(12) United States Patent
Jung et al.

(10) Patent No.: US 8,069,125 B2
(45) Date of Patent: Nov. 29, 2011

(54) METHODS AND SYSTEMS FOR COMPARING MEDIA CONTENT

(75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA
(US); Lowell L. Wood, Jr., Bellevue,
WA (US)

(73) Assignee: The Invention Science Fund I, Bellevue, WA (US)

( * ) Notice: Subject to any disclaimer, the term of this patent is extended or adjusted under 35 U.S.C. 154(b) by 979 days.

(21) Appl. No.: 12/005,115

(22) Filed: Dec. 20, 2007

(65) Prior Publication Data

US 2009/0163777 A1    Jun. 25, 2009

(51) Int. Cl.
*G06F 17/00* (2006.01)
*G06F 17/20* (2006.01)

(52) U.S. Cl. .......................................... 706/11

(58) Field of Classification Search .................. None
See application file for complete search history.

(56) References Cited

U.S. PATENT DOCUMENTS

| | | | |
|---|---|---|---|
| 6,009,458 A | 12/1999 | Hawkins et al. | |
| 6,081,660 A | 6/2000 | Macleod et al. | |
| 6,099,319 A | 8/2000 | Zaltman et al. | |
| 6,102,846 A | 8/2000 | Patton et al. | |
| 6,251,017 B1 | 6/2001 | Leason et al. | |
| 6,457,010 B1 | 9/2002 | Eldering et al. | |
| 6,817,979 B2 | 11/2004 | Nihtilä | |
| 6,904,408 B1 | 6/2005 | McCarthy et al. | |
| 7,115,034 B2 | 10/2006 | Kuwahara | |
| 7,468,729 B1 | 12/2008 | Levinson | |
| 7,788,188 B2 | 8/2010 | Kramer | |
| 2001/0034661 A1 | 10/2001 | Ferreira | |
| 2002/0090985 A1 | 7/2002 | Tochner et al. | |

(Continued)

FOREIGN PATENT DOCUMENTS
WO    WO 2008/063527 A2    5/2008

OTHER PUBLICATIONS

Krepki, R. The Berlin Brain—Computer Interface (BBCI). Submitted to the 9th International Conference on Distributed Multimedia Systems (DMS'03) [retrieved on Dec. 9, 2010]. Retrieved from the Internet:<URL:http://ml.cs.tu-berlin.de/publications/KreBlaCurMue03.pdf>.*

(Continued)

*Primary Examiner* — Omar Fernandez Rivas
*Assistant Examiner* — Peter Coughlan
(74) *Attorney, Agent, or Firm* — Keller LaPuma Woodard PC; Gerald M. Keller

(57) ABSTRACT

Avatars, methods, apparatuses, computer program products, devices and systems are described that carry out presenting to at least one member of a population a plurality of avatars associated with at least one instance of media content; measuring at least one physiologic activity of the at least one member of the population, the at least one physiologic activity proximate to at least one presented avatar among the plurality of avatars associated with at least one instance of media content; associating the at least one physiologic activity with at least one mental state; and identifying at least one instance of media content based on the at least one mental state.

46 Claims, 38 Drawing Sheets

U.S. PATENT DOCUMENTS

| | | | |
|---|---|---|---|
| 2002/0113820 | A1 | 8/2002 | Robinson et al. |
| 2003/0120140 | A1 | 6/2003 | Bango, Jr. |
| 2003/0142041 | A1 | 7/2003 | Barlow et al. |
| 2003/0177187 | A1 | 9/2003 | Levine et al. |
| 2004/0049490 | A1 | 3/2004 | Milov |
| 2004/0075677 | A1 | 4/2004 | Loyall et al. |
| 2004/0131998 | A1* | 7/2004 | Marom et al. ............... 434/236 |
| 2004/0199923 | A1 | 10/2004 | Russek |
| 2004/0210634 | A1 | 10/2004 | Ferrer et al. |
| 2004/0221224 | A1 | 11/2004 | Blattner et al. |
| 2005/0137015 | A1 | 6/2005 | Rogers et al. |
| 2005/0223328 | A1 | 10/2005 | Ashtekar et al. |
| 2005/0273017 | A1* | 12/2005 | Gordon ......................... 600/544 |
| 2006/0089543 | A1 | 4/2006 | Kim et al. |
| 2006/0129277 | A1* | 6/2006 | Wu et al. ....................... 700/245 |
| 2006/0195790 | A1 | 8/2006 | Beaupre et al. |
| 2006/0224546 | A1 | 10/2006 | Ballin et al. |
| 2006/0234795 | A1 | 10/2006 | Dhuniishaw et al. |
| 2006/0282304 | A1 | 12/2006 | Bedard et al. |
| 2006/0294084 | A1 | 12/2006 | Patel et al. |
| 2006/0294465 | A1 | 12/2006 | Ronen et al. |
| 2007/0002057 | A1 | 1/2007 | Danzig et al. |
| 2007/0050715 | A1 | 3/2007 | Behar |
| 2007/0082738 | A1 | 4/2007 | Fickie et al. |
| 2007/0101368 | A1 | 5/2007 | Jacoby et al. |
| 2007/0176921 | A1 | 8/2007 | Iwasaki et al. |
| 2007/0197274 | A1 | 8/2007 | Dugan |
| 2007/0207846 | A1* | 9/2007 | Burak et al. ...................... 463/9 |
| 2007/0214106 | A1 | 9/2007 | Johnston et al. |
| 2007/0218987 | A1 | 9/2007 | Van Luchene et al. |
| 2007/0233579 | A1 | 10/2007 | Saarinen et al. |
| 2007/0260984 | A1 | 11/2007 | Marks et al. |
| 2007/0282177 | A1 | 12/2007 | Pilz |
| 2007/0282913 | A1 | 12/2007 | Hurtis et al. |
| 2008/0030496 | A1 | 2/2008 | Lee et al. |
| 2008/0039204 | A1 | 2/2008 | Ackley et al. |
| 2008/0039737 | A1 | 2/2008 | Breiter et al. |
| 2008/0065468 | A1 | 3/2008 | Berg et al. |
| 2008/0081692 | A1 | 4/2008 | Pope et al. |
| 2008/0091692 | A1 | 4/2008 | Keith et al. |
| 2008/0120558 | A1 | 5/2008 | Nathan et al. |
| 2008/0120588 | A1 | 5/2008 | Becker |
| 2008/0158222 | A1 | 7/2008 | Li et al. |
| 2008/0163379 | A1 | 7/2008 | Robinson et al. |
| 2008/0172412 | A1 | 7/2008 | Gruhl et al. |
| 2008/0214902 | A1 | 9/2008 | Lee et al. |
| 2008/0222295 | A1 | 9/2008 | Robinson et al. |
| 2008/0262911 | A1 | 10/2008 | Altberg et al. |
| 2008/0263459 | A1 | 10/2008 | Altberg et al. |
| 2008/0275340 | A1 | 11/2008 | Beach et al. |
| 2009/0013002 | A1 | 1/2009 | Eggink et al. |
| 2009/0044113 | A1 | 2/2009 | Jones et al. |
| 2009/0109213 | A1 | 4/2009 | Hamilton, II et al. |
| 2009/0143695 | A1 | 6/2009 | Mullen et al. |
| 2009/0156907 | A1* | 6/2009 | Jung et al. ..................... 600/300 |
| 2009/0156955 | A1* | 6/2009 | Jung et al. ..................... 600/544 |
| 2009/0161856 | A1 | 6/2009 | Lurie |

OTHER PUBLICATIONS

Leuthardt, 'Electrocorticography—Based Brain Computer Interface—The Seattle Experience', Jun. 2006, IEEE, 1534-4320, pp. 194-198.*

Bloom, N. 'Parallel Brain Computer Interface signal processing', Oct. 23, 2007 [retrieved on Dec. 9, 2010]. Retrieved from the Internet:<http:janus.cs.utwente.nl:8000/twiki/pub/brainmedia/intermediateandfinalreports/afstudeerverslagneilsbloomfinal.pdf.>.*

'The Sims' (user manual), 2000, Electronis Arts.*

Parc Research; "Content-Centric Networking: Parc's Strategy for Pioneering a Self-Organizing Network That Meets Information Needs"; pp. 1-4; Xerox Corporation; located at: http://www.parc.xerox.com/research/projects/networking/contentcentric/mediabackgrounder.html; printed on Mar. 2, 2009.

Ambler, Tim, et al.; "Salience and Choice: Neural Correlates of Shopping Decisions"; Psychology & Marketing; bearing a date of Apr. 2004; pp. 247-261; vol. 21; Wiley Periodicals, Inc.

Axelrod, Lesley, et al., "Smoke and Mirrors: Gathering User Requirements for Emerging Affective Systems"; 26th Int. Conf. Information Technology Interfaces ITI 2004; bearing a date of Jun. 7-10, 2004; pp. 323-328, Cavtat, Croatia.

Cabeza, Roberto, et al.; "Imaging Cognition II: An Empirical Review of 275 PET and fMRI Studies"; Journal of Cognitive Neuroscience; bearing a date of 2000, pp. 1-47, vol. 12, No. 1.

Clarke, Peter; "IMEC has a brain wave: feed EEG emotion back into games"; EE Times online, bearing a date of Nov. 1, 2007; pp. 1-2; located at http://www.eetimes.eu/design/202801063 ; printed on Nov. 1, 2007.

Contreras, Marco, et al.; "Inactivation of the Interoceptive Insula Disrupts Drug Craving and Malaise Induced by Lithium"; Science; bearing a date of Oct. 26, 2007; pp. 655-658; vol. 318.

Gur, Raquel E. et al.; "An fMRI Study of Facial Emotion Processing in Patients with Schizophrenia"; Am. J. Psych., bearing a date of Dec. 2002; pp. 1992-1999; vol. 159; No. 12.

Henig, Robin Marantz; "Looking for the Lie," New York Times; bearing a date of Feb. 5, 2006; pp. 1-13; located at http://www.nytimes.com/2006/02/05/magazine/05lying.html?pagewanted=print; printed on Nov. 28, 2007.

Holroyd, Clay B., et al.; "Dorsal anterior cingulate cortex shows fMRI response to internal and external error signals"; Nature Neuroscience; bearing a date of May 2004; pp. 497-498; vol. 7; No. 5.

Kenning, Peter et al.; "NeuroEconomics: An overview from an economic perspective," Brain Research Bulletin; bearing a date of 2005; pp. 343-354; vol. 67; Elseiver, Inc.

King-Casas, Brooks et al.; "Getting to Know You: Reputation and Trust in a Two-Person Economic Exchange" Science, bearing a date of Apr. 1, 2005; pp. 78-83; vol. 308; No. 5718; AAAS.

Knoch, Daria, et al.; "Diminishing Reciprocal Fairness by Disrupting the Right Prefrontal Cortex"; Science; bearing a date of Nov. 3, 2006; pp. 829-832; vol. 314; No. 5800; AAAS.

Koechlin, Etienne and Hyafil, Alexandre; "Review: Anterior Prefrontal Function and the Limits of Human Decision-Making"; Science; bearing a date of Oct. 26, 2007; pp. 594-598; vol. 318.

Kording, Konrad; "Decision Theory: What "Should" the Nervous System Do?"; Science; bearing a date of Oct. 26, 2007; pp. 606-610; vol. 318.

Lee, Nick; "What is 'Neuromarketing'? A Discussion and Agenda for Future Research"; International Journal of Psychophysiology; bearing a date of 2007; pp. 199-204; vol. 63; Elseiver B.V.

Martin, Sarah B., et al.; "Human Experience Seeking Correlates with Hippocampus Volume: Convergent Evidence from Manual Tracing and Voxel-Based Morphometry"; Neuropsychologia; bearing a date of 2007; pp. 2874-2881 (abstract p. 1); vol. 45, Issue 12; Elseiver B.V.

"Men Motivated by 'Superior Wage'"; BBC News; bearing a date of Nov. 23, 2007; p. 1; located at http://newsvote.bbc.co.uk/mpapps/pagetools/print/news.bbc.co.uk/2/h; printed on Nov. 29, 2007.

"Mind-reading machine knows what you see," NewScientist.com; bearing a date of Apr. 25, 2005; pp. 1-3; located at http://www.newscientist.com/article.ns?id=dn7304&feedId=online-news_rss20; printed on Nov. 28, 2007.

"New mini-sensor may have biomedical and security applications"; Physorg.com; bearing a date of Nov. 1, 2007; pp. 1-4; located at http://www.physorg.com/news113151078.html; printed on Nov. 8, 2007**.

Paulus, Martin P.; "Review: Decision-Making Dysfunctions in Psychiatry-Altered Homeostatic Processing?"; Science, bearing a date of Oct. 26, 2007; pp. 602-606; vol. 318.

Potenza, Marc N. et al; "Gambling Urges in Pathological Gambling"; Arch Gen Psychiatry; bearing a date of Aug. 2003; pp. 828-836; vol. 60; downloaded from www.archgenpsychiatry.com on Oct. 6, 2007.

Schaefer, Michael, et al.; "Neural Correlates of Culturally Familiar Brands of Car Manufacturers"; NeuroImage; bearing dates of Oct. 8, 2005, and Feb. 17, 2006; pp. 861-865; vol. 31.

Stern, Peter; "Decisions, Decisions; Science"; bearing a date of Oct. 26, 2007; p. 593; vol. 318.

Stratonnikov, Alexander A., et al.; "Evaluation of Blood Oxygen Saturation in vivo from Diffuse Reflectance Spectra"; abstract; Journal of Biomedical Optics; bearing a date of Oct. 2001; pp. 457-467 (Abstract p. 1-2); vol. 6; printed on Nov. 28, 2007.

"Technology could enable computers to 'read the minds' of users" Physorg.com; pp. 1-2; located at http://www.physorg.com/news110463755.html; printed on Nov. 28, 2007; Tufts University.

Vasalou, Asimina, et al.; "Constructing My Online Self: Avatars that Increase Self-Focused Attention"; CHI 2007; bearing dates of Apr. 28-May 3, 2007; pp. 1-4; San Jose, California; ACM.

Wang, Gene-Jack, et al.; "Gastric stimulation in obese subject activates the hippocampus and other regions involved in brain reward circuitry"; PNAS, bearing a date of Oct. 17, 2006; pp. 15641-15645; vol. 103, No. 42.

Wise; Jeff; "Thought Police: How Brain Scans Could Invade Your Private Life"; Popular Mechanics; bearing a date of Nov. 2007; pp. 1-4; located at http://www.popularmechanics.com/science/researcy/4226614.html?d; printed on Nov. 8, 2007.

Ayanwale et al.; "The Influence of Advertising on Consumer Brand Preference"; J. Soc. Sci.; 2005; pp. 9-16; vol. 10(1); Kamla-Raj.

Illner et al.; "Functional brain imaging: Evaluation of the effects of violent media exposure"; Paediatr Child Health; May/Jun. 2003; pp. 283-284; vol. 8, No. 5.

Nakai et al.; "Scalable Collaborative Virtual Environment Considering User's Interests Based on P2P Overlay Network"; Proceedings of the First International Conference on Complex, Intelligent and Software Intensive Systems (CISIS'07); 2007; 5 pages; IEEE.

Rossiter et al.; "Brain-Imaging Detection of Visual Scene Encoding in Long-term Memory for TV Commercials"; Journal of Advertising Research; Mar./Apr. 2001; pp. 13-21.

Bellman, Steven et al.; "Predictors of Online Buying Behavior"; Communications of the ACM; Dec. 1999; pp. 32-38; vol. 42, No. 12; ACM.

Burke, Raymond R.; "Technology and the Customer Interface: What Consumers Want in the Physical and Virtual Store"; Journal of the Academy of Marketing Science; 2002; pp. 411-432; vol. 30, No. 4; Academy of Marketing Science.

Case, Thomas et al.; "Drivers of On-Line purchasing Among U.S. University Students" AMCIS 2001 Proceedings; Dec. 31, 2001 ; pp. 873-878; Paper 169; AIS Electronic Library.

Li, Hairong et al.; "The Impact of Perceived Channel Utilities, Shopping Orientations, and Demographics on the Consumer's Online Buying Behavior"; JCMC; Dec. 1999;pp. 1-20; vol. 5, No. 2.

Montgomery; Alan L. et al.; "Learning About Customers Without Asking"; Jan. 2002; pp. 1-33; Alan L. Montgomery and Kannan Srinivasan.

Van Den Poel, Dirk et al.; "Predicting online-purchasing behavior"; European Journal of Operational Research; 2005 pp. 557-575; vol. 166.

Wise, Jeff; "Thought Police, How Brain Scans Could invade Your Private Life"; Popular Mechanics; bearing a date of Nov. 2007; pp. 1-4; located at: www.popularmechanics.com/science/research/4226614.html; printed on Nov. 8, 2007.

Kim, Sonho et al.; "Usability Evaluation of Humanoid-Animation Avatar with Physiological Signals"; Frontiers in the Convergence of Bioscience and Information Technologies; IEEE; bearing a date of Oct. 11-13, 2007; pp. 628-629 & 636-639, 1 supplemental page.

Picard, Rosalind W. et al.; "Toward Machine Emotional Intelligence: Analysis of Affective Physiological State"; IEEE Transactions on Pattern Analysis and Machine Intelligence; bearing a date of Oct. 2001; vol. 23, No. 10; pp. 1175-1191.

\* cited by examiner

FIG. 4
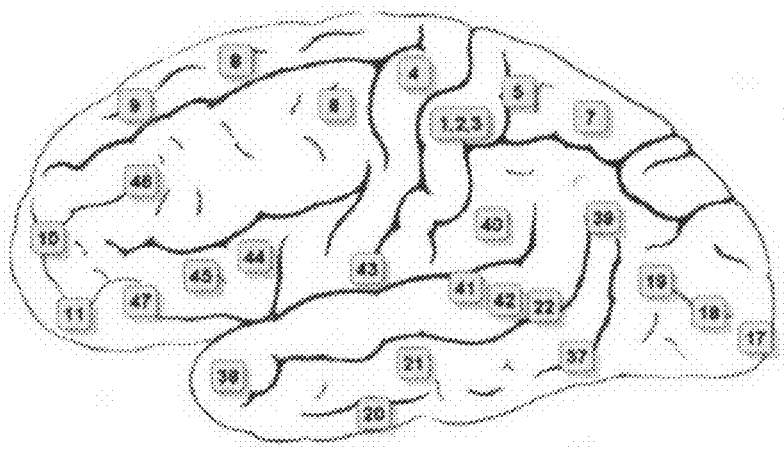
400 Lateral surface of
the brain with
Brodmann's areas
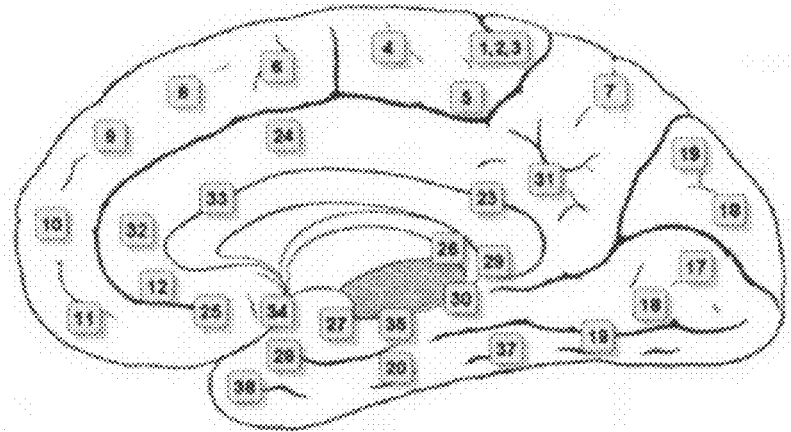
402 Medial surface of
the brain with
Brodmann's areas

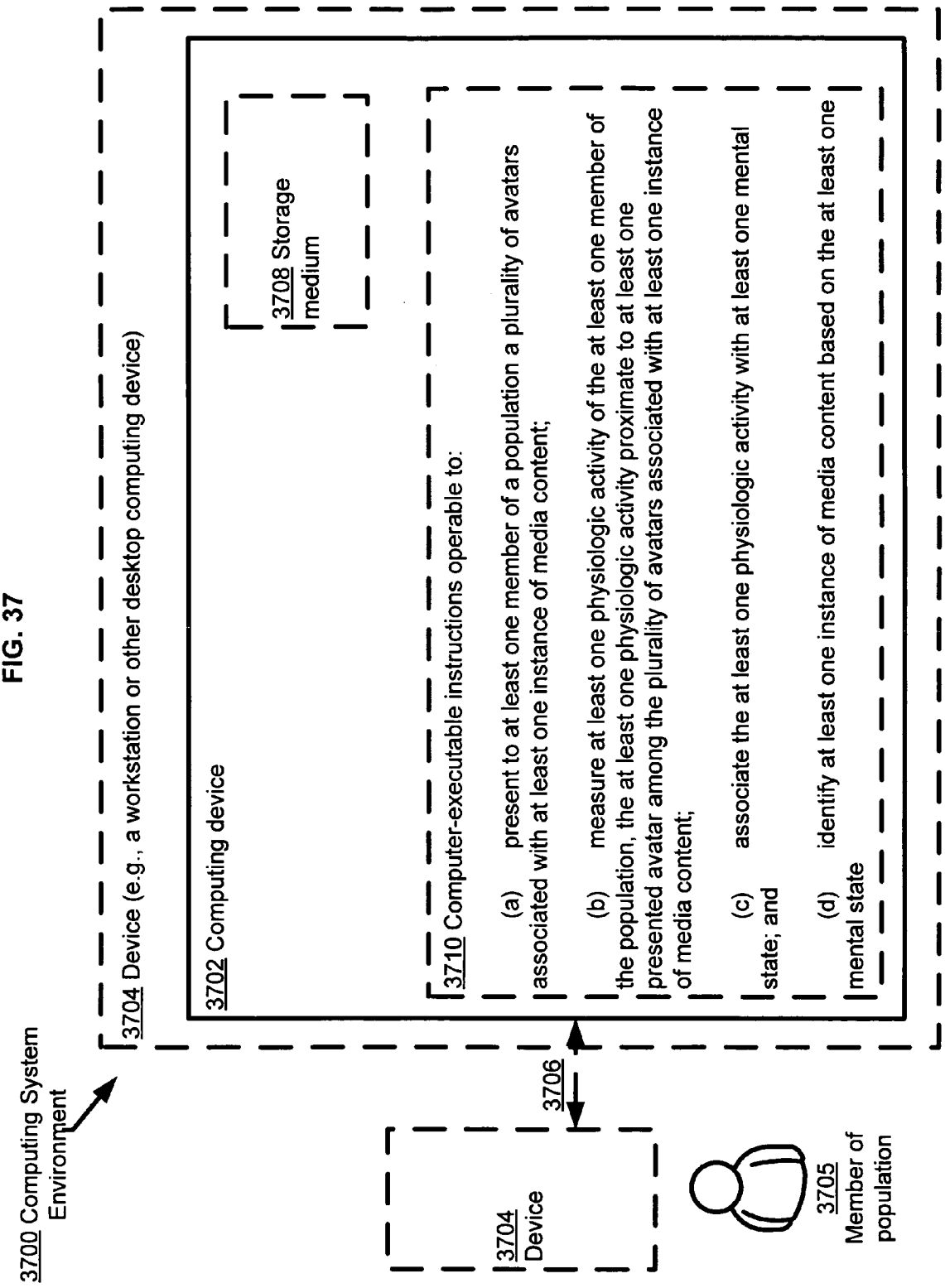

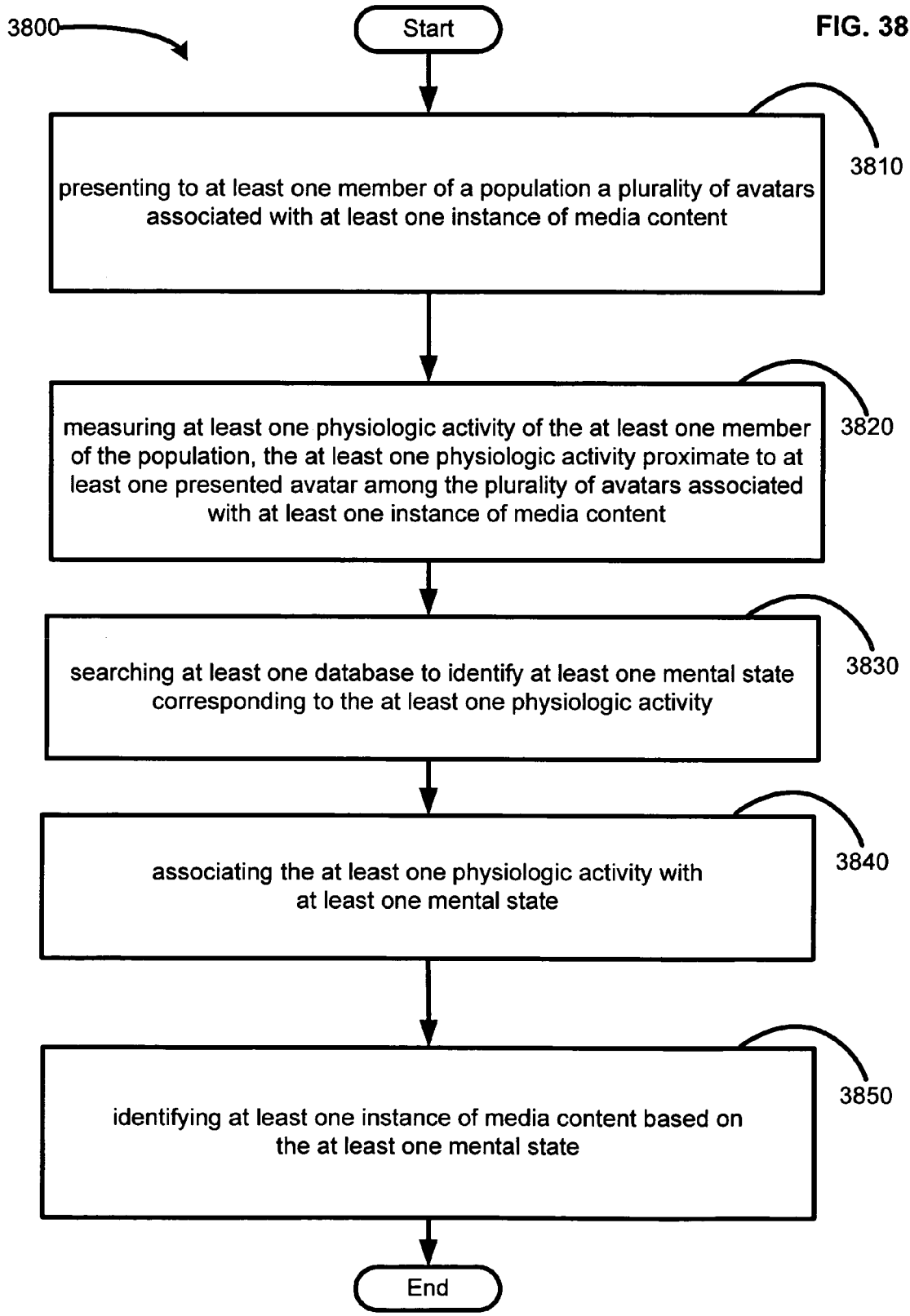

METHODS AND SYSTEMS FOR COMPARING MEDIA CONTENT

INCORPORATION-BY-REFERENCE TO OTHER APPLICATIONS

All subject matter of the Incorporated-by-reference Applications and of any and all parent, grandparent, great-grandparent, etc. applications of the Incorporated-by-reference Applications is incorporated herein by reference to the extent such subject matter is not inconsistent herewith.

INCORPORATED-BY-REFERENCE APPLICATIONS

U.S. patent application Ser. No. 12/002,289, entitled METHODS AND SYSTEMS FOR SPECIFYING AN AVATAR, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 13 Dec. 2007.

U.S. patent application Ser. No. 12/002,788, entitled METHODS AND SYSTEMS FOR IDENTIFYING AN AVATAR-LINKED COHORT, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 17 Dec. 2007.

TECHNICAL FIELD

This description relates to data capture and data handling techniques.

SUMMARY

An embodiment provides a method. In one implementation, the method includes but is not limited to presenting to at least one member of a population a plurality of avatars associated with at least one instance of media content; measuring at least one physiologic activity of the at least one member of the population, the at least one physiologic activity proximate to at least one presented avatar among the plurality of avatars associated with at least one instance of media content; associating the at least one physiologic activity with at least one mental state; and identifying at least one instance of media content based on the at least one mental state. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for presenting to at least one member of a population a plurality of avatars associated with at least one instance of media content; circuitry for measuring at least one physiologic activity of the at least one member of the population, the at least one physiologic activity proximate to at least one presented avatar among the plurality of avatars associated with at least one instance of media content; circuitry for associating the at least one physiologic activity with at least one mental state; and circuitry for identifying at least one instance of media content based on the at least one mental state. In addition to the foregoing, other system aspects are described in the claims, drawings, and text forming a part of the present disclosure.

An embodiment provides a computer program product. In one implementation, the computer program product includes but is not limited to a signal-bearing medium bearing (a) one or more instructions for presenting to at least one member of a population a plurality of avatars associated with at least one instance of media content; (b) one or more instructions for measuring at least one physiologic activity of the at least one member of the population, the at least one physiologic activity proximate to at least one presented avatar among the plurality of avatars associated with at least one instance of media content; (c) one or more instructions for associating the at least one physiologic activity with at least one mental state; and (d) one or more instructions for identifying at least one instance of media content based on the at least one mental state. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to (a) present to at least one member of a population a plurality of avatars, each avatar associated with at least one instance of media content; (b) measure at least one physiologic activity of the at least one member of the population, the at least one physiologic activity proximate to at least one presented avatar among the plurality of avatars associated with at least one instance of media content; (c) associate the at least one physiologic activity with at least one mental state; and (d) identify at least one instance of media content based on the at least one mental state. In addition to the foregoing, other system aspects are described in the claims, drawings, and text forming a part of the present disclosure.

In one or more various aspects, related systems include but are not limited to computing means and/or programming for effecting the herein referenced method aspects; the computing means and/or programming may be virtually any combination of hardware, software, and/or firmware configured to effect the herein referenced method aspects depending upon the design choices of the system designer.

In addition to the foregoing, various other method and/or system and/or program product aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE DRAWINGS

With reference now to FIG. 1, shown is an example of an avatar attribute specification system and/or a system for comparing media content in which embodiments may be implemented, perhaps in a device and/or through a network, which may serve: as a context for introducing one or more processes and/or devices described herein. Also depicted on FIG. 1 is the example operational flow of FIG. 22 described below.

FIG. 4 shows diagrammatic views of the surface of the human brain.

Figure 5:
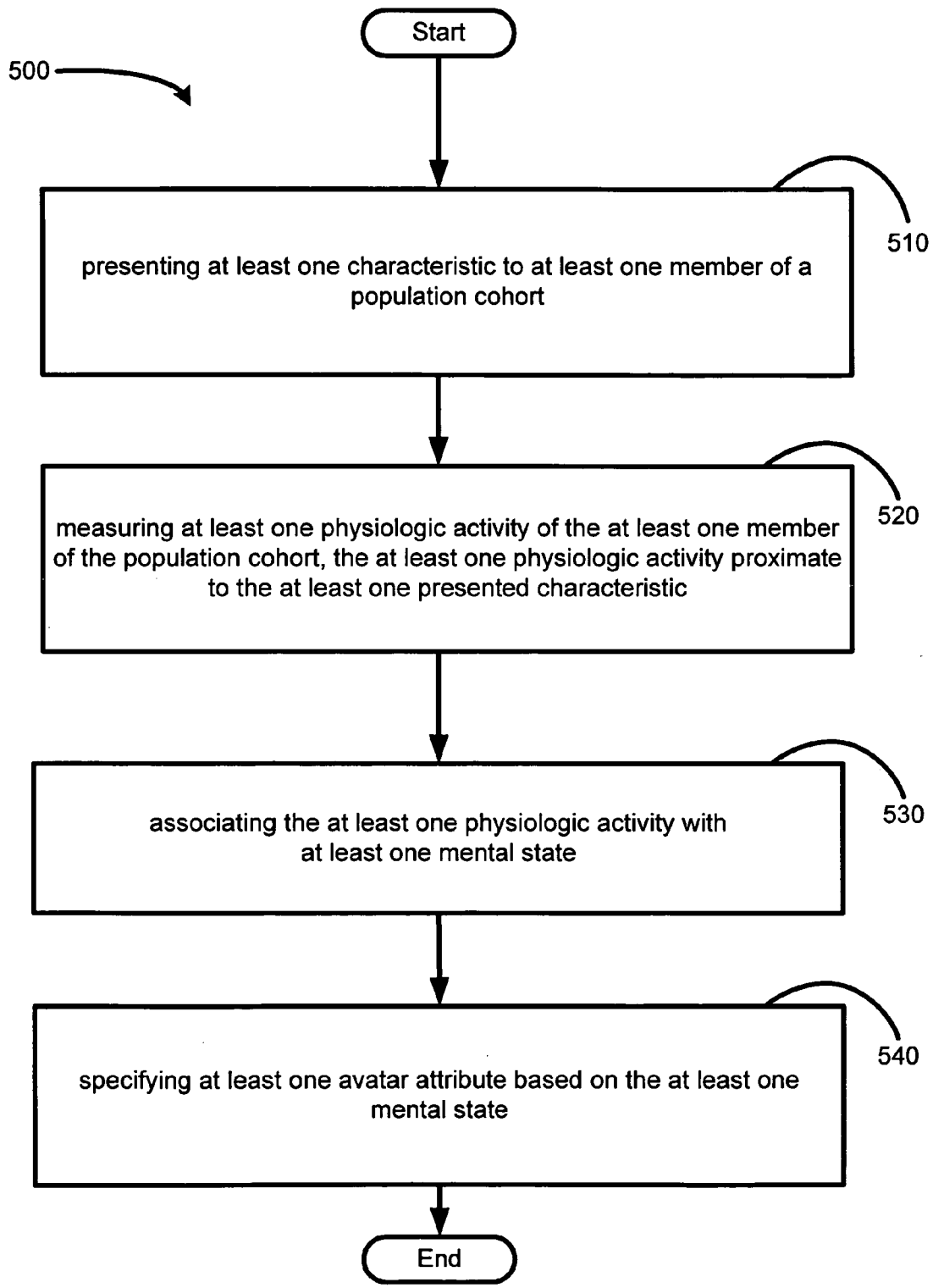

With reference now to FIG. 5, shown is an example of an operational flow representing example operations related to specifying an avatar attribute, which may serve as a context for introducing one or more processes and/or devices described herein.

Figure 6:
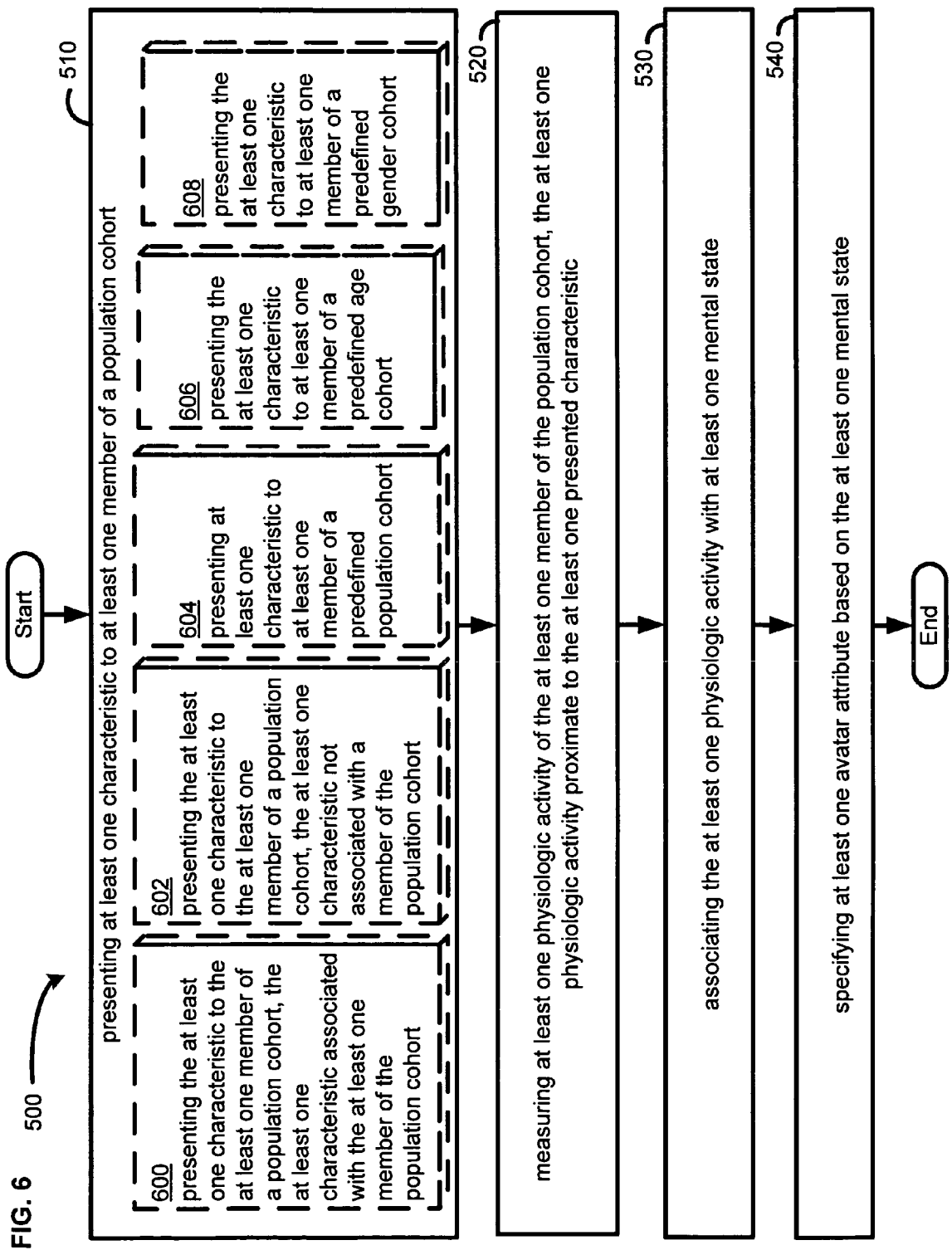

FIG. 6 illustrates an alternative embodiment of the example operational flow of FIG. 5.

Figure 7:
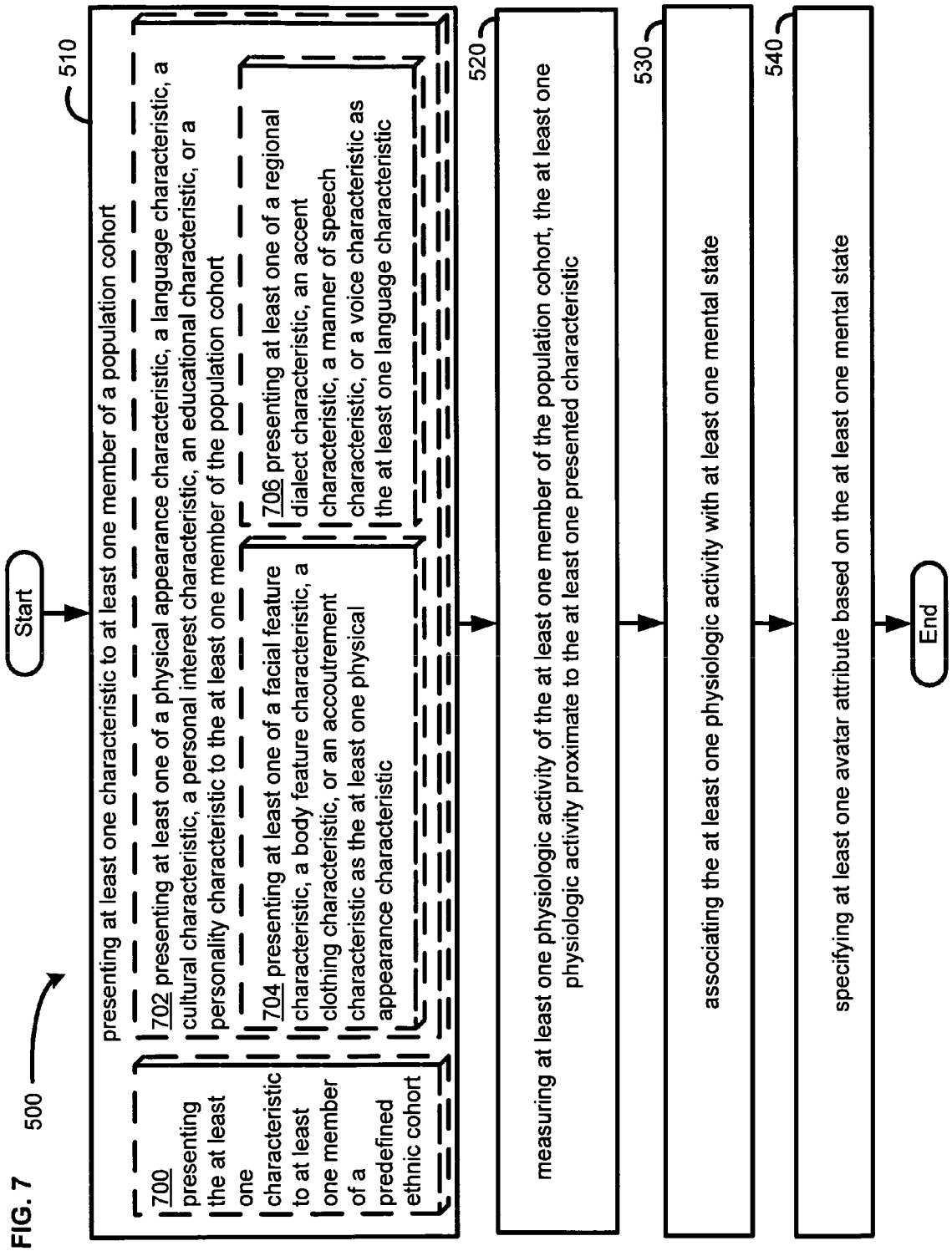

FIG. 7 illustrates an alternative embodiment of the example operational flow of FIG. 5.

Figure 8:
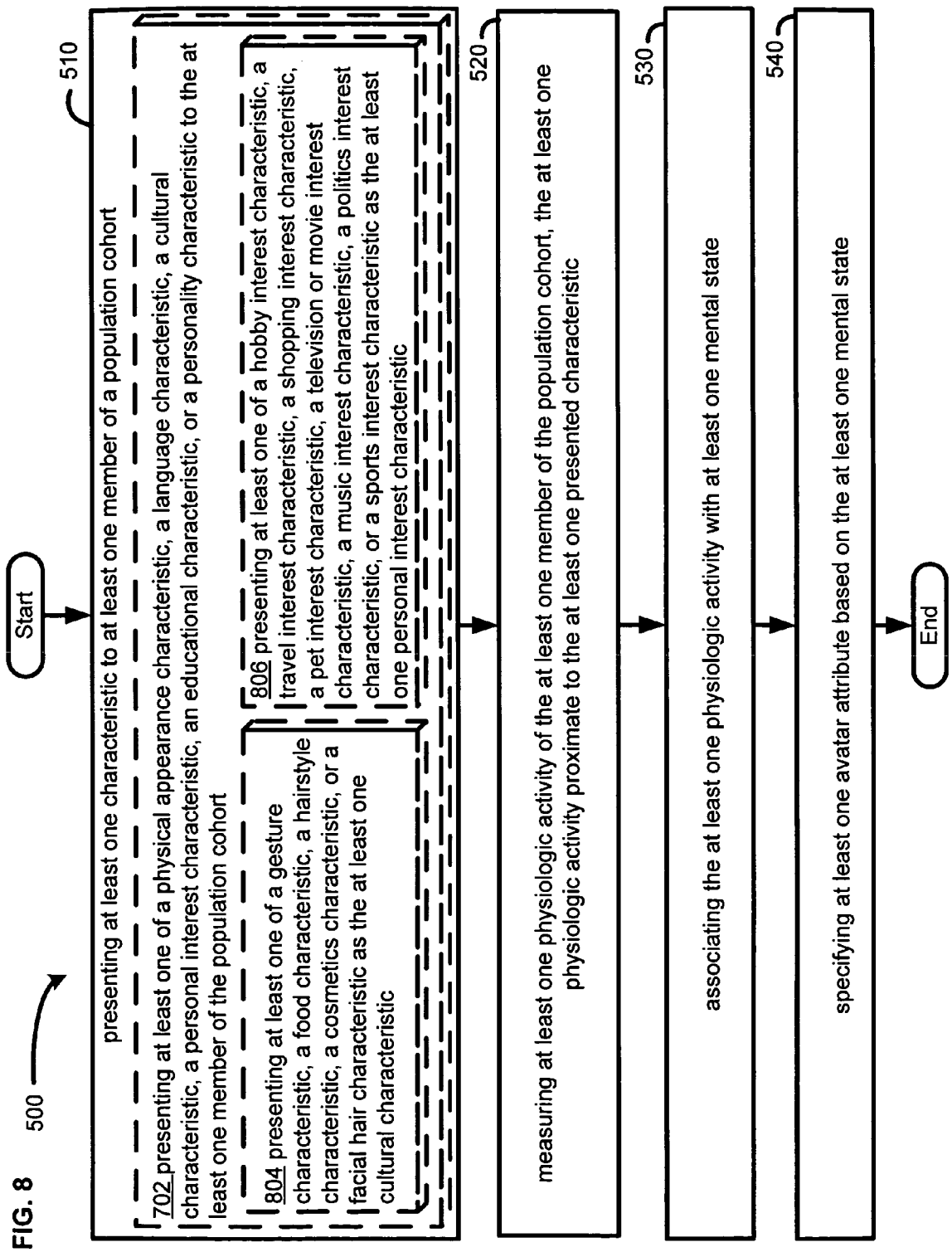

FIG. 8 illustrates an alternative embodiment of the example operational flow of FIG. 5.

Figure 9:
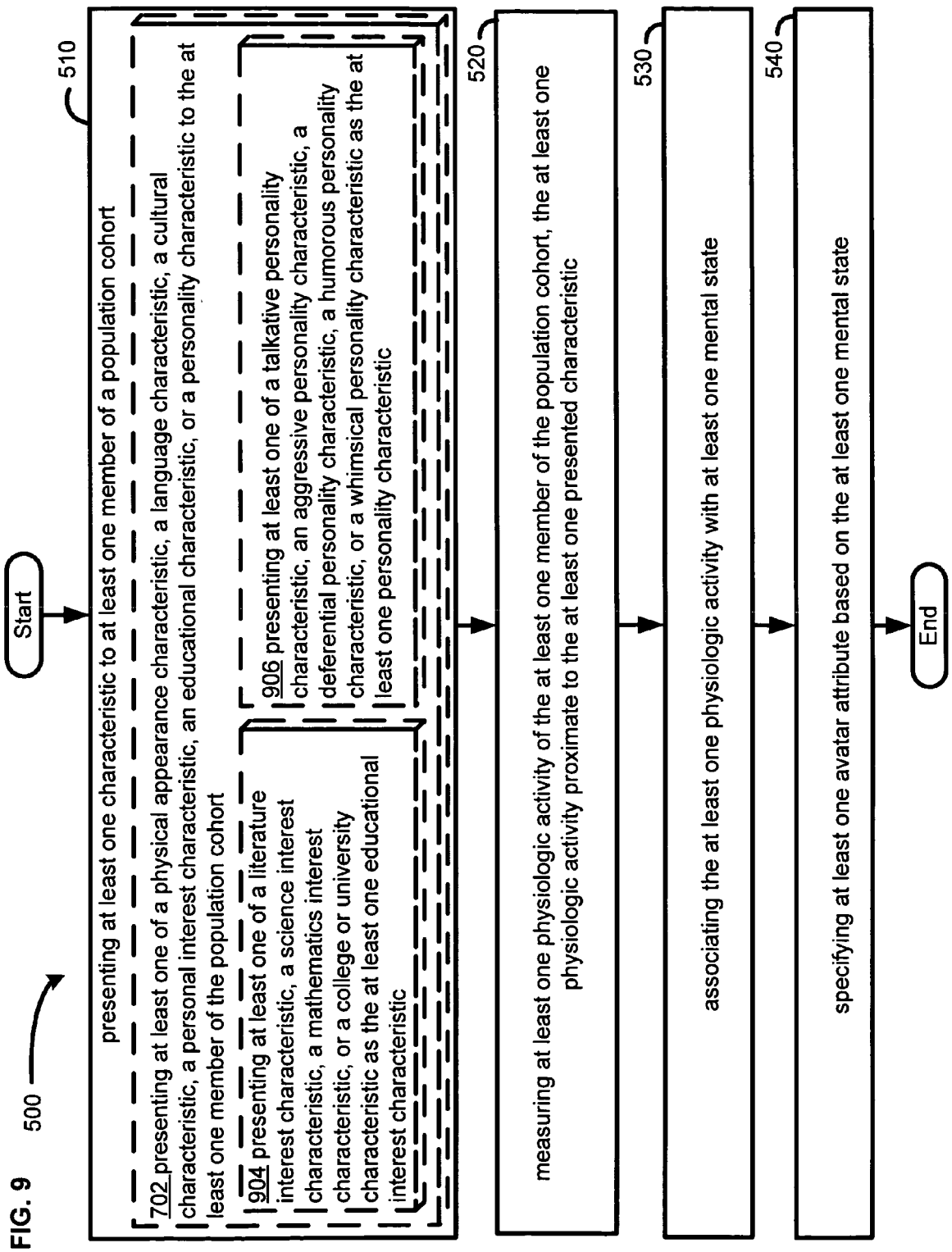

FIG. 9 illustrates an alternative embodiment of the example operational flow of FIG. 5.

Figure 10:
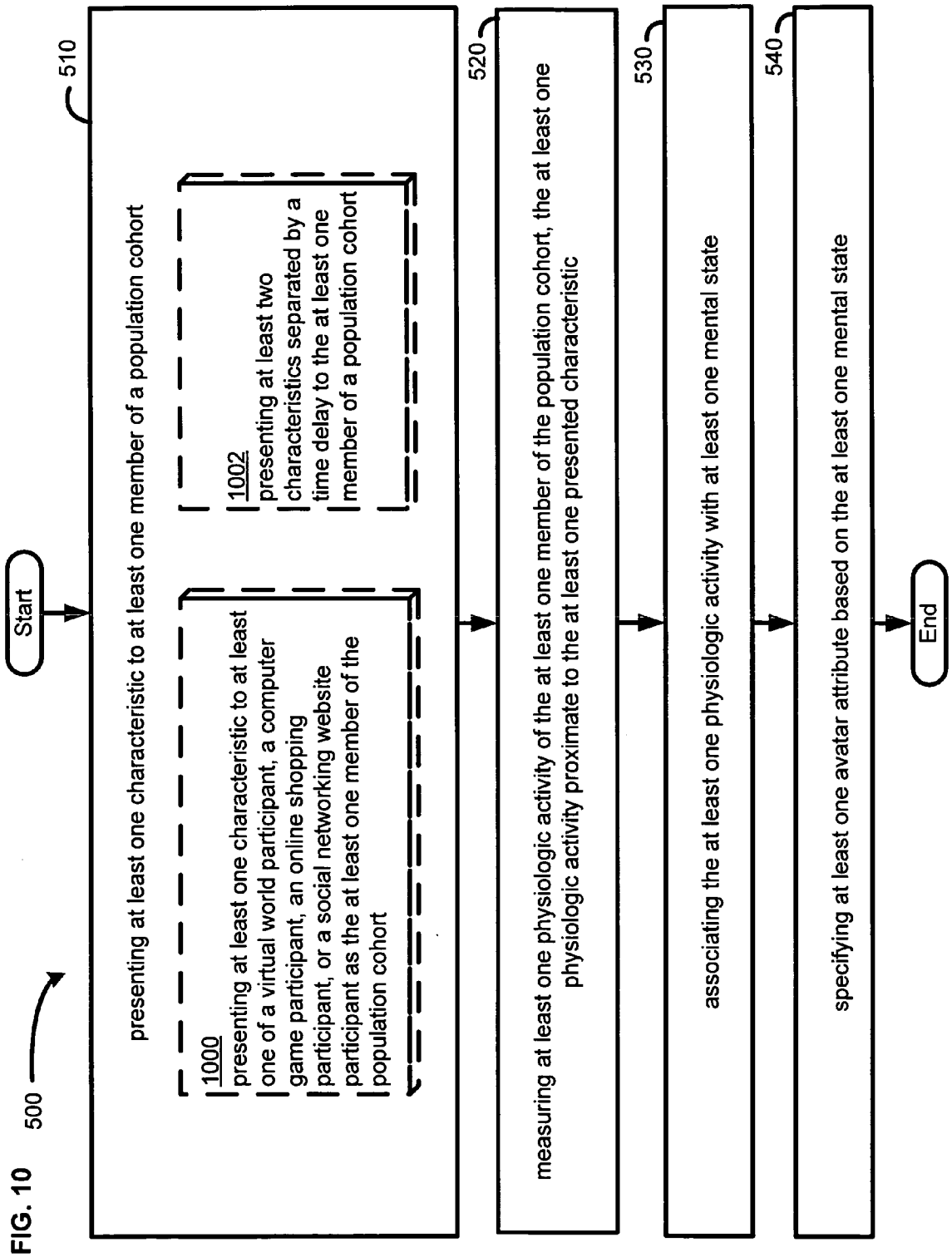

FIG. 10 illustrates an alternative embodiment of the example operational flow of FIG. 5.

Figure 11:
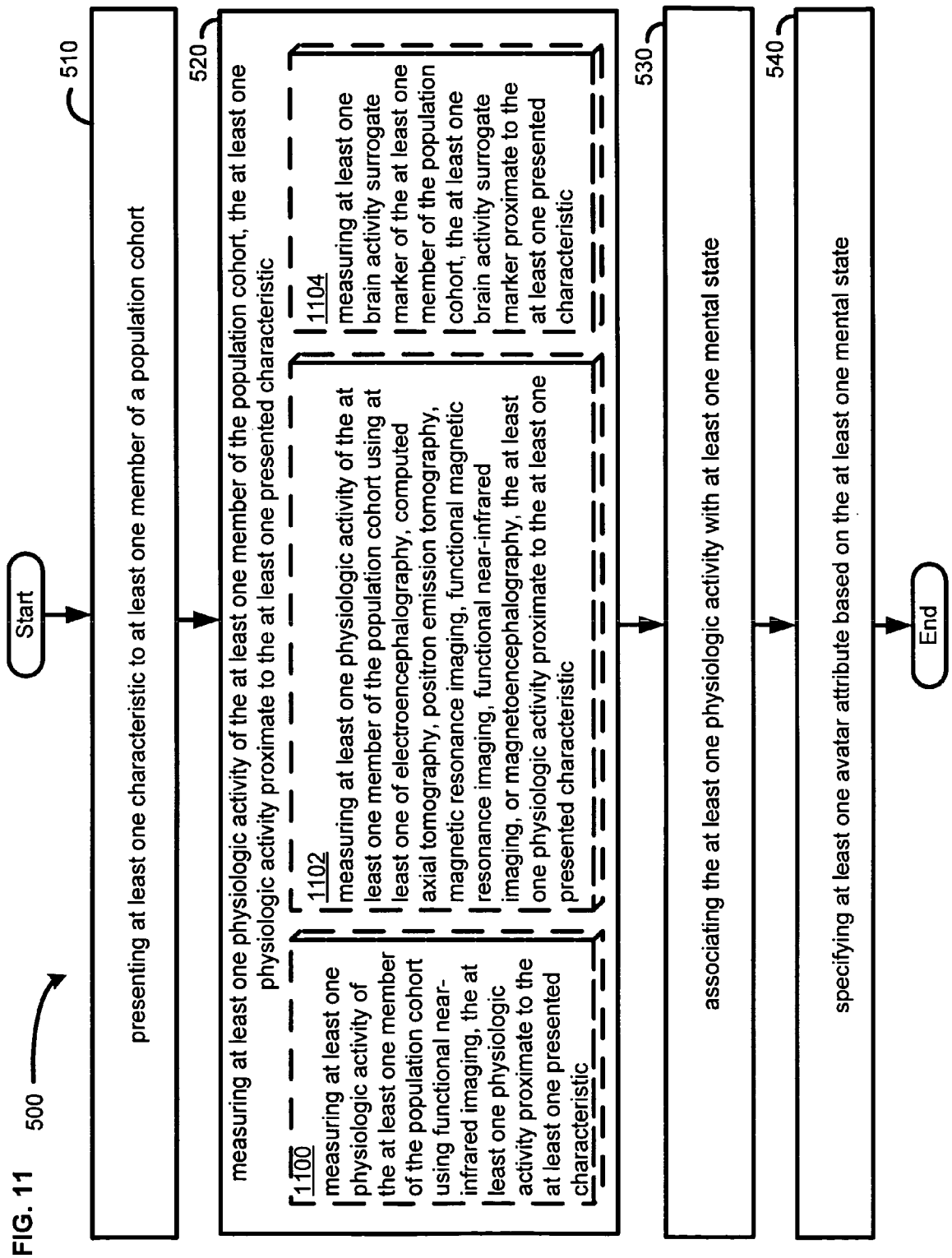

FIG. 11 illustrates an alternative embodiment of the example operational flow of FIG. 5.

Figure 12:
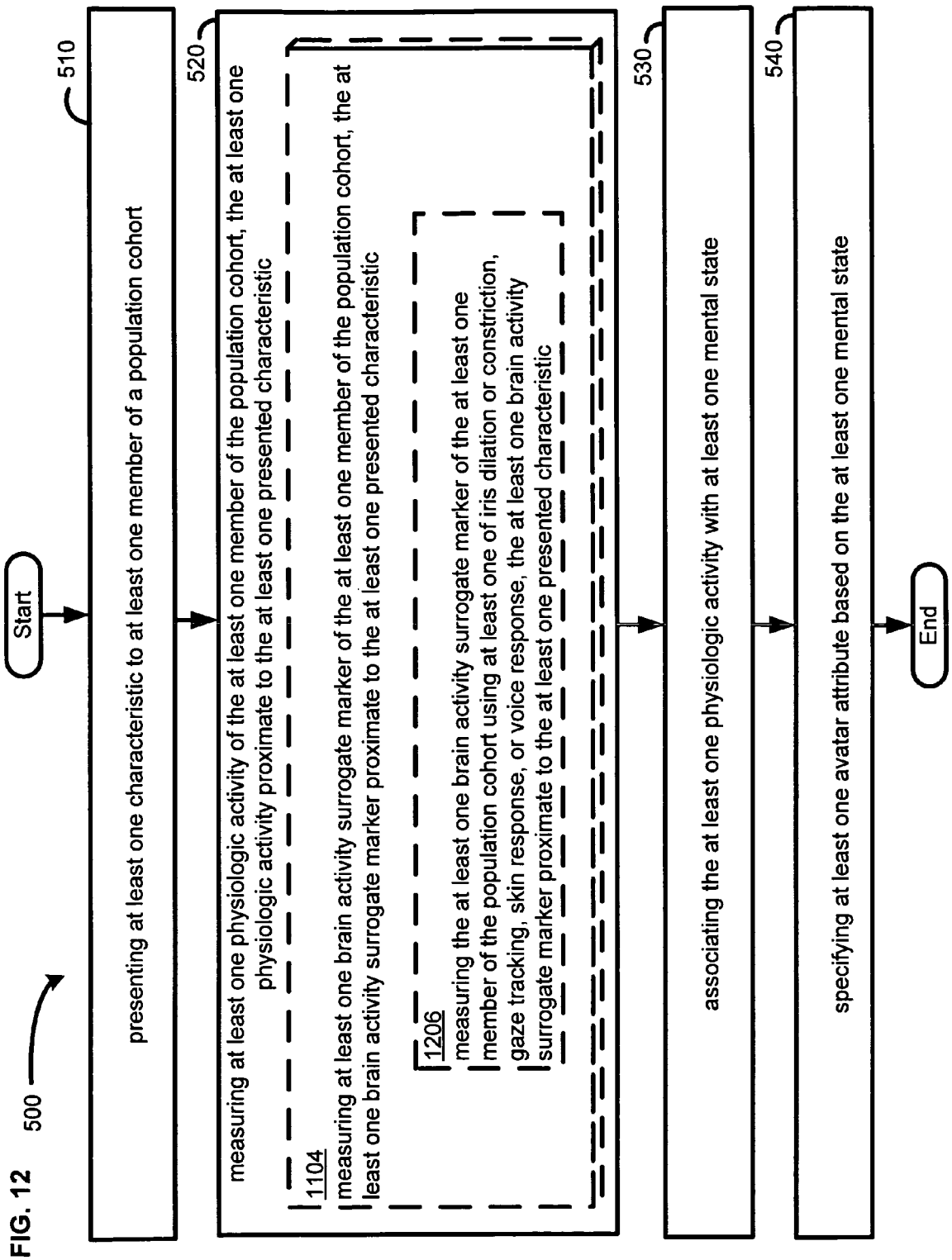

FIG. 12 illustrates an alternative embodiment of the example operational flow of FIG. 5.

Figure 13:
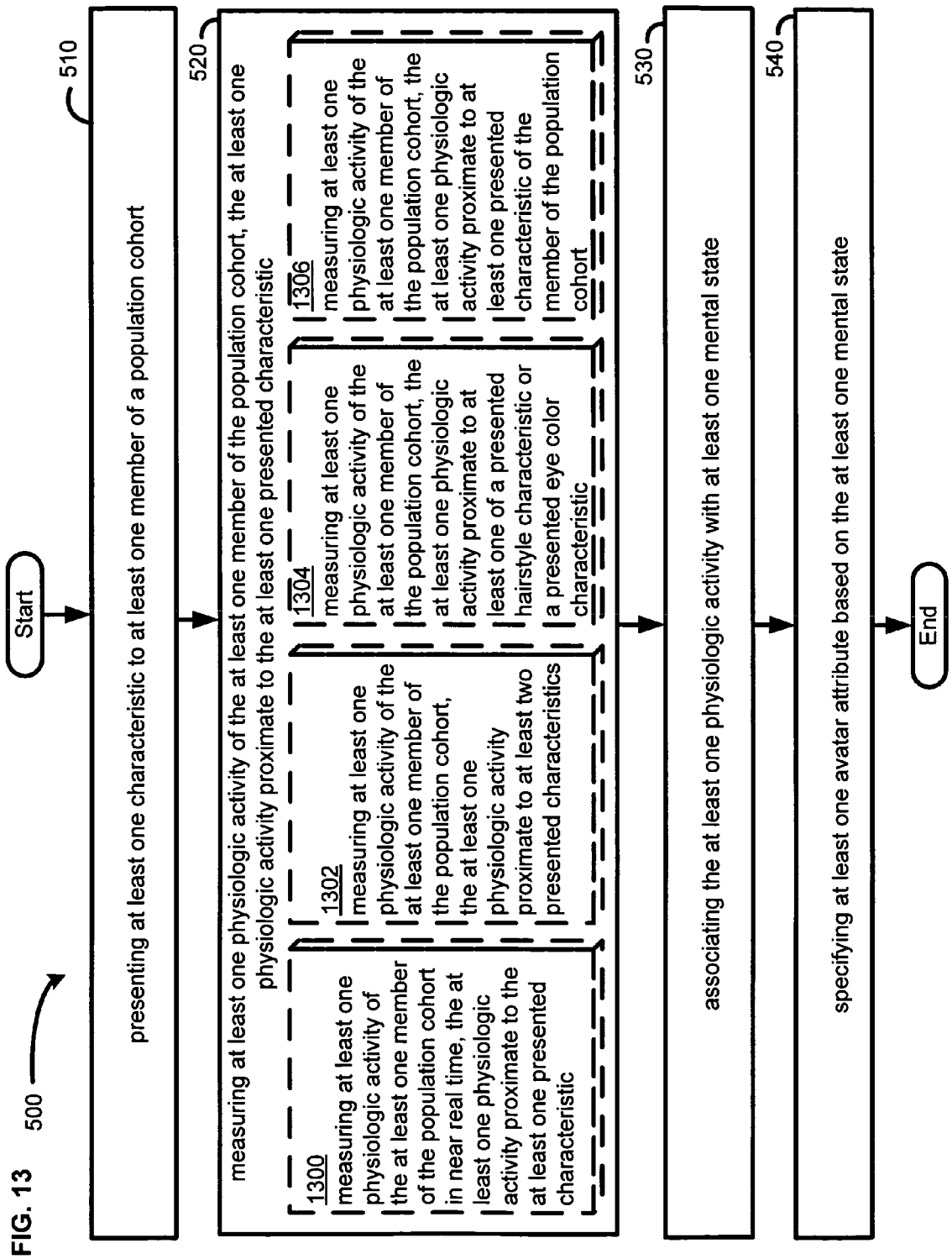

FIG. 13 illustrates an alternative embodiment of the example operational flow of FIG. 5.

Figure 14:
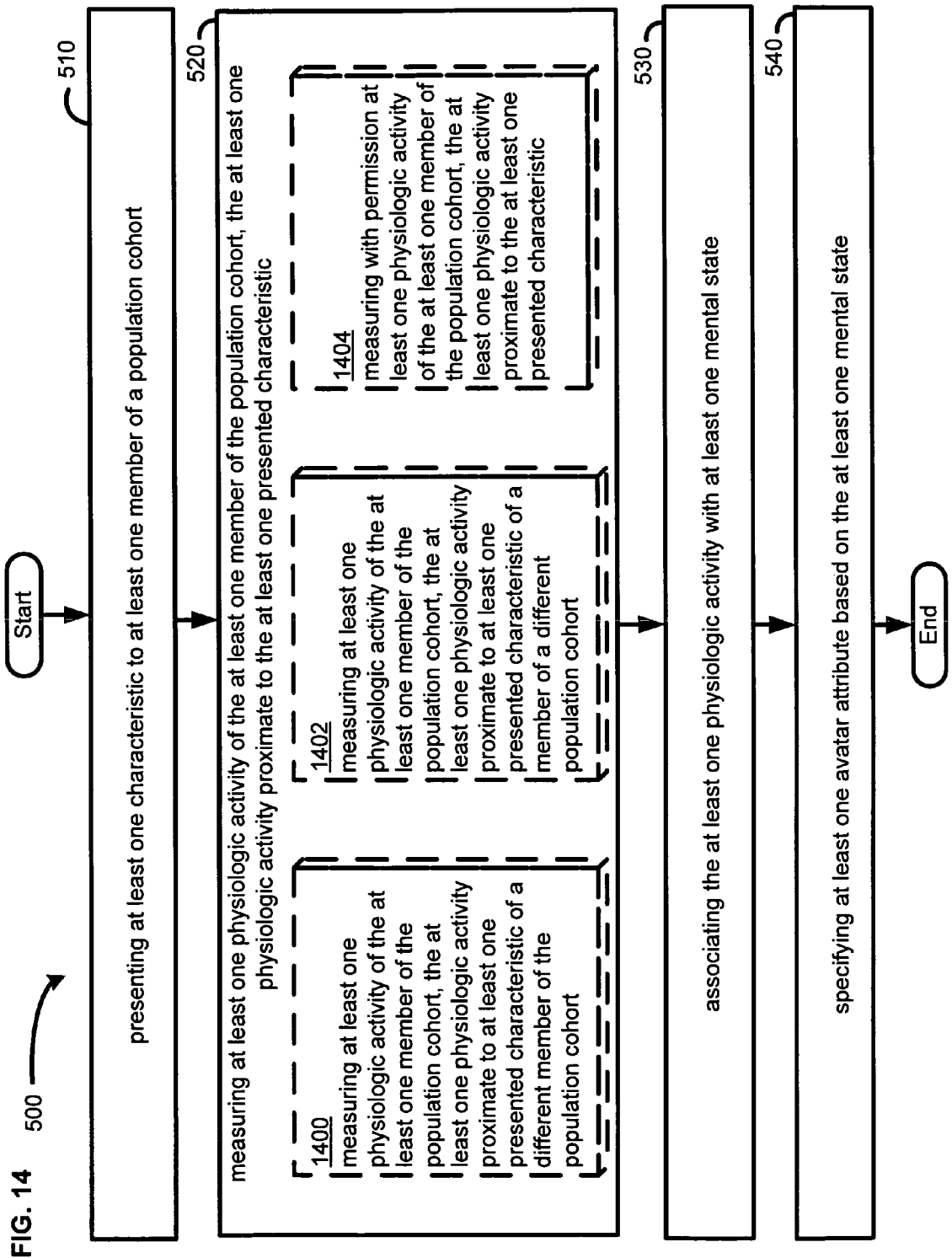

FIG. 14 illustrates an alternative embodiment of the example operational flow of FIG. 5.

Figure 15:
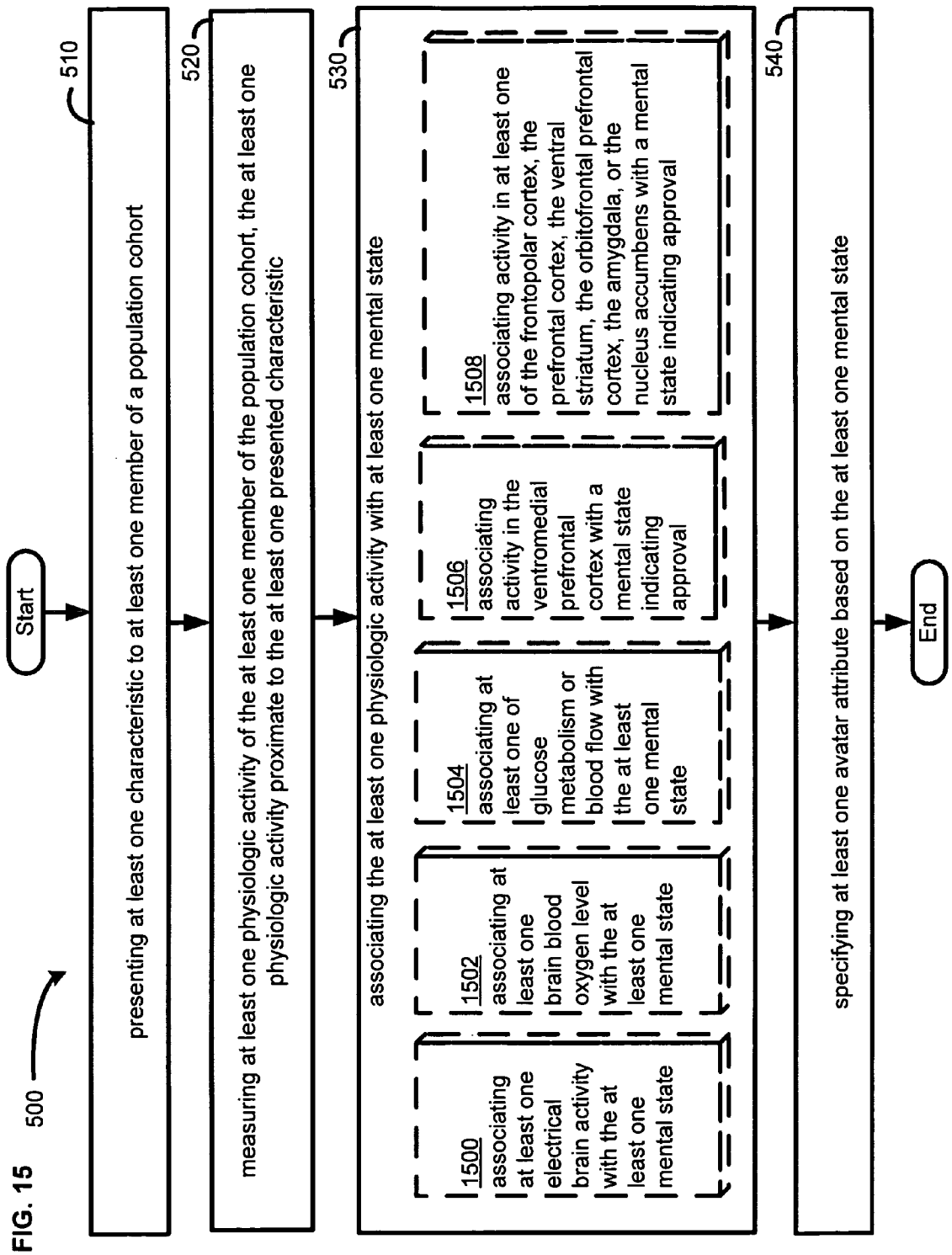

FIG. 15 illustrates an alternative embodiment of the example operational flow of FIG. 5.

Figure 16:
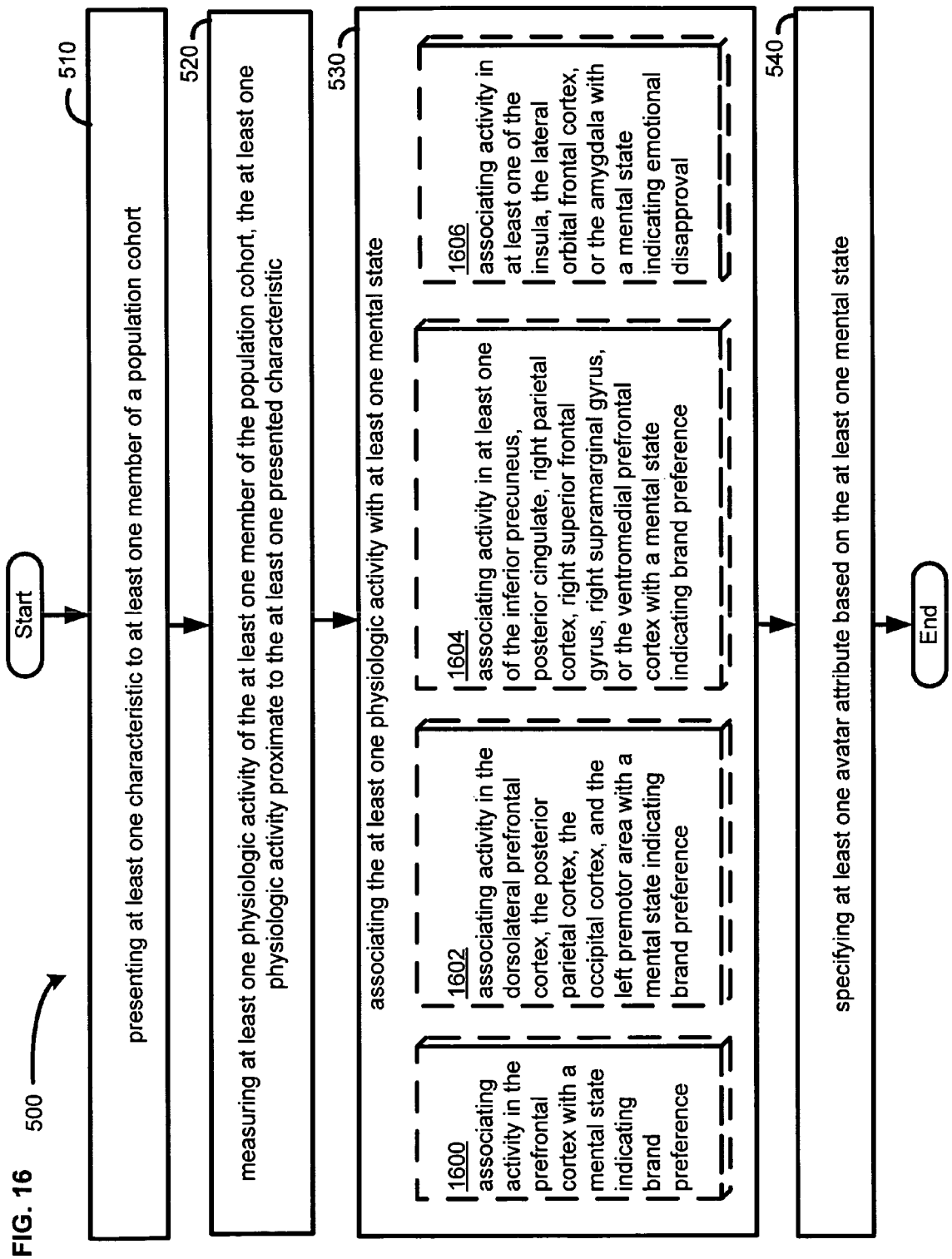

FIG. 16 illustrates an alternative embodiment of the example operational flow of FIG. 5.

Figure 17:
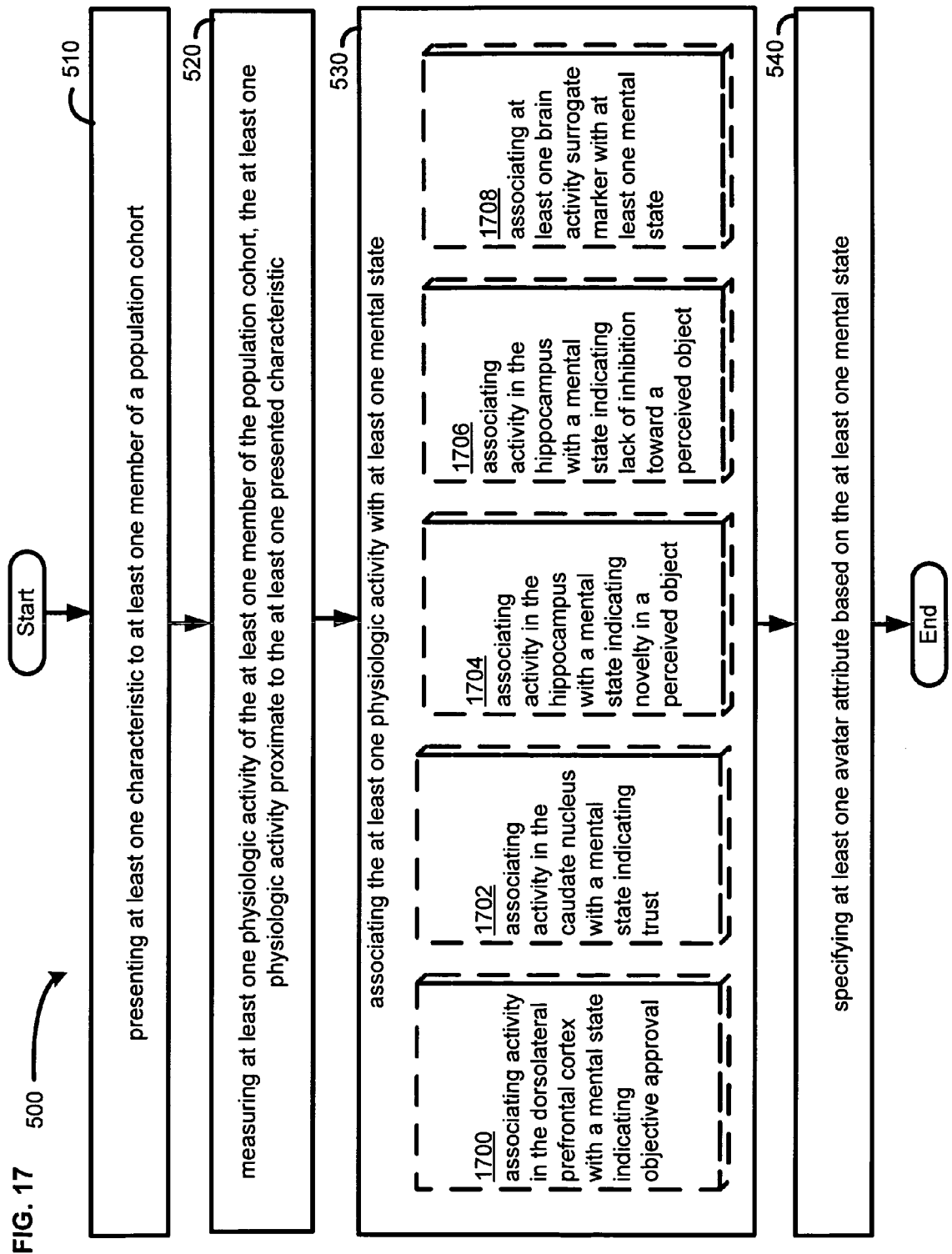

FIG. 17 illustrates an alternative embodiment of the example operational flow of FIG. 5.

Figure 18:
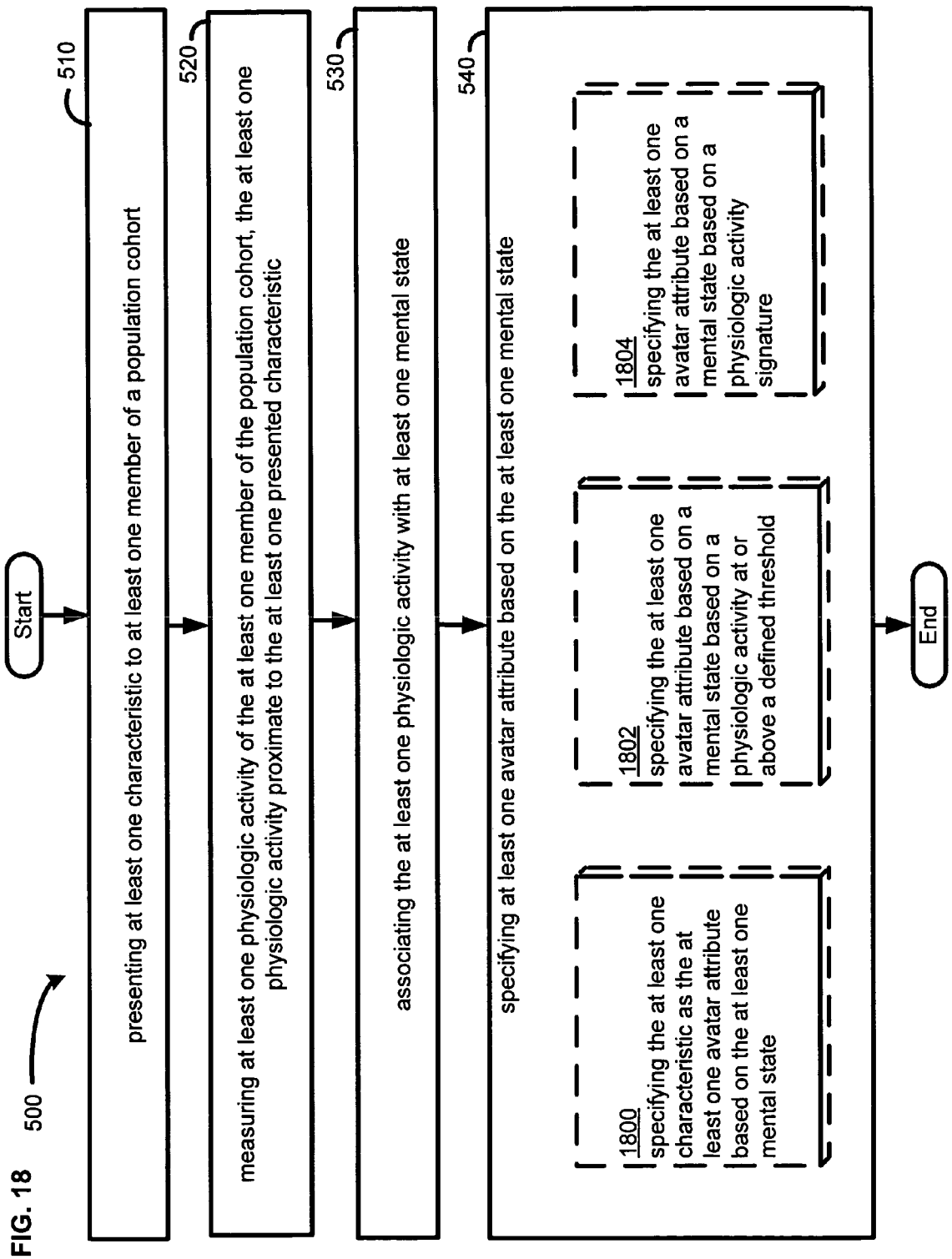

FIG. 18 illustrates an alternative embodiment of the example operational flow of FIG. 5.

Figure 19:
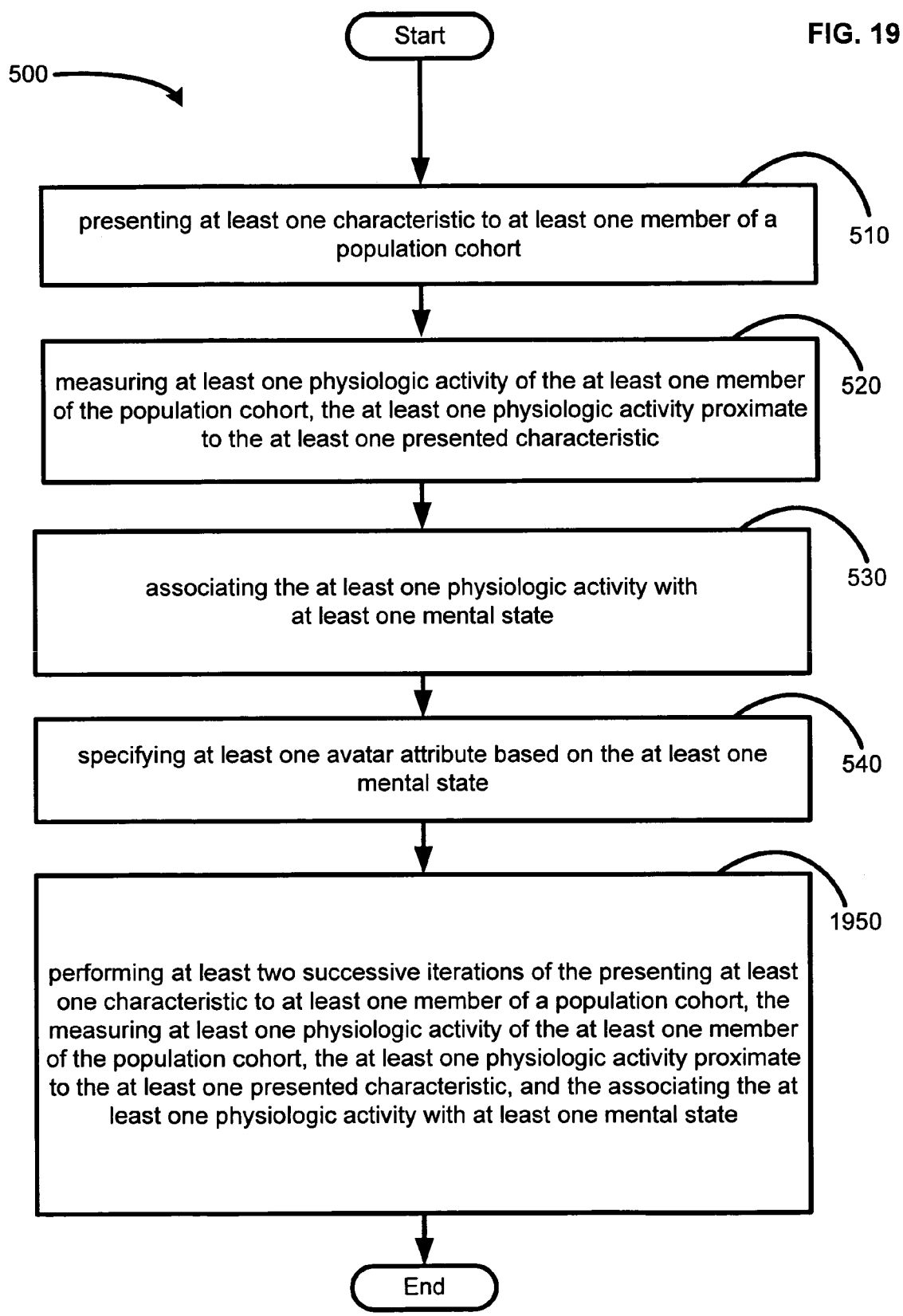

FIG. 19 illustrates an alternative embodiment of the example operational flow of FIG. 5.

Figure 20:
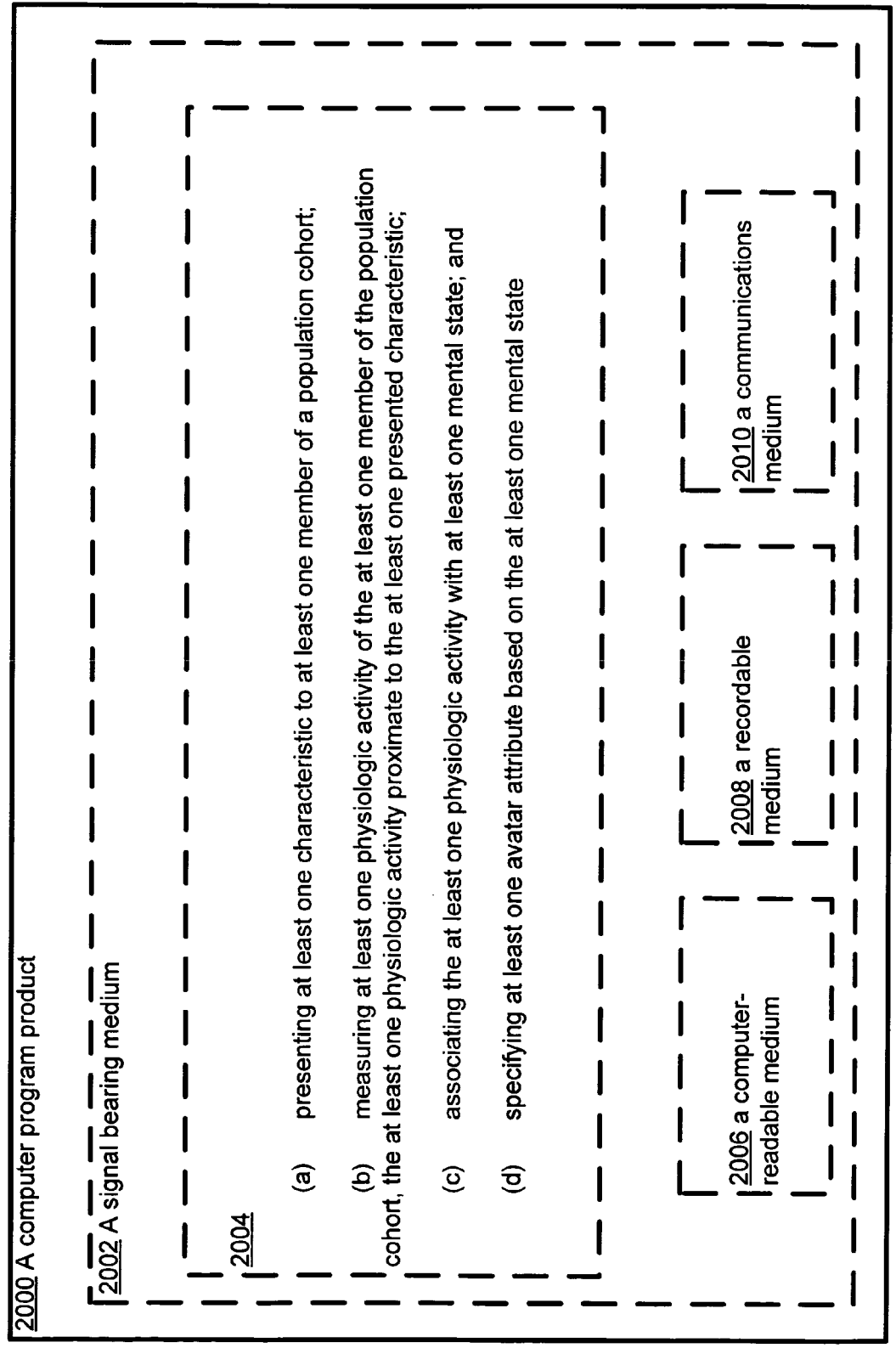

With reference now to FIG. 20, shown is a partial view of an example computer program product that includes a computer program for executing a computer process on a computing device related to specifying an avatar attribute, which may serve as a context for introducing one or more processes and/or devices described herein.

Figure 21:
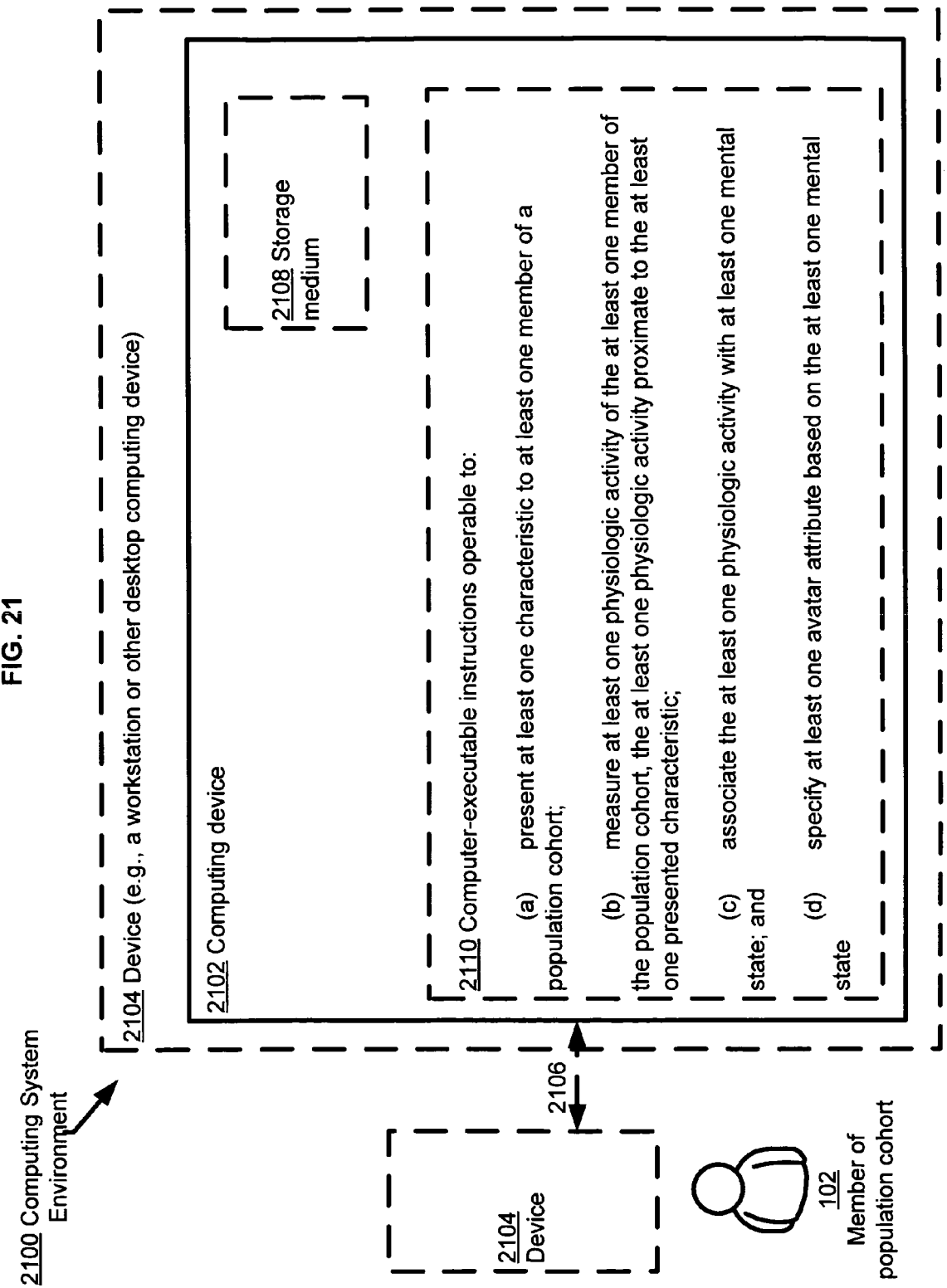

With reference now to FIG. 21, shown is an example device in which embodiments may be implemented related to specifying an avatar attribute, which may serve as a context for introducing one or more processes and/or devices described herein.

Figure 22:
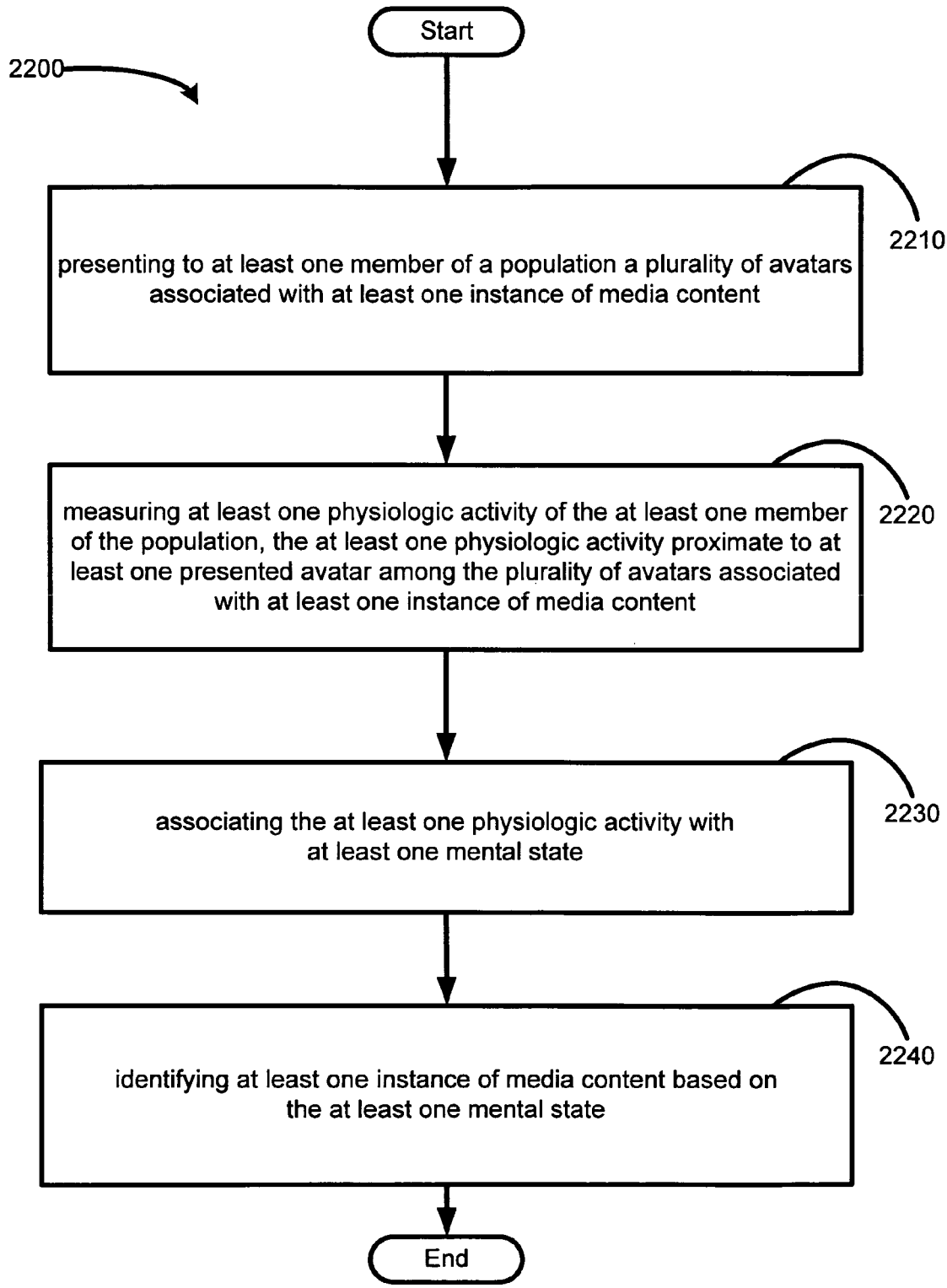

With reference now to FIG. 22 shown is an example of an operational flow representing example operations related to comparing media content, which may serve as a context for introducing one or more processes and/or devices described herein.

Figure 23:
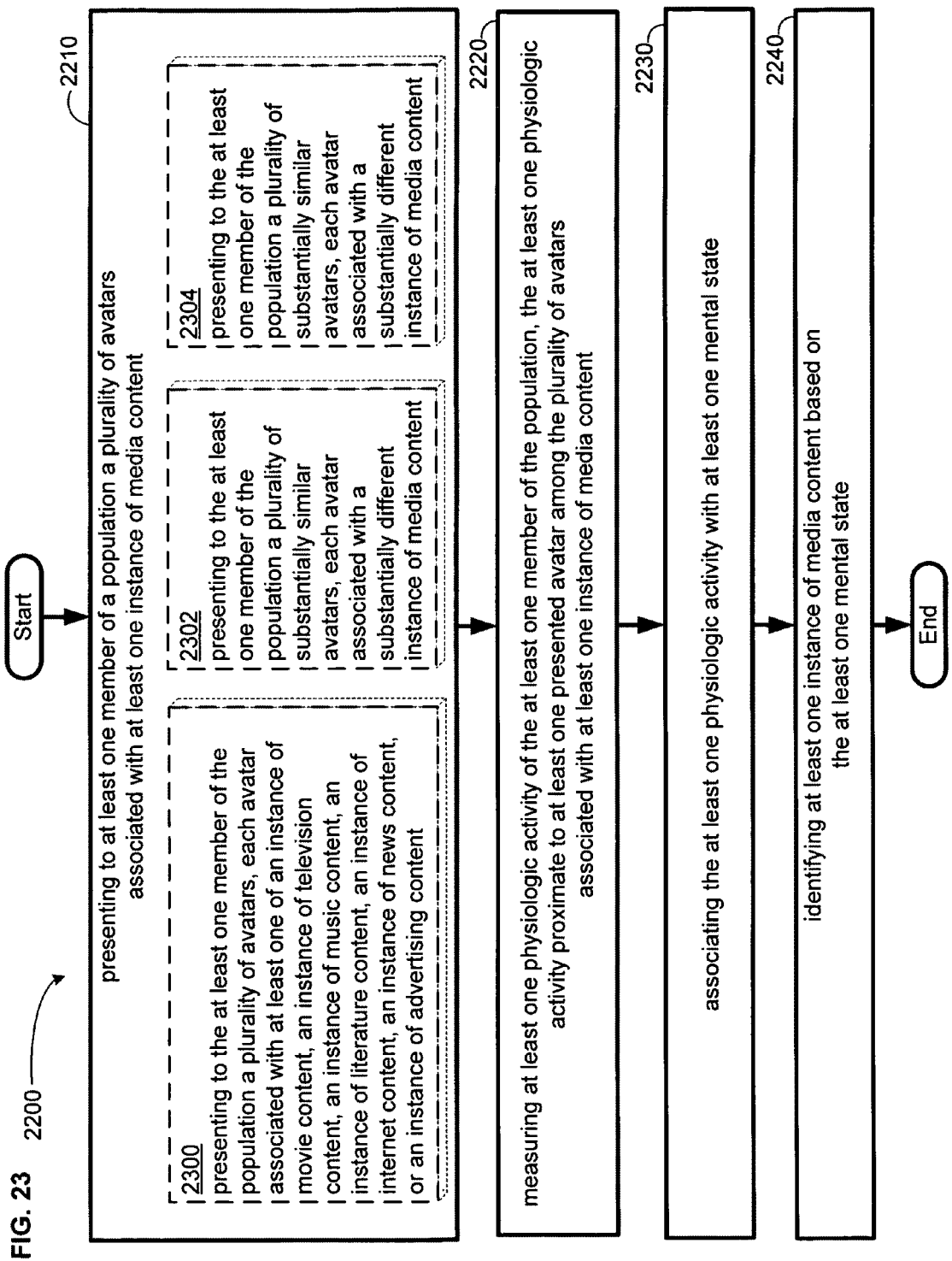

FIG. 23 illustrates an alternative embodiment of the example operational flow of FIG. 22.

Figure 24:
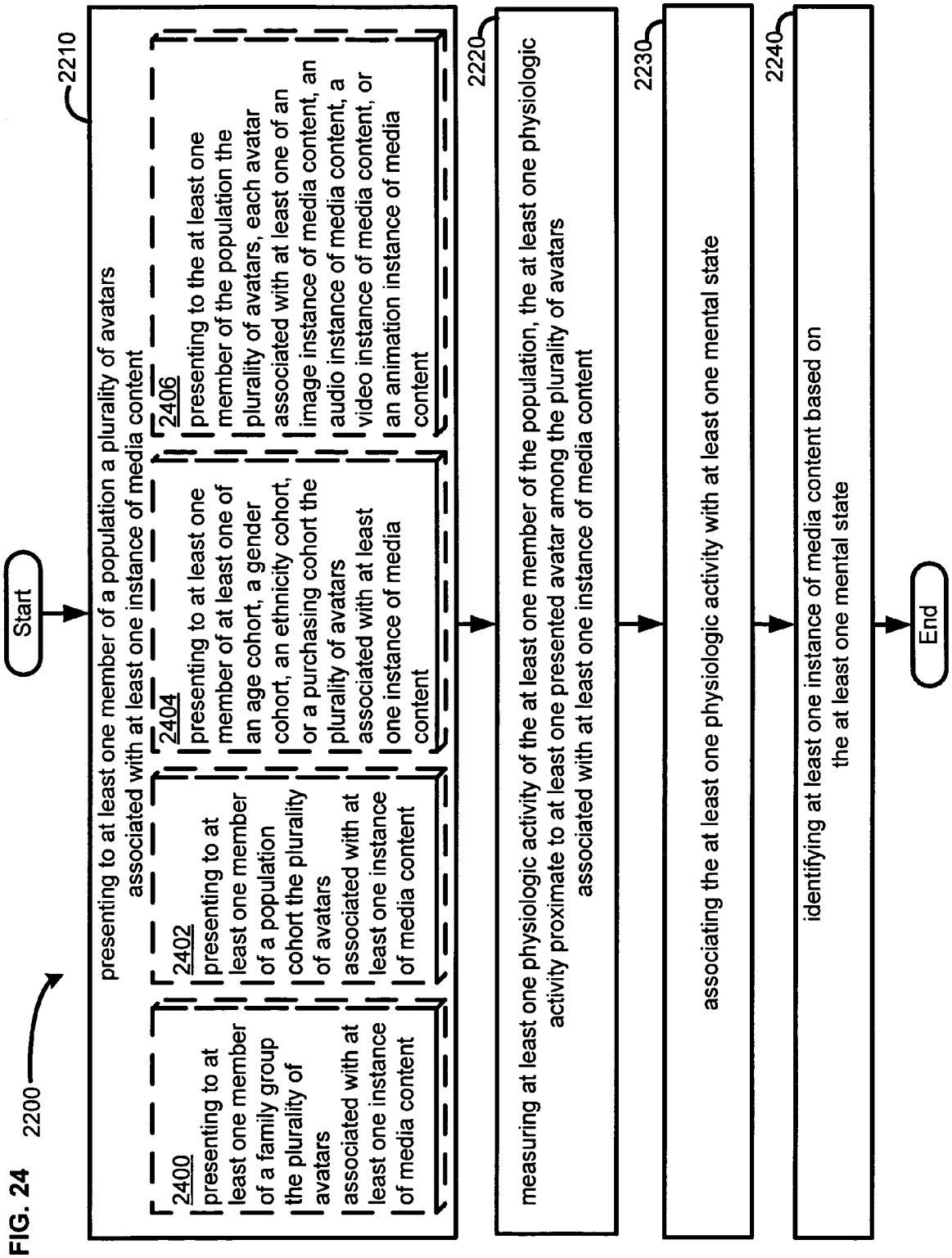

FIG. 24 illustrates an alternative embodiment of the example operational flow of FIG. 22.

Figure 25:
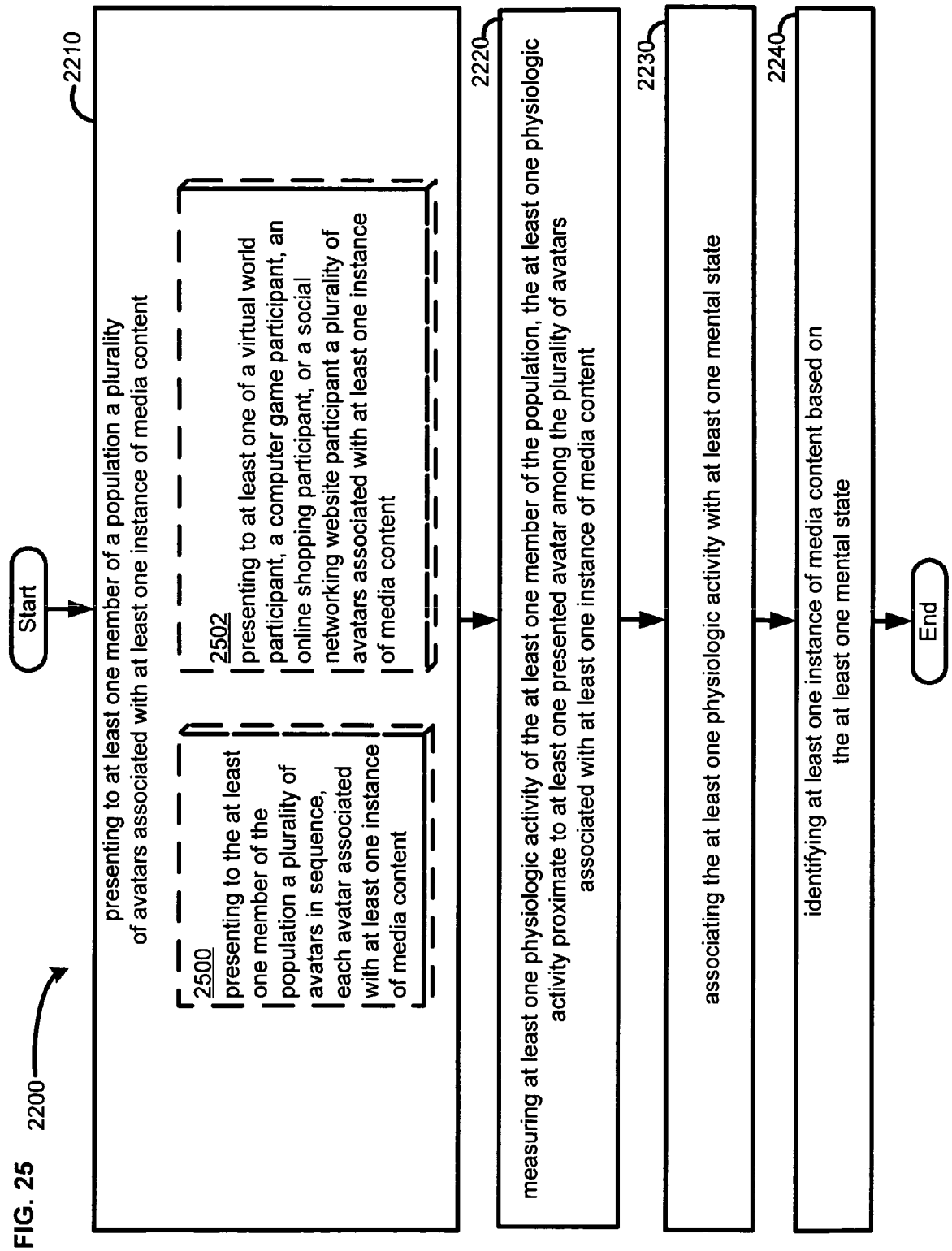

FIG. 25 illustrates an alternative embodiment of the example operational flow of FIG. 22.

Figure 26:
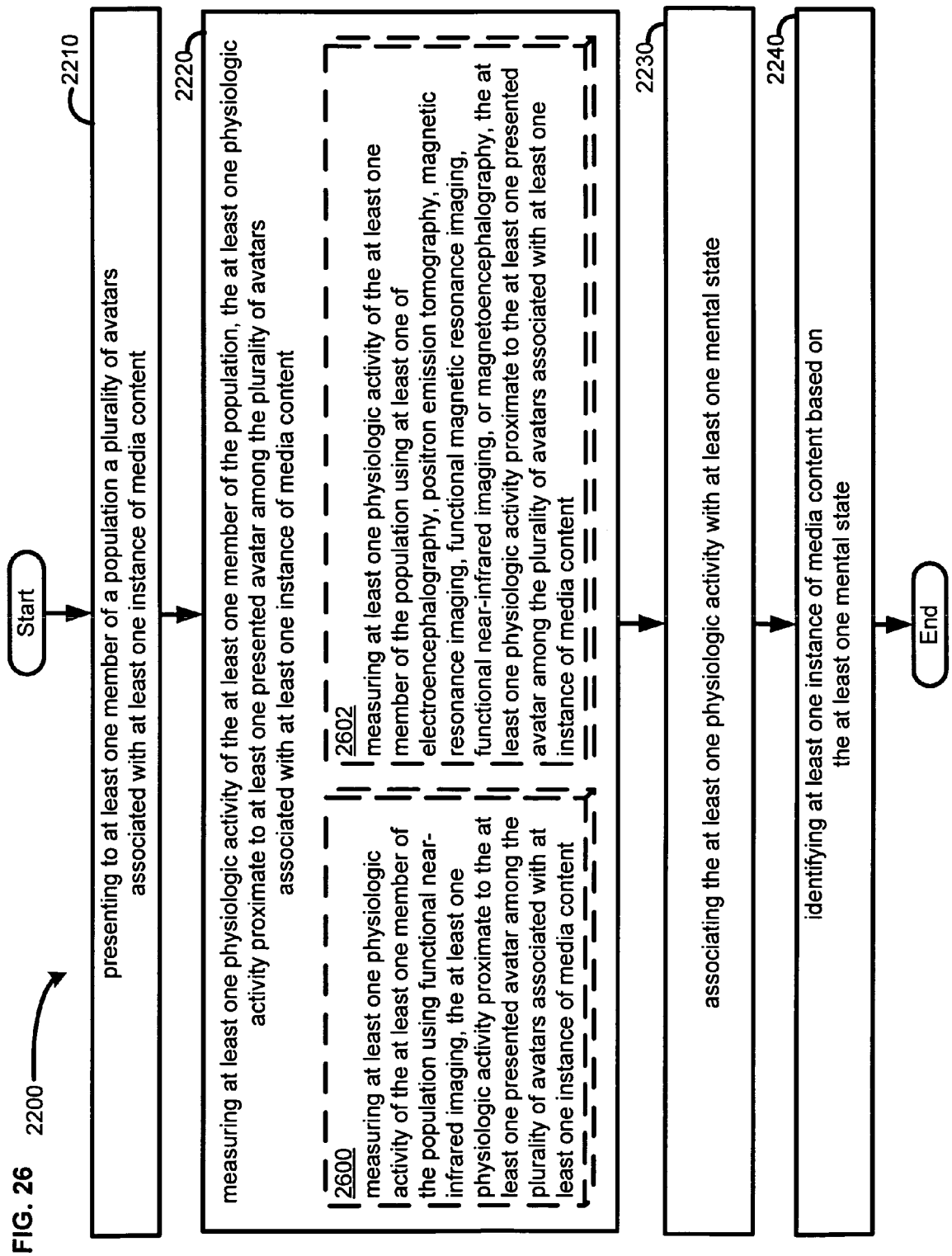

FIG. 26 illustrates an alternative embodiment of the example operational flow of FIG. 22.

Figure 27:
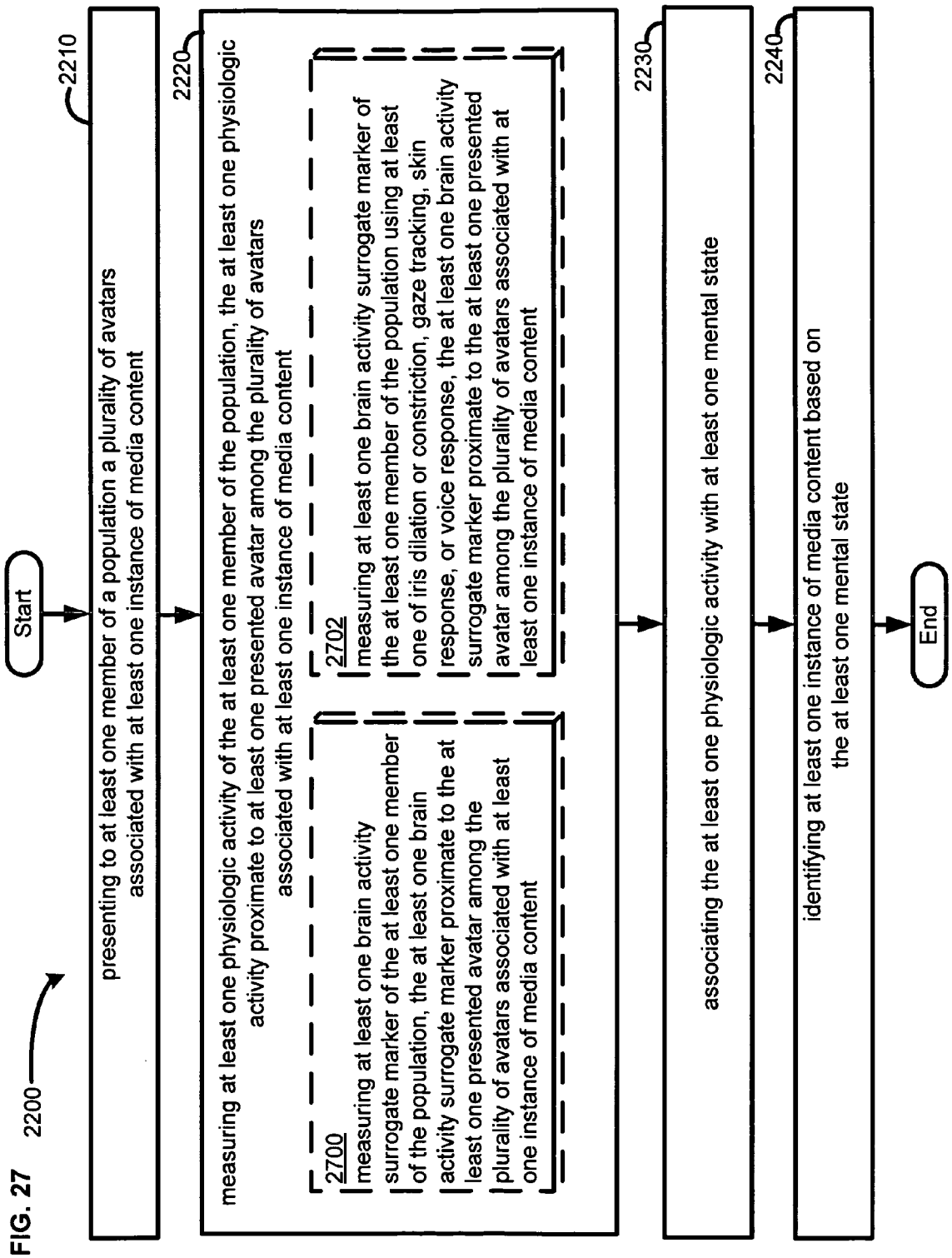

FIG. 27 illustrates an alternative embodiment of the example operational flow of FIG. 22.

Figure 28:
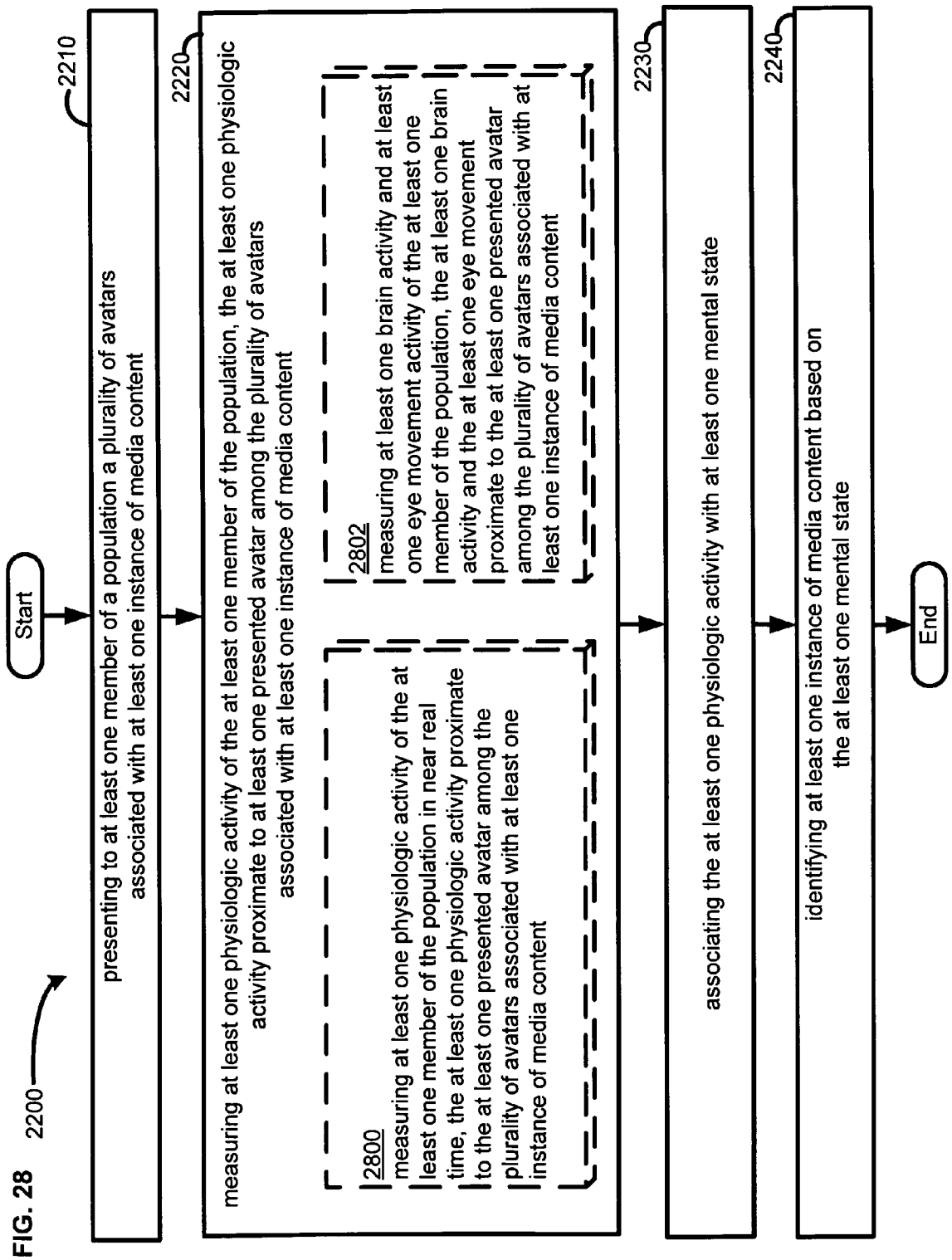

FIG. 28 illustrates an alternative embodiment of the example operational flow of FIG. 22.

Figure 29:
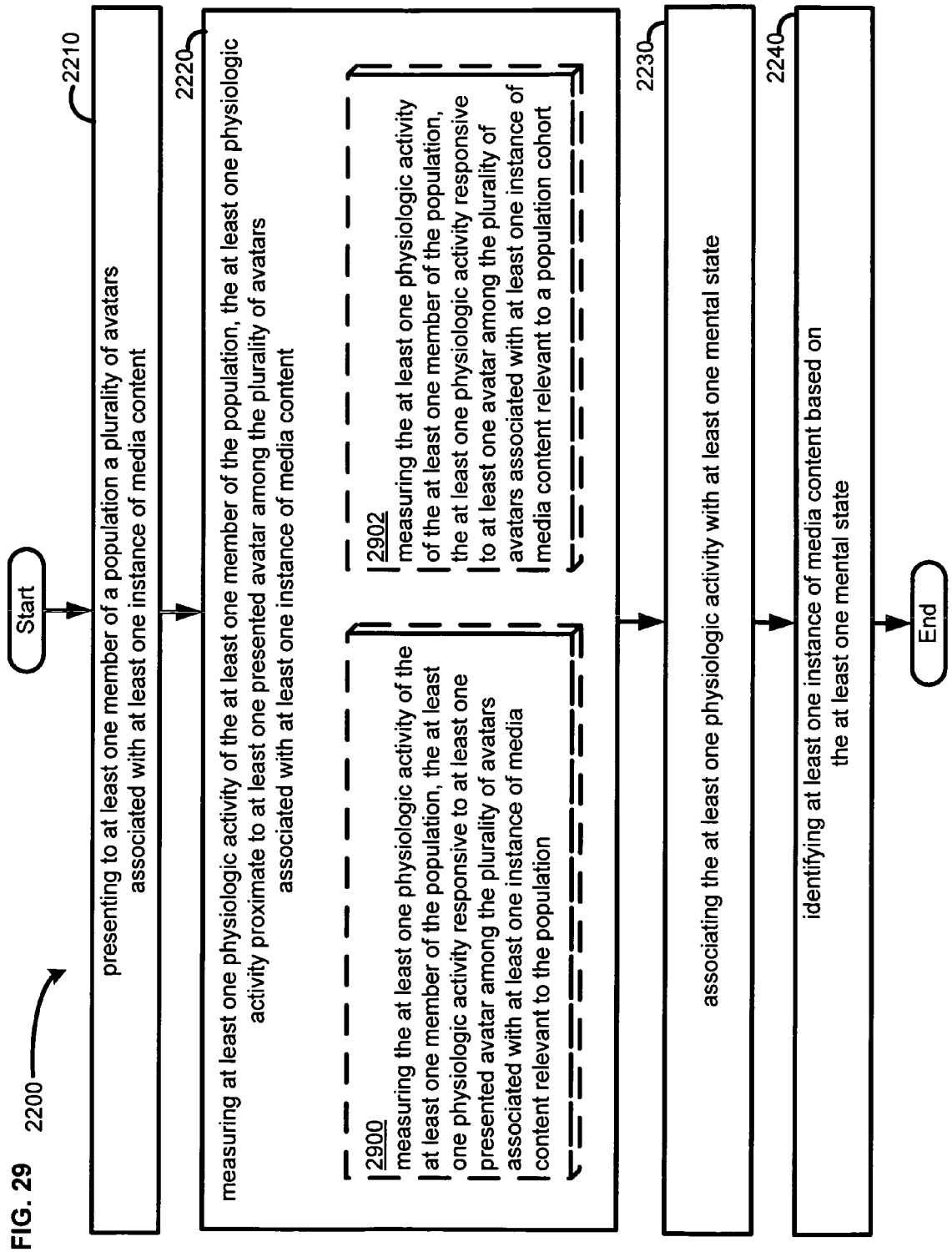

FIG. 29 illustrates an alternative embodiment of the example operational flow of FIG. 22.

Figure 30:
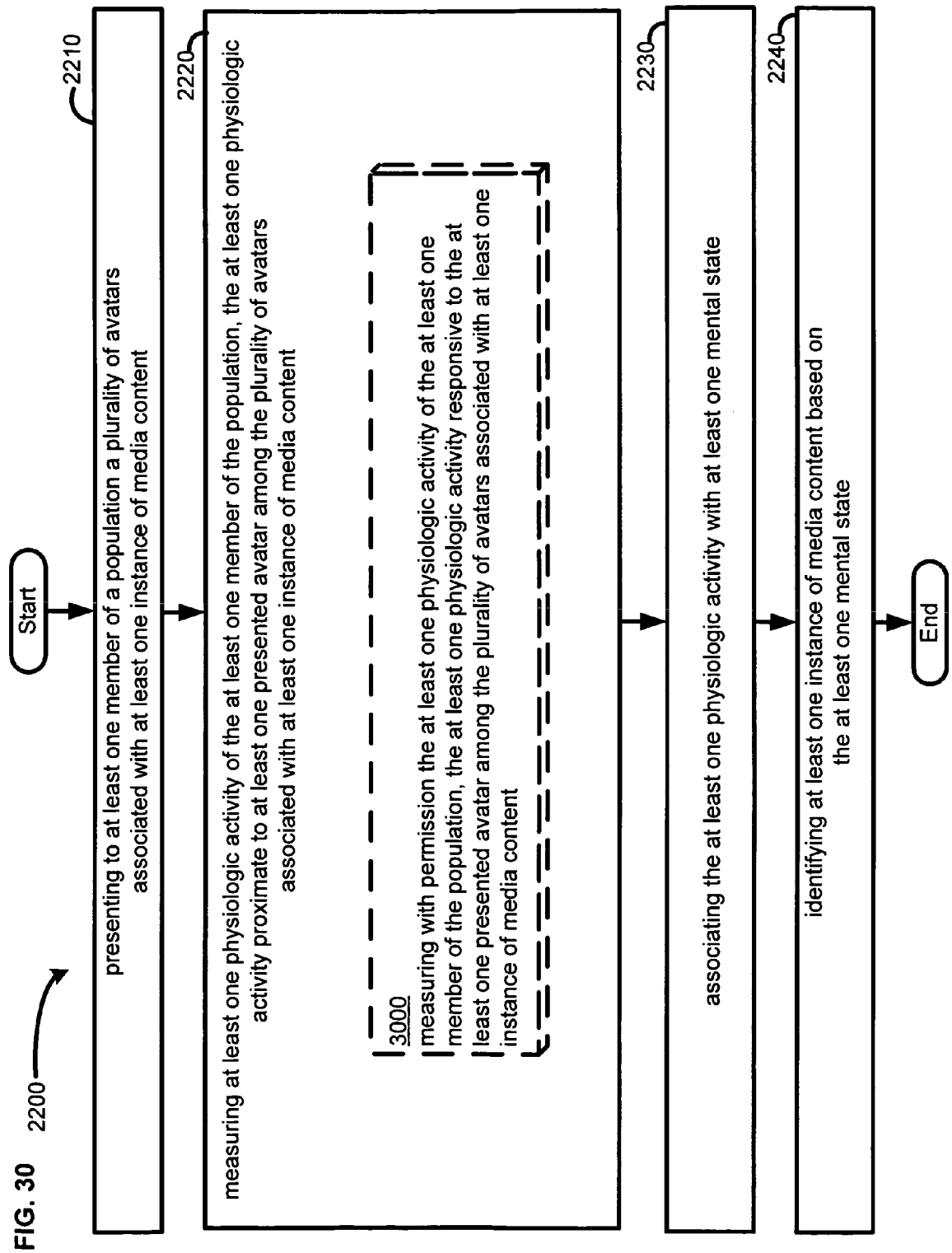

FIG. 30 illustrates an alternative embodiment of the example operational flow of FIG. 22.

Figure 31:
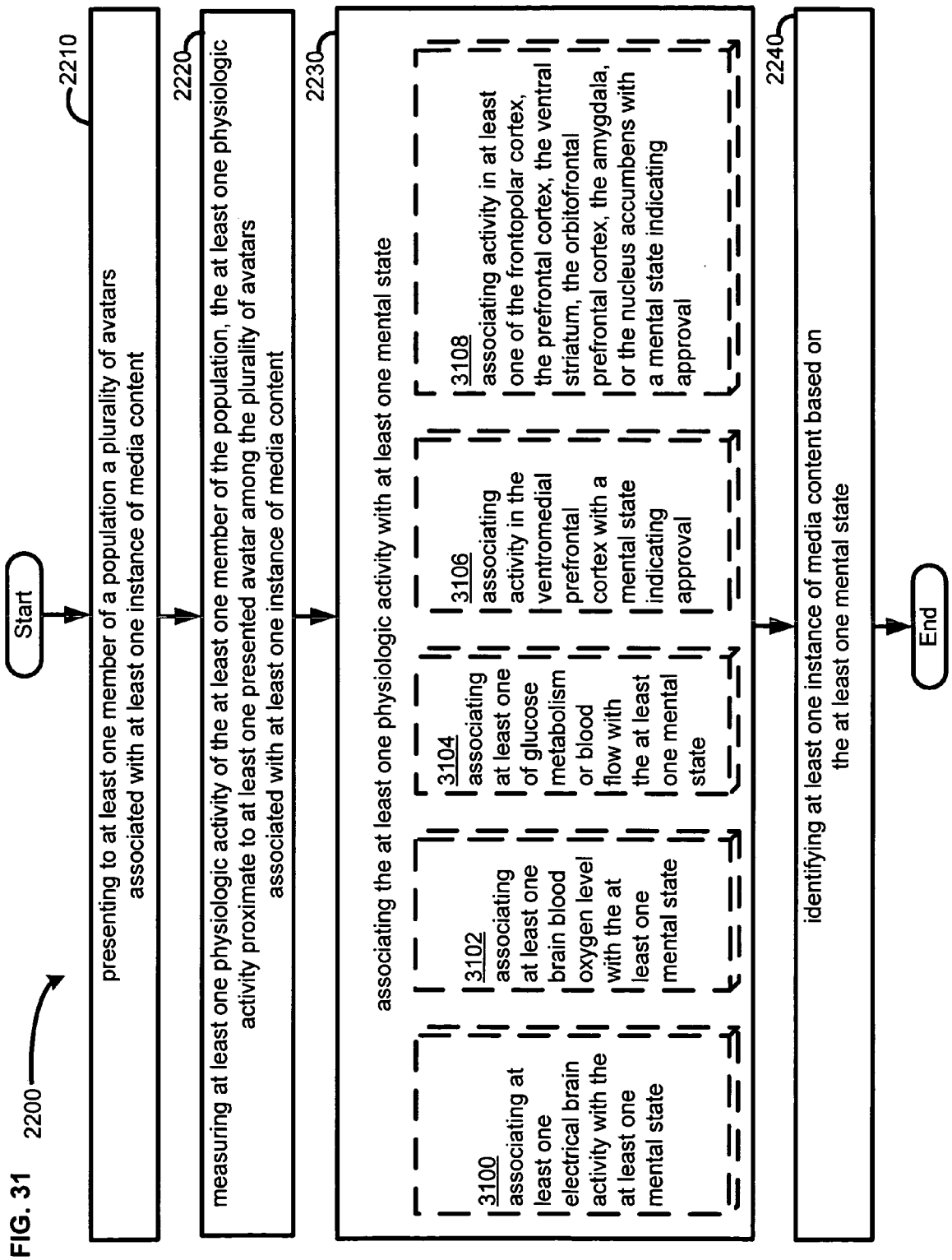

FIG. 31 illustrates an alternative embodiment of the example operational flow of FIG. 22.

Figure 32:
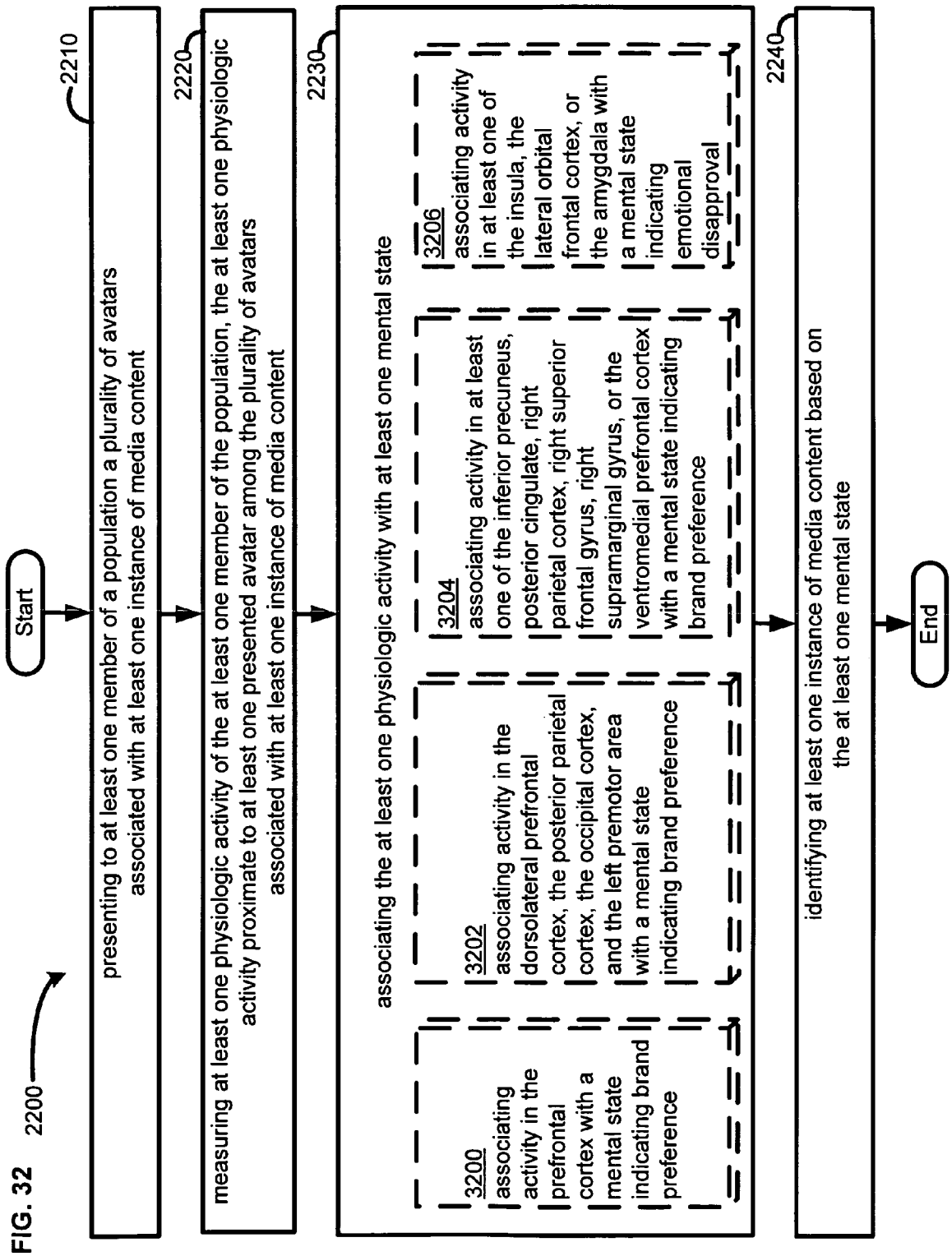

FIG. 32 illustrates an alternative embodiment of the example operational flow of FIG. 22.

Figure 33:
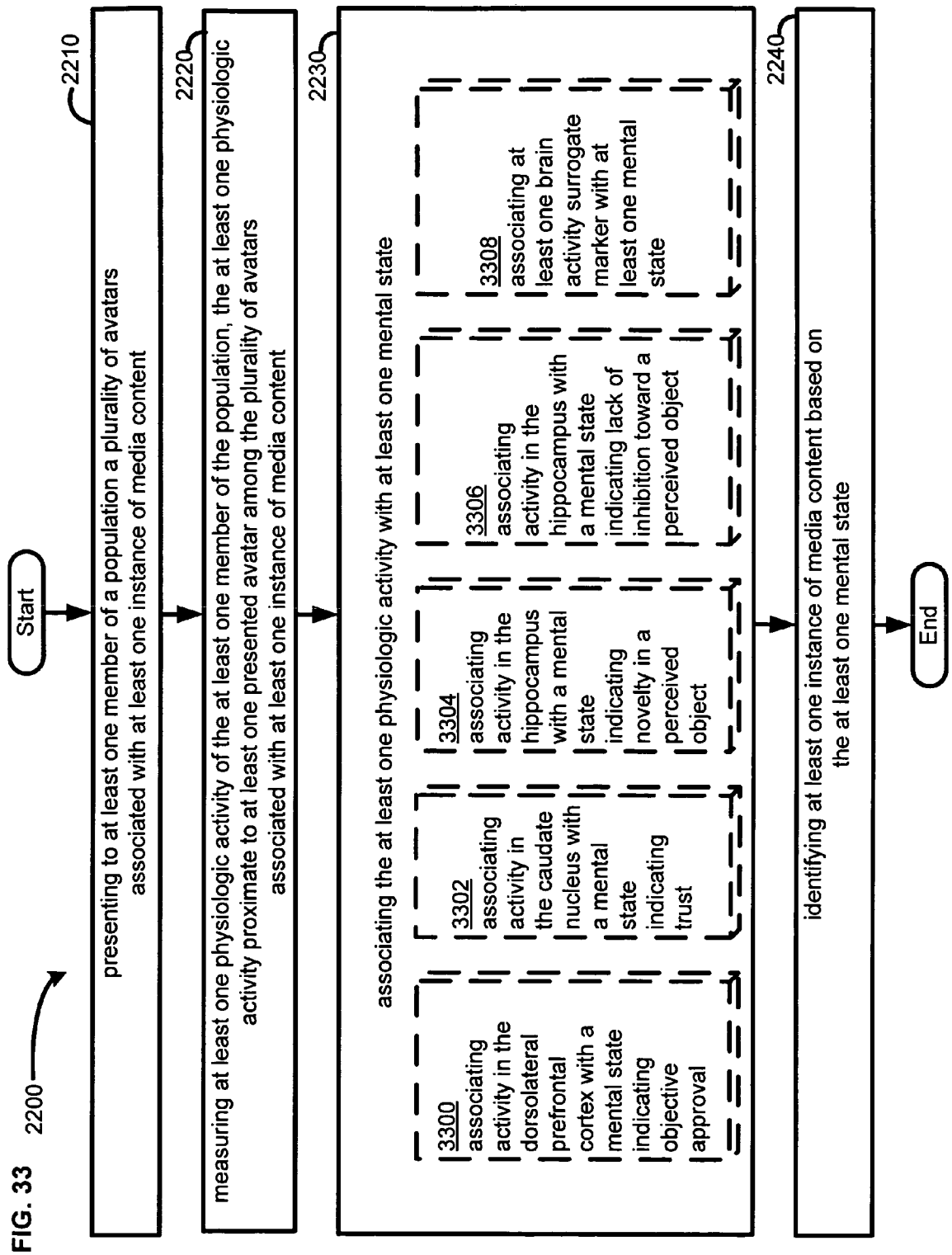

FIG. 33 illustrates an alternative embodiment of the example operational flow of FIG. 22.

Figure 34:
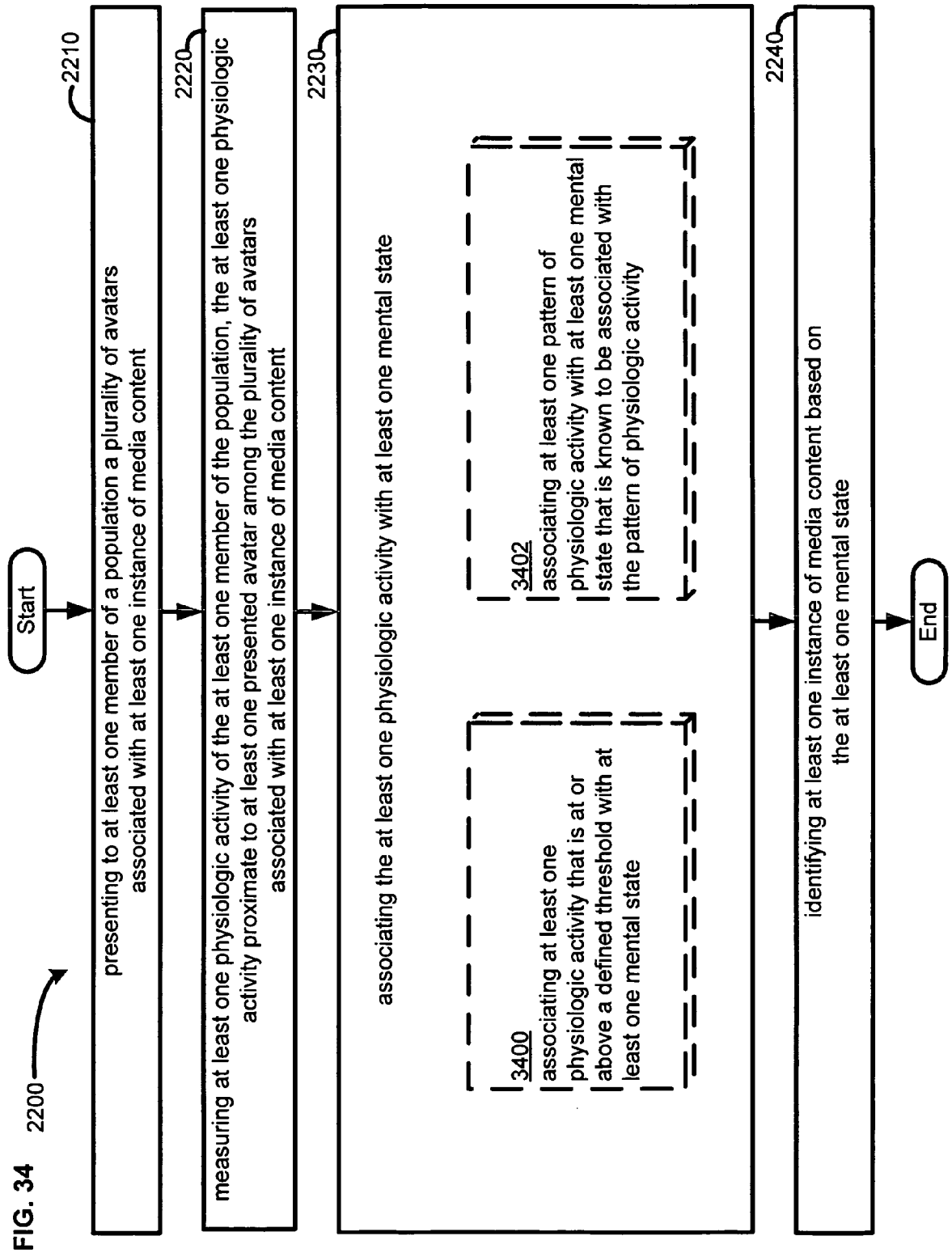

FIG. 34 illustrates an alternative embodiment of the example operational flow of FIG. 22.

Figure 35:
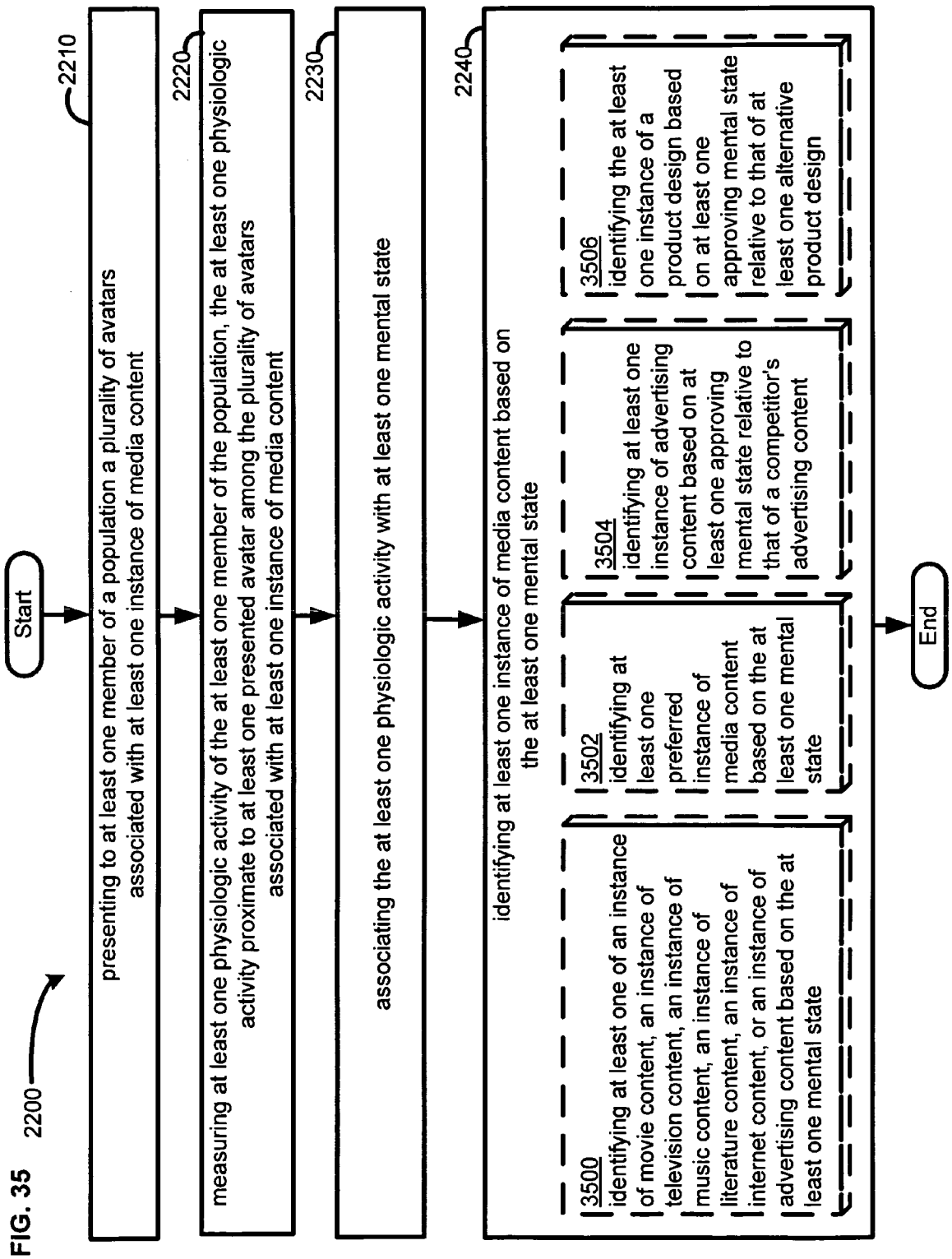

FIG. 35 illustrates an alternative embodiment of the example operational flow of FIG. 22.

Figure 36:
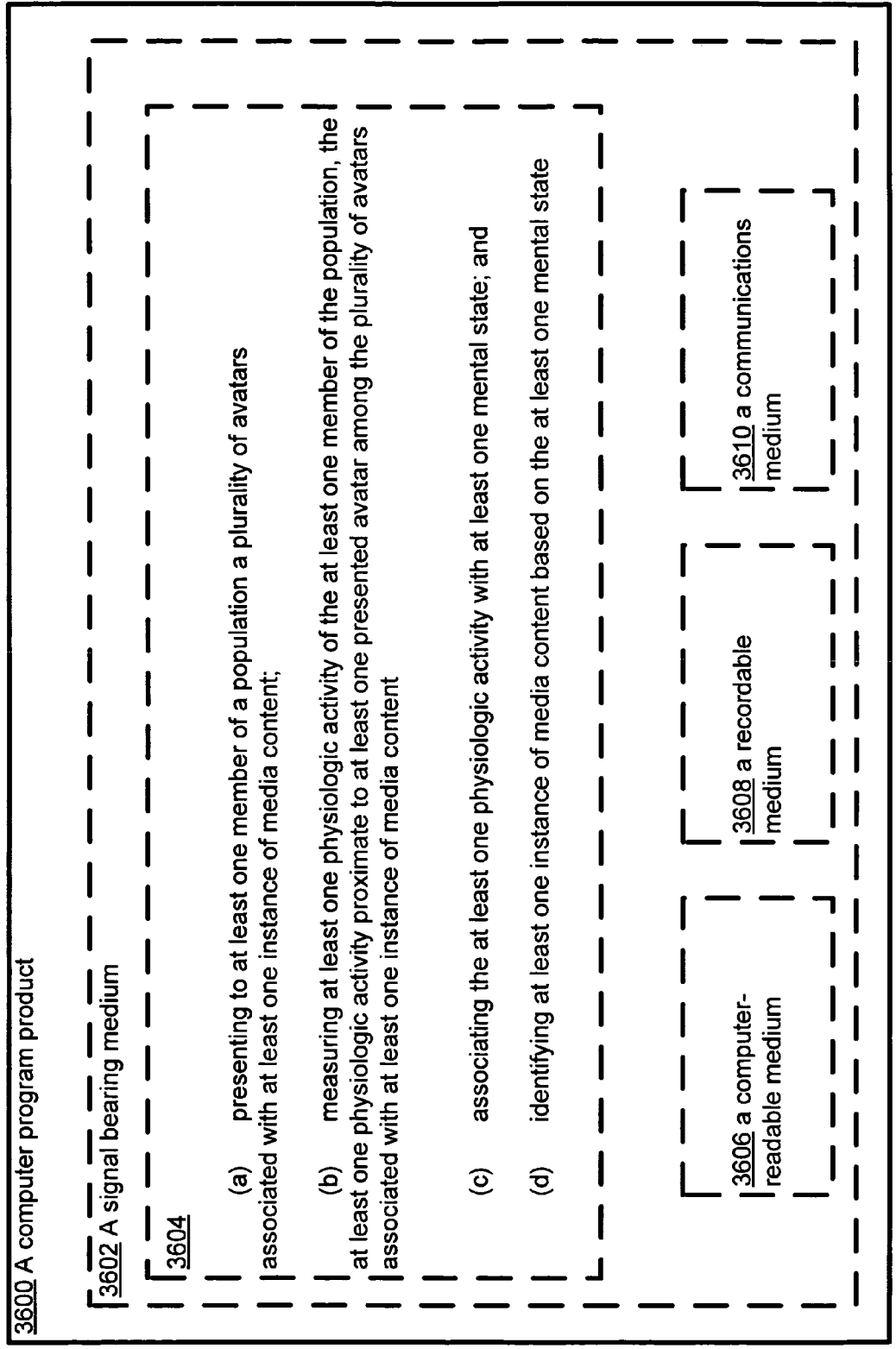

FIG. 36 illustrates an alternative embodiment of the example operational flow of FIG. 22.

With reference now to FIG. 37, shown is a partial view of an example computer program product that includes a computer program for executing a computer process on a computing device related to comparing media content, which may serve as a context for introducing one or more processes and/or devices described herein.

With reference now to FIG. 38, shown is an example device in which embodiments may be implemented related to comparing media content, which may serve as a context for introducing one or more processes and/or devices described herein.

The use of the same symbols in different drawings typically indicates similar or identical items.

DETAILED DESCRIPTION

Figure 1:
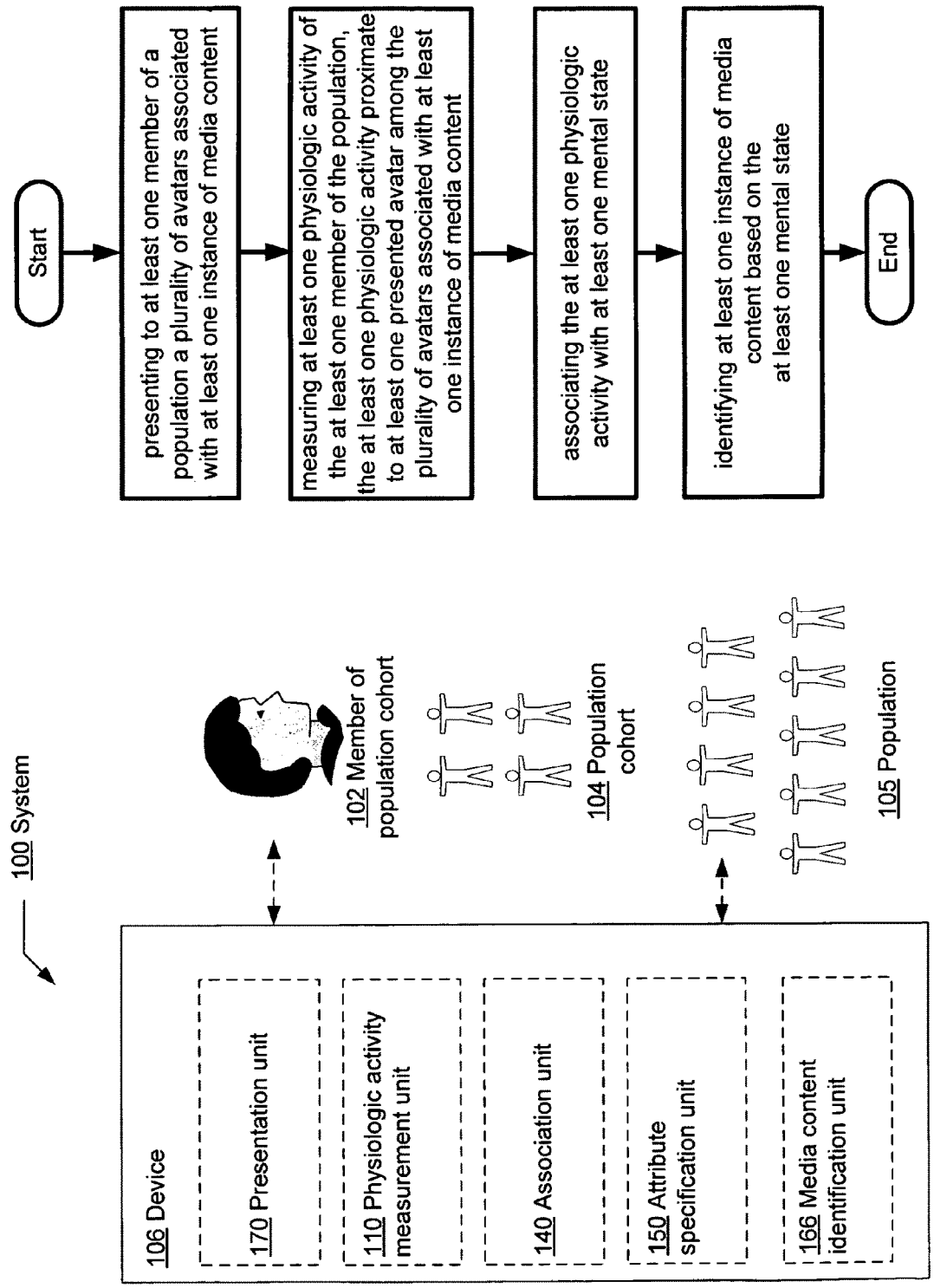

FIG. 1 illustrates an example system 100 in which embodiments may be implemented. The system 100 includes a device 106. The device 106 may contain, for example, a presentation unit 170, a physiologic activity measurement unit 110, an association unit 140, an attribute specification unit 150, and/or a media content identification unit 166. The device 106 may interact with one or more members of population cohort 104 and/or population 105. Population cohort 104 may be a part of a population 105.

Figure 2:
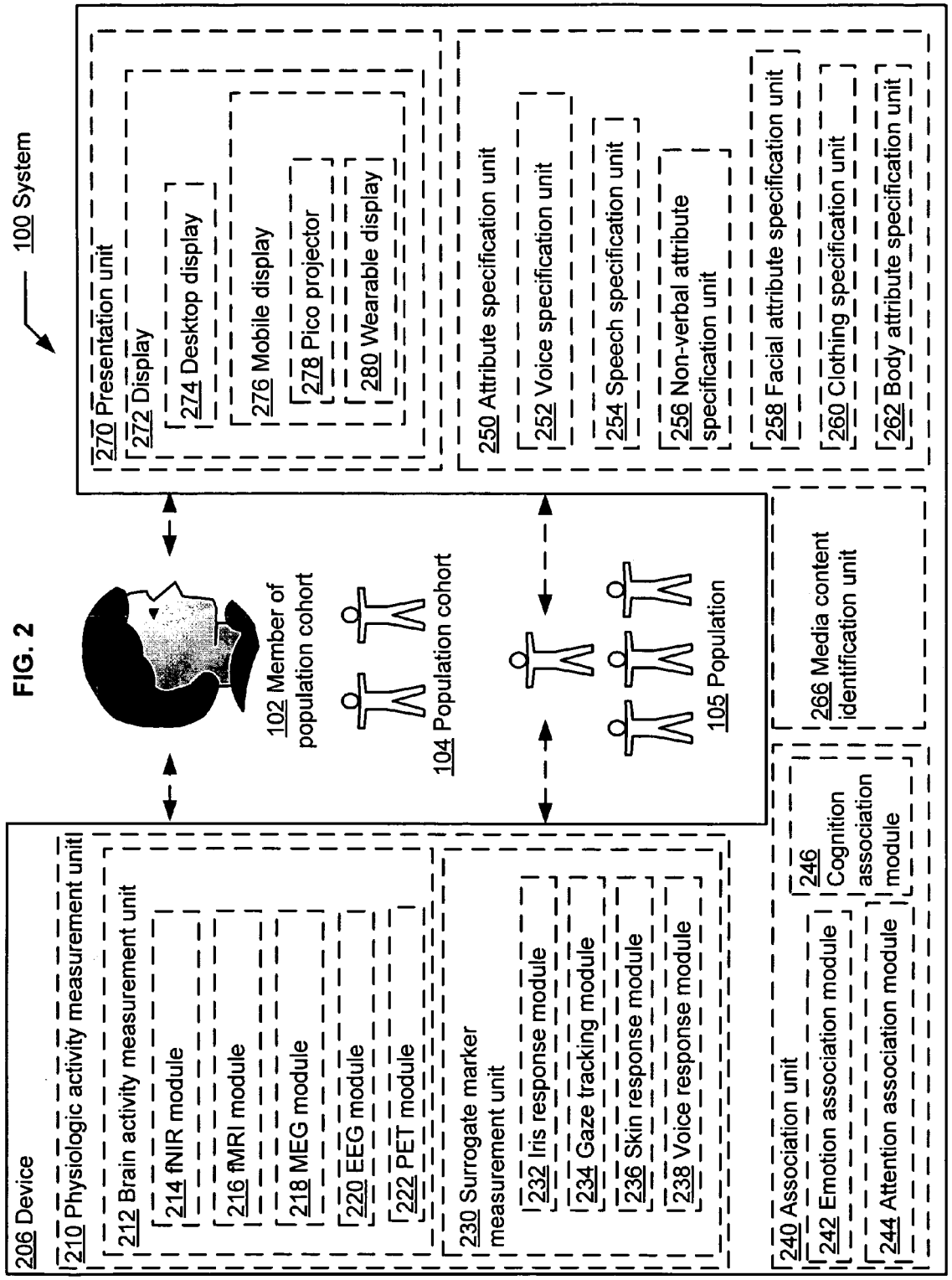
FIG. 2 illustrates certain alternative embodiments of the system of FIG. 1.

FIG. 2 illustrates the example system 100 in which embodiments may be implemented. The system 100 includes a device 206. Device 206 may include physiologic activity measurement unit 210, which may in turn include brain activity measurement unit 212, which may in turn include functional near-infrared imaging fNIR module 214, functional magnetic resonance imaging fMRI module 216, magnetoencephalography MEG module 218, electroencephalography EEG module 220, and/or positron emission topography PET module 222. Device 206 may also include surrogate marker measurement unit 230 including iris response module 232, gaze tracking module 234, skin response module 236, and/or voice response module 238. Device 206 may also include association unit 240, which in turn may include emotion association module 242, attention association module 244, and/or cognition association module 246. Device 206 may also include media content identification unit 266.

Device 206 may also include attribute specification unit 250, which may in turn include voice specification unit 252, speech specification unit 254, non-verbal attribute specification unit 256, facial attribute specification unit 258, clothing specification unit 260, and/or body attribute specification unit 262. Device 206 may also include presentation unit 270, which may in turn include display 272, which may in turn include desktop display 274 and/or mobile display 276, which may in turn include pico projector 278 and/or wearable display 280. Member of population cohort 102, multiple members of population cohort 104, and/or one or more members of population 105 may interact with device 206 including presentation unit 270, and/or be monitored by device 206 including physiologic activity measurement unit 210.

In FIG. 2, the device 206 is illustrated as possibly being included within a system 100. Of course, virtually any kind of computing device may be used to implement the physiologic activity measurement unit 210, surrogate marker measurement unit 230, association unit 340, attribute specification unit 350, and/or presentation unit 264, such as, for example, a workstation, a desktop computer, a networked computer, a server, a collection of servers and/or databases, a virtual machine running inside a computing device, a mobile computing device, or a tablet PC.

Additionally, not all of the physiologic activity measurement unit 210, surrogate marker measurement unit 230, association unit 240, attribute specification unit 250, and/or presentation unit 264 need be implemented on a single computing device. For example, one or more of the physiologic activity measurement unit 210, surrogate marker measurement unit 230, association unit 340, attribute specification unit 350, and/or presentation unit 264 may be implemented and/or operable on a remote computer, while one or more of these functions are implemented and/or occur on a local computer. Further, aspects of the physiologic activity measurement unit 210 may be implemented in different combinations and implementations than that shown in FIG. 1. For example, functionality of a physiologic activity measurement unit 210 may be incorporated into the surrogate marker measurement unit 230, association unit 240, attribute specification unit 250, and/or presentation unit 264. The association unit 240 and/or attribute specification unit 250 may perform simple data relay functions and/or complex data analysis, including, for example, fuzzy logic and/or traditional logic steps. Further, many methods of searching functional brain mapping and/or surrogate marker activity databases known in the art may be used, including, for example, unsupervised pattern discovery methods, coincidence detection methods, and/or entity relationship modeling. In some embodiments, the association unit 240 may process physiologic activity measurements according to activity profiles available as updates through a network. Similarly, in some embodiments, the attribute specification unit 250 may process association unit output according to population cohort, media content, avatar attribute, and/or avatar profiles available as updates through a network.

Outputs of physiologic activity measurement unit 210, surrogate marker measurement unit 230, association unit 240, attribute specification unit 250, and/or presentation unit 264 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 3:
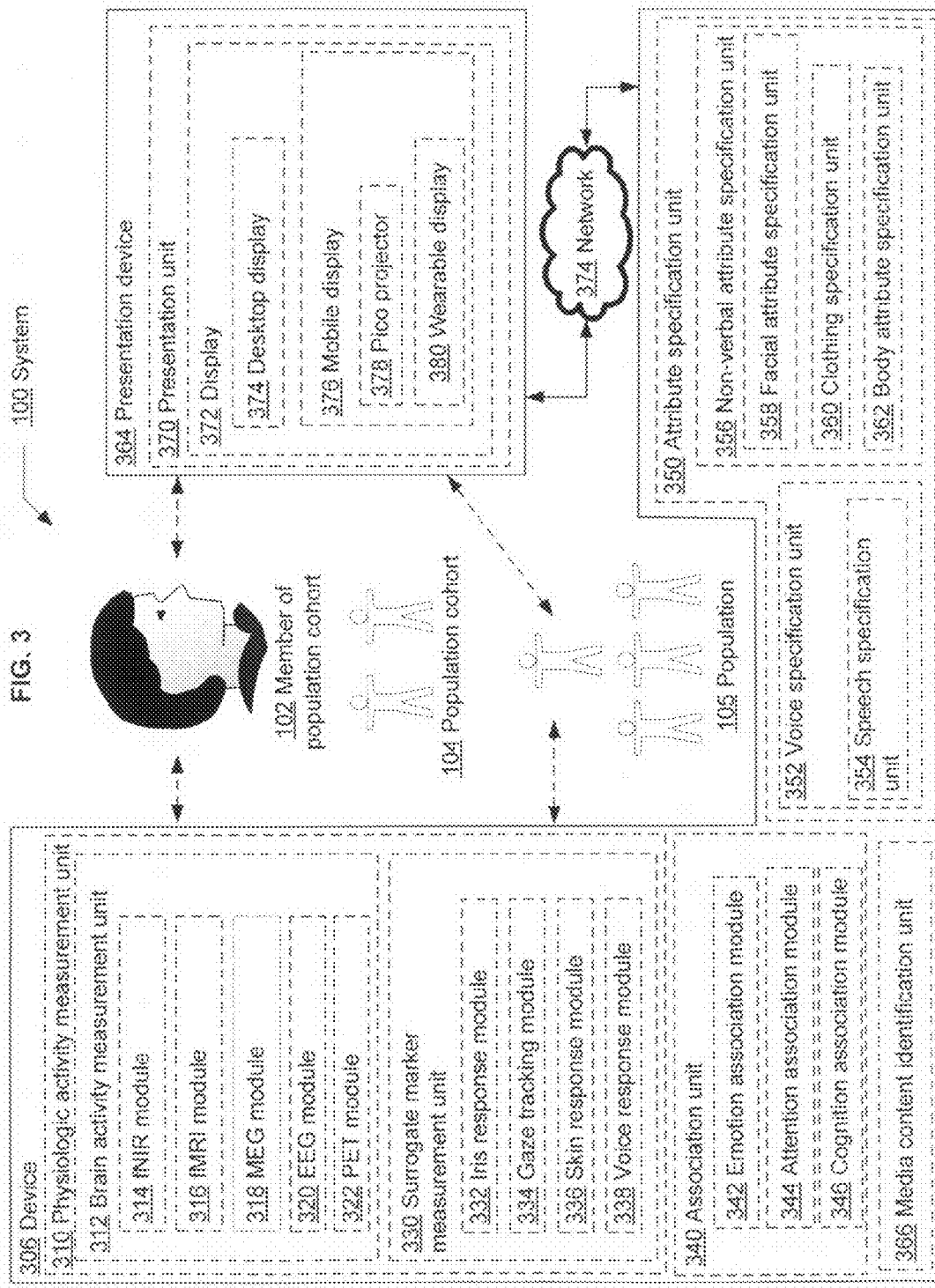
FIG. 3 illustrates certain alternative embodiments of the system of FIG. 1.

FIG. 3 illustrates the example system 100 in which embodiments may be implemented. The system 100 includes a device 306. The device 306 may communicate over a network 374 with a presentation device 364. Device 306 may include physiologic activity measurement unit 310, which may in turn include brain activity measurement unit 312, which may in turn include functional near-infrared imaging fNIR module 314, functional magnetic resonance imaging fMRI module 316, magnetoencephalography MEG module 318, electroencephalography EEG module 320, and/or positron emission topography PET module 322. Device 306 may also include surrogate marker measurement unit 330 including iris response module 332, gaze tracking module 334, skin response module 336, and/or voice response module 338. Device 306 may also include association unit 340, which in turn may include emotion association module 342, attention association module 344, and/or cognition association module 346. Device 306 may also include media content identification unit 366.

Device 306 may also include attribute specification unit 350, which may in turn include voice specification unit 352, which may in turn include speech specification unit 354. Attribute specification unit 350 may include non-verbal attribute specification unit 356, which may in turn include facial attribute specification unit 358, clothing specification unit 360, and/or body attribute specification unit 362.

Presentation device 364 may include presentation unit 370, which may in turn include display 372, which may in turn include desktop display 374 and/or mobile display 376, which may in turn include pico projector 378 and/or wearable display 380. Member of population cohort 102 and or multiple members of population cohort 104 may be monitored by device 306 including physiologic activity measurement unit 310. Member of population cohort 102, multiple members of population cohort 104, and/or one or more members of population 105 may interact with presentation device 364 including presentation unit 370.

In this way, a member of population cohort 102 or a member of population 105, who may be interacting with a presentation device 364 that is connected through a network 374 with a device 306 (e.g., in a home, an office, outdoors and/or in a public environment), may interact with the system 100 as if the member of population cohort 102 or member of population 105 were interacting locally with the device 306 on which the association unit 340 and/or attribute specification unit 350 is operable. In such an embodiment, the physiologic activity measurement unit 310 and/or surrogate marker measurement unit 330 may also be located locally with the member of population cohort 102, transmitting output via network to a remote association unit 340 and/or attribute specification unit 350.

As referenced herein, the device 306, association unit 340, and/or attribute specification unit 350 may be used to perform various data querying and/or recall techniques with respect to output of physiologic activity measurement unit 310, and/or output of association unit 340, respectively, in order to for example, obtain and/or transmit an avatar attribute based on a physiological activity of member of population cohort 102. For example, where the output of physiologic activity measurement unit 310 is organized, keyed to, and/or otherwise accessible using one or more reference physiologic activity profiles, association unit 340 may employ various Boolean, statistical, and/or semi-boolean searching techniques to match physiologic activity measurement output with one or more appropriate mental states. Similarly, for example, where association unit 340 output is organized, keyed to, and/or otherwise accessible using one or more reference population cohort profiles, various Boolean, statistical, and/or semi-boolean searching techniques may be performed by media content identification unit 366 to match the mental state of the member of population 105 with one or more appropriate instances of media content.

Many examples of databases and database structures may be used in connection with the device 3.06, association unit 340, media content identification unit 366, and/or attribute specification unit 350. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more reference physiologic activity measurement and/or reference mental state may be performed, or Boolean operations using a reference physiologic activity measurement and/or reference mental state may be performed. For example, weighted Boolean operations may be performed in which different weights or priorities are assigned to one or more of the reference physiologic activity measurements and/or reference mental states, including reference physiologic activity measurements and/or reference mental states associated with various reference avatar attributes, perhaps relative to one another. For example, a number-weighted, exclusive-OR operation may be performed to request specific weightings of desired (or undesired) physiologic activity reference data to be included or excluded. Reference physiologic activity measurements may include normal physiological values for an individual in a demographic group responding to a given stimulus. Such normal physiological activity values may be "normal" relative to the member of population cohort 102, to a group of population cohort 104, to the entire population cohort 104, to a member of population 105, and/or the entire population 105. Similarly, reference demographic characteristics may be associated with a general population or a sub-population defined by such things as age, gender, ethnicity, or other demographic measure known to those of ordinary skill in the art.

FIG. 4 shows diagrammatic views of the surface of the human brain. Lateral surface of the brain with Brodmann's areas 400 shows various numbered areas of a lateral aspect of the human brain. Medial surface of the brain with Brodmann's areas 402 shows various numbered areas of the medial aspect of the human brain.

Measuring at least one physiologic activity of a member of population cohort 102 may include measuring magnetic, electrical, hemodynamic, and/or metabolic activity in the brain.

Magnetoencephalography

One method of measuring at least one physiologic activity may include measuring the magnetic fields produced by electrical activity in the brain via magnetoencephalography (MEG) using magnetometers such as superconducting quantum interference devices (SQUIDs) or other devices. Such measurements are commonly used in both research and clinical settings to, e.g., assist researchers in determining the function of various parts of the brain. Synchronized neuronal currents induce very weak magnetic fields that can be measured by magnetoencephalography. However, the magnetic field of the brain is considerably smaller at 10 femtotesla (fT) for cortical activity and 103 fT for the human alpha rhythm than the ambient magnetic noise in an urban environment, which is on the order of 108 fT. Two essential problems of biomagnetism arise: weakness of the signal and strength of the competing environmental noise. The development of extremely sensitive measurement devices such as SQUIDs facilitates analysis of the brain's magnetic field in spite of the relatively low signal versus ambient magnetic signal noise. Magnetoencephalography (and EEG) signals derive from the net effect of ionic currents flowing in the dendrites of neurons during synaptic transmission. In accordance with Maxwell's equations, any electrical current will produce an orthogonally oriented magnetic field. It is this field that is measured with MEG. The net currents can be thought of as current dipoles, which are currents having an associated position, orientation, and magnitude, but no spatial extent. According to the right-hand rule, a current dipole gives rise to a magnetic field that flows around the axis of its vector component.

In order to generate a detectable signal, approximately 50,000 active neurons are needed. Because current dipoles must have similar orientations to generate magnetic fields that reinforce each other, it is often the layer of pyramidal cells in the cortex, which are generally perpendicular to its surface, that give rise to measurable magnetic fields. Further, it is often bundles of these neurons located in the sulci of the cortex with orientations parallel to the surface of the head that project measurable portions of their magnetic fields outside of the head.

Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news113151078.html.

Electroencephalography

Another method of measuring at least one physiologic activity may include measuring the electrical activity of the brain by recording from electrodes placed on the scalp or, in special cases, subdurally, or in the cerebral cortex. The resulting traces are known as an electroencephalogram (EEG) and represent a summation of post-synaptic potentials from a large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

The most robust ERPs are seen after many dozens or hundreds of individual presentations are averaged together. This technique cancels out noise in the data allowing only the voltage response to the stimulus to stand out clearly. While evoked potentials reflect the processing of the physical stimulus, event-related potentials are caused by higher processes, such as memory, expectation, attention, or other changes in mental state.

A two-channel wireless brain wave monitoring system powered by a thermoelectric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.eetimes.eu/design/202801063 (Nov. 1, 2007).

EEG can be recorded at the same time as MEG so that data from these complimentary high-time-resolution techniques can be combined.

Measuring at least one physiologic activity of a member of population cohort 102 may also include measuring metabolic or hemodynamic responses to neural activity. For example, in positron emission tomography (PET), positrons, the antiparticles of electrons, are emitted by certain radionuclides that have the same chemical properties as their non-radioactive isotopes and that can replace the latter in biologically-relevant molecules. After injection or inhalation of tiny amounts of these modified molecules, e.g., modified glucose (FDG) or neurotransmitters, their spatial distribution can be detected by a PET-scanner. This device is sensitive to radiation resulting from the annihilation of emitted positrons when they collide with ubiquitously-present electrons. Detected distribution information concerning metabolism or brain perfusion can be derived and visualized in tomograms. Spatial resolution is on the order of about 3-6 mm, and temporal resolution is on the order of several minutes to fractions of an hour.

Functional Near-Infrared Imaging

Another method for measuring physiologic activity is functional near-infrared imaging (fNIR). fNIR is a spectroscopic neuro-imaging method for measuring the level of neuronal activity in the brain. The method is based on neuro-vascular coupling, i.e., the relationship between neuronal metabolic activity and oxygen level (oxygenated hemoglobin) in blood vessels in proximity to the neurons.

Time-resolved frequency-domain spectroscopy (the frequency-domain signal is the Fourier transform of the original, time-domain signal) may be used in fNIR to provide quantitation of optical characteristics of the tissue and therefore offer robust information about oxygenation. Diffuse optical tomography (DOT) in fNIR enables researchers to produce images of absorption by dividing the region of interest into thousands of volume units, called voxels, calculating the amount of absorption in each (the forward model) and then putting the voxels back together (the inverse problem). fNIR systems commonly have multiple sources and detectors, signifying broad coverage of areas of interest, and high sensitivity and specificity. fNIR systems today often consist of little more than a probe with fiber optic sources and detectors, a piece of dedicated hardware no larger than a small suitcase and a laptop computer. Thus, fNIR systems can be portable; indeed battery operated, wireless continuous wave fNIR devices have been developed at the Optical Brain Imaging Lab of Drexel University. fNIR employs no ionizing radiation and allows for a wide range of movement; it's possible, for example, for a subject to walk around a room while wearing a fNIR probe. fNIR studies have examined cerebral responses to visual, auditory and somatosensory stimuli, as well as the motor system and language, and subsequently begun to construct maps of functional activation showing the areas of the brain associated with particular stimuli and activities.

For example, a fNIR spectroscopy device (fNIRS) has been developed that looks like a headband and uses laser diodes to send near-infrared light through the forehead at a relatively shallow depth e.g., (two to three centimeters) to interact with the brain's frontal lobe. Light ordinarily passes through the body's tissues, except when it encounters oxygenated or deoxygenated hemoglobin in the blood. Light waves are absorbed by the active, blood-filled areas of the brain and any remaining light is diffusely reflected to fNIRS detectors. See "Technology could enable computers to 'read the minds' of users," Physorg.com http://www.physorg.com/news110463755.html (1 Oct. 2007).

There are three types of fNIR: (1) CW—continuous wave—In this method, infrared light shines at the same intensity level during the measurement period. The detected signal is lower intensity static signal (dc valued); (2) FD—frequency domain—In this method, input signal is a modulated sinusoid at some frequency and detected output signal has changes in amplitude and phase; (3) TR—time resolved—In time resolve spectroscopy, a very short pulse is introduced to be measured and the pulse length is usually on the order of picoseconds. The detected signal is usually a longer signal and has a decay time.

In one approach, an infrared imager captures an image of a portion of the user. For example, the imager may capture a portion of the user's forehead. Infrared imaging may provide an indication of blood oxygen levels which in turn may be indicative of brain activity. With such imaging, the infrared imager may produce a signal indicative of brain activity. According to one method, hemoglobin oxygen saturation and relative hemoglobin concentration in a tissue may be ascertained from diffuse reflectance spectra in the visible wavelength range. This method notes that while oxygenated and deoxygenated hemoglobin contributions to light attenuation are strongly variable functions of wavelength, all other contributions to the attenuation including scattering are smooth wavelength functions and can be approximated by Taylor series expansion. Based on this assumption, a simple, robust algorithm suitable for real time monitoring of the hemoglobin oxygen saturation in the tissue was derived. This algorithm can be used with different fiber probe configurations for delivering and collecting light passed through tissue. See Stratonnikov et al., "Evaluation of blood oxygen saturation in vivo from diffuse reflectance spectra," J. Biomed. Optics, vol. 6, pp. 457-467 (2001).

Functional Magnetic Resonance Imaging

Another method of measuring at least one physiologic activity may include measuring blood oxygen level dependent effects by, for example, functional magnetic resonance imaging (fMRI). fMRI involves the use of magnetic resonance scanners to produce sets of cross sections—tomograms—of the brain, detecting weak but measurable resonance signals that are emitted by tissue water subjected to a very strong magnetic field after excitation with a high frequency electromagnetic pulse. Acquired resonance signals can be attributed to their respective spatial origins, and cross sectional images can be calculated. The signal intensity, often coded as a gray value of a picture element, depends on water content and certain magnetic properties of the local tissue. In general, structural MR imaging is used to depict brain morphology with good contrast and high resolution. Visualizing brain function by MRI relies on the relationship between increased neural activity of a brain region and increased hemodynamic response or blood flow to that brain region. The increased perfusion of activated brain tissue is the basis of the so-called Blood Oxygenation Level Dependent (BOLD)-effect: hemoglobin, the oxygen carrying molecule in blood, has different magnetic properties depending on its oxygenation state. While oxyhemoglobin is diamagnetic, deoxyhemoglobin is paramagnetic, which means that it locally distorts the magnetic field, leading to a local signal loss. In activated brain tissue the increased oxygen consumption is accompanied by a blood flow response. Thus, during activation of a brain region, deoxyhemoglobin is partly replaced by oxyhemoglobin, leading to less distortion of the local magnetic field and increased signal intensity. Color-coded statistical parametric activation maps (SPMs) are typically generated from statistical analyses of fMRI time series comparing signal intensity during different activation states.

Temporal and spatial resolution of fMRI depends on both scanning technology and the underlying physiology of the detected signal intensity changes. Structural images are usually obtained with a resolution of at least 1 mm×1 mm×1 mm voxels (the equivalent of a pixel in a volume), while fMRI voxels typically have edge lengths of about 3-5 mm. Temporal resolution of fMRI is on the order of between 1 and 3 seconds. The cerebral blood flow (CBF) response to a brain activation is delayed by about 3-6 seconds. There is a balance between temporal and spatial resolution, allowing whole brain scans in less than 3 seconds, and non-invasiveness, permitting repeated measurements without adverse events. In addition, the choice of scanning parameters allows increasing one parameter at the expense of the other. Recent fMRI approaches show that for some neural systems the temporal resolution can be improved down to milliseconds and spatial resolution can be increased to the level of cortical columns as basic functional units of the cortex.

In one embodiment, an fMRI protocol may include fMRI data may be acquired with an MRI scanner such as a 3 T Magnetom Trio Siemens scanner. T2*-weighted functional MR images may be obtained using axially oriented echo-planar imaging. For each subject, data may be acquired in three scanning sessions or functional runs. The first four volumes of each session may be discarded to allow for T1 equilibration effects. For anatomical reference, a high-resolution T1-weighted anatomical image may be obtained. Foam cushioning may be placed tightly around the side of the subject's head to minimize artifacts from head motion. Data preprocessing and statistical analysis may be carried out using a statistical parametric mapping function, such as SPM99 (Statistical Parametric Mapping, Wellcome Institute of Cognitive Neurology, London, UK). Individual functional images may be realigned, slice-time corrected, normalized into a standard anatomical space (resulting in isotropic 3 mm voxels) and smoothed with a Gaussian kernel of 6 mm. In one embodiment, a standard anatomical space may be based on the ICBM 152 brain template (MNI, Montreal Neurological Institute). A block-design model with a boxcar regressor convoluted with the hemodynamic response function may be used as the predictor to compare activity related to a stimulus versus a control object. High frequency noise may be removed using a low pass filter (e.g., Gaussian kernel with 4.0 s FWHM) and low frequency drifts may be removed via a high pass filter. Effects of the conditions for each subject may be compared using linear contrast, resulting in a t-statistic for each voxel. A group analysis may be carried out on a second level using a whole brain random-effect analysis (one-sample t-test). Regions that contain a minimum of five contiguous voxels thresholded at $P<0.001$ (uncorrected for multiple comparisons) may be considered to be active. See Schaefer et al., "Neural correlates of culturally familiar brands of car manufacturers," NeuroImage vol. 31, pp. 861-865 (2006).

Mapping Brain Activity

When brain activity data are collected from groups of individuals, data analysis across individuals may take into account variation in brain anatomy between and among individuals. To compare brain activations between individuals, the brains are usually spatially normalized to a template or control brain. In one approach they are transformed so that they are similar in overall size and spatial orientation. Generally, the goal of this transformation is to bring homologous brain areas into the closest possible alignment. In this context the Talairach stereotactic coordinate system is often used. The Talairach system involves a coordinate system to identify a particular brain location relative to anatomical landmarks; a spatial transformation to match one brain to another; and an atlas describing a standard brain, with anatomical and cytoarchitectonic labels. The coordinate system is based on the identification of the line connecting the anterior commissure (AC) and posterior commissure (PC)—two relatively invariant fiber bundles connecting the two hemispheres of the brain. The AC-PC line defines the y-axis of the brain coordinate system. The origin is set at the AC. The z-axis is orthogonal to the AC-PC-line in the foot-head direction and passes through the interhemispheric fissure. The x-axis is orthogonal to both the other axes and points from AC to the right. Any point in the brain can be identified relative to these axes.

Accordingly, anatomical regions may be identified using the Talairach coordinate system or the Talairach daemon (TD) and the nomenclature of Brodmann. The Talairach daemon is a high-speed database server for querying and retrieving data about human brain structure over the internet. The core components of this server are a unique memory-resident application and memory-resident databases. The memory-resident design of the TD server provides high-speed access to its data. This is supported by using TCP/IP sockets for communications and by minimizing the amount of data transferred during transactions. A TD server data may be searched using x-y-z coordinates resolved to 1×1×1 mm volume elements within a standardized stereotaxic space. An array, indexed by x-y-z coordinates, that spans 170 mm (x), 210 mm (y) and 200 mm (z), provides high-speed access to data. Array dimensions are approximately 25% larger than those of the Co-planar Stereotaxic Atlas of the Human Brain (Talairach and Tournoux, 1988). Coordinates tracked by a TD server are spatially consistent with the Talairach Atlas. Each array location stores a pointer to a relation record that holds data describing what is present at the corresponding coordinate. Data in relation records are either Structure Probability Maps (SP Maps) or Talairach Atlas Labels, though others can be easily added. The relation records are implemented as linked lists to names and values for brain structures. The TD server may be any computing device, such as a Sun Sparcstation 20 with 200 Mbytes of memory. Such a system provides 24-hour access to the data using a variety of client applications.

Some commercially available analysis software such as SPM5 (available for download from http://www.fil.ion.ucl.ac.uk/spm/software/spm5/) uses brain templates created by the Montreal Neurological Institute (MNI), based on the average of many normal MR brain scans. Although similar, the Talairach and the MNI templates are not identical, and care should be given to assigning localizations given in MNI coordinates correctly to, for example, cytoarchitectonically defined brain areas like the Brodmann areas (BA's), which are regions in the brain cortex defined in many different species based on its cytoarchitecture. Cytoarchitecture is the organization of the cortex as observed when a tissue is stained for nerve cells. Brodmann areas were originally referred to by numbers from 1 to 52. Some of the original areas have been subdivided further and referred to, e.g., as "23a" and "23b." The Brodmann areas for the human brain include the following:

Areas 1, 2 & 3—Primary Somatosensory Cortex (frequently referred to as Areas 3, 1, 2 by convention)
Area 4—Primary Motor Cortex
Area 5—Somatosensory Association Cortex
Area 6—Pre-Motor and Supplementary Motor Cortex (Secondary Motor Cortex)
Area 7—Somatosensory Association Cortex
Area 8—Includes Frontal eye fields
Area 9—Dorsolateral prefrontal cortex
Area 10—Frontopolar area (most rostral part of superior and middle frontal gyri)
Area 11—Orbitofrontal area (orbital and rectus gyri, plus part of the rostral part of the superior frontal gyrus)
Area 12—Orbitofrontal area (used to be part of BA11, refers to the area between the superior frontal gyrus and the inferior rostral sulcus)
Area 13—Insular cortex
Area 17—Primary Visual Cortex (V1)
Area 18—Visual Association Cortex (V2)
Area 19—V3
Area 20—Inferior Temporal gyrus
Area 21—Middle Temporal gyrus
Area 22—Superior Temporal Gyrus, of which the rostral part participates to Wernicke's area
Area 23—Ventral Posterior cingulate cortex
Area 24—Ventral Anterior cingulate cortex
Area 25—Subgenual cortex
Area 26—Ectosplenial area
Area 28—Posterior Entorhinal Cortex
Area 29—Retrosplenial cingular cortex
Area 30—Part of cingular cortex
Area 31—Dorsal Posterior cingular cortex
Area 32—Dorsal anterior cingulate cortex
Area 34—Anterior Entorhinal Cortex (on the Parahippocampal gyrus)
Area 35—Perirhinal cortex (on the Parahippocampal gyrus)
Area 36—Parahippocampal cortex (on the Parahippocampal gyrus)
Area 37—Fusiform gyrus
Area 38—Temporopolar area (most rostral part of the superior and middle temporal gyri
Area 39—Angular gyrus, part of Wernicke's area
Area 40—Supramarginal gyrus part of Wernicke's area
Areas 41 & 42—Primary and Auditory Association Cortex
Area 43—Subcentral area (between insula and post/precentral gyrus)
Area 44—pars opercularis, part of Broca's area
Area 45—pars triangularis Broca's area
Area 46—Dorsolateral prefrontal cortex
Area 47—Inferior prefrontal gyrus
Area 48—Retrosubicular area (a small part of the medial surface of the temporal lobe)
Area 52—Parainsular area (at the junction of the temporal lobe and the insula)

Associating Brain Activity with Brain Function or Mental State

The brain performs a multitude of functions. It is the location of memory, including working memory, semantic memory, and episodic memory. Attention is controlled by the brain, as is language, cognitive abilities, and visual-spatial functions. The brain also receives sensory signals and generates motor impulses. The frontal lobes of the brain are involved in most higher-level cognitive tasks as well as episodic and semantic memory. There is some degree of lateralization of the frontal lobes, e.g., the right frontal lobe is a locus for sustained attention and episodic memory retrieval, and the left frontal lobe is a locus for language, semantic memory retrieval, and episodic memory encoding.

The cingulated regions of the brain are associated with memory, initiation and inhibition of behavior, and emotion. The parietal regions of the brain are associated with attention, spatial perception and imagery, thinking involving time and numbers, working memory, skill learning, and successful episodic memory retrieval. The lateral temporal lobe of the brain is associated with language and semantic memory encoding and retrieval, while the medial temporal lobe is associated with episodic memory encoding and retrieval. The occipital temporal regions of the brain are associated with vision and visual-spatial processing.

Attention

Attention can be divided into five categories: sustained attention, selective attention, Stimulus-Response compatibility, orientation of attention, and division of attention. The tasks included in the sustained attention section involved continuous monitoring of different kinds of stimuli (e.g., somatosensory stimulation). The selective attention section includes studies in which subjects selectively attended to different attributes of the same set of stimuli (e.g., attend to color only for stimuli varying with respect to both color and shape). The stimulus-response (SR) compatibility section also includes studies examining selective attention, with the important difference that they involve a "conflict component." In all cases, this is implemented by employing the Stroop task.

Prefrontal and parietal areas, preferentially in the right hemisphere, are frequently engaged during tasks requiring attention. An fMRI study involving a visual vigilance task was in close agreement with the results of a PET study showing predominantly right-sided prefrontal and parietal activation. Observed data is consistent with a right fronto-parietal network for sustained attention. Selective attention to one sensory modality is correlated with suppressed activity in regions associated with other modalities. For example, studies have found deactivations in the auditory cortex during attention area activations. Taken together, the results suggest the existence of a fronto-parietal network underlying sustained attention. Direct support for fronto-parietal interactions during sustained attention has been provided by structural equation modeling of fMRI data. Studies on the effects of attention on thalamic (intralaminar nuclei) and brain stem (midbrain tegmentum) activity have shown that these areas may control the transition from relaxed wakefulness to high general attention.

Selective attention is characterized by increased activity in posterior regions involved in stimulus processing. Different regions seem to be involved depending on the specific attribute that is attended to. Studies have shown attentional modulation of auditory regions, and modulation of activity in the lingual and fusiform gyri during a color attention task has also been demonstrated. Attending to motion activates a region in occipito-temporal cortex, and it has also been shown that, in addition to extrastriate regions, attention to motion increased activity in several higher-order areas as well. It may be that activity in extrastriate regions may be modulated by prefrontal, parietal and thalamic regions. Similarly, modulation of activity in specific posterior regions is mediated by regions in parietal and anterior cingulate cortices, as well as the pulvinar. A role of parietal cortex, especially the inferior parietal lobe, in control of selective attention has also been suggested. The prefrontal cortex may also play a role in attentional modulation. As long as attentional load is low, task-irrelevant stimuli are perceived and elicit neural activity, however, when the attentional load is increased, irrelevant perception and its associated activity is strongly reduced.

The stimulus-response compatibility panel includes selective attention studies on the Stroop test. The Stroop test is associated with activations in the anterior cingulate cortex. SR compatibility studies point to a role of both the anterior cingulate and the left prefrontal cortex. See Cabeza et al, "Imaging Cognition II: An Empirical Review of 275 PET and fMRI Studies," J. Cognitive Neurosci., vol. 12, pp. 1-47 (2000).

Activation of the thalamic reticular nucleus is also associated with selective attention. See Contreras et al., "Inactivation of the Interoceptive Insula Disrupts Drug Craving and Malaise Induced by Lithium," Science, vol. 318, pp. 655-658 (26 Oct. 2007).

The category "orientation of attention" includes studies associating shifts of spatial attention to parietal and prefrontal regions. Another study found activations in superior parietal regions during a visual search for conjunction of features. Based on the similarities in activation patterns, it appears that serial shifts of attention took place during the search task. There is also evidence for a large-scale neural system for visuospatial attention that includes the right posterior parietal cortex. PET and fMRI have been employed to study attentional orienting to spatial locations (left vs. right) and to time intervals (short vs. long stimulus onset times). Both spatial and temporal orienting were found to activate a number of brain regions, including prefrontal and parietal brain regions. Other analyses revealed that activations in the intraparietal sulcus were right-lateralized for spatial attention and left lateralized for temporal attention. Moreover, simultaneous spatial and temporal attention activate mainly parietal regions, suggesting that the parietal cortex, especially in the right hemisphere, is a site for interactions between different attentional processes. Parietal activation has also been demonstrated in an fMRI study of nonspatial attention shifting. In addition, the cerebellum has been implicated in attention shifting, and this is consistent with other findings of attentional activation of the cerebellum. It has also been shown that spatial direction of attention can influence the response of the extrastriate cortex. Specifically, it was demonstrated that while multiple stimuli in the visual field interact with each other in a suppressive way, spatially directed attention partially cancels out the suppressive effects.

With respect to division of attention, activity in the left prefrontal cortex increases under divided-attention conditions. In this context, it is also relevant to mention that if two tasks activate overlapping brain areas, there may be significant interference effects when the tasks are performed simultaneously. See Cabeza et al, "Imaging Cognition II: An Empirical Review of 275 PET and fMRI Studies," J. Cognitive Neurosci., vol. 12, pp. 1-47 (2000).

Perception

Perception processes can be divided into object, face, space/motion, smell and "other" categories. Object perception is associated with activations in the ventral pathway (ventral brain areas 18, 19, and 37). The ventral occipito-temporal pathway is associated with object information, whereas the dorsal occipito-parietal pathway is associated with spatial information. For example, it has been shown that viewing novel, as well as familiar, line drawings, relative to scrambled drawings, activated a bilateral extrastriate area near the border between the occipital and temporal lobes. Based on these findings, it appears that this area is concerned with bottom-up construction of shape descriptions from simple visual features. It has also been shown that a region termed the "lateral occipital complex" (LO) is selectively activated by different kinds of shapes (e.g., shapes defined by motion, texture, and luminance contours). Greater activity in lingual gyrus (Area 19) and/or inferior fusiform gyrus (Area 37) is seen when subjects make judgments about appearance than when they make judgments about locations, providing confirmation that object identity preferentially activates regions in the ventral pathway. Both ventral and dorsal activations during shape-based object recognition suggests that visual object processing involves both pathways to some extent (a similar conclusion has been drawn based on network analysis of PET data).

Face perception involves the same ventral pathway as object perception, but there is a tendency for right-lateralization of activations for faces, but not for objects. For example, bilateral fusiform gyrus activation is seen for faces, but with more extensive activation in the right hemisphere. Faces are perceived, at least in part, by a separate processing stream within the ventral object pathway. In an fMRI study, a region was identified that is more responsive to faces than to objects, termed the "fusiform face area" or FF area.

Whereas perception of objects and faces tends to preferentially activate regions in the ventral visual pathway, perception of spatial location tends to selectively activate more dorsal regions located in parietal cortex. Greater activity in the superior parietal lobe (area 7) as well as in the premotor cortex is seen during location judgments than during object judgments. The dorsal pathway is not only associated with space perception, but also with action. For example, perception of scripts of goal-directed hand action engage parts of the parietal cortex. Comparison have been done of meaningful actions (e.g., pantomime of opening a bottle) and meaningless actions (e.g., signs from the American Sign Language that were unknown to subjects). Whereas meaningless actions activated the dorsal pathway, meaningful actions activated the ventral pathway. Meaningless actions appear to be decoded in terms of spatiotemporal layout, while meaningful actions are processed by areas that allow semantic processing and memory storage. Thus, as object perception, location/action perception may involve both dorsal and ventral pathways to some extent.

Activations in the orbitofrontal cortex (where the secondary olfactory cortex is located), particularly in the right hemisphere, and the cerebellum are associated with smelling, as well as increased activity in the primary olfactory cortex (piriform cortex). Odorants (regardless of sniffing) activate the posterior lateral cerebellum, whereas sniffing (nonodorized air) activate anterior parts of the cerebellum. Thus the cerebellum receives olfactory information for modulating sniffing. Odorants (regardless of sniffing) activate the anterior and lateral orbitofrontal cortex whereas sniffing (even in the absence of odorants) activates the piriform and medial/posterior orbitofrontal cortices. In sum, smell perception involves primarily the orbitofrontal cortex and parts of the cerebellum and its neural correlates can be dissociated from those of sniffing.

With respect to the "other" category, fMRI has been employed to define a "parahippocampal place area" (PPA) that responds selectively to passively viewed scenes. A region probably overlapping with PPA responds selectively to buildings, and this brain region may respond to stimuli that have orienting value (e.g., isolated landmarks as well as scenes). The neural correlates of music perception have been localized to specialized neural systems in the right superior temporal cortex, which participate in perceptual analysis of melodies. Attention to changes in rhythm activate Broca's/insular regions in the left hemisphere, pointing to a role of this area in the sequencing of auditory input. Further, studies of "emotional perception" suggest that perception of different kinds of emotion are based on separate neural systems, with a possible convergence in prefrontal regions (area 47). Consistent with the role of the amygdala in fear conditioning, the amygdala is more activated for fearful faces relative to happy faces. See Cabeza et al, "Imaging Cognition II: An Empirical Review of 275 PET and fMRI Studies," J. Cognitive Neurosci., vol. 12, pp. 1-47 (2000).

Imagery

Imagery can be defined as manipulating sensory information that comes not from the senses, but from memory. The memory representations manipulated can be in working memory (e.g., holding three spatial locations for 3 seconds), episodic memory (e.g., retrieving the location of an object in the study phase), or semantic memory (e.g., retrieving the shape of a bicycle). Thus, imagery-related contrasts could be classified within working memory, episodic retrieval, and semantic retrieval sections. Imagery contrasts can be described as visuospatial retrieval contrasts, and vice versa.

A central issue in the field of imagery has been whether those visual areas that are involved when an object is perceived are also involved when an object is imagined. In its strictest form, this idea would imply activation of the primary visual cortex in the absence of any visual input. A series of PET experiments provides support for similarities between visual perception and visual imagery by showing increased blood flow in Area 17 during imagery. In particular, by comparing tasks involving image formation for small and large letters, respectively, these studies provide evidence that imagery activates the topographically mapped primary visual cortex. A subsequent PET study, involving objects of three different sizes, provides additional support that visual imagery activates the primary visual cortex.

Increased activation in extrastriate visual regions is also associated with imaging tasks. The left inferior temporal lobe (area 37) is most reliably activated across subjects (for some subjects the activation extended into area 19 of the occipital lobe). Compared with a resting state, a left posterior-inferior temporal region was also activated. Moreover, mental imagery of spoken, concrete words has been shown to activate the inferior-temporal gyrus/fusiform gyrus bilaterally. Thus, right temporal activation may be related to more complex visual imagery.

Color imagery and color perception engage overlapping networks anterior to region V4 (an area specialized for color perception), whereas areas V1-V4 were selectively activated by color perception. There is an increase in primary visual-cortex activity during negative imagery, as compared to neutral imagery. The primary visual cortex therefore appears to have a role in visual imagery, and emotion appears to affect the quality of the image representations.

Mental rotation of visual stimuli involves lateral parietal areas (BA47 and BA40). The bulk of the computation for this kind of mental rotation is performed in the superior parietal lobe. PET has been employed to study a mental-rotation task in which subjects were asked to decide whether letters and digits, tilted in 120°, 180°, or 240°, were in normal or mirror image form. The left parietal cortex is activated in this task.

Mental "exploration" of maps or routes has been studied using PET, revealing that this task is associated with increased activity in the right superior occipital cortex, the supplementary motor area (SMA) and the cerebellar vermis. The latter two activations are related to eye movements, and it appears that the superior occipital cortex has a specific role in generation and maintenance of visual mental images. In a subsequent PET study, occipital activation was again observed, although this time the peak was in left middle occipital gyrus. This activation was specific to a task involving mental navigation—static visual imagery was not associated with occipital activation. Mental navigation tasks appears to tap visual memory to a high extent, and feedback influences from areas involved in visual memory may activate visual (occipital) areas during certain imagery tasks.

Thus, visual mental imagery is a function of the visual association cortex, although different association areas seem to be involved depending on the task demands. In addition, prefrontal areas have been activated in many of the reported comparisons. Partly, these effects may be driven by eye movements (especially for areas 6 and 8), but other factors, such as image generation and combination of parts into a whole, may account for some activations as well.

Neuroanatomical correlates of motor imagery via a mental writing task implicate a left parietal region in motor imagery, and, more generally, show similarities between mental writing and actual writing. Similarities between perception and imagery are seen in both musical imagery and perception. For example, relative to a visual baseline condition, an imagery task is associated with increased activity in the bilateral secondary auditory cortex. This was so despite the fact that the contrast included two entirely silent conditions. Similarly, a comparison of a task involving imaging a sentence being spoken in another person's voice with a visual control task reveals left temporal activation. Activation of the supplementary motor area was also seen, suggesting that both input and output speech mechanisms are engaged in auditory mental imagery. See Cabeza et al, "Imaging Cognition II: An Empirical Review of 275 PET and fMRI Studies," J. Cognitive Neurosci., vol. 12, pp. 1-47 (2000).

Language

Language mapping studies are commonly divided into four categories: spoken and written word recognition crossed with spoken or no-spoken response. Word recognition, regardless of input modality and whether or not a spoken response is required, has consistently been found to activate areas 21 and 22 in the temporal cortex. In general, this activation tends to be bilateral, although in the category of written word recognition all activations are left-lateralized. The cortical surface covered by these areas is most likely made up by several distinct regions that can be functionally dissociated. Involvement of left superior temporal gyrus/Wernicke's area in word recognition is in agreement with the traditional view implicating this area in comprehension.

Whereas left temporal brain regions have been associated with word comprehension, left inferior prefrontal cortex/Broca's area has traditionally been linked to word production. However, comparing conditions involving spoken response with conditions involving no spoken response do not suggest that (left) prefrontal involvement is greater when spoken responses are required. Instead, the major difference between these two classes is that conditions involving spoken responses tend to activate the cerebellum to a higher extent. Broca's area is involved in word perception, as well as in word production, and in addition to having an output function, the left prefrontal areas may participate in receptive language processing in the uninjured state. An fMRI study has shown that cerebellar activation is related to the articulatory level of speech production.

Visual areas are more frequently involved in the case of written word recognition, and regardless of output (spoken/no spoken), written word recognition tends to differentially activate left prefrontal and anterior cingulate regions. Moreover, left inferior prefrontal activation has been associated with semantic processing.

A posterior left temporal region (BA 37) is a multimodal language region. Both blind and sighted subjects activate this area during tactile vs. visual reading (compared to non-word letter strings). This area may not contain linguistic codes per se, but may promote activity in other areas that jointly lead to lexical or conceptual access. Area 37 has been activated in several studies of written word recognition but not in studies of spoken word recognition. Lip-reading activates the auditory cortex in the absence of auditory speech sounds. The activation was observed for silent speech as well as pseudospeech, but not for nonlinguistic facial movements, suggesting that lip-reading modulates the perception of auditory speech at a prelexical level.

There are few differences between sign language and spoken language, and sign language in bilingual persons activates a similar network as that underlying spoken language. The difference in activation in ventral temporal cortex (area 37) related to sign language appears to relate to an attention mechanism that assigns importance to signing hands and facial expressions. With respect to the processing of native and foreign languages, native-language processing, relative to processing of a foreign language, selectively activates several brain regions leading to the conclusion that some brain areas are shaped by early exposure to the maternal language, and that these regions may not be activated when people process a language that they have learned later in life. In Broca's area, second languages acquired in adulthood are spatially separated from native languages, whereas second languages acquired at an early age tend to activate overlapping regions within Broca's area. In Wernicke's area, no separation based on age of language acquisition is observed. Further, fMRI has been used to determine brain activity related to aspects of language processing. During phonological tasks, brain activation in males was lateralized to the left inferior frontal gyrus, whereas the pattern was more diffuse for females.

Activation patterns related to the processing of particular aspects of information show that a set of brain regions in the right hemisphere is selectively activated when subjects try to appreciate the moral of a story as opposed to semantic aspects of the story. Brain activation associated with syntactic complexity of sentences indicates that parts of Broca's area increase their activity when sentences increase in syntactic complexity. See Cabeza et al, "Imaging Cognition II: An Empirical Review of 275 PET and fMRI Studies," J. Cognitive Neurosci., vol. 12, pp. 1-47 (2000).

Working Memory

Working memory consists of three main components: a phonological loop for the maintenance of verbal information, a visuospatial sketchpad for the maintenance of visuospatial information, and a central executive for attentional control. Dozens of functional neuroimaging studies of working memory have been carried out. Working memory is associated with activations in prefrontal, parietal, and cingulate regions. There also may be involvement of occipital and cerebellar regions discriminations between different Brodmann's areas.

Working memory is almost always associated with increased activity in the prefrontal cortex. This activity is typically found in areas 6, 44, 9 and 46. Area 44 activations are more prevalent for verbal/numeric tasks than for visuospatial tasks, and tend to be lateralized to the left hemisphere (i.e., Broca's area), suggesting that they reflect phonological processing. Area 6 activations are common for verbal, spatial, and problem-solving tasks, and, hence, they are likely related to general working memory operations (i.e., they are not material or task-specific). In contrast, activations in areas 9 and 46 seem to occur for certain kinds of working memory tasks but not others. Activations in these two areas tend to be more prevalent for tasks that require manipulation of working memory contents, such as N-back tasks, than for tasks that require only uninterrupted maintenance, such as delayed response tasks. Ventrolateral prefrontal regions are involved in simple short-term operations, whereas mid-dorsal prefrontal regions perform higher-level executive operations, such as monitoring. Object working memory may be left-lateralized while spatial-working memory is right-lateralized.

In addition to prefrontal activations, working memory studies normally show activations in parietal regions, particularly areas 7 and 40. In the case of verbal/numeric tasks, these activations tend to be left-lateralized, suggesting that they are related to linguistic operations. The phonological loop consists of a phonological store, where information is briefly stored, and a rehearsal process, which refreshes the contents of this store. Left parietal activations may reflect the phonological store, whereas left prefrontal activations in area 44 (Broca's area) may reflect the rehearsal process. When nonverbal materials are employed, parietal activations, particularly those in area 7, tend to be bilateral, and to occur for spatial but not for object working memory. Thus the distinction between a ventral pathway for object processing and a dorsal pathway for spatial processing may also apply to working memory.

Working memory tasks are also associated with anterior cingulate, occipital, and cerebellar activations. Anterior cingulate activations are often found in Area 32, but they may not reflect working memory operations per se. Activity in dorsolateral prefrontal regions (areas 9 and 46) varies as a function of delay, but not of readability of a cue, and activity in the anterior cingulate (and in some right ventrolateral prefrontal regions) varies as a function of readability but not of delay of a cue. Thus, the anterior cingulate activation seems to be related to task difficulty, rather than to working memory per se. Occipital activations are usually found for visuospatial tasks, and may reflect increased visual attention under working memory conditions. Cerebellar activations are common during verbal working memory tasks, particularly for tasks involving phonological processing (e.g., holding letters) and tasks that engage Broca's area (left area 44).

Consistent with the idea that mid-dorsal areas 9/46 are involved in higher-level working memory operations, activations in these areas are prominent in the reasoning and planning tasks. Area 10 activations are also quite prevalent, and may be related to episodic memory aspects of problem-solving tasks (see episodic memory retrieval section above). Tasks involving sequential decisions, such as conceptual reasoning and card sorting consistently engage the basal ganglia, thalamic, and cerebellar regions. These regions are typical skill learning regions and may reflect the skill-learning aspects of sequential problem-solving tasks. Also, the basal ganglia, thalamus, and prefrontal cortex are intimately linked and dysfunction of this circuitry could underlie planning deficits in Parkinson disease. See Cabeza et al, "Imaging Cognition II: An Empirical Review of 275 PET and fMRI Studies," J. Cognitive Neurosci., vol. 12, pp. 1-47 (2000).

Semantic Memory Retrieval

Semantic memory refers to knowledge we share with other members of our culture, such as knowledge about the meaning of words (e.g., a banana is a fruit), the properties of objects (e.g., bananas are yellow), and facts (e.g., bananas grow in tropical climates). Semantic memory may be divided into two testing categories, categorization tasks and generation tasks. In categorization tasks, subjects classify words into different categories (e.g., living vs. nonliving), whereas in generation tasks, they produce one (e.g., word stem completion) or several (for example, fluency tasks) words in response to a cue. Semantic memory retrieval is associated with activations in prefrontal, temporal, anterior cingulate, and cerebellar regions.

Prefrontal activity during semantic memory tasks frequently found in the left hemisphere but not in the right. This is so even when the stimuli are nonverbal materials, such as objects and faces. This striking left-lateralization is in sharp contrast with the right-lateralization of prefrontal activity typically observed during episodic memory retrieval. This asymmetric pattern has been conceptualized in terms of a hemispheric encoding/retrieval asymmetry (HERA) model. This model consists of three hypotheses: (1) the left prefrontal cortex is differentially more involved in semantic memory retrieval than is the right prefrontal cortex; (2) the left prefrontal cortex is differentially more involved in encoding information into episodic memory than is the right prefrontal cortex; and (3) the right prefrontal cortex is differentially more involved in episodic memory retrieval than is the left prefrontal cortex. Thus, the left-lateralization of prefrontal activations supports the first hypothesis of the model. The second and third hypotheses are addressed by episodic memory encoding and episodic memory retrieval testing, respectively, as discussed above.

Within the frontal lobes, activations are found in most prefrontal regions, including ventrolateral (areas 45 and 47), ventromedial (area 11), posterior (areas 44 and 6), and mid-dorsal (areas 9 and 46) regions. Activations in ventrolateral regions occur during both classification and generation tasks and under a variety of conditions, suggesting that they are related to generic semantic retrieval operations. In contrast, area 11 activations are more common for classification than for generation tasks, and could be related to a component of classification tasks, such as decision-making. Conversely, activations in posterior and dorsal regions are more typical for generation tasks than for classification tasks. Many posterior activations (areas 44 and 6) occur at or near Broca's area, thus they may reflect overt or covert articulatory processes during word generation. Activations in dorsal regions (areas 9 and 46) are particularly frequent for fluency tasks. Because fluency tasks require the monitoring of several items in working memory, these activations may reflect working memory, rather than semantic memory, per se. Accordingly, when subjects complete word stems, areas 9/10 are more active for stems with many completions than for stems with few completions. These areas may therefore be involved in selecting among competing candidate responses.

Semantic retrieval tasks are also commonly associated with temporal, anterior cingulate, and cerebellar regions. Temporal activations occur mainly in the left middle temporal gyrus (area 21) and in bilateral occipito-temporal regions (area 37). Left area 21 is activated not only for words but also pictures and faces, suggesting it is involved in higher-level semantic processes that are independent of input modality. In contrast, area 37 activations are more common for objects and faces, so they could be related to the retrieval of visual properties of these stimuli. Anterior cingulate activations are typical for generation tasks. The anterior cingulate—like the dorsal prefrontal cortex—is more active for stems with many than with few completions, whereas the cerebellum shows the opposite pattern. The anterior cingulate may therefore be involved in selecting among candidate responses, while the cerebellum may be involved in memory search processes. Accordingly cerebellar activations are found during single-word generation, but not during fluency tasks.

The retrieval of animal information is associated with left occipital regions and the retrieval of tool information with left prefrontal regions. Occipital activations could reflect the processing of the subtle differences in physical features that distinguish animals, whereas prefrontal activations could be related to linguistic or motor aspects of tool utilization. Animal knowledge activates a more anterior region (area 21) of the inferior temporal lobe than the one associated with tool knowledge (area 37). Whereas generating color words activates fusiform areas close to color perception regions, generating action words activates a left temporo-occipital area close to motion perception regions. Thus knowledge about object attributes is stored close to the regions involved in perceiving these attributes. See Cabeza et al, "Imaging Cognition II: An Empirical Review of 275 PET and fMRI Studies," J. Cognitive Neurosci., vol. 12, pp. 1-47 (2000).

Episodic Memory Encoding

Episodic memory refers to memory for personally experienced past events, and it involves three successive stages: encoding, storage, and retrieval. Encoding refers to processes that lead to the formation of new memory traces. Storage designates the maintenance of memory traces over time, including consolidation operations that make memory traces more permanent. Retrieval refers to the process of accessing stored memory traces. Encoding and retrieval processes are amenable to functional neuroimaging research, because they occur at specific points in time, whereas storage/consolidation processes are not, because they are temporally distributed. It is very difficult to differentiate the neural correlates of encoding and retrieval on the basis of the lesion data, because impaired memory performance after brain damage may reflect encoding deficits, retrieval deficits, or both. In contrast, functional neuroimaging allows separate measures of brain activity during encoding and retrieval.

Episodic encoding can be intentional, when subjects are informed about a subsequent memory test, or incidental, when they are not. Incidental learning occurs, for example, when subjects learn information while performing a semantic retrieval task, such as making living/nonliving decisions. Semantic memory retrieval and incidental episodic memory encoding are closely associated. Semantic processing of information (semantic retrieval) usually leads to successful storage of new information. Further, when subjects are instructed to learn information for a subsequent memory test (intentional encoding), they tend to elaborate the meaning of the information and make associations on the basis of their knowledge (semantic retrieval). Thus, most of the regions (for example, left prefrontal cortex) associated with semantic retrieval tasks are also associated with episodic memory encoding.

Episodic encoding is associated primarily with prefrontal, cerebellar, and medial temporal brain regions. In the case of verbal materials, prefrontal activations are always left lateralized. This pattern contrasts with the right lateralization of prefrontal activity during episodic retrieval for the same kind of materials. In contrast, encoding conditions involving nonverbal stimuli sometimes yield bilateral and right-lateralized activations during encoding. Right-lateralized encoding activations may reflect the use of non-nameable stimuli, such as unfamiliar faces and textures, but encoding of non-nameable stimuli has been also associated with left-lateralized activations with unfamiliar faces and locations. Contrasting encoding of verbal materials with encoding of nonverbal materials may speak to the neural correlates of different materials rather than to the neural correlates of encoding per se.

The prefrontal areas most commonly activated for verbal materials are areas 44, 45, and 9/46. Encoding activations in left area 45 reflects semantic processing while those in left area 44 reflects rote rehearsal. Areas 9/46 may reflect higher-order working memory processes during encoding. Activation in left area 9 increases as a function of organizational processes during encoding, and is attenuated by distraction during highly organizational tasks. Cerebellar activations occur only for verbal materials and show a tendency for right lateralization. The left-prefrontal/right-cerebellum pattern during language, verbal-semantic memory, and verbal-episodic encoding tasks is consistent with the fact that fronto-cerebellar connections are crossed.

Medial-temporal activations are seen with episodic memory encoding and can predict not only what items will be remembered, but also how well they will be remembered. Medial-temporal activations show a clear lateralization pattern: they are left-lateralized for verbal materials and bilateral for nonverbal materials. Under similar conditions, medial-temporal activity is stronger during the encoding of pictures than during the encoding of words, perhaps explaining why pictures are often remembered better than words. In the case of nonverbal materials, medial-temporal activity seems to be more pronounced for spatial than for nonspatial information, consistent with the link between the hippocampus and spatial mapping shown by animal research. See Cabeza et al, "Imaging Cognition II: An Empirical Review of 275 PET and fMRI Studies," J. Cognitive Neurosci., vol. 12, pp. 1-47 (2000).

Episodic Memory Retrieval

Episodic memory retrieval refers to the search, access, and monitoring of stored information about personally experienced past events, as well as to the sustained mental set underlying these processes. Episodic memory retrieval is associated with seven main regions: prefrontal, medial temporal, medial parieto-occipital, lateral parietal, anterior cingulate, occipital, and cerebellar regions.

Prefrontal activations during episodic memory retrieval are sometimes bilateral, but they show a clear tendency for right-lateralization. The right lateralization of prefrontal activity during episodic memory retrieval contrasts with the left lateralization of prefrontal activity during semantic memory retrieval and episodic memory encoding. Left prefrontal activations during episodic retrieval tend to occur for tasks that require more reflectively complex processing. These activations may be related to semantic retrieval processes during episodic retrieval. Semantic retrieval can aid episodic retrieval particularly during recall, and bilateral activations tend to be more frequent during recall than during recognition. Moreover, left prefrontal activity during episodic retrieval is associated with retrieval effort, and is more common in older adults than in young adults.

Prefrontal activity changes as a function of the amount of information retrieved during the scan have been measured by varying encoding conditions (e.g., deep vs. shallow), or by altering the proportion of old items (e.g., targets) during the scan. As more information is retrieved during the scan, prefrontal activity may increase (retrieval success), decrease (retrieval effort), or remain constant (retrieval mode). These three outcomes are not necessarily contradictory; they may correspond to three different aspects of retrieval: maintaining an attentional focus on a particular past episode (retrieval mode), performing a demanding memory search (retrieval effort), and monitoring retrieved information (retrieval success).

These different aspects of retrieval may map to distinct prefrontal regions. The region most strongly associated to retrieval mode is the right anterior prefrontal cortex (area 10). A combined PET/ERP study associated a right area 10 activation with task-related rather than item-related activity during episodic retrieval. Activations associated with retrieval effort show a tendency to be left lateralized, specifically in left areas 47 and 10. Bilateral Areas 10, 9, and 46 are sometimes associated with retrieval success. Prefrontal activity is also seen to increase with success activations when subjects are warned about the proportion of old and new items during the scan (biasing).

Medial-temporal activations have been seen in the typical pattern of episodic retrieval in PET and fMRI studies, for both verbal and nonverbal materials. In contrast with medial-temporal activations during episodic encoding, those during episodic retrieval tend to occur in both hemispheres, regardless of the materials employed. That they are sometimes found in association with retrieval success, but never in association with retrieval effort or retrieval mode, suggest that they are related to the level of retrieval performance. Medial-temporal activity increases as linear function of correct old word recognition, and this activity may reflect successful access to stored-memory representations. Further, hippocampal activity has been associated with conscious recollection. Hippocampal activity is also sensitive to the match between study and test conditions, such as the orientation of study and test objects. However, recollection need not be accurate; for example in the case of significant hippocampal activations during the recognition of false targets. Accurate recognition yields additional activations in a left temporoparietal region, possibly reflecting the retrieval of sensory properties of auditorily studied words. Further, intentional retrieval is not a precondition for hippocampal activity; activations in this area are found for old information encountered during a non-episodic task, suggesting that they can also reflect spontaneous reminding of past events.

After the right prefrontal cortex, the most typical region in PET/fMRI studies of episodic retrieval is the medial parieto-occipital area that includes retrosplenial (primarily areas 29 and 30), precuneus (primarily medial area 7 and area 31), and cuneus (primarily medial areas 19, 18, and 17) regions. The critical role of the retrosplenial cortex in memory retrieval is supported by evidence that lesions in this region can cause severe memory deficits (e.g., retrosplenial amnesia. The role of the precuneus has been attributed to imagery and to retrieval success. Retrieval-related activations in the precuneus are more pronounced for imageable than for nonimageable words. However, the precuneus region was not more activated for object recall than for word recall. Imagery-related activations are more anterior than activations typically associated with episodic retrieval. The precuneus is activated for both imageable and abstract words, and for both visual and auditory study presentations. Thus this region appears to be involved in episodic retrieval irrespective of imagery content. The precuneus cortex is more active in a high-target than in low-target recognition condition.

Episodic memory retrieval is also associated with activations in lateral parietal, anterior cingulate, occipital, and cerebellar regions. Lateral parietal regions have been associated with the processing of spatial information during episodic memory retrieval and with the perceptual component of recognition. Anterior cingulate activations (areas 32 and 24) have been associated with response selection and initiation of action. Anterior cingulate activations may be related to language processes because they are more frequent for verbal than for nonverbal materials. As expected, occipital activations are more common during nonverbal retrieval, possibly reflecting not only more extensive processing of test stimuli but also memory-related imagery operations. Cerebellar activations have been associated with self-initiated retrieval operations. This idea of initiation is consistent with the association of cerebellar activations with retrieval mode and effort, rather than with retrieval success.

With respect to context memory, a fusiform region is more active for object identity than for location retrieval, whereas an inferior parietal region shows the opposite pattern. Thus the ventral/dorsal distinction applies also to episodic retrieval. In the time domain, recognition memory (what) has been contrasted with recency memory (when). Medial-temporal regions are more active during item memory than during temporal-order memory, whereas dorsal prefrontal and parietal regions are more active during temporal-order memory than during item memory. Parietal activations during temporal-order memory suggest that the dorsal pathway may be associated not only with "where" but also with "when."

Prefrontal regions were similarly activated in both recall and recognition tests. This may signify the use of associative recognition—a form of recognition with a strong recollection component, or to the careful matching of task difficulty in the two tests. A comparison of free and cued recall found a dissociation in the right prefrontal cortex between dorsal cortex (areas 9 and 46), which is more active during free recall, and the ventrolateral cortex (area 47/frontal insula), which is more active during cued recall. Thus some of the activations observed during episodic-memory retrieval tasks may reflect the working-memory components of these tasks. Autobiographic retrieval is associated with activations along a right fronto-temporal network.

Episodic memory retrieval is associated with activations in prefrontal, medial temporal, posterior midline, parietal, anterior cingulate, occipital, and cerebellar regions. Prefrontal activations tend to be right-lateralized, and have been associated with retrieval mode, retrieval effort, and retrieval success. The engagement of medial temporal regions has been linked to retrieval success and recollection. Posterior midline activations also seem related to retrieval success. Parietal activations may reflect processing of spatial context, and anterior cingulate activations may reflect selection/initiation processes. Cerebellar involvement has been attributed to self-initiated retrieval. Spatial retrieval engaged parietal regions, and object retrieval activated temporal regions. Parietal regions are also activated during temporal-order retrieval, suggesting a general role in context memory. See Cabeza et al, "Imaging Cognition II: An Empirical Review of 275 PET and fMRI Studies," J. Cognitive Neurosci., vol. 12, pp. 1-47 (2000).

Priming

Priming can be divided into perceptual and conceptual priming. In several studies, perceptual priming has been explored by studying completion of word-stems. In the primed condition, it is possible to complete the stems with previously presented words, whereas this is not possible in the unprimed condition. Visual perceptual priming is associated with decreased activity in the occipital cortex. PET and fMRI studies on non-verbal visual perceptual priming have revealed priming-related reduction in activation of regions in the occipital and inferior temporal brain regions. Priming effects can persist over days; repetition priming (item-specific learning) as measured by fMRI shows that learning-related neural changes that accompany these forms of learning partly involve the same regions.

Comparisons of blood flow responses associated with novel vs. familiar stimuli (across memory tasks) show that novel stimuli are associated with higher activity in several regions, including fusiform gyrus and cuneus. Thus, priming-related reductions in activity in visual areas occur even after subliminal presentation.

Priming cannot only facilitate perceptual processes, but may also influence conceptual processes. The primed condition is associated with decreased activity in several regions, including the left inferior prefrontal cortex. Similarly, several fMRI studies that have included repeated semantic processing of the same items have found reduced left prefrontal activation associated with the primed condition. Left prefrontal reduction of activation is not seen when words are non-semantically reprocessed, suggesting that the effect reflects a process-specific change (not a consequence of mere repeated exposure). This process-specific effect can be obtained regardless of the perceptual format of the stimuli (e.g., pictures or words). Many memory tests rely upon a mixture of processes, and even the stem-completion task, which has been used in several studies of perceptual priming, has been associated with priming-related left prefrontal reductions. This may be taken as evidence that this task, too, taps both perceptual and conceptual processes.

With respect to a neural correlate of priming, repeating items during performance of the same task, or even during performance of different tasks, can lead to decreases in the amount of activation present in specific brain areas. This effect may reflect enhanced processing of the involved neurons or/and a specification of the involved neuronal population, resulting in a spatially less diffuse response. See Cabeza et al, "Imaging Cognition II: An Empirical Review of 275 PET and fMRI Studies," J. Cognitive Neurosci., vol. 12, pp. 1-47 (2000).

Procedural Memory

Procedural memory processes can be divided into three subcategories: conditioning, motor-skill learning, and non-motor skill learning. With respect to conditioning, studies on eye-blink conditioning point to a consistent role of the cerebellum in this form of learning (e.g., decreased activity in the cerebellum following conditioning). Conditioning is also associated with increased activity in the auditory cortex.

Motor-skill learning is associated with activation of motor regions. Area 6 is involved, and learning-related changes have also repeatedly been demonstrated in the primary motor cortex. (area 4). The size of the activated area in the primary motor cortex increases as a function of training. There is also parietal involvement in motor skill learning; fronto-parietal interactions may underlie task performance. With respect to nonmotor skill learning, cerebellar activation is observed across tasks, as is consistent involvement of parietal brain regions. This is in line with the pattern observed for motor-skill learning, and the overlap in activation patterns may reflect common processes underlying these two forms of procedural memory. See Cabeza et al, "Imaging Cognition II: An Empirical Review of 275 PET and fMRI Studies," J. Cognitive Neurosci., vol. 12, pp. 1-47 (2000).

Preference

Neural correlates of preference can be detected through neuroimaging studies. For example, in a simulated buying decision task between similar fast moving consumer goods, only a subject's preferred brand elicited a reduced activation in the dorsolateral prefrontal, posterior parietal and occipital cortices and the left premotor area (Brodmann areas 9, 46, 7/19 and 6), and only when the target brand was the subjects' favorite one. Simultaneously, activity was increased in the inferior precuneus and posterior cingulated (BA 7), right superior frontal gyrus (BA 10), right supramarginal gyrus (BA 40) and most pronounced in the ventromedial prefrontal cortex ("VMPFC", BA 10).

In fMRI analyses, activation of the nucleus accumbens is associated with product preference, and the medial prefrontal cortex is associated with evaluation of gains and losses. When these areas of the brain are activated, subjects bought a product at an accuracy rate of 60%. In other fMRI analyses, early stage romantic love has been associated with activation of subcortical reward regions such as the right ventral tegmental area and the dorsal caudate area. Subjects in more extended romantic love showed more activity in the ventral pallidum. In still another fMRI analysis, in subjects experiencing a mistake, activation of the rostral anterior cingulated cortex increased in proportion to a financial penalty linked to the mistake. See Wise, "Thought Police: How Brain Scans Could Invade Your Private Life," Popular Mechanics, (November 2007).

With respect to brand discrimination, brain activations in product choice differ from those for height discrimination, and there is a positive relationship between brand familiarity and choice time. Neural activation during choice tasks involves brain areas responsible for silent vocalization. Decision processes take approximately 1 second as measured by magnetoencephalography and can be seen as two halves. The first period involves gender-specific problem recognition processes, and the second half concerns the choice itself (no gender differences). MEG measurements can be categorized in four stages:

Stage 1—V (visual): Activation of the primary visual cortices at around 90 ms after stimulus onset.

Stage 2—T (temporal): Neuronal activity predominantly over left anterior-temporal and middle-temporal cortices at approximately 325 ms after stimulus onset. Some specific activity was also found over the left frontal and right extrastriate cortical areas.

Stage 3—F (frontal): Activation of the left inferior frontal cortices at about 510 ms after stimulus onset. These signals are consistent with activation of Broca's speech area.

Stage 4—P (parietal): Activation of the right posterior parietal cortices (P) at around 885 ms after stimulus onset.

Male brain activity differed from female in the second stage (T) but not in the other three stages (V, F and P). Left anterior temporal activity is present in both groups, but males seem to activate right hemispherical regions much more strongly during memory recall than females do. As noted above, response times also differed for male and female subjects. See Amber et al., "Salience and Choice: Neural Correlates of Shopping Decisions," Psychology & Marketing, Vol. 21(4), pp. 247-261 (April 2004).

In an fMRI study, a consistent neural response in the ventromedial prefrontal cortex was associated with subjects' behavioral preferences for sampled anonymized beverages. In a brand-cued experiment, brand knowledge of one of the beverages had a dramatic influence on expressed behavioral preferences and on the measured brain responses. See Kenning et al., "Neuroeconomics: an overview from an economic perspective," Brain Res. Bull., vol. 67, pp. 343-354 (2005).

In an fMRI study, only the presence of a subject's favorite brand indicating a distinctive mode of decision-making was associated with activation of regions responsible for integrating emotions. See Kenning et al., "Neuroeconomics: an overview from an economic perspective," Brain Res. Bull., vol. 67, pp. 343-354 (2005).

Emotion

Various emotions may be identified through detection of brain activity. As discussed below, activation of the anterior insula has been associated with pain, distress, and other negative emotional states. Conversely, as discussed below, positive emotional processes are reliably associated with a series of structures representing a reward center, including the striatum and caudate, and areas of the midbrain and cortex to which they project, such as the ventromedial prefrontal cortex, orbitofrontal cortex, and anterior cingulated cortex, as well as other areas such as the amygdala and the insula.

In addition, approval and/or disapproval may be determined based on brain activity. For example, in an fMRI study, blood-oxygen-level-dependent signal changes were measured in subjects viewing facial displays of happiness, sadness, anger, fear, and disgust, as well as neutral faces. Subjects were tasked with discriminating emotional valence (positive versus negative) and age (over 30 versus under 30) of the faces. During the task, normal subjects showed activation in the fusiform gyrus, the occipital lobe, and the inferior frontal cortex relative to the resting baseline condition. The increase was greater in the amygdala and hippocampus during the emotional valence discrimination task than during the age discrimination task. See Gur et al., "An fMRI study of Facial Emotion Processing in Patients with Schizophrenia," Am. J. Psych., vol. 159, pp. 1992-1999 (2002).

Frustration is associated with decreased activation in the ventral striatum, and increased activation in the anterior insula and the right medial prefrontal cortex by fMRI. See Kenning et al., "Neuroeconomics: an overview from an economic perspective," Brain Res. Bull., vol. 67, pp. 343-354 (2005).

Fairness, Altruism and Trust fMRI has been used to show that perceived unfairness correlates with activations in the anterior insula and the dorsolateral, prefrontal cortex ("DLPFC"). Anterior insula activation is consistently seen in neuroimaging studies focusing on pain and distress, hunger and thirst, and autonomic arousal. Activation of the insula has also been associated with negative emotional states, and activation in the anterior insula has been linked to a negative emotional response to an unfair offer, indicating an important role for emotions in decision-making.

In contrast to the insula region, the DLPFC has been linked to cognitive processes such as goal maintenance and executive control. Thus, DLPFC activation may indicate objective recognition of benefit despite an emotional perception of unfairness.

Event-related hyperscan-fMRI ("hfMRI" which means that two volunteers are measured parallel in two scanners) has been used to measure the neural correlates of trust. By this method, the caudate nucleus has been shown to be involved in trust-building and reciprocity in economic exchange. The caudate nucleus is commonly active when learning about relations between stimuli and responses. See Kenning et al., "Neuroeconomics: an overview from an economic perspective," Brain Res. Bull., vol. 67, pp. 343-354 (2005).

In a PET study, sanctions against defectors were associated with activity in reward-processing brain regions. See Kenning et al., "Neuroeconomics: an overview from an economic perspective," Brain Res. Bull., vol. 67, pp. 343-354 (2005).

Reward

In an fMRI study, activation changes in the sublenticular extended amygdala (SLEA) and orbital gyrus were associated with expected values of financial gain. Responses to actual experience of rewards increased monotonically with monetary value in the nucleus accumbens, SLEA, and thalamus. Responses to prospective rewards and outcomes were generally, but not always, seen in the same regions. Overlaps with activation changes seen previously in response to tactile stimuli, gustatory stimuli, and euphoria-inducing drugs were found. See Kenning et al., "Neuroeconomics: an overview from an economic perspective," Brain Res. Bull., vol. 67, pp. 343-354 (2005).

In another fMRI study, within a group of cooperative subjects the prefrontal cortex showed activation changes when subjects playing a human compared to playing a computer. Within a group of non-cooperators, no significant activation changes in the prefrontal cortex were seen between computer and human conditions. See Kenning et al., "Neuroeconomics: an overview from an economic perspective," Brain Res. Bull., vol. 67, pp. 343-354 (2005).

In an fMRI study, products symbolizing wealth and status were associated with increased activity in reward-related brain areas. See Kenning et al., "Neuroeconomics: an overview from an economic perspective," Brain Res. Bull., vol. 67, pp. 343-354 (2005).

In a PET study, participants were risk averse in gains and risk-seeking in losses; and ambiguity-seeking in neither gains nor losses. Interactions between attitudes and beliefs were associated with neural activation changes in dorsomedial and ventromedial brain areas. See Kenning et al., "Neuroeconomics: an overview from an economic perspective," Brain Res. Bull., vol. 67, pp. 343-354 (2005).

In an fMRI study, increasing monetary gains were associated with increased activity in a subcortical region of the ventral striatum in a magnitude-proportional manner. This ventral striatal activation was not evident during anticipation of losses. Actual gain outcomes were associated with activation of a region of the medial prefrontal cortex. During anticipation of gain, ventral striatal activation was associated with feelings characterized by increasing arousal and positive valence. See Kenning et al., "Neuroeconomics: an overview from an economic perspective," Brain Res. Bull., vol. 67, pp. 343-354 (2005).

In an fMRI study, activation of parts of the limbic system were associated with decisions involving immediate rewards. Activity changes in the lateral prefrontal cortex and posterior parietal cortex were associated with inter-temporal choices. Greater relative fronto-parietal activity was associated with a subject's choice of longer term options. See Kenning et al., "Neuroeconomics: an overview from an economic perspective," Brain Res. Bull., vol. 67, pp. 343-354 (2005).

Brain Activation by Region

Prefrontal Regions

The prefrontal cortex is involved in almost all high-level cognitive tasks. Prefrontal activations are particularly prominent during working memory and memory retrieval (episodic and semantic), and less prevalent during perception and perceptual priming tasks. This pattern is consistent with the idea that the prefrontal cortex is involved in working memory processes, such as monitoring, organization, and planning. However, some of the same prefrontal regions engaged by working tasks are also recruited by simple detection tasks that do not involve a maintenance component. Thus the prefrontal cortex is not devoted solely to working memory operations.

Regarding lateralization, prefrontal activations during language, semantic memory retrieval, and episodic memory encoding are usually left-lateralized, those during sustained attention and episodic retrieval are mostly right-lateralized, and those during working memory are typically bilateral.

With respect to distinctions between different prefrontal areas, ventrolateral regions (areas 45 and 47) are involved in selecting, comparing, or deciding on information held in short-term and long-term memory, whereas mid-dorsal regions (areas 9 and 46) are involved when several pieces of information in working memory need to be monitored and manipulated. Area 45/47 activations were found even in simple language tasks, while activations in areas 9/46 were associated with working memory and episodic encoding and retrieval. However, areas 9/46 were also activated during sustained attention tasks, which do not involve the simultaneous consideration of several pieces of information. See Cabeza et al, "Imaging Cognition II: An Empirical Review of 275 PET and fMRI Studies," J. Cognitive Neurosci., vol. 12, pp. 1-47 (2000).

Humans restrain self-interest with moral and social values. They are the only species known to exhibit reciprocal fairness, which implies the punishment of other individuals' unfair behaviors, even if it hurts the punisher's economic self-interest. Reciprocal fairness has been demonstrated in the Ultimatum Game, where players often reject their bargaining partner's unfair offers. It has been shown that disruption of the right, but not the left, dorsolateral prefrontal cortex (DLPFC) by low-frequency repetitive transcranial magnetic stimulation substantially reduces subjects' willingness to reject their partners' intentionally unfair offers, which suggests that subjects are less able to resist the economic temptation to accept these offers. Importantly, however, subjects still judge such offers as very unfair, which indicates that the right DLPFC plays a key role in the implementation of fairness-related behaviors. See Knoch et al., "Diminishing Reciprocal Fairness by Disrupting the Right Prefrontal Cortex," Science, vol. 314, pp. 829-832 (3 Nov. 2006).

Differences across tasks can be found in frontopolar (area 10), opercular (area 44), and dorsal (areas 6 and 8) prefrontal regions. Frontopolar activations were typical for episodic memory retrieval and problem-solving tasks. In the case of episodic retrieval, they are found for both retrieval success and retrieval mode, suggesting they are probably not related to performance level or task difficulty. Area 10 is involved in maintaining the mental set of episodic retrieval, but also has an involvement in problem-solving tasks. Activations in left area 44, which corresponds to Broca's area, were commonly found for reading, verbal working memory and semantic generation. Right area 44 is engaged by nonverbal episodic retrieval tasks. Area 6 plays a role in spatial processing (orientation of attention, space/motion perception and imagery), working memory, and motor-skill learning. Midline area 6 activations correspond to SMA and are common for silent reading tasks. Area 8 is involved in problem-solving tasks, possibly reflecting eye movements. See Cabeza et al, "Imaging Cognition II: An Empirical Review of 275 PET and fMRI Studies," J. Cognitive Neurosci., vol. 12, pp. 1-47 (2000).

The frontopolar cortex has been shown to be active during the initial stages of learning, gradually disengaging over the course of learning. Frontopolar cortex activity specifically correlates with the amount of uncertainty remaining between multiple putative options that subjects are simultaneously tracking. The frontopolar cortex is also active whenever subjects depart from an a priori optimal option to check alternative ones. Thus the frontopolar cortex contribution to learning and exploration appears to be associated with maintaining and switching back and forth between multiple behavioral alternatives in search of optimal behavior. The frontopolar cortex has also been implicated in memory retrieval, relational reasoning, and multitasking behaviors. These subfunctions are thought to be integrated in the general function of contingently switching back and forth between independent tasks by maintaining distractor-resistant representations of postponed tasks during the performance of another task. For example, the frontopolar cortex is specifically activated when subjects suspend execution of an ongoing task set associated with a priori the largest expected future rewards in order to explore a possibly more-rewarding task set. See Keochlin et al., "Anterior Prefrontal Function and the Limits of Human Decision-Making," Science, vol. 318, pp. 594-598 (26 Oct. 2007).

Activation of the medial prefrontal cortex and anterior paracingulate cortex indicate that a subject is thinking and acting on the beliefs of others, for example, either by guessing partner strategies or when comparing play with another human to play with a random device, such as a computer partner. Accordingly, these regions may be involved in intention detection, i.e., assessing the meaning of behavior from another agent. The tempo-parietal junction is also implicated in this function. Further, publication brand-related bias in the credibility of ambiguous news headlines is associated with activation changes in the medial prefrontal cortex. See Kenning et al., "Neuroeconomics: an overview from an economic perspective," Brain Res. Bull., vol. 67, pp. 343-354 (2005).

In situations in which people gain some useful good (e.g., money, juice, or other incentive) by using judgment, activation can be observed in the so-called "reward areas" of the brain. Therefore, a "feeling" of approval or utility may correlate with the activation in the reward areas of the brain. Reward areas of the brain include the ventral striatum and the orbitofrontal prefrontal cortex-amygdala-nucleus accumbens circuit. Monetary payoffs induce activation in the nucleus accumbens. The nucleus accumbens is densely innervated by dopaminergic fibers originating from neurons in the midbrain. Sudden release of dopamine after an unexpected reward may lead to acceptance of risk. Accordingly, defects in the orbitofrontal cortex-amygdala-nucleus accumbens reward circuit may accompany extreme risk-seeking behavior. This reward system is also associated with the perception of utility of objects.

Cingulate Regions

Cingulate regions can be roughly classified as anterior (for example, areas 32 and 24), central (areas 23 and 31), and posterior (posterior area 31, retrosplenial). Posterior cingulate activations are consistently seen during successful episodic memory retrieval, as are other posterior midline activations (e.g., medial parietal, cuneus, precuneus). Anterior cingulate activations occur primarily in area 32 and are consistently found for S-R compatibility (Stroop test), working memory, semantic generation, and episodic memory tasks.

There are three main views of the anterior cingulate function: initiation, inhibitory, and motor. According to the initiation view, the anterior cingulate cortex is involved in "attention to action," that is, in attentional processes required to initiate behavior. This is consistent with evidence that damage to this region sometimes produces akinetic mutism, that is, an almost complete lack of spontaneous motor or verbal behavior. This is also consistent with the involvement of this region in demanding cognitive tasks, such as working memory and episodic retrieval.

The inhibitory view postulates that the anterior cingulate is involved in suppressing inappropriate responses. This idea accounts very well not only for its involvement in the Stroop task, in which prepotent responses must be inhibited, but also in working memory, in which interference from previous trials must be controlled. The initiation and inhibition views are not incompatible: the anterior cingulate cortex may both initiate appropriate responses and suppress inappropriate ones. Moreover, these views share the idea that the anterior cingulate cortex plays an "active" role in cognition by controlling the operations of other regions, including the prefrontal cortex.

In contrast, the motor view conceptualizes the anterior cingulate as a more "passive" structure: it receives cognitive/motor "commands" from various regions (for example, prefrontal cortex), and "funnels" them to the appropriate motor system. This view assumes that different anterior cingulate regions are engaged, depending on whether responses are ocular, manual, or verbal. For example, due to its close connections to the auditory cortex, area 32 is assumed to play a role in vocalization and speech. This idea accounts for activations during tasks involving verbal materials, such as Stroop, semantic generation, and verbal episodic retrieval tasks. See Cabeza et al, "Imaging Cognition II: An Empirical Review of 275 PET and fMRI Studies," J. Cognitive Neurosci., vol. 12, pp. 1-47 (2000).

Lying is associated with increased activity in several areas of the cortex, including the anterior cingulate cortex, the parietal cortex, and the superior frontal gyrus. See Henig, "Looking for the Lie," New York Times http://www.nytimes.com/2006/02/05/magazine/05lying.html?pagewanted=print (5 Feb. 2006).

Parietal Regions

Parietal regions are consistently activated during tasks involving attention, spatial perception and imagery, working memory, spatial episodic encoding, episodic retrieval, and skill learning. Medial parietal activations are frequently found during episodic memory retrieval. In general, lateral parietal activations relate either to spatial perception/attention or to verbal working memory storage. Parietal regions may be part of a dorsal occipito-parietal pathway involved in spatial perception, and/or part of a "posterior attention system" involved in disengaging spatial attention. These spatial views account for parietal activations during spatial tasks of perception, imagery, and episodic encoding, as well as for those during skill-learning tasks, which, typically, involve an important spatial component.

According to the working memory interpretation, parietal regions are involved in the storage of verbal information in working memory. This is consistent with evidence that left posterior parietal lesions can impair verbal short-term memory. See Cabeza et al, "Imaging Cognition II: An Empirical Review of 275 PET and fMRI Studies," J. Cognitive Neurosci., vol. 12, pp. 1-47 (2000).

Temporal Regions

The temporal lobes can be subdivided into four broad regions: lateral (insula, 42, 22, 21, and 20), medial (areas 28, 34-36, and hippocampal regions), posterior (area 37), and polar (area 38). Area 38 is likely to have a very important role in cognition, for example, by linking frontal-lobe and temporal-lobe regions.

Lateral temporal activations are consistently found for language and semantic memory retrieval and are mostly left-lateralized. Spoken word-recognition tasks usually yield bilateral activations, possibly reflecting the auditory component of these tasks. The involvement of the left superior and middle temporal gyrus (areas 22 and 21) in language operations is consistent with research on aphasic patients. Since area 21 is also consistently activated during semantic retrieval tasks—not only for verbal but also for nonverbal materials—it is possible that this area reflects semantic, rather than linguistic, operations. This is supported by the involvement of this region in object perception.

Medial-temporal lobe activations are repeatedly found for episodic memory encoding and nonverbal episodic memory retrieval. The involvement of medial temporal regions in episodic memory is consistent with lesion data. Based on PET data, encoding-related activations are more common in anterior hippocampal regions, whereas retrieval-related activations are more prevalent in posterior hippocampal regions, a pattern described as the hippocampal encoding/retrieval (HIPER) model. See Cabeza et al, "Imaging Cognition II: An Empirical Review of 275 PET and fMRI Studies," J. Cognitive Neurosci., vol. 12, pp. 1-47 (2000).

Occipito-Temporal Regions

The engagement of temporo-occipital regions (areas 37, 19, 18, and 17) in cognitive tasks seems to be of two kinds: activations associated with perceiving and manipulating visuospatial information, and deactivations associated with perceptual priming. Visual processing along the ventral pathway is assumed to be organized hierarchically, with early image analyses engaging areas close to the primary visual cortex and higher-order object recognition processes involving more anterior areas. Consistent with this idea, activations in areas 18 and 19 occur for most visuospatial tasks, whereas activations in area 37 are associated with object processing. For example, area 37 activation is found when subjects perceive objects and faces, maintain images of objects in working memory, and intentionally encode objects. Perception-related occipital activations are enhanced by visual attention and they therefore can be expected during visual-attentional tasks, as well as during demanding visual-skill learning tasks (e.g., mirror reading).

Most activations in occipito-temporal regions occur during the processing of visual information coming from eyes (perception) or from memory (imagery), and weaken when the same information is repeatedly processed (priming). See Cabeza et al, "Imaging Cognition II: An Empirical Review of 275 PET and fMRI Studies," J. Cognitive Neurosci., vol. 12, pp. 1-47 (2000).

Subcortical Regions

With respect to activations in the basal ganglia, the thalamus, and the cerebellum, basal ganglia activations were common during motor-skill learning, and the cerebellum was consistently activated in several different processes. Evolutionary, anatomical, neuropsychological, and functional neuroimaging evidence indicates that the cerebellum plays an important role in cognition. The cognitive role of the cerebellum has been related as motor-preparation, sensory acquisition, timing, and attention/anticipation. Each of these views can account for some cerebellar activations, but not for all of them. For example, the motor preparation view accounts well for activations during tasks involving motor responses, such as word production and conditioning, while the sensory-acquisition view can accommodate activations during perceptual tasks, such as smelling. The timing view accounts for activations during tasks involving relations between successive events, such as conditioning and skill learning, while the attention/anticipation view explains activations during attention and problem solving. See Cabeza et al, "Imaging Cognition II: An Empirical Review of 275 PET and fMRI Studies," J. Cognitive Neurosci., vol. 12, pp. 1-47 (2000).

Mesolimbic Dopamine System

Activity in the striatum scales directly with the magnitude of monetary reward or punishment. The striatum is also involved in social decisions, above and beyond a financial component. The striatum also encodes abstract rewards such as positive feeling as a result of mutual cooperation. In addition, the caudate is activated in situations where a subject has an intention to trust another. Emotional processes are reliably associated with a series of structures including the striatum and caudate, and areas of the midbrain and cortex to which they project, such as the ventromedial prefrontal cortex, orbitofrontal cortex, and anterior cingulated cortex, as well as other areas such as the amygdala and the insula. Indeed, subjects with lesions in the ventromedial prefrontal cortex and having associated emotional deficits are impaired in performing gambling tasks. The anterior insula is associated with increased activation as unfairness or inequity of an offer is increased. Activation of the anterior insula predicts an Ultimatum Game player's decision to either accept or reject an offer, with rejections associated with significantly higher activation than acceptances. Activation of the anterior insula is also associated with physically painful, distressful, and/or disgusting stimuli. Thus, the anterior insula and associated emotion-processing areas may play a role in marking an interaction as aversive and undeserving of trust in the future. See Sanfey, "Social Decision-Making: Insights from Game Theory and Neuroscience," Science, vol. 318, pp. 598-601 (26 Oct. 2007).

Activation in the ventral striatum is seen by fMRI when subjects provide a correct answer to a question, resulting in a reward. Similarly, a wrong answer and no payment results in a reduction in activity (i.e., oxygenated blood flow) to the ventral striatum. Moreover, activation of the reward centers of the brain including the ventral striatum over and above that seen from a correct response and reward is seen when a subject receives a reward that is known to be greater than that of a peer in the study. Thus, stimulation of the reward center appears to be linked not only to individual success and reward, but also to the success and rewards of others. See BBC news story "Men motivated by 'superior wage,'" http://news.bbc.co.uk/1/hi/sci/tech/7108347.stm, (23 Nov. 2007).

In a multi-round trust game, reciprocity expressed by one player strongly predicts future trust expressed by their partner—a behavioral finding mirrored by neural responses in the dorsal striatum as measured by fMRI. Analyses within and between brains show two signals—one encoded by response magnitude, and the other by response timing. Response magnitude correlates with the "intention to trust" on the next play of the game, and the peak of these "intention to trust" responses shifts its time of occurrence by 14 seconds as player reputations develop. This temporal transfer resembles a similar shift of reward prediction errors common to reinforcement learning models, but in the context of a social exchange. See King-Casas et al., "Getting to Know You: Reputation and Trust in a Two-Person Economic Exchange," Science, vol. 308, pp. 78-83 (1 Apr. 2005).

Activity in the head of the caudate nucleus is associated with the processing of information about the fairness of a social partner's decision and the intention to repay with trust, as measured by hyperscan-fMRI. See Kenning et al., "Neuroeconomics: an overview from an economic perspective," Brain Res. Bull., vol. 67, pp. 343-354 (2005).

Activation of the insular cortex is associated with the perception of bodily needs, providing direction to motivated behaviors. For example, imaging studies have shown activation of the insula in addicts with cue-induced drug craving, and activation of the insular cortex has been associated with subjective reports of drug craving. See Contreras et al., "Inactivation of the Interoceptive Insula Disrupts Drug Craving and Malaise Induced by Lithium," Science, vol. 318, pp. 655-658 (26 Oct. 2007).

Visual Cortex

The visual cortex is located in and around the calcarine fissure in the occipital lobe. In one visual cortex study, subjects were shown two patterns in quick succession. The first appeared for just 15 milliseconds, too fast to be consciously perceived by the viewer. By examining fMRI images of the brain, a specific image that had been flashed in front of the subjects could be identified. The information was perceived in the brain even if the subjects were not consciously aware of it. The study probed the part of the visual cortex that detects a visual stimulus, but does not perceive it. It encodes visual information that the brain does not process as "seen." See "Mind-reading machine knows what you see," NewScientist. com http://www.newscientist.corn/article.ns?id=dn7304&feedId=online-news_rss20 (25 Apr. 2005).

Hippocampus

Activation of the hippocampus can modulate eating behaviors linked to emotional eating and lack of control in eating. Activation of brain areas known to be involved in drug craving in addicted subjects, such as the orbitofrontal cortex, hippocampus, cerebellum, and striatum, suggests that similar brain circuits underlie the enhanced motivational drive for food and drugs seen in obese and drug-addicted subjects. See Wang et al., "Gastric stimulation in obese subjects activates the hippocampus and other regions involved in brain reward circuitry," PNAS, vol. 103, pp. 15641-45 (2006).

Surrogate Markers of Brain Activity and/or Mental State

Surrogate markers of mental state may include indicators of attention, approval, disapproval, recognition, cognition, memory, trust, or the like in response to a stimulus, other than direct measurement of brain activity associated with the stimulus.

Examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Conversely, conflict between brain activity and a surrogate marker may decrease confidence in a predictive or interpretational outcome. For example, a pattern of activation of the insula diagnostic for fear, together with a visual face image showing a smile may decrease the level of confidence that the subject is truly frightened by a stimulus.

For example, emotion links to cognition, motivation, memory, consciousness, and learning and developmental systems. Affective communication depends on complex, rule-based systems with multiple channels and redundancy built into the exchange system, in order to compensate if one channel fails. Channels can include all five senses: for example, increased heart-rate or sweating may show tension or agitation and can be heard, seen, touched, smelt or tasted. Emotional exchanges may be visible displays of body tension or movement, gestures, posture, facial expressions or use of personal space; or audible displays such as tone of voice, choice of pitch contour, choice of words, speech rate, etc. Humans also use touch, smell, adornment, fashion, architecture, mass media, and consumer products to communicate our emotional state. Universals of emotion that cross cultural boundaries have been identified, and cultural differences have also been identified. For example 'love' is generally categorized as a positive emotion in Western societies, but in certain Eastern cultures there is also a concept for 'sad love.' Accordingly, universal emotional triggers may be used to transcend cultural barriers.

When communicating with computers, people often treat new media as if they were dealing with real people. They often follow complex social rules for interaction and modify their communication to suit their perceived conversation partner. Much research has focused on the use of facial actions and ways of coding them. Speech recognition systems have also attracted attention as they grow in capability and reliability, and can recognize both verbal messages conveyed by spoken words, and non verbal messages, such as those conveyed by pitch contours.

System responses and means of expressing emotions also vary. Innovative prototypes are emerging designed to respond indirectly, so the user is relatively unaware of the response: for example by adaptation of material, such as changing pace or simplifying or expanding content. Other systems use text, voice technology, visual agents, or avatars to communicate. See Axelrod et al., "Smoke and Mirrors: Gathering User Requirements for Emerging Affective Systems," 26th Int. Conf. Information Technology Interfaces/TI 2004, Jun. 7-10, 2004, Cavtat, Croatia, pp. 323-328.

Skin Response

Mental state may be determined by detection of a skin response associated with a stimulus. One skin response that may correlate with mental state and/or brain activity is galvanic skin response (GSR), also known as electrodermal response (EDR), psychogalvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals.

For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007). Other skin responses may include flushing, blushing, goose bumps, sweating, or the like.

Face Pattern Recognition

Mental state may also be determined by detection of facial feature changes associated with a stimulus, via pattern recognition, emotion detection software, face recognition software, or the like.

For example, an emotional social intelligence prosthetic device has been developed that consists of a camera small enough to be pinned to the side of a pair of glasses, connected to a hand-held computer running image recognition software plus association software that can read the emotions these images show. If the wearer seems to be failing to engage his or her listener, the software makes the hand-held computer vibrate. The association software can detect whether someone is agreeing, disagreeing, concentrating, thinking, unsure, or interested, just from a few seconds of video footage. Previous computer programs have detected the six more basic emotional states of happiness, sadness, anger, fear, surprise and disgust. The system can detect a sequence of movements beyond just a single facial expression. The association program is based on a machine-learning algorithm that was trained by showing it more than 100 8-second video clips of actors expressing particular emotions. The software picks out movements of the eyebrows, lips and nose, and tracks head movements such as tilting, nodding, and shaking, which it then associates with the emotion the actor was showing. When presented with fresh video clips, the software gets people's emotions right 90 percent of the time when the clips are of actors, and 64 percent of the time on footage of ordinary people. See "Device warns you if you're boring or irritating," NewScientist http://www.newscientist.com/article/mg19025456.500-device-warns-you-if-youre-boring-or-irritating.html (29 Mar. 2006).

In another approach, an imager, such as a CCD camera, may observe expressed features of the user. For example, the imager may monitor pupil dilation, eye movement, expression, or a variety of other expressive indicators. Such expressive indicators may indicate a variety of emotional, behavioral, intentional, or other aspects of the user. For example, in one approach, systems have been developed for identifying an emotional behavior of a person based upon selected expressive indicators. Similarly, eye movement and pupil dilation may be correlated to truthfulness, stress, or other user characteristics.

Eye Movement Analysis

Eye movement or pupil movement can be tested, for example, by measuring user pupil and/or eye movements, perhaps in relation to items on a display. For example, a user's eye movement to a part of the screen containing an advertisement may be of interest to an advertiser for purposes of advertisement placement or determining advertising noticeability and/or effectiveness within a computerized game world. For example, knowing that a user's eyes have been attracted by an advertisement may be of interest to an advertiser. For example, a merchant may be interested in measuring whether a user notices a virtual world avatar having particular design characteristics. If the user exhibits eye movements toward the avatar on a display, then the merchant may derive a mental state from repeated eye movements vis a vis the avatar, or the merchant may correlate eye movements to the avatar with other physiological activity data such as brain activation data indicating a mental state such as brand preference, approval or reward.

In another embodiment, a smart camera may be used that can capture images of a user's eyes, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving, e.g., forward and backward. This can provide real-time data relating to pupil accommodation relative to objects on a display, which information may be of interest to an entity 170 (e.g., http://jp.hamamatsu.com/en/rd/publication/scientific_american/common/pdf/scientific_06 08.pdf).

Eye movement and/or pupil movement may also be measured by video-based eye trackers. In these systems, a camera focuses on one or both eyes and records eye movement as the viewer looks at a stimulus. Contrast may be used to locate the center of the pupil, and infrared and near-infrared non-collunmated light may be used to create a corneal reflection. The vector between these two features can be used to compute gaze intersection with a surface after a calibration for a subject.

Two types of eye tracking techniques include bright pupil eye tracking and dark pupil eye tracking. Their difference is based on the location of the illumination source with respect to the optics. If the illumination is coaxial with the optical path, then the eye acts as a retroreflector as the light reflects off the retina, creating a bright pupil effect similar to red eye. If the illumination source is offset from the optical path, then the pupil appears dark.

Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright light. However, bright pupil techniques are not recommended for tracking outdoors as extraneous IR sources may interfere with monitoring.

Eye tracking configurations can vary; in some cases the measurement apparatus may be head-mounted, in some cases the head should be stable (e.g., stabilized with a chin rest), and in some cases the eye tracking may be done remotely to automatically track the head during motion. Most eye tracking systems use a sampling rate of at least 30 Hz. Although 50/60 Hz is most common, many video-based eye trackers run at 240, 350 or even 1000/1250 Hz, which is recommended in order to capture the detail of the very rapid eye movements during reading, or during studies of neurology.

Eye movements are typically divided into fixations, when the eye gaze pauses in a certain position, and saccades, when the eye gaze moves to another position. A series of fixations and saccades is called a scanpath. Most information from the eye is made available during a fixation, not during a saccade. The central one or two degrees of the visual angle (the fovea) provide the bulk of visual information; input from larger eccentricities (the periphery) generally is less informative. Therefore the locations of fixations along a scanpath indicate what information loci on the stimulus were processed during an eye tracking session. On average, fixations last for around 200 milliseconds during the reading of linguistic text, and 350 milliseconds during the viewing of a scene. Preparing a saccade towards a new goal takes around 200 milliseconds.

Scanpaths are useful for analyzing cognitive intent, interest, and salience. Other biological factors (some as simple as gender) may affect the scanpath as well. Eye tracking in human-computer interaction typically investigates the scanpath for usability purposes, or as a method of input in gaze-contingent displays, also known as gaze-based interfaces.

There are two primary components to most eye tracking studies: statistical analysis and graphic rendering. These are both based mainly on eye fixations on specific elements. Statistical analyses generally sum the number of eye data observations that fall in a particular region. Commercial software packages may analyze eye tracking and show the relative probability of eye fixation on each feature on an avatar. This allows for a broad analysis of which avatar elements received attention and which ones were ignored. Other behaviors such as blinks, saccades, and cognitive engagement can be reported by commercial software packages. Statistical comparisons can be made to test, for example, competitors, prototypes or subtle changes to an avatar. They can also be used to compare participants in different demographic groups. Statistical analyses may quantify where users look, sometimes directly, and sometimes based on models of higher-order phenomena (e.g., cognitive engagement).

In addition to statistical analysis, it is often useful to provide visual depictions of eye tracking results. One method is to create a video of an eye tracking testing session with the gaze of a participant superimposed upon it. This allows one to effectively see through the eyes of the consumer during interaction with a target medium. Another method graphically depicts the scanpath of a single participant during a given time interval. Analysis may show each fixation and eye movement of a participant during a search on a virtual shelf display of breakfast cereals, analyzed and rendered with a commercial software package. For example, a different color may represent one second of viewing time, allowing for a determination of the order in which products are seen. Analyses such as these may be used as evidence of specific trends in visual behavior.

A similar method sums the eye data of multiple participants during a given time interval as a heat map. A heat map may be produced by a commercial software package, and shows the density of eye fixations for several participants superimposed on the original stimulus, for example, an avatar on a magazine cover. Red and orange spots represent areas with high densities of eye fixations. This allows one to examine which regions attract the focus of the viewer.

Commercial eye tracking applications include web usability, advertising, sponsorship, package design and automotive engineering. Eye tracking studies may presenting a target stimulus to a sample of consumers while an eye tracker is used to record the activity of the eye. Examples of target stimuli may include avatars in the context of websites, television programs, sporting events, films, commercials, magazines, newspapers, packages, shelf displays, consumer systems (ATMs, checkout systems, kiosks), and software. The resulting data can be statistically analyzed and graphically rendered to provide evidence of specific visual patterns. By examining fixations, saccades, pupil dilation, blinks, and a variety of other behaviors, researchers can determine a great deal about the effectiveness of a given avatar in a given medium or associated with a given product.

A prominent field of eye tracking research is web usability. While traditional usability techniques are often quite powerful in providing information on clicking and scrolling patterns, eye tracking offers the ability to analyze user interaction between the clicks. This provides insight into which features are the most eye-catching, which features cause confusion, and which ones are ignored altogether. Specifically, eye tracking can be used to assess impressions of an avatar in the context of search efficiency, branding, online advertisement, navigation usability, overall design, and/or many other site components. Analyses may target an avatar on a prototype or competitor site in addition to the main client site.

Eye tracking is commonly used in a variety of different advertising media. Commercials, print ads, online ads, and sponsored programs are all conducive to analysis with eye tracking technology. Analyses may focus on visibility of a target avatar, product, or logo in the context of a magazine, newspaper, website, virtual world, or televised event. This allows researchers to assess in great detail how often a sample of consumers fixates on the target avatar, logo, product, or advertisement. In this way, an advertiser can quantify the success of a given campaign in terms of actual visual attention.

Eye tracking also provides avatar designers with the opportunity to examine the visual behavior of a consumer while interacting with a target avatar. This may be used to analyze distinctiveness, attractiveness and the tendency of the avatar to be chosen for recognition and/or purchase. Eye tracking can be used while the target avatar is in the prototype stage. Prototype avatars can be are tested against each other and against competitors to examine which specific elements are associated with high visibility and/or appeal.

Another application of eye tracking research is in the field of automotive design. Eye tracking cameras may be integrated into automobiles to provide the vehicle with the capacity to assess in real-time the visual behavior of the driver. The National Highway Traffic Safety Administration (NHTSA) estimates that drowsiness is the primary causal factor in 100,000 police-reported accidents per year. Another NHTSA study suggests that 80% of collisions occur within three seconds of a distraction. By equipping automobiles with the ability to monitor drowsiness, inattention, and cognitive engagement driving safety could be dramatically enhanced. Lexus® claims to have equipped its LS 460 automobile with the first driver monitor system in 2006, providing a warning if the driver takes his or her eye off the road.

Eye tracking is also used in communication systems for disabled persons, allowing the user to speak, mail, surf the web and so on with only the eyes as tool. Eye control works even when the user has involuntary body movement as a result of cerebral palsy or other disability, and/or when the user wears glasses.

Eye movement or pupil movement may be gauged from a user's interaction with an application.

An example of a measure of pupil movement may be an assessment of the size and symmetry of a user's pupils before and after a stimulus, such as light or focal point. In one embodiment, where the user interacts with a head mounted display, the display may include image capturing features that may provide information regarding expressive indicators. Such approaches have been described in scanned-beam display systems such as those found in U.S. Pat. No. 6,560,028.

Voice Stress Analysis

Voice stress analysis (VSA) technology records psychophysiological stress responses that ate present in the human voice when a person experiences a psychological stress in response to a stimulus. Psychological stress may be detected as acoustic modifications in the fundamental frequency of a speaker's voice relative to normal frequency modulation of the vocal signal between 8-14 Hz during speech in an emotionally neutral situation. In situations involving a stress response, the 8-14 Hz modulation may decrease as the muscles surrounding the vocal cords contract in response to the reaction.

VSA typically records an inaudible component of human voice, commonly referred to as the Lippold Tremor. Under normal circumstances, the laryngeal muscles are relaxed, producing recorded voice at approximately 12 Hz. Under stress however, the tensed laryngeal muscles produce voice significantly lower than normal. The higher the stress, the lower down the Hertz scale voice waves are produced. One application for VSA is in the detection of deception.

Dektor Counterintelligence manufactured the PSE 1000, an analog machine that was later replaced by the PSE 2000. The National Institute Of Truth Verification (NITV) then produced and marketed a digital application based on the McQuiston-Ford algorithm. The primary commercial suppliers are Dektor (PSE5128-software); Diogenes (Lantern-software); NITV (CVSA Software); and Baker (Baker-software).

VSA is distinctly different from LVA (Layered Voice Analysis). LVA is used to measure different components of voice, such as pitch and tone. LVA is available in the form of hand-held devices and software. LVA produces readings such as 'love,' excitement, and fear.

One example of a commercially available layered voice analysis system is the SENSE system, sold by Nemesysco Ltd (Natania, Israel). SENSE can analyze different layers within the voice, using multiple parameters to analyze each speech segment. SENSE can detect various cognitive states, such as whether a subject is excited, confused, stressed, concentrating, anticipating a response, or unwillingly sharing information. The technology also can provide an in-depth view of the subject's range of emotions, including those relating to love. SENSE technology can be further utilized to identify psychological issues, mental illness, and other behavioral patterns. The LVA technology is the security version of the SENSE technology, adapted to identify the emotional situations a subject is expected to have during formal/security investigations.

The SENSE technology is made up of 4 sub-processes:

1. The vocal waveform is analyzed to measure the presence of local micro-high frequencies, low frequencies, and changes in their presence within a single voice sample.

2. A precise frequency spectrum of the vocal input is sampled and analyzed.

3. The parameters gathered by the previous steps are used to create a baseline profile for the subject.

4. The new voice segments to be tested are compared with the subject's baseline profile, and the analysis is generated.

This input can be further processed by statistical learning algorithms to predict the probability of a deceptive or fraudulent sentence in a subject's speech. Another layer that is used in certain applications evaluates the conversation as a whole, and produces a final risk or QA value.

The SENSE technology can detect the following emotional and cognitive states:

Excitement Level: Each of us becomes excited (or depressed) from time to time. SENSE compares the presence of the Micro-High-frequencies of each sample to the basic profile to measure the excitement level in each vocal segment.

Confusion Level: Is your subject sure about what he or she is saying? SENSE technology measures and compares the tiny delays in a subject's voice to assess how certain he or she is.

Stress Level: Stress may include the body's reaction to a threat, either by fighting the threat, or by fleeing. However, during a spoken conversation neither option may be available. The conflict caused by this dissonance affects the micro-low-frequencies in the voice during speech.

Thinking Level: How much is your subject trying to find answers? Might he or she be "inventing" stories?

S.O.S.: (Say Or Stop)—Is your subject hesitating to tell you something?

Concentration Level: Extreme concentration might indicate deception.

Anticipation Level: Is your subject anticipating your responses according to what he or she is telling you?

Embarrassment Level: Is your subject feeling comfortable, or does he feel some level of embarrassment regarding what he or she is saying?

Arousal Level: What triggers arousal in the subject? Is he or she interested in an object?. Aroused by certain visual stimuli?

Deep Emotions: What long-standing emotions does a subject experience? Is he or she "excited" or "uncertain" in general?

SENSE's "Deep" Technology: Is a subject thinking about a single topic when speaking, or are there several layers to a response (e.g., background issues, something that may be bothering him or her, planning, or the like). SENSE technology can detect brain activity operating at a pre-conscious level.

The speaking mechanism is one of the most complicated procedures the human body is capable of. First, the brain has to decide what should be said, then air is pushed from the lungs upward to the vocal cords, that must vibrate to produce the main frequency. Now, the vibrated air arrives to the mouth.

The tongue, the lips, the teeth, and the nose space turns the vibrated air into the sounds that we recognize as phrases. The brain is closely monitoring all these events, and listens to what comes out; if we speak too softly, too loudly, and if it is understandable to a listener. SENSE Technology ignores what your subject is saying, and focuses only on what the brain is broadcasting.

Humans, unlike other mammals, are capable of predicting or imagining the future. Most people can tell whether or not a certain response will cause them pleasure or pain. Lying is not a feeling, it is a tool. The feeling structure around it will be the one causing us to lie, and understanding the differences is crucial for making an analysis.

The SENSE technology differentiates among 5 types of lies:

1. Jokes—Jokes are not so much lies as they are untruths, used to entertain. No long gain profit or loss will be earned from it, and usually, little or no extra feelings will be involved.

2. White Lies—You know you don't want to say the truth, as it may hurt someone else. White lies are lies, but the teller usually experiences little stress or guilt.

3. Embarrassment Lies—Same as for white lies, but this time directed internally. Nothing will be lost except the respect of the listener, most likely for the short term.

4. Offensive Lies—This is a unique lie, for it's intention is to gain something extra that could not be gained otherwise.

5. Defensive Lie—The common lie to protect one's self.

The SENSE technology IS the old "Truster" technology, with several additions and improvements. The old Truster was all about emotions in the context of Truth/Lie; SENSE looks at emotions in general.

When people get sexually aroused or feel "in love," the pupils get wider, the lips get reddish, the skin of the face gets red. The voice changes too. Increased excitement makes the whole voice higher and more concentrated. The SENSE technology can detect the increased excitement and the associated heightened concentration and anticipation.

While each of the above described approaches to providing expressive indicators has been described independently, in some approaches, a combination of two or more of the above described approaches may be implemented to provide additional information that may be useful in evaluating user behavior and/or mental state.

Specifying a cohort-linked avatar attribute and/or a cohort-linked avatar

FIG. 5 illustrates an operational flow 500 representing example operations related to specifying an avatar attribute. In FIG. 5 and in following figures that include various examples of operational flows, discussion and explanation may be provided with respect to the above-described system environments of FIGS. 1-4, and/or with respect to other examples and contexts. However, it should be understood that the operational flows may be executed in a number of other environment and contexts and/or in modified versions of FIGS. 1-3. Also, although the various operational flows are presented in the sequences illustrated, it should be understood that the various operations may be performed in other orders than those which are illustrated, or may be performed concurrently.

After a start operation, operation 510 depicts presenting at least one characteristic to at least one member of a population cohort. For example, an attribute specification unit 250 can transmit a characteristic for display to a member of population cohort 102 on a presentation unit and/or display 272. Optionally, a presented avatar characteristic may be encountered during an interaction of the member of population cohort 102 with a virtual world; alternatively, the characteristic may be one presented in a real world context, for subsequent incorporation into an avatar. In one embodiment, a clothing specification unit 260 can present a photograph of a particular item of clothing independent of an avatar via mobile display 276. In another embodiment, a facial attribute specification unit 258 can present an eye shape and color to a member of population cohort 102 in the context of an avatar in an online game via a desktop display 274.

For example, a device 106, attribute specification unit 250, and/or presentation unit 270 may present at least one characteristic to at least one member of a population cohort 102. In one embodiment, a body attribute specification unit 362 may communicate via a network 374, for example, with a presentation device 364 to present a characteristic to member of population cohort 102. A population cohort may include an ad hoc population cohort, or an established population cohort such as an age-defined demographic group.

In another embodiment, a speech specification unit of the device 306 may present a speech characteristic such as accent, dialect, tone, or pitch to a member of population cohort 102 via, for example, a personal communication device such as a video-capable cellular phone. For example, the attribute specification unit 350 may initiate the presentation of an avatar with a particular characteristic such as a hair color or hair style to a member of population cohort 102 in response to the member of population cohort 102 signing on to a social networking website. The presentation may be through, for example, a widget on the social networking website.

It should be understood that characteristics may be profitably combined to provide feedback about composite features of presented attributes and/or avatars. For example, an attribute specification unit 350 may present a composite voice, facial attribute, clothing attribute, and body attribute characteristic to a member of population cohort 102 via an online shopping experience, such as a virtual personal shopper.

Verbal attributes or characteristics may be presented, such as foreign language or accented speech, such as a southern accent, a Boston accent, a Spanish accent, a British accent, or the like. Such voice variations may be computer-detectable and/or computer-implemented. See, for example, U.S. Pat. No. 7,263,489 "Detection of characteristics of human-machine interactions for dialog customization and analysis." Prosodic features of speech such as intonation, stress, and other paralinguistic features of speech such as voice quality, emotion, and speaking style may also be presented as characteristic.

A characteristic may also include paralanguage, a.k.a., vocalics, which involves nonverbal cues of the voice. Various acoustic properties of speech such as tone, pitch, accent, or the like, collectively known as prosody, can be presented as nonverbal characteristics. Paralanguage may be used to present a characteristic, as well as voice qualities including volume, pitch, tempo, rhythm, articulation, resonance, nasality, and/or accent. Vocalization cues also may be presented as the characteristic, including emotions expressed during or associated with speech, such as laughing, crying, and/or yawning. Vocalization cues also may include delivery nuances such as volume and/or pitch modulation such as whispering and shouting. Vocalization cues also may include vocal segregates such as "um" in between spoken expressions, or "uh-huh," "like," "no way," or other phrase in response to another's speech to indicate comprehension, to punctuate speech, and/or to manage contact during dialogue. See, for example, U.S. Pat. No. 6,356,868, "Voiceprint identification system."

Alternatively, a non-verbal attribute or characteristic including physical appearance and/or non-verbal communication may be presented. For example, body language such as use of American Sign Language may be presented as the characteristic.

Non-verbal communication characteristics may also include, for example, a facial expression, a gesture, a gaze, and/or a posture. A characteristic may also include clothing, hairstyle, adornment, shoes, and/or other communicative props; or even architecture, a symbol, and/or an infographic.

Kinesic behaviors such as body movements, facial expressions, and gestures may also be presented characteristics. Kinesic behaviors may include, mutual gaze, smiling, facial warmth or pleasantness, childlike behaviors, direct body orientation, and the like. An attribute specification unit 250 and/or presentation unit 270 can present a movement characteristic such as a kineme, which is a unit of visual expression analogous to a phoneme, a unit of speech. Presentable gestures may include emblems, illustrators, affect displays, regulators, and/or adaptors. An emblem is a gesture with a direct verbal translation such as a wave of the hand; an illustrator is a gesture that depicts a concept that is substantially simultaneously spoken, such as turning an imaginary steering wheel while speaking about driving; an affect display is a gesture that conveys emotions, such as a smile or a frown; a regulator is a gesture that controls interaction such as a "shhh" sign placing an index finger vertically at the center of the lips; and finally, an adaptor is a gesture that facilitates release of body tension, such as quick, repetitive leg movements or stretching.

A presented characteristic may also include an advertising symbol and/or a brand name, design, symbol, or logo (e.g., trademarks of corporations such as a Bic® pen, a Rolex® watch, a McDonald's® restaurant, a Hermes® scarf, a Louis Vuitton® bag, or a Les Paul® guitar). Service marks may also be presented as a characteristic.

A presented characteristic may also include, for example, a characteristic that is not typically presented in the context of an avatar, and/or a characteristic that an avatar cannot have.

Operation 520 depicts measuring at least one physiologic activity of the at least one member of the population cohort, the at least one physiologic activity proximate to the at least one characteristic. For example, a physiologic activity measurement unit 210, brain activity measurement unit 212, and/or surrogate marker measurement unit 230 may measure at least one physiologic activity of the at least one member of the population cohort, the at least one physiologic activity proximate to the at least one characteristic. For example, during presentation of the characteristic to the member of the population cohort 102, a fNIR module may detect brain activity in the member of the population cohort 102 indicative of approval of the characteristic. Of course other measurement methods may be used including fMRI, MEG, EEG, singly or in combination. Optionally, surrogate markers of brain activity may be employed to detect physiologic activity, such as a voice response to a characteristic, an eye movement response to an object, a skin response to an object, or the like. Detected brain activity may be proximate in time to presentation and/or viewing of the characteristic by the member of the population cohort 102, as determined by one or more of brain activity indicative of visual activity (e.g., activity in the visual cortex), selective attention (e.g., activity in fronto-parietal areas), and/or perception (e.g., activity in the ventral pathway). Detected physiologic activity may be determined to be proximate in time using an eye movement or gaze tracking measurement to identify times when a member of the population cohort 102 looks at a characteristic. In one embodiment, eye movement or gaze tracking data may be matched with a time course of brain activity to associate a particular brain area activation with visual contact of the member of the population cohort 102 with a presented characteristic.

As used herein, the term "proximate" may refer to "proximate in time," for example, a physiologic measurement that is proximate in time to a presentation of a characteristic to a member of population cohort 102 and/or member of population 105.

In another embodiment, eye movement or gaze tracking data may be matched with a time course of voice response, skin response, or other surrogate marker of brain activity to associate a particular physiologic activity with visual contact of the member of the population cohort 102 with a presented characteristic.

In the context of storing physiologic activity measurement data, it should be understood that a data signal may first be encoded and/or represented in digital form (i.e., as digital data), prior to an assignment to at least one memory. For example, a digitally-encoded representation of user eye movement data may be stored in a local memory, or may be transmitted for storage in a remote memory.

Thus, an operation may be performed relating either to a local or remote storage of the digital data, or to another type of transmission of the digital data. Of course, as discussed herein, operations also may be performed relating to accessing, querying, processing, recalling, or otherwise obtaining the digital data from a memory, including, for example, transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

Operation 530 depicts associating the at least one physiological activity with at least one mental state. For example, a device 206 and/or association unit 240 may associate the at least one physiologic activity with at least one mental state. For example, association unit 240 may associate approval with a pattern of activation of the reward center, including for example, the striatum and caudate, and areas of the midbrain and cortex to which they project, such as the ventromedial prefrontal cortex, orbitofrontal cortex, and anterior cingulated cortex. In one embodiment, an association unit 240 may search a database of functional brain mapping that contains information about which brain regions are associated with particular mental states and/or functions. Such a database search may be keyed to brain activation pattern, and/or to mental state and/or function. For example, an association unit 240 may search measured brain activation information and/or surrogate marker information for data consistent with trust. For example, a measured activation of a region of the brain associated with trust, such as the caudate nucleus, may be associated with trust as the at least one mental state. Alternatively or in addition, measurement of a surrogate marker such as an approving voice response proximate to the at least one characteristic may be associated with approval as the at least one mental state by an association unit 140.

Operation 540 depicts specifying at least one avatar attribute based on the at least one mental state. For example, a device 206 and/or attribute specification unit 250 may specify at least one avatar attribute based on the at least one mental state. For example, a device 206 and/or attribute specification unit 250 may specify at least one facial feature or facial dimension as an avatar attribute for use in an avatar based on an approving mental state identified in association with a measured physiologic activity proximate to a presented characteristic. In one embodiment, an association of a characteristic with a high degree of attention on the part of a member of population cohort 102 may provide the basis for an attribute specification unit 250 to specify the characteristic as an attribute for incorporation into a cohort-linked avatar.

In another embodiment, a voice specification unit 252 may specify a particular tonal quality of voice as the at least one avatar attribute based on an association between the tonal voice quality and a positive emotional response as measured by a brain activity measurement unit 212 and/or a surrogate marker measurement unit 230 and as associated by association unit 240. In another embodiment, a non-verbal specification unit 356 may specify an object as an avatar attribute based on a positive mental state associated with the object by emotion association module 342, for example.

In another embodiment, an attribute specification unit 250 may specify an attribute that is a variant of the initially-presented characteristic that provided the basis for the identification of mental state. In this case, specification of the variant of the characteristic may allow the system 100 to titrate the reactions of a member of population cohort 102 among various flavors of an attribute. For example, the system may be used to explore reactions of a member of population cohort 102 to various hairstyles of an avatar. Accordingly, a short hairstyle may be presented, brain activity may be measured proximate to the presentation of the short hairstyle, a positive emotional reaction may be associated with the brain activity, and based on the positive emotional mental state, a body attribute specification unit 262 may specify a medium hairstyle as an avatar attribute for subsequent presentation to the member of population cohort 102. As the process repeats, differential reactions indicating preference, approval, and/or disapproval of the member of population cohort 102 for variations on the attribute will emerge to suggest a "most preferred attribute" for an avatar.

Accordingly, in one embodiment, an attribute specification unit 350 may send an avatar attribute and/or other avatar output to a presentation device 364 for subsequent presentation to a member of population cohort 102. The process may be repeated reiteratively as a means of refining an avatar to include characteristics or attributes that are linked to a cohort in terms of preference or other mental state-eliciting quality.

In some embodiments, an avatar attribute may include, for example, an attribute of a three dimensional model, an attribute of a two dimensional icon or image, an attribute of a text construct, an attribute of an audio construct, and/or an attribute of a personality connected with a screen name. An avatar attribute may include an attribute of a real world object. In other embodiments, an avatar attribute may include, for example, an attribute of an embodiment, as of a quality or a concept. In another example, an avatar attribute may include an attribute of an archetype. In another embodiment, an avatar attribute may include a manifestation or aspect of a continuing entity, not necessarily a person. For example, a manifestation or aspect of a corporation may be an avatar attribute, as may be a specification for a class of robots. Accordingly, a specified avatar attribute may be an overall representation of what is happening in the population cohort with respect to a presented characteristic, Other examples of an avatar attribute are known to those of ordinary skill in the art.

FIG. 6 illustrates alternative embodiments of the example operational flow 500 of FIG. 5. FIG. 6 illustrates example embodiments where the presenting operation 510 may include at least one additional operation. Additional operations may include operation 600, 602, 604, 606, and/or operation 608.

Operation 600 depicts presenting the at least one characteristic to the at least one member of a population cohort, the at least one characteristic associated with the at least one member of the population cohort. For example, an attribute specification unit 150, presentation device 364, presentation unit 270, and/or device 106 may present at least one characteristic to at least one member of a population cohort 102, the at least one characteristic associated with the at least one member of the population cohort 102. For example, if the member of the population cohort 102 has brown hair and brown eyes, an attribute specification unit 150 may present an avatar with brown hair and brown eyes to the member of population cohort 102 via presentation unit 170.

In another embodiment, a clothing specification unit 360 may specify a particular color and/or style of clothing that matches the clothing of the at least one member of a population cohort 102, for presentation to the at least one member of a population cohort 102. Similarly, a speech specification unit may present a particular speech attribute such as a low pitch in an instance where the at least one member of a population cohort 102 is determined to have a low-pitched voice.

Operation 602 depicts presenting the at least one characteristic to the at least one member of a population cohort, the at least one characteristic not associated with a member of the population cohort. For example, an attribute specification unit 150, presentation device 364, presentation unit 270, and/or device 106 may present at least one characteristic to at least one member of a population cohort 102, the at least one characteristic not associated with the at least one member of the population cohort 102. For example, if the member of the population cohort 102 has short curly hair, an attribute specification unit 150 may present an avatar with long straight hair to the member of population cohort 102 via presentation unit 170.

In another embodiment, a clothing specification unit 260 may specify a particular color and/or style of clothing that contrasts with the clothing of the at least one member of a population cohort 102, for presentation to the at least one member of a population cohort 102. Similarly, a speech specification unit may present a particular speech attribute such as a low pitch in an instance where the at least one member of a population cohort 102 is determined to have a high-pitched voice. Such contrasting characteristic presentations may elicit interesting mental state responses, particularly in cases where gender-opposite characteristics (such as the voice pitch example above) are found to elicit favorable physiologic responses in the member of a population cohort 102.

Operation 604 depicts presenting at least one characteristic to at least one member of a established population cohort. For example, an attribute specification unit 150, presentation device 364, presentation unit 270, and/or device 106 may present at least one characteristic to at least one member of a established population cohort. For example, an attribute specification unit 250 may present an avatar wearing Hello Kitty brand clothing as the at least one characteristic to a member of a demographic group including girls ages 6-10 as the established population cohort. Alternatively, a speech specification unit 254 may present an avatar that speaks with a British accent as the at least one characteristic to a demographic group including people living in Britain as the established population cohort. In another embodiment, a facial attribute specification unit 258 may present an avatar that includes a heavy beard as the at least one characteristic to a male demographic as the established population cohort.

Operation 606 depicts presenting the at least one characteristic to at least one member of a established age cohort. For example, an attribute specification unit 150, presentation device 364, presentation unit 270, and/or device 106 may present at least one characteristic to at least one member of a established age cohort. For example, an attribute specification unit 250 may present an avatar wearing Van Dutch brand clothing as the at least one characteristic to a member of a demographic group including women aged 18-24 as the established age cohort. Alternatively, a speech specification unit 254 may present an avatar that speaks with a British accent as the at least one characteristic to a demographic group including British people aged 45-65 as the established age cohort. In another embodiment, a facial attribute specification unit 258 may present an avatar that includes an approximation of Jennifer Aniston's nose as the at least one characteristic to an age demographic between 18-24 years of age as the established age cohort.

Operation 608 depicts presenting the at least one characteristic to at least one member of a established gender cohort. For example, an attribute specification unit 150, presentation device 364, presentation unit 270, and/or device 106 may present at least one characteristic to at least one member of a established gender cohort. For example, an attribute specification unit 250 may present an avatar having an Oprah-like appearance as the at least one characteristic to a member of a demographic group including women as the established gender cohort. Alternatively, a speech specification unit 254 may present an avatar that speaks with a lilting tone as the at least one characteristic to a demographic group including men as the established gender cohort. In another embodiment, a body attribute specification unit 362 may present an avatar that includes a body builder's physique as the at least one characteristic to at least one member of a male cohort as the established gender cohort.

FIG. 7 illustrates alternative embodiments of the example operational flow 500 of FIG. 5. FIG. 7 illustrates example embodiments where the presenting operation 510 may include at least one additional operation. Additional operations may include operation 700, 702, 704, and/or operation 706.

Operation 700 depicts presenting the at least one characteristic to at least one member of a established ethnic cohort. For example, an attribute specification unit 150, presentation device 364, presentation unit 270, and/or device 106 may present at least one characteristic to at least one member of a established ethnic cohort, perhaps via a presentation unit 270. For example, an attribute specification unit 250 may present an image including, for example, plaid clothing or a bagpipe as the at least one characteristic to a member of an ethnic group including Scotsmen as the established ethnic cohort. Alternatively, a speech specification unit 254 may present an avatar that speaks with a southern drawl as the at least one characteristic to a member of an ethnic group including inhabitants of northern states as the established gender cohort. In another embodiment, a facial attribute specification unit 258 may present a sun-tanned face as the at least one characteristic to at least one member of a Canadian cohort as the established ethnic cohort.

A number of methods of identifying ethnicity based on facial features are known in the art, for example, ethnicity identification may be formulated as a two-category classification problem, for example, to classify the subject as an Asian or non-Asian. The input images may be resized to different scales. At each scale, a classic appearance-based face recognizer based on a linear discriminant analysis representation may be developed under a Bayesian statistical decision framework. An ensemble may then be constructed by integrating classification results to arrive at a final decision. The product rule may be used as an integration strategy. See Lu et al., "Ethnicity Identification from Face Images," Biometric Technology for Human Identification, Eds. Jain et al., Proc. SPIE, Vol. 5404, pp. 114-123 (2004).

Subject ethnicity identification may be based on a number of factors including skin and/or hair characteristics associated with ethnicity, such as red hair among caucasians; voice and/or speech associated with ethnicity, such as French-accented English indicating French or French-Canadian ethnicity; face pattern associated with ethnicity, such as eye shape, nose shape, face shape, or the like; and eye attributes such as blue eyes among Caucasians. In one embodiment, Gabor wavelets transformation and retina sampling from physiologic measurement data may be combined to extract key facial features, and support vector machines may be used for ethnicity classification. An experimental system has used Gabor wavelets transformation and retina sampling in combination to extract key facial features, and support vector machines were used for ethnicity classification, resulting in approximately 94% success for ethnicity estimation under various lighting conditions. See Hosoi et al., "Ethnicity estimation with facial images," Sixth IEEE International Conference on Automatic Face and Gesture Recognition, pp. 195-200 (2004). Of course other methods of ethnicity identification known in the art may be used.

An age, gender, and/or ethnicity characteristic may be based on, for example, an iris pattern associated with an asian user. For example, a bank of multichannel 2D Gabor filters may be used to capture global texture information about an a user's iris, and AdaBoost, a machine learning algorithm, may be used to allow a presentation unit 370 to learn a discriminant classification principle from a pool of candidate iris feature sets. Iris image data may be thus grouped into race categories, for example, Asian and non-Asian. See Qui et al., "Global Texture Analysis of Iris Images for Ethnic Classification," Lecture notes in computer science, Springer:Berlin/Heidelberg, Advances in Biometrics, pp. 411-418 (2005).

Operation 702 depicts presenting at least one of a physical appearance characteristic, a language characteristic, a cultural characteristic, a personal interest characteristic, an educational characteristic, or a personality characteristic to the at least one member of the population cohort. For example, an attribute specification unit 150, presentation device 364, presentation unit 270, and/or device 106 may present at least one of a physical appearance characteristic, a language characteristic, a cultural characteristic, a personal interest characteristic, an educational characteristic, or a personality characteristic to the at least one member of the population cohort, perhaps via a presentation unit 270. For example, an attribute specification unit 250 may present an image including, for example, a tattoo as the at least one physical appearance characteristic to a member of a population cohort. Alternatively, a speech specification unit 254 may present an avatar that speaks with a French accent as the at least one language characteristic to a member of a population cohort. In another embodiment, an attribute specification unit 258 may present an item of sports equipment such as a tennis racquet as the at least one personal interest characteristic to at least one member of a population cohort.

Operation 704 depicts presenting at least one of a facial feature characteristic, a body feature characteristic, a clothing characteristic, or an accoutrement characteristic as the at least one physical appearance characteristic. For example, an attribute specification unit 150, clothing specification unit 260, facial attribute specification unit 258, presentation device 364, presentation unit 270, and/or device 106 may present at least one of a facial feature characteristic, a body feature characteristic, a clothing characteristic, or an accoutrement characteristic as the at least one physical appearance characteristic, perhaps via a presentation unit 270. For example, an attribute specification unit 250 may present an image including, for example, a piece of jewelry such as a ring or a necklace as an accoutrement characteristic. Alternatively, a facial attribute specification unit 258 may present an avatar having dimples as the facial feature characteristic. In another embodiment, a body attribute specification unit 262 may present a slender body type as the body feature characteristic.

Operation 706 depicts presenting at least one of a regional dialect characteristic, an accent characteristic, a manner of speech characteristic, or a voice characteristic as the at least one language characteristic. For example, an attribute specification unit 150, voice specification unit 352, speech specification unit 354, presentation device 364, presentation unit 270, and/or device 106 may present at least one of a regional dialect characteristic, an accent characteristic, a manner of speech characteristic, or a voice characteristic as the at least one language characteristic, perhaps via a presentation unit 270. For example, a voice specification unit 252 may present an avatar's speech having, for example, a Boston dialect as the at least one language characteristic. Alternatively, a speech specification unit 254 may present an avatar having an authoritative tone as the at least one language characteristic. In another embodiment, a voice specification unit 252 may present speech including colloquialisms such as "y'all" or "yins" as the manner of speech characteristic.

FIG. 8 illustrates alternative embodiments of the example operational flow 500 of FIG. 5. FIG. 8 illustrates example embodiments where the presenting operation 510 may include at least one additional operation. Additional operations may include operation 804, and/or operation 806.

Operation 804 depicts presenting at least one of a gesture characteristic, a food characteristic, a hairstyle characteristic, a cosmetics characteristic, or a facial hair characteristic as the at least one cultural characteristic. For example, an attribute specification unit 150, clothing specification unit 260, non-verbal attribute specification unit 256, voice specification unit 352, presentation device 364, presentation unit 270, and/or device 106 may present at least one of a gesture characteristic, a food characteristic, a hairstyle characteristic, a cosmetics characteristic, or a facial hair characteristic as the at least one cultural characteristic, perhaps via a presentation unit 270. For example, an attribute specification unit 350 may present an avatar's speech accompanied by emphatic gesturing as the gesture characteristic. Alternatively, a non-verbal attribute specification unit 356 may present an avatar wearing traditional dress of an ethnicity as the at least one cultural characteristic. In another embodiment, a facial attribute specification unit 358 may present facial hair such as a mustache or a goatee as the facial hair characteristic.

Operation 806 depicts presenting at least one of a hobby interest characteristic, a travel interest characteristic, a shopping interest characteristic, a pet interest characteristic, a television or movie interest characteristic, a music interest characteristic, a politics interest characteristic, or a sports interest characteristic as the at least one personal interest characteristic. For example, an attribute specification unit 150, clothing specification unit 260, non-verbal attribute specification unit 256, voice specification unit 352, presentation device 364, presentation unit 270, and/or device 106 may present at least one of a hobby interest characteristic, a travel interest characteristic, a shopping interest characteristic, a pet interest characteristic, a television or movie interest characteristic, a music interest characteristic, a politics interest characteristic, or a sports interest characteristic as the at least one personal interest characteristic, perhaps via a presentation unit 270. For example, an attribute specification unit 350 may present an avatar together with a musical instrument as the music interest characteristic. Alternatively, a non-verbal attribute specification unit 356 may present an avatar wearing a Star Trek t-shirt as the television or movie interest characteristic. In another embodiment, a facial attribute specification unit 358 may present an avatar's face painted with a sports team's colors as the sports interest characteristic.

FIG. 9 illustrates alternative embodiments of the example operational flow 500 of FIG. 5. FIG. 9 illustrates example embodiments where the presenting operation 510 may include at least one additional operation. Additional operations may include operation 904, and/or operation 906.

Operation 904 depicts presenting at least one of a literature interest characteristic, a science interest characteristic, a mathematics interest characteristic, or a college or university characteristic as the at least one educational interest characteristic. For example, an attribute specification unit 150, clothing specification unit 260, non-verbal attribute specification unit 256, voice specification unit 352, presentation device 364, presentation unit 270, and/or device 106 may present at least one of a literature interest characteristic, a science interest characteristic, a mathematics interest characteristic, or a college or university characteristic as the at least one educational interest characteristic, perhaps via a presentation unit 270. For example, an attribute specification unit 350 may present an avatar together with a book as the literature interest characteristic. Alternatively, a non-verbal attribute specification unit 356 may present an avatar wearing a computer as the science interest characteristic. In another embodiment, a clothing specification unit 260 may present an avatar wearing the logo of a school as the college or university characteristic.

Operation 906 depicts presenting at least one of a talkative personality characteristic, an aggressive personality characteristic, a deferential personality characteristic, a humorous personality characteristic, or a whimsical personality characteristic as the at least one personality characteristic. For example, an attribute specification unit 150, clothing specification unit 260, non-verbal attribute specification unit 256, voice specification unit 352, presentation device 364, presentation unit 270, and/or device 106 may present at least one of a talkative personality characteristic, an aggressive personality characteristic, a deferential personality characteristic, a humorous personality characteristic, or a whimsical personality characteristic as the at least one personality characteristic, perhaps via a presentation unit 270. For example, an attribute specification unit 350 may present an avatar that rarely makes eye contact as the deferential personality characteristic. Alternatively, a speech specification unit 354 may present an avatar that talks often and at a rapid rate as the talkative personality characteristic. In another embodiment, a facial attribute specification unit 358 may present an avatar that smiles and or laughs frequently as the humorous personality characteristic.

FIG. 10 illustrates alternative embodiments of the example operational flow 500 of FIG. 5. FIG. 10 illustrates example embodiments where the presenting operation 510 may include at least one additional operation. Additional operations may include operation 1000, and/or operation 1002.

Operation 1000 depicts presenting at least one characteristic to at least one of a virtual world participant, a computer game participant, an online shopping participant, or a social networking website participant as the at least one member of the population cohort. For example, an attribute specification unit 150, clothing specification unit 260, non-verbal attribute specification unit 256, voice specification unit 352, presentation device 364, presentation unit 270, and/or device 106 may present at least one characteristic to at least one of a virtual world participant, a computer game participant, an online shopping participant, or a social networking website participant as the at least one member of the population cohort, perhaps via a presentation unit 270. For example, an attribute specification unit 350 may present an avatar to a Second Life user as the virtual world participant. Alternatively, a non-verbal attribute specification unit 256 may present an avatar to a player of an online game, such as World of Warcraft as the computer game participant. In another embodiment, a facial attribute specification unit 358 may present an avatar to a person visiting a myspace page or a facebook page as the social networking website participant.

Operation 1002 depicts presenting at least two characteristics separated by a time delay to the at least one member of a population cohort. For example, an attribute specification unit 150, clothing specification unit 260, non-verbal attribute specification unit 256, voice specification unit 352, presentation device 364, presentation unit 270, and/or device 106 may present at least two characteristics separated by a time delay to the at least one member of a population cohort, perhaps via a presentation unit 270. For example, an attribute specification unit 350 may present an avatar having a particular advertising logo displayed on an item of clothing, followed some time later by another avatar having a different logo displayed on the same avatar. Thus physiologic responses to the different logos may be measured and compared. Alternatively, a non-verbal attribute specification unit 256 may present an avatar having a particular physical feature such as blue eye color, followed some time later by an avatar the same in all respects but for a change to green eye color. Thus physiologic responses to the different eye colors may be measured and compared.

FIG. 11 illustrates alternative embodiments of the example operational flow 500 of FIG. 5. FIG. 11 illustrates example embodiments where the measuring operation 520 may include at least one additional operation. Additional operations may include operation 1100, 1102, and/or operation 1104.

Operation 1100 depicts measuring at least one physiologic activity of the at least one member of the population cohort using functional near-infrared imaging, the at least one physiologic activity proximate to the at least one presented characteristic. For example, the device 206, physiologic activity measurement unit 210, brain activity measurement unit 212, and/or fNIR module 214 can measure at least one physiologic activity of the at least one member of the population cohort using functional near-infrared imaging, the at least one physiologic activity proximate to the at least one presented characteristic. In one embodiment, a member of the population cohort 102 can be monitored by fNIR module 214 during presentation of a characteristic to a member of population cohort 102. fNIR module 214 can measure brain activity as the physiologic activity of the at least one member of the population cohort.

Proximity of the fNIR measurement to presentation, viewing, and/or perception of the characteristic can be determined by presentation unit 270, device 206, physiologic activity measurement unit 210, brain activity measurement unit 212, and/or fNIR module 214. For example, the time of presentation of the characteristic can be matched with brain activity measured by fNIR module 214. In another embodiment, eye movement and/or gaze tracking analysis can determine the time that a subject's eyes contact a presented characteristic, and this can be matched to the time of a measured brain activity by fNIR module 214. In still another embodiment, brain activity in the visual cortex or other perception-indicative brain area or areas can be measured by fNIR module 214 as an indicator of a subject's viewing of a presented characteristic; continued measurement of physiologic activity by fNIR module 214 can then measure a response to the viewing of the characteristic.

In one embodiment, the fNIR module 214 may be located in a kiosk in a public area such as a shopping mall. In such an environment, images of individuals may be captured by photography or videography and compared with reference population cohort 104 image profiles to identify members of population cohort 102. In another embodiment, presentation of a characteristic by, for example, presentation unit 270 and measurement of physiologic activity by, for example fNIR module 214 may occur in a home computing environment, with characteristic presentation data sent by, for example, a remote attribute specification unit 350 to a presentation device 364 located in the home. The physiologic activity measurement unit 310 unit may be located in the home environment and send measurement data via a network to a remote device 306 for processing of the data, or all functions of device 106 may be located in the home environment.

In one embodiment, fNIR module 214 may measure brain activation within milliseconds of a subject encountering a presented characteristic. For example, fNIR module 214 may detect increased brain activity in the nucleus accumbens, SLEA, and thalamus within milliseconds of presentation of a prepared food item to a member of population cohort 102. Such a response may be considered proximate to the presentation of the prepared food item.

Operation 1102 depicts measuring at least one physiologic activity of the at least one member of the population cohort using at least one of electroencephalography, computed axial tomography, positron emission tomography, magnetic resonance imaging, functional magnetic resonance imaging, functional near-infrared imaging, or magnetoencephalography, the at least one physiologic activity proximate to the at least one presented characteristic. For example, the device 206, physiologic activity measurement unit 210, brain activity measurement unit 212, fMRI module 216, MEG module 218, EEG module, PET module, and/or fNIR module 214 can measure at least one physiologic activity of the at least one member of the population cohort using at least one of electroencephalography, computed axial tomography, positron emission tomography, magnetic resonance imaging, functional magnetic resonance imaging, functional near-infrared imaging, or magnetoencephalography, the at least one physiologic activity proximate to the at least one presented characteristic. In one embodiment, a member of the population cohort 102 can be monitored by MEG module 218 during presentation of a characteristic to a member of population cohort 102. fMRI module 216, MEG module 218, EEG module, PET module, and/or fNIR module 214 can measure brain activity as the physiologic activity of the at least one member of the population cohort.

Operation 1104 depicts measuring at least one brain activity surrogate marker of the at least one member of the population cohort, the at least one brain activity surrogate marker proximate to the at least one presented characteristic. For example, the device 206, physiologic activity measurement unit 210, surrogate marker measurement unit 230, iris response module 232, gaze tracking module 234, skin response module 236, and/or voice response module can measure at least one brain activity surrogate marker of the at least one member of the population cohort, the at least one brain activity surrogate marker proximate to the at least one presented characteristic. In one embodiment, surrogate marker measurement unit 230 can measure any of a variety of physiological responses to a presented characteristic, the physiological responses indicative of a brain activation and/or mental state response to the presented characteristic. For example, surrogate marker measurement unit 230 may measure a physiological attribute such as heart rate, respiration, perspiration, temperature, skin coloring, skin electrical response, eye movement, pupil dilation, voice stress, body or facial tic, or the like, before, during, and/or after presentation of a characteristic to a member of population cohort 102. Such measurements may include, for example, an increase in heart rate over a time interval as measured by a heart rate monitor embedded in a user interface; increased eye movements as measured by an image capture device such as a video camera, or changes in the galvanic skin response as measured by electrodes embedded in a user interface or included in device 106.

In one embodiment, an iris response module 232 and/or gaze tracking module 234 may acquire data from a user monitoring device such as a video capture device or a video communication device, for example, when a subject's image is captured as a photograph or video when using an application, such as a webcam, or when a subject's image is captured when communicating via a photography or video-based application. Other sources of image data may include biometric data such as facial pattern data, eye scanning data, or the like. Such image data may indicate, for example, alertness, attention, approval, disapproval, or the like, as discussed below.

Image data may include results of visual spectrum imaging that can image changes in facial expression, body movement, or the like that can be indicative of a physiological activity, brain activity, and/or mental state. User image data may also be obtained from other kinds of imaging such as infrared imaging that can read a heat signature and/or ultrasound imaging. Further, reflected image or refracted image data may also be obtained by physiologic activity measurement unit 210 and/or surrogate marker measurement unit 230. Near infrared imaging may be used to test for baseline physiologic states and metabolism, as well as physiologic and metabolic changes. Image data may be of all or a portion of a member of population cohort 102 such as a head-to-toe image, a face image, an image of fingers, an image of an eye, or the like. Such images may be in the visual or non-visual wavelength range of the electromagnetic spectrum.

Alertness or attention can be measured, for example, by measuring eye movements, body movements, pointing device manipulation, and/or task proficiency (e.g., are a subject's eyelids drooping, is a subject's head nodding, is a subject failing or succeeding to activate on-screen items when prompted, does a subject respond to a sound, or the like). Alertness or attention to, for example, an advertisement may be gauged from a subject's interaction with the advertisement. Interest in the advertisement as the presented characteristic in the form of face pattern data (e.g., a smile on an image of the subject's face), pointing device manipulation data (e.g., a mouse click on an onscreen advertisement icon as the presented characteristic), and/or eye movement data (e.g., repeated eye movements toward the advertisement as the presented characteristic), or the like.

FIG. 12 illustrates alternative embodiments of the example operational flow 500 of FIG. 5. FIG. 12 illustrates example embodiments where the measuring operation 520 may include at least one additional operation. Additional operations may include operation 1206.

Operation 1206 depicts measuring the at least one brain activity surrogate marker of the at least one member of the population cohort using at least one of iris dilation or constriction, gaze tracking, skin response, or voice response, the at least one brain activity surrogate marker proximate to the at least one characteristic. For example, the device 206, physiologic activity measurement unit 210, surrogate marker measurement unit 230, iris response module 232, gaze tracking module 234, skin response module 236, and/or voice response module can measure the at least one brain activity surrogate marker of the at least one member of the population cohort using at least one of iris dilation or constriction, gaze tracking, skin response, or voice response, the at least one brain activity surrogate marker proximate to the at least one presented characteristic. In one embodiment, a voice response module can measure speech captured by a microphone during presentation of a characteristic. Speech or voice can be measured, for example, by examining voice, song, and/or other vocal utterances of a subject before, during, and/or after presentation of a characteristic to a member of population cohort 102. Such measurements may include, for example, as discussed above, layered voice analysis, voice stress analysis, or the like.

The reaction of a subject to a presented characteristic such as an advertisement in a computerized game world or in another virtual world may be a recognizable vocal exclamation such as "Wow, that's nice!" that may be detectable by a voice response module 338 such as a microphone monitoring an interaction between the subject and, for example, a presentation device 364 and/or device 306. A voice response module 338 may also include a speech recognition function such as a software program or computational device that can identify and/or record an utterance of a subject as speech or voice data.

In another embodiment, an iris response module may record changes in the movement of a subject's iris (with corresponding changes in the size of the pupil) before, during, and/or after presentation of a characteristic to a member of a population cohort 102. Such measurements of physiologic activity that indicate brain activity and/or mental state may be carried out at a time that is proximate to presentation of a characteristic to a member of population cohort 102.

In one embodiment, a gaze tracking module 334 may include a camera that can monitor a subject's eye movements in order to determine whether the subject looks at a presented characteristic, for example, during a certain time period.

Gaze tracking module 334 and/or iris response module 332 may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, a display 372. (e.g., http://jp.hamamatsu.com/en/rd/publication/scientific_american/common/pdf/scientific_06 08.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an user 106.

Two types of gaze tracking or eye tracking techniques include bright pupil eye tracking and dark pupil eye tracking. Their difference is based on the location of the illumination source with respect to the optics. If the illumination is coaxial with the optical path, then the eye acts as a retroreflector as the light reflects off the retina, creating a bright pupil effect similar to red eye. If the illumination source is offset from the optical path, then the pupil appears dark.

Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright light. However, bright pupil techniques are not recommended for tracking outdoors as extraneous IR sources may interfere with monitoring.

Eye tracking configurations can vary; in some cases the measurement apparatus may be head-mounted, in some cases the head should be stable (e.g., stabilized with a chin rest), and in some cases the eye tracking may be done remotely to automatically track the head during motion. Most eye tracking systems use a sampling rate of at least 30 Hz. Although 50/60 Hz is most common, many video-based eye trackers run at 240, 350 or even 1000/1250 Hz, which is recommended in order to capture the detail of the very rapid eye movements during reading, or during studies of neurology.

Eye movements are typically divided into fixations, when the eye gaze pauses in a certain position, and saccades, when the eye gaze moves to another position. A series of fixations and saccades is called a scanpath. Most information from the eye is made available during a fixation, not during a saccade. The central one or two degrees of the visual angle (the fovea) provide the bulk of visual information; input from larger eccentricities (the periphery) generally is less informative. Therefore the locations of fixations along a scanpath indicate what information loci on the stimulus were processed during an eye tracking session. On average, fixations last for around 200 milliseconds during the reading of linguistic text, and 350 milliseconds during the viewing of a scene. Preparing a saccade towards a new goal takes around 200 milliseconds.

Scanpaths are useful for analyzing cognitive intent, interest, and salience. Other biological factors (some as simple as gender) may affect the scanpath as well. Eye tracking in human-computer interaction typically investigates the scanpath for usability purposes, or as a method of input in gaze-contingent displays, also known as gaze-based interfaces.

There are two primary components to most eye tracking studies: statistical analysis and graphic rendering. These are both based mainly on eye fixations on specific elements. Statistical analyses generally sum the number of eye data observations that fall in a particular region. Commercial software packages may analyze eye tracking and show the relative probability of eye fixation on each feature in a website. This allows for a broad analysis of which site elements received attention and which ones were ignored. Other behaviors such as blinks, saccades, and cognitive engagement can be reported by commercial software packages. Statistical comparisons can be made to test, for example, competitors, prototypes or subtle changes to an avatar and/or web design. They can also be used to compare participants in different demographic groups and/or population cohorts. Statistical analyses may quantify where subjects look, sometimes directly, and sometimes based on models of higher-order phenomena (e.g., cognitive engagement).

In addition to statistical analysis, it is often useful to provide visual depictions of eye tracking results. One method is to create a video of an eye tracking testing session with the gaze of a participant superimposed upon it. This allows one to effectively see through the eyes of the subject during interaction with a presented characteristic. Another method graphically depicts the scanpath of a single participant during a given time interval. Analysis may show each fixation and eye movement of a participant during a search on a virtual shelf display of breakfast cereals, analyzed and rendered with a commercial software package. For example, a different color may represent one second of viewing time, allowing for a determination of the order in which products are seen. Analyses such as these may be used as evidence of specific trends in visual behavior.

A similar method sums the eye data of multiple participants during a given time interval as a heat map. A heat map may be produced by a commercial software package, and shows the density of eye fixations for several participants superimposed on the original stimulus, for example, a magazine cover. Red and orange spots represent areas with high densities of eye fixations. This allows one to examine which regions attract the attention and focus of the viewer.

Commercial eye tracking applications include web usability, advertising, sponsorship, package design and automotive engineering. Eye tracking studies often present a target stimulus to a sample of consumers while an eye tracker is used to record the activity of the eye. Examples of target stimuli may include websites, television programs, sporting events, films, commercials, magazines, newspapers, packages, shelf displays, consumer systems (e.g., ATMs, checkout systems, kiosks), and software. The resulting data can be statistically analyzed and graphically rendered to provide evidence of specific visual patterns. By examining fixations, saccades, pupil dilation, blinks, and a variety of other behaviors, researchers can determine a great deal about the effectiveness of a given medium or product.

A prominent field of eye tracking research is web usability. While traditional usability techniques are often quite powerful in providing information on clicking and scrolling patterns, eye tracking offers the ability to analyze user interaction between the clicks. This provides insight into which features are the most eye-catching, which features cause confusion, and which ones are ignored altogether. Specifically, eye tracking can be used to assess search efficiency, branding, online advertisement, navigation usability, overall design, and many other site components, including avatar attributes. Analyses may target a prototype avatar or competitor avatars in addition to the main avatar.

Eye tracking is commonly used in a variety of different advertising media. Commercials, print ads, online ads, and sponsored programs are all conducive to analysis with eye tracking technology. Analyses may focus on visibility of a target product or logo in the context of a magazine, newspaper, website, virtual world, or televised event. This allows researchers to assess in great detail how often a sample of consumers fixates on the target logo, product, or advertisement. In this way, an advertiser can quantify the success of a given campaign in terms of actual visual attention.

Eye tracking also provides package designers with the opportunity to examine the visual behavior of a consumer while interacting with a target package. This may be used to analyze distinctiveness, attractiveness and the tendency of the package to be chosen for purchase. Eye tracking is often used while the target product is in the prototype stage. Prototypes are tested against each other and against competitors to examine which specific elements are associated with high visibility and/or appeal.

Another application of eye tracking research is in the field of automotive design. Eye tracking cameras may be integrated into automobiles to provide the vehicle with the capacity to assess in real-time the visual behavior of the driver. The National Highway Traffic Safety Administration (NHTSA) estimates that drowsiness is the primary causal factor in 100,000 police-reported accidents per year. Another NHTSA study suggests that 80% of collisions occur within three seconds of a distraction. By equipping automobiles with the ability to monitor drowsiness, inattention, and cognitive engagement driving safety could be dramatically enhanced. Lexus® claims to have equipped its LS 460 automobile with the first driver monitor system in 2006, providing a warning if the driver takes his or her eye off the road.

Eye tracking is also used in communication systems for disabled persons, allowing the user to speak, mail, surf the web and so with only the eyes as tool. Eye control works even when the user has involuntary body movement as a result of cerebral palsy or other disability, and/or when the user wears glasses.

A surrogate marker measurement unit may also measure face pattern, for example, by measuring user facial features, perhaps in relation to a control user face pattern image captured when the user was not interacting with a presented characteristic. Alternatively, a subject's face pattern may be compared to an average face pattern compiled from a large number of faces in the population cohort. In one embodiment, the reaction of a member of population cohort 102 to an onscreen avatar may be a smile or a frown that may be detectable by a camera monitoring the interaction. Information suggesting that a user smiles in response to viewing a presented characteristic may be transmitted to association unit 340.

A surrogate marker measurement unit 330 may include a pen including electronic sensing capability that may include the capability to monitor a subject's hand for temperature, blood flow, tremor, fingerprints, or other attributes. Reaction time among young males aged 18-28 that play video games with some frequency may be distinguishable from average reaction times of women and/or users in older age groups.

In another embodiment, a surrogate marker measurement unit 330 and/or device 306 may anonymize physiologic activity measurement data acquired during a subject's interaction with one or more presented characteristics. Anonymization of member of population cohort 102 data may be accomplished through various methods known in the art, including data coding, k-anonymization, de-association, pseudonymization, or the like.

FIG. 13 illustrates alternative embodiments of the example operational flow 500 of FIG. 5. FIG. 13 illustrates example embodiments where the measuring operation 520 may include at least one additional operation. Additional operations may include operation 1300, 1302, 1304, and/or 1306.

Operation 1300 depicts measuring at least one physiologic activity of the at least one member of the population cohort in near real time, the at least one physiologic activity proximate to the at least one presented characteristic. For example, the device 206, physiologic activity measurement unit 210, brain activity measurement unit 212, and/or surrogate marker measurement unit 230 can measure at least one physiologic activity of the at least one member of the population cohort 102 in near real time, the at least one physiologic activity proximate to the at least one presented characteristic. In one embodiment, the brain activity measurement unit 212 can measure brain activity in the member of population cohort 102 at the milliseconds-to-seconds time frame, inclusive of processing time. Accordingly, the methods discussed herein, including surrogate marker measurement functions, can measure responses of a member of the population cohort 102 in near real time, which may include a delay between the occurrence of a proximate and/or response event and the use of the processed proximate measurement data, e.g., for further processing and/or for subsequent display.

Operation 1302 depicts measuring at least one physiologic activity of the at least one member of the population cohort, the at least one physiologic activity proximate to at least two presented characteristics. For example, the device 206, physiologic activity measurement unit 210, brain activity measurement unit 212, and/or surrogate marker measurement unit 230 can measure at least one physiologic activity of the at least one member of the population cohort, the at least one physiologic activity proximate to at least two presented characteristics. In one embodiment, a combination of characteristics can be presented to a member of population cohort 102 in the context of, for example an avatar. For example, brain activity measurement unit 212 may measure brain activity during presentation of a set of avatar features, such as a facial feature and a voice feature, to a member of population cohort 102.

Operation 1304 depicts measuring at least one physiologic activity of the at least one member of the population cohort, the at least one physiologic activity proximate to at least one of a presented hairstyle characteristic or a presented eye color characteristic. For example, the device 206, physiologic activity measurement unit 210, brain activity measurement unit 212, and/or surrogate marker measurement unit 230 can measure at least one physiologic activity of the at least one member of the population cohort, the at least one physiologic activity proximate to at least one of a presented hairstyle characteristic or a presented eye color characteristic. In one embodiment, physiologic activity measurement unit 210 can measure brain activity and/or eye movement activity during presentation of an avatar to a member of population cohort 102, the avatar having, for example, wavy blond hair and/or blue eyes. Choice of hairstyle characteristic may be based on a population cohort 104 characteristic, a member of population cohort 102 characteristic, and/or previous avatar specification data.

Operation 1306 depicts measuring at least one physiologic activity of the at least one member of the population cohort, the at least one physiologic activity proximate to at least one presented characteristic of the member of the population cohort. For example, the device 206, physiologic activity measurement unit 210, brain activity measurement unit 212, and/or surrogate marker measurement unit 230 can measure at least one physiologic activity of the at least one member of the population cohort, the at least one physiologic activity proximate to at least one presented characteristic of the member of the population cohort. In one embodiment, physiologic activity measurement unit 210 can measure brain activity and/or iris movement activity during presentation of an appearance characteristic of the member of the population cohort 102, for example, as detected by a camera monitoring the member of the population cohort. In another embodiment, physiologic activity measurement unit 210 can measure brain activity and/or voice stress response during presentation of a voice characteristic of the member of the population cohort 102, for example, as detected by a microphone monitoring the member of the population cohort.

FIG. 14 illustrates alternative embodiments of the example operational flow 500 of FIG. 5. FIG. 14 illustrates example embodiments where the measuring operation 520 may include at least one additional operation. Additional operations may include operation 1400, 1402, 1404, and/or 1406.

Operation 1400 depicts measuring at least one physiologic activity of the at least one member of the population cohort, the at least one physiologic activity proximate to at least one presented characteristic of a different member of the population cohort. For example, the device 206, physiologic activity measurement unit 210, brain activity measurement unit 212, and/or surrogate marker measurement unit 230 can measure at least one physiologic activity of the at least one member of the population cohort, the at least one physiologic activity proximate to at least one presented characteristic of a different member of the population cohort 104. In one embodiment, brain activity measurement unit 312 can measure brain activity during presentation of an appearance characteristic of a member of population cohort 104 different from the member of population cohort 102 that is responding to the characteristic. For example, a middle-aged member of population cohort 102 may be presented with a characteristic of a child-aged member of the population cohort 104, during which physiologic activity measurement unit 210, brain activity measurement unit 212, and/or surrogate marker measurement unit 230 can measure a physiological response to the presentation of the characteristic.

Operation 1402 depicts measuring at least one physiologic activity of the at least one member of the population cohort, the at least one physiologic activity proximate to at least one presented characteristic of a member of a different population cohort. For example, the device 206, physiologic activity measurement unit 210, brain activity measurement unit 212, and/or surrogate marker measurement unit 230 can measure at least one physiologic activity of the at least one member of the population cohort, the at least one physiologic activity proximate to at least one presented characteristic of a member of a different population cohort. In one embodiment, brain activity measurement unit 312 can measure brain activity during presentation of a speech characteristic of a member of a population cohort that is different from the population cohort 104 to which member of population cohort 102 belongs. For example, for a population cohort 104 including males aged 18-24, a member of population cohort 102 (i.e., a male aged 18-24) may be presented with a characteristic of a female, and thus a member of a different population cohort, during which physiologic activity measurement unit 210, brain activity measurement unit 212, and/or surrogate marker measurement unit 230 can measure a physiological response to the presentation of the female characteristic.

Operation 1404 depicts measuring with permission at least one physiologic activity of the at least one member of the population cohort, the at least one physiologic activity proximate to the at least one presented characteristic. For example, the device 206, physiologic activity measurement unit 210, brain activity measurement unit 212, and/or surrogate marker measurement unit 230 can measure with permission at least one physiologic activity of the at least one member of the population cohort, the at least one physiologic activity proximate to the at least one presented characteristic. In one embodiment, after receiving permission from a member of population cohort 102, brain activity measurement unit 312 can measure brain activity during presentation of a physical characteristic to the member of population cohort 102. For example, a member of population cohort 102 may click an acceptance box asking for permission to measure a physiologic activity, for example, during a virtual world session, an online gaming session, an online shopping session, a social networking session, or the like.

FIG. 15 illustrates alternative embodiments of the example operational flow 500 of FIG. 5. FIG. 15 illustrates example embodiments where the associating operation 530 may include at least one additional operation. Additional operations may include operation 1500, 1502, 1504, 1506, and/or 1508.

Operation 1500 depicts associating at least one electrical brain activity with the at least one mental state. For example, the device 106, association unit 140, emotion association module 242, attention association module 244, and/or cognition association module 346 can associate at least one electrical brain activity with at least one mental state. In one embodiment, association unit 240 can receive an electrical brain activity measurement, such as measurement of electrical activation of the hippocampus, in response to presentation of a characteristic to a member of population cohort 102.

The electrical brain activity measurement may be received from, for example, EEG module 220. Association unit 240 can then search one or more functional brain mapping databases based on the electrical brain activity measurement to find one or more matching mental states. For example, activation of the hippocampus is associated in the literature with enhanced motivational drive for food and drugs. Thus an association may be made between hippocampus activation and enhanced motivational drive, for example, based on research findings (e.g., Wang et al., "Gastric stimulation in obese subjects activates the hippocampus and other regions involved in brain reward circuitry," PNAS, vol. 103, pp. 15641-45 (2006).

In another embodiment, attention association module 244 can receive a brain activity measurement based on electrical brain activity, such as a measurement from MEG module 218. In this embodiment, an avatar with a specific set of facial features as the at least one characteristic may be presented to a member of population cohort 102, during which presentation MEG module 218 can measure the brain's electrical activity based on induced magnetic fields. For example, presentation of the avatar with the specific set of facial features may elicit electrical activity in the prefrontal and/or parietal areas of the brain. Association unit 240 may thus match the activation measurement pattern with a known pattern of brain activation from research indicating which brain areas are activated when attention is required. For example, activation of the thalamic reticular nucleus is also associated with selective attention. See Contreras et al., "Inactivation of the Interoceptive Insula Disrupts Drug Craving and Malaise Induced by Lithium," Science, vol. 318, pp. 655-658 (26 Oct. 2007).

Operation 1502 depicts associating at least one brain blood oxygen level with the at least one mental state. For example, the device 106, association unit 140, emotion association module 242, attention association module 244, and/or cognition association module 346 can associate at least one hemodynamic brain activity with at least one mental state. In one embodiment, association unit 240 can receive a brain blood oxygen level activity measurement, such as measurement of activation of the right prefrontal and parietal areas, in response to presentation of a characteristic to a member of population cohort 102. The hemodynamic brain activity measurement indicating activation of the right prefrontal and parietal areas may be received from, for example, fNIR module 214. Association unit 240 can then search one or more functional brain mapping databases based on the brain activity measurement to find one or more matching mental states. For example, activation of the right prefrontal and parietal areas is associated in the literature with attention. Thus an association may be made between right prefrontal and parietal areas activation and increased attention to the presented characteristic by association unit 240, for example, based on research findings. See Cabeza et al, "Imaging Cognition II: An Empirical Review of 275 PET and fMRI Studies," J. Cognitive Neurosci., vol. 12, pp. 1-47 (2000).

Operation 1504 depicts associating at least one of glucose metabolism or blood flow with the at least one mental state. For example, the device 106, association unit 140, emotion association module 242, attention association module 244, and/or cognition association module 346 can associate at least one of glucose metabolism or blood flow with at least one mental state. In one embodiment, association unit 240 can receive a glucose metabolism measurement, such as measurement of activation of the right hemisphere of the bilateral fusiform gyrus, in response to presentation of a face characteristic to a member of population cohort 102. The glucose metabolism brain activity measurement indicating activation of the right hemisphere of the bilateral fusiform gyrus may be received from, for example, PET module 222. Attention association module 244 can then match the brain activity measurement to one or more corresponding mental states. For example, activation of the right hemisphere of the bilateral fusiform gyrus is associated in the literature with increased attention to faces. Thus an association can be made between activation of the right hemisphere of the bilateral fusiform gyrus and increased attention to the presented face characteristic by association unit 240, for example, based on research findings. See Cabeza et al, "Imaging Cognition II: An Empirical Review of 275 PET and fMRI Studies," J. Cognitive Neurosci., vol. 12, pp. 1-47 (2000).

Operation 1506 depicts associating activity in the ventromedial prefrontal cortex with a mental state indicating approval. For example, the device 106, association unit 140, emotion association module 242, attention association module 244, and/or cognition association module 346 can associate activity in the ventromedial prefrontal cortex with a mental state indicating approval. In one embodiment, association unit 240 can receive a brain activity measurement indicating activation of the ventromedial prefrontal cortex, in response to presentation to a member of population cohort 102 of an avatar having a characteristic of interest. The brain activity measurement indicating activation of the ventromedial prefrontal cortex may be received from, for example, fMRI module 216. Emotion association module 242 and/or attention association module 244 can then match the ventromedial prefrontal cortex activation measurement to one or more corresponding mental states. For example, activation of the ventromedial prefrontal cortex is associated in the literature with preference or approval. Thus an association unit 240 can make an association between activation of the ventromedial prefrontal cortex and approval of the presented avatar having the characteristic of interest, for example, based on research findings. See Cabeza et al, "Imaging Cognition II: An Empirical Review of 275 PET and fMRI Studies," J. Cognitive Neurosci., vol. 12, pp. 1-47 (2000).

Operation 1508 depicts associating activity in at least one of the frontopolar cortex, the prefrontal cortex, the ventral striatum, the orbitofrontal prefrontal cortex, the amygdala, or the nucleus accumbens with a mental state indicating approval. For example, the device 106, association unit 140, emotion association module 242, attention association module 244, and/or cognition association module 346 can associate activity in at least one of the frontopolar cortex, the prefrontal cortex, the ventral striatum, the orbitofrontal prefrontal cortex, the amygdala, or the nucleus accumbens with a mental state indicating approval. In one embodiment, association unit 240 can receive a brain activity measurement indicating activation of the nucleus accumbens in response to presentation to a member of population cohort 102 of an avatar possessing a product as the at least one characteristic. The brain activity measurement indicating activation of the nucleus accumbens may be received from, for example, MEG module 218. Emotion association module 242 and/or attention association module 244 can then match the nucleus accumbens activation measurement to one or more corresponding mental states. For example, activation of the nucleus accumbens is associated in the literature with product preference. Thus an association can be made between activation of the nucleus accumbens and preference for the presented avatar possessing a product, by association unit 240, for example, based on research findings. See Wise, "Thought Police: How Brain Scans Could Invade Your Private Life," Popular Mechanics, (November 2007).

FIG. 16 illustrates alternative embodiments of the example operational flow 500 of FIG. 5. FIG. 16 illustrates example embodiments where the associating operation 530 may include at least one additional operation. Additional operations may include operation 1600, 1602, 1604, 1606, and/or 1608.

Operation 1600 depicts associating activity in the prefrontal cortex with a mental state indicating brand preference. For example, the device 106, association unit 140, emotion association module 242, attention association module 244, and/or cognition association module 346 can associate activity in the prefrontal cortex with a mental state indicating brand preference. In one embodiment, association unit 240 can receive a brain activity measurement indicating activation of the prefrontal cortex in response to presentation to a member of population cohort 102 of an image of a product brand as the at least on characteristic. The brain activity measurement indicating activation of the prefrontal cortex may be received from, for example, fNIR module 314. Emotion association module 242, attention association module 244, and/or cognition association module 346 can then match the prefrontal cortex activation measurement to one or more corresponding mental states. For example, activation of the prefrontal cortex is associated in the literature with brand preference. Thus an association can be made between activation of the prefrontal cortex and preference for the presented image of a product brand, by association unit 240, for example, based on research findings. See Kenning et al., "Neuroeconomics: an overview from an economic perspective," Brain Res. Bull., vol. 67, pp. 343-354 (2005).

Operation 1602 depicts associating activity in the dorsolateral prefrontal cortex, the posterior parietal cortex, the occipital cortex, and the left premotor area with a mental state indicating brand preference. For example, the device 106, association unit 140, emotion association module 242, attention association module 244, and/or cognition association module 346 can associate activity in the dorsolateral prefrontal cortex, the posterior parietal cortex, the occipital cortex, and the left premotor area with a mental state indicating brand preference. In one embodiment, association unit 240 can receive a brain activity measurement indicating activation of the dorsolateral prefrontal cortex, the posterior parietal cortex, the occipital cortex, and the left premotor area in response to presentation to a member of population cohort 102 of a brand embodied in an avatar as the at least on characteristic. The brain activity measurement indicating activation of the dorsolateral prefrontal cortex, the posterior parietal cortex, the occipital cortex, and the left premotor area may be received from, for example, fNIR module 314. Emotion association module 242, attention association module 244, and/or cognition association module 346 can then match the dorsolateral prefrontal cortex, the posterior parietal cortex, the occipital cortex, and the left premotor area activation measurement to one or more corresponding mental states. For example, activation of the dorsolateral prefrontal cortex, the posterior parietal cortex, the occipital cortex, and the left premotor area is associated in the literature with brand preference. Thus an association can be made by association unit 240 between preference for the presented image of a product brand and activation of the dorsolateral prefrontal cortex, the posterior parietal cortex, the occipital cortex, and the left premotor area, for example, based on research findings. This is particularly true when the target brand is the subject's favorite brand. See Kenning et al., "Neuroeconomics: an overview from an economic perspective," Brain Res. Bull., vol. 67, pp. 343-354 (2005). Further, there is evidence for a large-scale neural system for visuospatial attention that includes the right posterior parietal cortex. See Cabeza et al, "Imaging Cognition II: An Empirical Review of 275 PET and fMRI Studies," J. Cognitive Neurosci., vol. 12, pp. 1-47 (2000).

Operation 1604 depicts associating activity in at least one of the inferior precuneus, posterior cingulate, right parietal cortex, right superior frontal gyrus, right supramarginal gyrus, or the ventromedial prefrontal cortex with a mental state indicating brand preference. For example, the device 106, association unit 140, emotion association module 242, attention association module 244, and/or cognition association module 346 can associate activity in at least one of the inferior precuneus, posterior cingulate, right parietal cortex, right superior frontal gyrus, right supramarginal gyrus, or the ventromedial prefrontal cortex with a mental state indicating brand preference. In one embodiment, association unit 240 can receive a brain activity measurement indicating activation of the inferior precuneus and the ventromedial prefrontal cortex in response to presentation to a member of population cohort 102 of an avatar associated with a brand as the at least on characteristic. The brain activity measurement indicating activation of the inferior precuneus and the ventromedial prefrontal cortex may be received from, for example, EEG module 320 and/or fMRI module 316. Emotion association module 242, attention association module 244, and/or cognition association module 346 can then match the inferior precuneus and ventromedial prefrontal cortex activation measurement to one or more corresponding mental states. For example, activation of the inferior precuneus and the ventromedial prefrontal cortex is associated in the literature with brand preference. Thus an association can be made between preference for the presented avatar associated with a brand and activation of the inferior precuneus and the ventromedial prefrontal cortex, by association unit 240, for example, based on research findings. See Kenning et al., "Neuroeconomics: an overview from an economic perspective," Brain Res. Bull., vol. 67, pp. 343-354 (2005).

Operation 1606 depicts associating activity in at least one of the insula, the lateral orbital frontal cortex, or the amygdala with a mental state indicating emotional disapproval. For example, the device 106, association unit 140, and/or emotion association module 242 can associate activity in at least one of the insula, the lateral orbital frontal cortex, or the amygdala with a mental state indicating emotional disapproval. In one embodiment, association unit 240 and/or emotion association module 342 can receive a brain activity measurement indicating activation of the insula in response to presentation of a characteristic to a member of population cohort 102. The brain activity measurement indicating activation of the insula may be received from, for example, fNIR module 314 and/or EEG module 320. Emotion association module 242 and/or association unit 340 can then match the insula activation measurement to one or more corresponding mental states. For example, activation of the insula is associated in the literature with pain, distress, and other negative emotional states. Thus an association can be made between emotional disapproval of the presented characteristic and activation of the insula, by emotional association module 242 and/or association unit 240, for example, based on research findings. See Kenning et al., "Neuroeconomics: an overview from an economic perspective," Brain Res. Bull., vol. 67, pp. 343-354 (2005).

FIG. 17 illustrates alternative embodiments of the example operational flow 500 of FIG. 5. FIG. 17 illustrates example embodiments where the associating operation 530 may include at least one additional operation. Additional operations may include operation 1700, 1702, 1704, 1706, and/or 1708.

Operation 1700 depicts associating activity in the dorsolateral prefrontal cortex with a mental state indicating objective approval. For example, the device 106, association unit 140, emotion association module 242, attention association module 244, and/or cognition association module 346 can associate activity in the dorsolateral prefrontal cortex with a mental state indicating objective approval. In one embodiment, association unit 240 can receive a brain activity measurement indicating activation of the dorsolateral prefrontal cortex proximate to presentation of a characteristic to a member of population cohort 102. The brain activity measurement indicating activation of the dorsolateral prefrontal cortex may be received from, for example, MEG module 218. Emotion association module 242 and/or association unit 340 can then match the dorsolateral prefrontal cortex activation measurement to one or more corresponding mental states. For example, activation of the dorsolateral prefrontal cortex is associated in the literature with objective recognition of benefit despite an emotional perception of unfairness. Thus an association can be made between activation of the DLPFC and objective approval a presented characteristic, for example by emotion association module 342, for example, based on research findings. See Kenning et al., "Neuroeconomics: an overview from an economic perspective," Brain Res. Bull., vol. 67, pp. 343-354 (2005).

Operation 1702 depicts associating activity in the caudate nucleus with a mental state indicating trust. For example, the device 106, association unit 140, emotion association module 242, attention association module 244, and/or cognition association module 346 can associate activity in the caudate nucleus with a mental state indicating trust. In one embodiment, association unit 240 can receive a brain activity measurement indicating activation of the caudate nucleus proximate to presentation of a characteristic to a member of population cohort 102. The brain activity measurement indicating activation of the caudate nucleus may be received from, for example, MEG module 218 and/or fNIR module 214. Emotion association module 242 and/or association unit 340 can then match the caudate nucleus activation measurement to one or more corresponding mental states. For example, activation of the caudate nucleus is associated in the literature with trust-building and reciprocity in economic exchange. Thus an association can be made between activation of the caudate nucleus and a mental state indicating trust in the context of presentation of a characteristic, for example by emotion association module 342, for example, based on research findings. See Kenning et al., "Neuroeconomics: an overview from an economic perspective," Brain Res. Bull., vol. 67, pp. 343-354 (2005).

Operation 1704 depicts associating activity in the hippocampus with a mental state indicating novelty in a perceived object. For example, the device 106, association unit 140, emotion association module 242, attention association module 244, and/or cognition association module 346 can associate activity in the hippocampus with a mental state indicating novelty in a perceived object. In one embodiment, association unit 240 can receive a brain activity measurement indicating activation of the hippocampus proximate to presentation of a characteristic to a member of population cohort 102. The brain activity measurement indicating activation of the hippocampus may be received from, for example, MEG module 218 and/or fMRI module 316. Emotion association module 242, cognition association module 346, and/or association unit 340 can then match the hippocampus activation measurement to one or more corresponding mental states. For example, activation of the hippocampus is associated in the literature with a central role in processing novel stimuli. Thus an association can be made between activation of the hippocampus and a mental state indicating perceived novelty in the context of presentation of a characteristic, for example by cognition association module 346, for example, based on research findings. See Martin et al., "Human experience seeking correlates with hippocampus volume: Convergent evidence from manual tracing and voxel-based morphometry," Neuropsychologia, vol. 45, pp. 2874-81 (2007).

Operation 1706 depicts associating activity in the hippocampus with a mental state indicating lack of inhibition toward a perceived object. For example, the device 106, association unit 140, emotion association module 242, attention association module 244, and/or cognition association module 346 can associate activity in the hippocampus with a mental state indicating lack of inhibition toward a perceived object. In one embodiment, association unit 240 can receive a brain activity measurement indicating activation of the hippocampus proximate to presentation of a characteristic to a member of population cohort 102. The brain activity measurement indicating activation of the hippocampus may be received from, for example, PET module 222 and/or fNIR module 214. Emotion association module 242, cognition association module 346, and/or association unit 340 can then match the hippocampus activation measurement to one or more corresponding mental states. For example, activation of the hippocampus is associated in the literature with a lack of inhibition toward a perceived object. Thus an association can be made between activation of the hippocampus and a mental state indicating a lack of inhibition toward a perceived object in the context of presentation of a characteristic, for example by emotion association module 342, for example, based on research findings. See Wang et al., "Gastric stimulation in obese subjects activates the hippocampus and other regions involved in brain reward circuitry," PNAS, vol. 103, pp. 15641-45 (2006).

Operation 1708 depicts associating at least one brain activity surrogate marker with at least one mental state. For example, the device 106, association unit 140, emotion association module 242, attention association module 244, and/or cognition association module 346 can associate at least one brain activity surrogate marker with at least one mental state. In one embodiment, association unit 240 can receive a brain activity surrogate marker such as a skin response measurement, voice stress measurement, eye movement measurement, and/or iris response measurement proximate to presentation of a characteristic to a member of population cohort 102. The brain activity surrogate marker may be received from, for example, iris response module 232, gaze tracking module 234, skin response module 236, and/or voice response module 238. Emotion association module 242, attention association module 244, cognition association module 246, and/or association unit 240 can then match the brain activity surrogate marker to one or more corresponding mental states. For example, detection of voice patterns indicative of a calm mental state may indicate approval toward a characteristic, particularly in combination with brain activation measurement of caudate nucleus activation as a predictor of trust toward the characteristic. Thus an association can be made between a calm voice pattern and a mental state indicating approval toward a presented characteristic, for example by emotion association module 342, for example, based on research findings. See Sanfey, "Social Decision-Making: Insights from Game Theory and Neuroscience," Science, vol. 318, pp. 598-601 (26 Oct. 2007).

FIG. 18 illustrates alternative embodiments of the example operational flow 500 of FIG. 5. FIG. 18 illustrates example embodiments where the specifying operation 540 may include at least one additional operation. Additional operations may include operation 1800, 1802, and/or 1804.

Operation 1800 depicts specifying the at least one presented characteristic as the at least one avatar attribute based on the at least one mental state. For example, device 306, attribute specification unit 350, voice specification unit 352, and/or non-verbal attribute specification unit 356 can specify the at least one presented characteristic as the at least one avatar attribute based on the at least one mental state. In one embodiment, attribute specification unit 350 can specify a characteristic for presentation to a member of population cohort 102 such as a photographic image of a girl's face with a specific hairstyle. After measurement of a physiologic activity proximate to the presentation, and association of the physiologic activity with a mental state, an attribute specification unit 250, non-verbal attribute specification unit 256, and/or body attribute specification unit 262 can specify the specific hairstyle as the at least one avatar attribute for incorporation into an avatar design. For example, if viewing the hairstyle elicited approval in the member of population cohort 102, specification of an approximation of the hairstyle in the design of an avatar may result in an avatar that is attractive to the member of population cohort 102 and/or population cohort 104 in general.

Operation 1802 depicts specifying the at least one avatar attribute based on a mental state based on a physiologic activity at or above a defined threshold. For example, device 306, attribute specification unit 350, voice specification unit 352, and/or non-verbal attribute specification unit 356 can specify at least one avatar attribute based on a mental state based on a physiologic activity at or above a defined threshold. In one embodiment, attribute specification unit 350 can specify an avatar attribute that is based on a presented characteristic that elicits, for example, activity in the frontopolar cortex above a specified intensity level, as measured by, for example, fMRI or fNIR. Because low level activations of the frontopolar cortex may occur frequently having little or no significance in terms of indicating mental state (an association unit 240 may nevertheless make an association based on low level activation of a brain area or surrogate marker), a filter may be employed to allow only mental state associations founded on activations above a certain threshold to pass to an attribute specification unit 250. Such a filter may be employed at the level of the physiologic measurement unit 210 such that measurements that do not meet or exceed the defined threshold level or intensity are not transmitted to the association unit 240. Alternatively, a filter may be employed at the stage of the association unit 240 such that only associations between mental state and physiologic measurements at or above the defined threshold are transmitted to attribute specification unit 250. In addition or alternatively, a filter may be employed at the level of the attribute specification unit 250 such that mental states grounded on physiological measurements below the defined threshold are not specified.

Operation 1804 depicts specifying the at least one avatar attribute based on a mental state based on a physiologic activity signature. For example, device 306, attribute specification unit 350, voice specification unit 352, and/or non-verbal attribute specification unit 356 can specify at least one avatar attribute based on a mental state based on a physiologic activity signature. In one embodiment, attribute specification unit 350 can specify an avatar attribute that is based on a presented characteristic that elicits, for example, a specific constellation of brain activity and/or surrogate marker(s) of brain activity, as measured by, for example, fMRI module 216, fNIR module 214, and/or by surrogate marker measurement unit 230. For example, presentation of a face characteristic to a member of population cohort 102 may coincide with detection of activation of the visual cortex (perhaps indicating visual contact with the characteristic); activation of the right prefrontal and parietal areas (perhaps indicating visual vigilance, i.e., attention); activation of the right hemisphere of the bilateral fusiform gyrus (perhaps indicating perception of the face characteristic); activation of the medial temporal regions (perhaps indicating retrieval of an item-specific memory); and activation of the ventral striatum and decreased activity in the insula (perhaps indicating a positive emotional response such as approval); increased frequency of eye movements to the face characteristic; and iris dilation. An association unit 240 may associate some or all of the above physiological measurements with one or more mental states, in effect creating a signature mental state for the reaction of member of population cohort 102 to the face characteristic; alternatively, association unit 240 may identify a known physiologic activity signature or pattern that corresponds to a known mental state, i.e., a known association.

FIG. 19 illustrates alternative embodiments of the example operational flow 500 of FIG. 5. FIG. 19 illustrates example embodiments where the flow 500 may include additional operation 1950.

Operation 1950 depicts performing successive iterations of the presenting at least one characteristic to at least one member of a population cohort, the measuring at least one physiologic activity of the at least one member of the population cohort, the at least one physiologic activity proximate to the at least one presented characteristic, and the associating the at least one physiological activity with at least one mental state. For example, device 106, presentation device 364, physiologic activity measurement unit 310, association unit 340, and/or attribute specification unit 350 may perform successive iterations of the presenting at least one characteristic to at least one member of a population cohort, the measuring at least one physiologic activity of the at least one member of the population cohort, the at least one physiologic activity proximate to the at least one characteristic, and the associating the at least one physiological activity with at least one mental state.

In one embodiment, device 206 can present a characteristic to member of population cohort 102, during which time physiologic activity measurement unit 210, brain activity measurement unit 212, and/or surrogate marker measurement unit 230 can measure a physiologic activity that is proximate to the presentation of the characteristic to the member of population cohort 102. Association unit 240, emotion association module 242, attention association module 244, and/or cognition association module 246 may then associate the physiologic measurement with at least one mental state. Attribute specification unit 250 may then specify an avatar attribute based on the mental state, for example an approving mental state. In a successive iteration, the attribute specification unit 250 may send an avatar including the characteristic previously associated with an approving mental state to presentation unit 270 for presentation, perhaps to a different member of population cohort 104. Alternatively, an avatar may be sent including a variant of the characteristic previously associated with an approving mental state to presentation unit 270 for presentation to the same member of population cohort 102 or to a different member of population cohort 104. Alternatively, an avatar may be sent including a different characteristic to presentation unit 270 for presentation to the same member of population cohort 102 or to a different member of population cohort 104. This process may be repeated in rapid succession to gauge preferences of a member of population cohort 102 and/or other members of population cohort 104 for attributes of an avatar and/or an avatar as whole.

FIG. 20 illustrates a partial view of an example computer program product 2000 that includes a computer program 2004 for executing a computer process on a computing device. An embodiment of the example computer program product 2000 is provided using a signal bearing medium 2002, and may include one or more instructions for presenting at least one characteristic to at least one member of a population cohort; one or more instructions for measuring at least one physiologic activity of the at least one member of the population cohort, the at least one physiologic activity proximate to the at least one presented characteristic; one or more instructions for associating the at least one physiological activity with at least one mental state; and one or more instructions for specifying at least one avatar attribute based on the at least one mental state. The one or more instructions may be, for example, computer executable and/or logic-implemented instructions. In one implementation, the signal-bearing medium 2002 may include a computer-readable medium 2006. In one implementation, the signal bearing medium 2002 may include a recordable medium 2008. In one implementation, the signal bearing medium 2002 may include a communications medium 2010.

FIG. 21 illustrates an example system 2100 in which embodiments may be implemented. The system 2100 includes a computing system environment. The system 2100 also illustrates a member of population cohort 102 using a device 2104, which is optionally shown as being in communication with a computing device 2102 by way of an optional coupling 2106. The optional coupling 2106 may represent a local, wide-area, or peer-to-peer network, or may represent a bus that is internal to a computing device (e.g., in example embodiments in which the computing device 2102 is contained in whole or in part within the device 2104). A storage medium 2108 may be any computer storage media. In one embodiment, the computing device 2102 may include a virtual machine operating within another computing device. In an alternative embodiment, the computing device 2102 may include a virtual machine operating within a program running on a remote server.

The computing device 2102 includes computer-executable instructions 2110 that when executed on the computing device 2102 cause the computing device 2102 to (a) present at least one characteristic to at least one member of a population cohort; (b) measure at least one physiologic activity of the at least one member of the population cohort, the at least one physiologic activity proximate to the at least one presented characteristic; (c) associate the at least one physiological activity with at least one mental state; and (d) specify at least one avatar attribute based on the at least one mental state. As referenced above and as shown in FIG. 21, in some examples, the computing device 2102 may optionally be contained in whole or in part within the device 2104.

In FIG. 21, then, the system 2100 includes at least one computing device (e.g., 2102 and/or 2104). The computer-executable instructions 2110 may be executed on one or more of the at least one computing device. For example, the computing device 2102 may implement the computer-executable instructions 2110 and output a result to (and/or receive data from) the computing device 2104. Since the computing device 2102 may be wholly or partially contained within the computing device 2104, the device 2104 also may be said to execute some or all of the computer-executable instructions 2110, in order to be caused to perform or implement, for example, various ones of the techniques described herein, or other techniques.

The device 2104 may include, for example, a portable computing device, workstation, or desktop computing device. In another example embodiment, the computing device 2102 is operable to communicate with the device 2104 associated with the member of population cohort 102 to receive information about physiologic activity of the member of population cohort 102 for performing data access and data processing, and to specify at least one avatar attribute based on at least one mental state, the mental state based on the physiologic activity of the member of population cohort 102.

Although a member of population cohort 102 is shown/described herein as a single illustrated figure, those skilled in the art will appreciate that a member of population cohort 102 and/or a member of population 105 may be composed of two or more entities. Those skilled in the art will appreciate that, in general, the same may be said of "sender" and/or other entity-oriented terms as such terms are used herein.

Comparison of Media Content

FIG. 22 illustrates an operational flow 2200 representing example operations related to comparing media content. In FIG. 22 and in following figures that include various examples of operational flows, discussion and explanation may be provided with respect to the above-described system environments of FIGS. 1-4, and/or with respect to other examples and contexts. However, it should be understood that the operational flows may be executed in a number of other environment and contexts and/or in modified versions of FIGS. 1-3. Also, although the various operational flows are presented in the sequences illustrated, it should be understood that the various operations may be performed in other orders than those which are illustrated, or may be performed concurrently.

After a start operation, operation 2210 depicts presenting to at least one member of a population a plurality of avatars associated with at least one instance of media content. For example, a device 206, attribute specification unit 250, and/or presentation unit 270 may present to at least one member of a population a plurality of avatars associated with at least one instance of media content. In one embodiment, an attribute specification unit 250 can transmit a plurality of avatars having a media content attribute, for example, on an item of clothing or as a facial feature, for display to a member of population 105 on a presentation unit 270 and/or display 272.

Optionally, presented avatars and associated media content may be encountered during an interaction of the member of population 105 with a virtual world. In one embodiment, a clothing specification unit 260 can present a photograph of a particular item of clothing featuring, for example, Paris Hilton as an instance of media content, on an avatar via mobile display 276, e.g., a cellular phone. Other avatars may be similarly sent to a member of population 105, in sequence or simultaneously. If a plurality of avatars is sent simultaneously, eye tracking technology may be used to determine which avatar is being viewed at any given time. In this way the system 100 may be used to carry out comparative advertising of one or more instances of media content as a way to gauge an individual's reactions to various instances of media content and/or avatars, perhaps including cohort-linked avatars. In another embodiment, a facial attribute specification unit 258 can present to a member of population 105 a likeness of various public figures on a plurality of avatars in the context a virtual world or social networking website via, for example, a desktop display 274.

For example, a device 106, attribute specification unit 250, and/or presentation unit 270 may present to at least one member of population 105 a set of avatars associated with audio media content, for example music samples or clips, or recognizable voice sounds or verbal content. In one embodiment, a body attribute specification unit 362 may communicate via a network 374, for example, with a presentation device 364 to present to member of population 105 a plurality of avatars with distinguishing body features that portray media content, such as a famous tattoo or an animal form, such as a famous dog.

In another embodiment, a speech specification unit 254 of the device 306 may present a plurality of avatars with media content in the form of a speech characteristic such as accent, dialect, tone, or pitch associated with, for example, a politician, to a member of population 105 via, for example, a personal communication device such as a video-capable cellular phone. For example, attribute specification unit 250 may initiate the presentation of a set of avatars associated with particular media content characteristics such as various hair care products or skin care products to a member of population 105 in response to the member of population 105 signing on to a social networking website. The presentation of the set of avatars may be through, for example, a widget on the social networking website.

It should be understood that instances of media content may be combined to provide feedback about composite features of presented attributes with one or more avatars. For example, an attribute specification unit 350 may present to a member of population 105 a composite of voice attribute, facial attribute, clothing attribute, and body attribute characteristics that approximates the appearance of a celebrity such as Angelina Jolie via an online shopping experience, such as a virtual personal shopping assistant. A plurality of such assistants may be presented in order to compare reactions of the member of population 105 to, for example, an Angelina Jolie avatar and a Jessica Simpson avatar.

A verbal attribute or characteristic may be presented as an instance of media content, such as foreign language or accented speech associated with a public figure. Examples include John Edwards' southern accent, Ted Kennedy's Boston accent, Antonio Banderas' Spanish accent, James Bonds' British accent, or the like. Such voice variations may be computer-detectable and/or computer-implemented. See, for example, U.S. Pat. No. 7,263,489 "Detection of characteristics of human-machine interactions for dialog customization and analysis." Prosodic features of speech such as intonation, stress, and other paralinguistic features of speech such as voice quality, emotion, and speaking style may also be presented as an instance of media content.

An instance of media content may also include paralanguage, a.k.a., vocalics, which involves nonverbal cues of the voice. Various acoustic properties of speech such as tone, pitch, accent, or the like, collectively known as prosody, can be presented as nonverbal characteristics. Paralanguage may be used to present a characteristic, as well as voice qualities including volume, pitch, tempo, rhythm, articulation, resonance, nasality, and/or accent. For example, various celebrities exhibit identifiable paralanguage patterns, such as Ed McMahon's laugh, or Tom Waits' gravelly voice, which has been described on Wikipedia as distinctive and "sounding 'like it was soaked in a vat of bourbon, left hanging in the smokehouse for a few months and then taken outside and run over with a car.'" Vocalization cues also may be presented as the characteristic, including emotions expressed during or associated with speech, such as laughing, crying, and/or yawning. Vocalization cues also may include delivery nuances such as volume and/or pitch modulation such as whispering and shouting. Vocalization cues also may include vocal segregates such as "um" in between spoken expressions, or "uh-huh," "like," "no way," or other phrase in response to another's speech to indicate comprehension, to punctuate speech, and/or to manage contact during dialogue. See, for example, U.S. Pat. No. 6,356,868, "Voiceprint identification system." Such a vocalization cue may be an instance of media content, such as an imitation of Jeff Spicoli from the movie Fast Times at Ridgemont High, e.g., "Hey Bud, what's your problem?" or "Don't hassle it" said in a distinctive California surfer style.

Alternatively, a non-verbal attribute or characteristic including physical appearance and/or non-verbal communication may be presented as an instance of media content. For example, body language used by a celebrity or an accessory such as Elton John's glasses and/or platform shoes. Non-verbal communication characteristics may also include, for example, a facial expression, a gesture, a gaze, and/or a posture. Such behaviors carried out by an avatar in the likeness of a public media figure such as a celebrity may be an instance of media content. An instance of media content may also include clothing, hairstyle, adornment, shoes, and/or other communicative props; or even architecture, a symbol, and/or an infographic. Accordingly, a trademarked item in the popular or traditional culture may be an instance of media content.

Kinesic behaviors such as body movements, facial expressions, and gestures may also be presented instances of media content. Kinesic behaviors may include mutual gaze, smiling, facial warmth or pleasantness, childlike behaviors, direct body orientation, and the like. An attribute specification unit 250 and/or presentation unit 270 can present a movement characteristic such as a kineme, which is a unit of visual expression analogous to a phoneme, a unit of speech. Presentable gestures may include emblems, illustrators, affect displays, regulators, and/or adaptors that are identifiable as media content. An emblem is a gesture with a direct verbal translation such as a wave of the hand; an illustrator is a gesture that depicts a concept that is substantially simultaneously spoken, such as turning an imaginary steering wheel while speaking about driving; an affect display is a gesture that conveys emotions, such as a smile or a frown; a regulator is a gesture that controls interaction such as a "shhh" sign placing an index finger vertically at the center of the lips; and finally, an adaptor is a gesture that facilitates release of body tension, such as quick, repetitive leg movements or stretching. Such behaviors carried out by an avatar in the likeness of a public media figure may be an instance of media content.

A presented set of avatars with an instance of media content may include an advertising symbol and/or a brand name, design, symbol, or logo (e.g., trademarks of corporations such as a Bic® pen, a Rolex® watch, a McDonald's® restaurant, a Hermes® scarf, a Louis Vuitton® bag, or a Les Paul® guitar). A service mark may also be presented as an instance of media content.

In some embodiments, an avatar may include, for example, a three dimensional model, a two dimensional icon or image, a text construct, an audio construct, and/or an attribute of a personality connected with a screen name. In one embodiment, an avatar may be an attribute of a real world object, and/or a real world object. In other embodiments, an avatar may include, for example, an embodiment, as of a quality or a concept. In another example, an avatar may include an archetype. In another embodiment, an avatar may include a manifestation or aspect of a continuing entity, not necessarily a person. For example, a manifestation or aspect of a corporation may be an avatar attribute, as may be a specification for a class of robots. Accordingly, a cohort-linked avatar may be an overall representation of what is happening in a population cohort with respect to a presented characteristic and/or set of characteristics. Other examples of an avatar are known to those of ordinary skill in the art.

Operation 2220 depicts measuring at least one physiologic activity of the at least one member of the population, the at least one physiologic activity proximate to at least one presented avatar among the plurality of avatars associated with at least one instance of media content. For example, a physiologic activity measurement unit 210, brain activity measurement unit 212, and/or surrogate marker measurement unit 230 may measure at least one physiologic activity of the at least one member of the population, the at least one physiologic activity proximate to at least one presented avatar among the plurality of avatars associated with at least one instance of media content. For example, during presentation of the plurality of avatars associated with the at least one instance of media content to the member of the population 105, a fNIR module may detect brain activity in the member of the population 105, perhaps indicative of approval of one or more instances of media content in one or more measured instances of visual contact with one or more avatars among the plurality of avatars. Of course other measurement methods may be used including fMRI, MEG, EEG, PET, either singly or in combination. Optionally, surrogate markers of brain activity may be employed to detect physiologic activity in the member of population 105, such as a voice response to an avatar associated with the at least one instance of media content, an eye movement response to an avatar associated with the at least one instance of media content, a skin response to an avatar associated with the at least one instance of media content, or the like. Surrogate markers of brain activity may be used alone or in combination with other physiologic activity measurements such as brain activity measurement to characterize activity in the member of population 105 that is proximate to presentation of one or more avatars among a plurality of presented avatars.

For example, detected brain activity may be proximate in time to presentation and/or viewing of one avatar associated with the at least one instance of media content among a plurality of avatars by the member of the population 105, as determined by one or more of brain activity indicative of visual activity (e.g., activity in the visual cortex), selective attention (e.g., activity in fronto-parietal areas), and/or perception (e.g., activity in the ventral pathway). Detected physiologic activity may be determined to be proximate in time using an eye movement or gaze tracking measurement to identify times when a member of the population 105 looks at an avatar associated with the at least one instance of media content. In one embodiment, eye movement or gaze tracking data may be matched with a time course of brain activity to associate a particular brain area activation with visual contact of the member of the population 105 with a presented avatar associated with the at least one instance of media content.

In another embodiment, eye movement or gaze tracking data may be matched with a time course of voice response, skin response, or other surrogate marker of brain activity to associate a particular physiologic activity with visual contact of the member of the population 105 with a presented avatar associated with the at least one instance of media content.

In the context of storing physiologic activity measurement data, it should be understood that a data signal may first be encoded and/or represented in digital form (i.e., as digital data), prior to an assignment to at least one memory. For example, a digitally-encoded representation of user eye movement data may be stored in a local memory, or may be transmitted for storage in a remote memory.

Thus, an operation may be performed relating either to a local or remote storage of the digital data, or to another type of transmission of the digital data. Of course, as discussed herein, operations also may be performed relating to accessing, querying, processing, recalling, or otherwise obtaining the digital data from a memory, including, for example, transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

Operation 2230 depicts associating the at least one physiologic activity with at least one mental state. For example, a device 206 and/or association unit 240 may associate the at least one physiologic activity with at least one mental state. For example, association unit 240 may associate approval with a pattern of activation of the reward center, including for example, the striatum and caudate, and areas of the midbrain and cortex to which they project, such as the ventromedial prefrontal cortex, orbitofrontal cortex, and anterior cingulated cortex. In one embodiment, an association unit 240 may search a database of functional brain mapping that contains information about which brain regions are associated with particular mental states and/or functions. Such a database search may be keyed to brain activation pattern, and/or to mental state and/or function. For example, an association unit 240 may search measured brain activation information and/or surrogate marker information for data consistent with trust. For example, a measured activation of a region of the brain associated with trust, such as the caudate nucleus, may be associated with trust as the at least one mental state. Alternatively or in addition, measurement of a surrogate marker such as an approving voice response proximate to the at least one avatar associated with an instance of media content may be associated with approval as the at least one mental state by an association unit 140.

Operation 2240 depicts identifying at least one instance of media content based on the at least one mental state. For example, a device 206 and/or media content identification unit 166 may identify at least one instance of media content based on the at least one mental state. For example, a device 206 and/or media content identification unit 266 may identify at least one trade dress as an instance of media content based on an approving mental state among a member of population 105 identified by association with a measured physiologic activity proximate to a presented avatar associated with an instance of media content. Such an approving mental state for an identified instance of media content may be relative to measured physiological activity and/or associated mental states identified for comparators among the plurality of presented avatars associated with instances of media content. In one embodiment, an association of a high degree of attention on the part of a member of population 105 with a specific avatar associated with a specific instance of media content may provide the basis for a media content identification unit 266 to identify the specific instance of media content as one that is particularly appealing and/or noticeable, by virtue of the measured display of attention relative to other presented avatars with instance of media content.

In another embodiment, a media content identification unit 366 may identify an instance of media content based on the at least one mental state. The identification may be based on an association by association unit 240 of a positive emotional response between, for example, a tonal voice quality of the member of population 105 proximate to viewing one avatar associated with an instance of media content among a presented plurality of avatars, as measured by, for example, brain activity measurement unit 212 and/or a surrogate marker measurement unit 230.

Accordingly, in one embodiment, a media content identification unit 366 may send an positively identified avatar associated with an instance of media content to a presentation device 364 for subsequent presentation with a plurality of avatars to another member of population 105 for comparative testing in other individuals to obtain additional data points for the population 105 and/or population cohort 104. The process may be repeated reiteratively as a means of obtaining more data points toward an optional goal of achieving a statistical confidence that an identified avatar and/or instance of media content is, for example, preferred relative to other instances of media content and/or avatars.

FIG. 23 illustrates alternative embodiments of the example operational flow 2200 of FIG. 22. FIG. 23 illustrates example embodiments where the presenting operation 2210 may include at least one additional operation. Additional operations may include operation 2300, 2302, and/or operation 2304.

Operation 2300 depicts presenting to the at least one member of the population a plurality of avatars, each avatar associated with at least one of an instance of movie content, an instance of television content, an instance of music content, an instance of literature content, an instance of internet content, an instance of news content, or an instance of advertising content. For example, an attribute specification unit 150, presentation device 364, presentation unit 270, and/or device 106 may present to the at least one member of the population a plurality of avatars, each avatar associated with at least one of an instance of movie content, an instance of television content, an instance of music content, an instance of literature content, an instance of internet content, an instance of news content, or an instance of advertising content. For example, attribute specification unit 150 and/or presentation device 364 may present a plurality of avatars with computer-generated likenesses of Harry Potter characters such as Ron Weasley and Hermione Granger to the member of population 105 via, for example, presentation unit 170.

In another embodiment, attribute specification unit 250 may specify a plurality of avatars in the likeness of characters from the movie Cars, such as Lightning McQueen, Mater, and Luigi, for presentation to the at least one member of a population 105. Similarly, an attribute specification unit 350 and/or presentation device 364 may present a plurality of speech attributes of a movie star, such as Arnold Schwarzenegger's accented speech and one-liners from one of his movies such as "I'll be back" from the Terminator and/or "Hasta la vista, baby" from Terminator 2). Another example includes lines from the Star Wars franchise such as "May the force be with you," "Use the force, Luke," and/or "No. I am your father").

As another example, attribute specification unit 150 and/or presentation device 364 may present a plurality of avatars with computer-generated likenesses of Jay Leno saying various things to the member of population 105 via, for example, presentation unit 170.

In another embodiment, attribute specification unit 250 may specify a set of avatars with the likenesses of Seinfeld characters such as Jerry, George, Elaine, Kramer, and/or Newman, perhaps in combination with a product for advertising purposes, for presentation to the at least one member of a population 105. Similarly, an attribute specification unit 350 and/or presentation device 364 may present a particular speech attribute of a television show, such as Kramer's "Giddy up!", Jerry's "that's a shame," and/or "Here's Johnny!" from the Tonight Show. Another example is Homer Simpson's catchphrase "D'oh!"

As another example, attribute specification unit 150 and/or presentation device 364 may present a plurality of avatars, each with a music clip, for example a variety of Coldplay songs, or clips of songs from different bands to the member of population 105 via, for example, presentation unit 170.

In another embodiment, attribute specification unit 250 may specify a plurality of avatars each with a shirt that displays the name of a band, such as "Led Zeppelin," "Grateful Dead," "Yo-Yo Ma," and/or "Nora Jones," for presentation to the at least one member of a population 105. Similarly, an attribute specification unit 350 and/or presentation device 364 may present a particular lyrical attribute of a song, such as "Bust a move" from the song of the same name by Young MC. Another example is an avatar singing a child's song such as "Mary had a little lamb." For example, attribute specification unit 150 and/or presentation device 364 may present a plurality of avatars each with a music clip as an identifier, a jingle associated with a product, or the like. Similarly, an attribute specification unit 350 and/or presentation device 364 may present a plurality of avatars each with a musical attribute such as a music sample from a well-known song, such as Beethoven's Fifth Symphony, or a sample from a popular music song.

In another example, attribute specification unit 150 and/or presentation device 364 may present a plurality of avatars in the likeness of Moby Dick's white whale, Queequeg, and/or Captain Ahab to the member of population 105 via, for example, presentation unit 170. In another embodiment, attribute specification unit 250 may specify a plurality of avatars each associated with an item of clothing that has the name of a book character or theme, or the name of a magazine on it, for example, Goliath or The New Yorker, respectively, for presentation to the at least one member of a population 105. Similarly, an attribute specification unit 350 and/or presentation device 364 may present an avatar with a non-human literary characteristic, such as Treebeard from Tolkien's "The Lord of the Rings." Another example is an avatar in the likeness of a nursery rhyme character such as Peter Peter pumpkin eater.

In another example, attribute specification unit 150 and/or presentation device 364 may present a plurality of avatars each in the likeness of an internet character, such as Homestar from homestarrunner.com or Kelly from Liamshow.com to the member of population 105 via, for example, presentation unit 170. Such avatars may be accompanied by sound, video, or other characteristic from any source. In another embodiment, attribute specification unit 250 may specify a plurality of avatars with an item of clothing that has a reference to internet content on it, for example, Slate and/or Google, for presentation to the at least one member of a population 105. Similarly, an attribute specification unit 350 and/or presentation device 364 may present a plurality of avatars with an attribute of a blog, such as a Steelers football fan blog like www.pittsburghsteelersfanatic.com or a news blog. Another example is an avatar in the likeness of a social networking website persona, such as a person having a facebook page, a myspace page; and/or an identity and/or video on youtube.com.

In another embodiment, attribute specification unit 150 and/or presentation device 364 may present a plurality of avatars in the likeness of a news anchor or an avatar associated with an item of current events to the member of population 105 via, for example, presentation unit 170. In another embodiment, attribute specification unit 250 may specify a plurality of avatars each with a news source logo on an item of clothing, for example, CNN or Fox News, for presentation to the at least one member of a population 105. Similarly, an attribute specification unit 350 and/or presentation device 364 may present a plurality of avatars with an attribute of a news blog, such as http://www.topix.com/news/blogs. Another example is a plurality of avatars in the likeness of news commentators, such as Walter Kronkite, Don Imus, or Rush Limbaugh.

In another embodiment, an attribute specification unit 250, presentation unit 270, display 272, and/or device 106 may present to the at least one member of the population a plurality of avatars associated with at least one instance of advertising. For example, attribute specification unit 150 and/or presentation device 364 may present a plurality of avatars incorporating a logo, brand name, and/or item, for example, an item of clothing, for example, a photograph of an ipod, a whopper sandwich, a can of Budweiser beer, or the like, for presentation to the at least one member of a population 105.

In another example, attribute specification unit 150 and/or presentation device 364 may present a plurality of avatars with a short video clip playing, for example on the chest of an avatar, the back of an avatar, or the like. Such a video in association with an avatar may be clickable for better viewing of the video, for example via expansion in size and/or opening of a separate viewing window and/or media player program.

In another embodiment, attribute specification unit 250 may specify one of a plurality of avatars associated with a video playing an advertisement, a logo and/or brand name video clip or montage, and/or a video depiction on an item on a piece of clothing, for example, a Porsche automobile driving, a diamond sparkling, or the like, for presentation to the at least one member of a population 105. Similarly, an attribute specification unit 350 and/or presentation device 364 may present one of a plurality of avatars with a video attribute of a celebrity, such as a sports figure in action.

Operation 2302 depicts presenting to the at least one member of the population a plurality of substantially similar avatars, each avatar associated with a substantially different instance of media content. For example, attribute specification unit 250, presentation unit 270, display 272, and/or device 106 may present to the at least one member of the population a plurality of substantially similar avatars, each avatar associated with a substantially different instance of media content. In one embodiment, a set of five identical cohort-linked avatars with demonstrated appeal to a population cohort 104 may be each assigned a different instance of media content, for example, five different brands of coffee. In this case, presentation to a member of population cohort 102 of the five avatars together with a displayed coffee brand may elicit different physiologic activity proximate to the presentation of the avatars, either one at a time in sequence, or in some combination presentation. In another example, synergistic marketing of complementary products may be investigated by, for example, presenting avatars with complementary brands to a member of population 105. For example, the measured physiologic activity proximate to the presentation of an avatar with a particular coffee brand logo alone may be compared with measured physiologic activity proximate to presentation of the particular coffee brand logo together with a song clip from a popular band, for example, after a 30 second time delay.

Operation 2304 depicts presenting to the at least one member of the population a plurality of substantially distinct avatars, each avatar associated with a substantially similar instance of media content. For example, attribute specification unit 250, presentation unit 270, display 272, and/or device 106 may present to the at least one member of the population a plurality of substantially distinct avatars, each avatar associated with a substantially similar instance of media content. In one embodiment, a group of cohort-linked avatars may be assembled that appeal preferentially to various demographic groups, for example, three cohort-linked avatars that appeal preferentially to females aged 8-12, males aged 18-25, and all people over the age of 50, respectively. These three avatars can then be presented to a member of a population 105 either sequentially or together in order to measure presentation-proximate physiologic activity that may be associated with a particular mental state, as discussed below. Accordingly, media content appeal may be gauged in the member of population 105, and/or the member of population 105 may be assigned to a population cohort 104 based on a presentation-proximate mental state associated with a particular cohort-linked avatar. For example, if the member of population 105 exhibits disapproval of two of the three presented avatars, the member of population 105 may be assigned to the population cohort represented by the third presented avatar.

FIG. 24 illustrates alternative embodiments of the example operational flow 2200 of FIG. 22. FIG. 24 illustrates example embodiments where the presenting operation 2210 may include at least one additional operation. Additional operations may include operation 2400, 2402, 2404, and/or operation 2406.

Operation 2400 depicts presenting to at least one member of a family group the plurality of avatars associated with at least one instance of media content. For example, an attribute specification unit 250, presentation unit 270, display 272, and/or device 106 may present to at least one member of a family group the plurality of avatars associated with at least one instance of media content. For example, an attribute specification unit 350 may present a plurality of avatars each associated with an instance of media content to a mother and daughter as the at least one member of a family group. Such a comparison of physiological activity proximate to presentation of the avatars among related family members may provide information about two population cohorts (e.g., young female and old female within a certain ethnic and/or income demographic). Such comparison if done between or among siblings may investigate cultural and/or finely graded age distinctions with respect to reactions to the avatars associated with the at least one instance of media content.

Operation 2402 depicts presenting to at least one member of a population cohort the plurality of avatars associated with at least one instance of media content. For example, an attribute specification unit 250, presentation unit 270, display 272, and/or device 106 may present to at least one member of a population cohort the plurality of avatars associated with at least one instance of media content. In one embodiment, a plurality of avatars each bearing the likeness of a politician or otherwise bearing an association with a specific politician may be presented to a member of population cohort 102, e.g., a middle-aged male living in California. Differential physiologic responses and associated mental states among the avatars may give an indication of which politician is preferred by that population cohort 104, e.g., middle-aged male Californians.

Operation 2404 depicts presenting to at least one member of at least one of an age cohort, a gender cohort, an ethnicity cohort, or a purchasing cohort the plurality of avatars associated with at least one instance of media content. For example, an attribute specification unit 250, presentation unit 270, display 272, and/or device 106 may present to at least one member of at least one of an age cohort, a gender cohort, an ethnicity cohort, or a purchasing cohort the plurality of avatars associated with at least one instance of media content. In one embodiment, a plurality of avatars associated with at least one instance of media content may be presented to a group of people known to have purchased a Porsche automobile in cash within the last five years as a purchasing cohort. Another example includes a group of people who have bought makeup from a particular retailer as both a gender and a purchasing cohort; to such a group a plurality of avatars associated with skin care advertising may be presented for comparison.

Identification of age, gender, ethnicity, and/or purchasing characteristics of an individual may be ascertained through information given by the individual, through measurement of external characteristics of the individual, or indirectly through inference (e.g., as in the makeup purchasing case above, it can reasonably be inferred that a makeup purchaser is a female, though that may not be true in every instance). For example, device 106, physiologic activity measurement unit 110, and/or media content identification unit 266 may attach demographic or other identifying information to a population member 105.

For example, an age, gender, ethnicity, and/or purchasing characteristic may be derived from facial features, body features, iris characteristic, physiologic measurements, or the like. For example, a specific eye shape and/or iris pattern can be associated with an asian population cohort. For example, a bank of multichannel 2D Gabor filters may be used to capture global texture information about an a subject's iris, and AdaBoost, a machine learning algorithm, may be used to allow a surrogate marker measurement unit 330, for example, to learn a discriminant classification principle from a pool of candidate iris feature sets. Iris image data may be thus grouped into race categories, for example, Asian and non-Asian. See Qui et al., "Global Texture Analysis of Iris Images for Ethnic Classification," Lecture notes in computer science, Springer:Berlin/Heidelberg, Advances in Biometrics, pp. 411-418 (2005).

In addition, a number of methods of identifying ethnicity based on facial features are known in the art, for example, ethnicity identification may be formulated as a two-category classification problem, for example, to classify the subject as an Asian or non-Asian. The input images may be resized to different scales. At each scale, a classic appearance-based face recognizer based on a linear discriminant analysis representation may be developed under a Bayesian statistical decision framework. An ensemble may then be constructed by integrating classification results to arrive at a final decision. The product rule may be used as an integration strategy. See Lu et al., "Ethnicity Identification from Face Images," Biometric Technology for Human Identification, Eds. Jain et al., Proc. SPIE, Vol. 5404, pp. 114-123 (2004).

Subject ethnicity identification may be based on a number of factors including skin and/or hair characteristics associated with ethnicity, such as red hair among Caucasians; voice and/or speech associated with ethnicity, such as French-accented English indicating French or French-Canadian ethnicity; face pattern associated with ethnicity, such as eye shape, nose shape, face shape, or the like; and eye attributes such as blue eyes among Caucasians. In one embodiment, Gabor wavelets transformation and retina sampling from physiologic measurement data may be combined to extract key facial features, and support vector machines may be used for ethnicity classification. An experimental system has used Gabor wavelets transformation and retina sampling in combination to extract key facial features, and support vector machines were used for ethnicity classification, resulting in approximately 94% success for ethnicity estimation under various lighting conditions. See Hosoi et al., "Ethnicity estimation with facial images," Sixth IEEE International Conference on Automatic Face and Gesture Recognition, pp. 195-200 (2004). Of course other methods of ethnicity, age, gender or other demographic identification known in the art may be used.

Alternatively, media content identification unit 266 may identify a population cohort 104 based on information provided by the member of population 105 directly, for example as part of a registration or permission process. Such information may convey geographic residence information, income level information, shopping habit information, age, gender, ethnicity, or other demographic information.

Operation 2406 depicts presenting to the at least one member of the population the plurality of avatars, each avatar associated with at least one of an image instance of media content, an audio instance of media content, a video instance of media content, or an animation instance of media content. For example, an attribute specification unit 250, presentation unit 270, display 272, and/or device 106 may present to the at least one member of the population the plurality of avatars, each avatar associated with at least one of an image instance of media content, an audio instance of media content, a video instance of media content, or an animation instance of media content. For example, attribute specification unit 150 and/or presentation device 364 may present a plurality of avatars each with an image of the likeness of an advertising campaign character such as Smokey the Bear, Mr. Peanut, Mr. Clean, or the like.

In another embodiment, attribute specification unit 250 may specify a plurality of avatars each with a logo, brand name, and/or item depiction on an item of clothing, for example, coca-cola, pepsi, ibm, intel, or the like, for presentation to the at least one member of a population 105. Similarly, an attribute specification unit 350 and/or presentation device 364 may present a set of avatars with an attribute of an advertising campaign, such as a jingle like intel's 5-note "D-flat D-flat G-flat D-flat A-flat" sonic logo, also known as a tag or audio mnemonic. Another example is a set of avatars in the likeness of a product, such as a personification of an item, such as the California Raisins or Mrs. Butterworth.

FIG. 25 illustrates alternative embodiments of the example operational flow 2200 of FIG. 22. FIG. 25 illustrates example embodiments where the presenting operation 2210 may include at least one additional operation. Additional operations may include operation 2500, 2502, and/or operation 2504.

Operation 2500 depicts presenting to the at least one member of the population a plurality of avatars in sequence, each avatar associated with at least one instance of media content. For example, an attribute specification unit 250, presentation unit 270, display 272, and/or device 106 may present to the at least one member of the population a plurality of avatars in sequence, each avatar associated with at least one instance of media content. For example, attribute specification unit 150 and/or presentation device 364 may present two avatars in sequence, each with a variant of an instance of media content. For example, avatars each driving a different model of an automobile line may be presented in sequence to a member of a population 105 in order to identify a preferred car model. In this example, presentation of two models of BMW in sequence, such as the Z4 roadster and the M6 Coupe, may elicit different physiologic activity within an individual, or among individuals in different age and/or income demographics. Such information may be of interest to BMW, advertisers, or other auto manufacturers.

In another embodiment, attribute specification unit 250 may specify for presentation in sequence an avatar associated with a visual image of a product as the instance of media content. Such an avatar may be presented to a member of population 105 on at least two occasions. Such sequential presentation of a substantially identical avatar as the plurality of avatars may provide information about memory encoded and/or retrieved by a first presentation of the avatar. Multiple presentations of an avatar and associated instance of media content over time may provide a time course of reactions of a member of population 105 to the avatar, providing information about, for example, memorability of the avatar, memorability of the instance of media content, novelty of the instance of media content novelty of the avatar over the course of repeated exposure, and/or approval/disapproval of the avatar after repeated exposure. One question that may be addressed by such an approach is "What is the rate at which a given avatar and associated instance of media content gets stale for an otherwise approving member of a population 105 and/or population cohort 104?"

Operation 2502 depicts presenting to at least one of a virtual world participant, a computer game participant, an online shopping participant, or a social networking website participant a plurality of avatars associated with at least one instance of media content. For example, an attribute specification unit 250, presentation unit 270, display 272, and/or device 106 may present to at least one of a virtual world participant, a computer game participant, an online shopping participant, or a social networking website participant a plurality of avatars associated with at least one instance of media content. For example, an attribute specification unit 350 may present a plurality of avatars associated with an instance of media content to a Second Life user as the virtual world participant. Alternatively, a non-verbal attribute specification unit 256 may present a plurality of avatars associated with an instance of media content to a player of an online game, such as World of Warcraft, as the computer game participant. In another embodiment, a facial attribute specification unit 358 may present a plurality of avatars each associated with an instance of media content to a member of population 105 visiting a myspace page or a facebook page as the social networking website participant.

FIG. 26 illustrates alternative embodiments of the example operational flow 2200 of FIG. 22. FIG. 26 illustrates example embodiments where the measuring operation 2220 may include at least one additional operation. Additional operations may include operation 2600, and/or operation 2602.

Operation 2600 depicts measuring at least one physiologic activity of the at least one member of the population using functional near-infrared imaging, the at least one physiologic activity proximate to the at least one presented avatar among the plurality of avatars associated with at least one instance of media content. For example, the device 206, physiologic activity measurement unit 210, brain activity measurement unit 212, and/or fNIR module 214 can measure at least one physiologic activity of the at least one member of the population using functional near-infrared imaging, the at least one physiologic activity proximate to the at least one presented avatar among the plurality of avatars associated with at least one instance of media content. In one embodiment, a member of the population 105 can be monitored by fNIR module 214 during presentation of one of a plurality of avatars associated with the at least one instance of media content to a member of population 105. For example, fNIR module 214 can measure brain activity as the physiologic activity of the at least one member of the population 105.

Proximity of the fNIR measurement to presentation, viewing, and/or perception of the at least one presented avatar associated with the at least one instance of media content can be determined by presentation unit 270, device 206, physiologic activity measurement unit 210, brain activity measurement unit 212, and/or fNIR module 214. For example, the time of presentation of the at least one avatar associated with the at least one instance of media content can be matched with brain activity measured by fNIR module 214. In another embodiment, eye movement and/or gaze tracking analysis can determine the time that a subject's eyes contact a presented avatar associated with the at least one instance of media content, and this can be matched to the time of a measured brain activity by fNIR module 214. In still another embodiment, brain activity in the visual cortex or other perception-indicative brain area or areas can be measured by fNIR module 214 as an indicator of a subject's viewing of a presented avatar associated with an instance of media content; continued measurement of physiologic activity by fNIR module 214 can then measure additional brain activation beyond that of visual/perception activations proximate to the at least one avatar associated with the at least one instance of media content.

In one embodiment, the fNIR module 214 may be located in a kiosk in a public area such as a shopping mall. In such an environment, images of individuals may be captured by photography or videography and compared with reference population 105 image profiles to identify members of population 105 and/or population cohort 104. Accordingly, specific individuals corresponding to a population 105 and/or population cohort 104 may be approached for analysis. In another embodiment, presentation of an avatar associated with at least one instance of media content by, for example, presentation unit 270 and measurement of physiologic activity by, for example fNIR module 214 may occur in a home computing environment, with avatar presentation data sent by, for example, a remote attribute specification unit 350 to a presentation device 364 located in the home. The physiologic activity measurement unit 310 unit may be located in the home environment and send measurement data via a network to a remote device 306 for processing of the data, or all functions of device 106 may be located in the home environment. In one embodiment, the physiologic activity measurement unit 310 and/or fNIR module 314 may be a portable device.

In a further embodiment, fNIR module 214 may measure brain activation within milliseconds of a subject encountering a presented avatar associated with at least one instance of media content. For example, fNIR module 214 may detect increased brain activity in the nucleus accumbens, SLEA, and thalamus within milliseconds of presentation of an Emeril Lagasse-associated food item to a member of population 105. Such a response may be considered proximate to the presentation of the Emeril Lagasse-associated food item.

Operation 2602 depicts measuring at least one physiologic activity of the at least one member of the population using at least one of electroencephalography, positron emission tomography, magnetic resonance imaging, functional magnetic resonance imaging, functional near-infrared imaging, or magnetoencephalography, the at least one physiologic activity proximate to the at least one presented avatar among the plurality of avatars associated with at least one instance of media content. For example, the device 206, physiologic activity measurement unit 210, brain activity measurement unit 212, fMRI module 216, MEG module 218, EEG module, PET module, and/or fNIR module 214 can measure at least one physiologic activity of the at least one member of the population using at least one of electroencephalography, positron emission tomography, magnetic resonance imaging, functional magnetic resonance imaging, functional near-infrared imaging, or magnetoencephalography, the at least one physiologic activity proximate to the at least one presented avatar among the plurality of avatars associated with at least one instance of media content. In one embodiment, a member of the population 105 can be monitored by MEG module 218 during presentation to the member of population 105 of an avatar associated with at least one instance of media content, among a plurality of avatars presented in sequence or in combination. fMRI module 216, MEG module 218, EEG module, PET module, and/or fNIR module 214 can measure brain activity as the physiologic activity of the at least one member of the population 105.

FIG. 27 illustrates alternative embodiments of the example operational flow 2200 of FIG. 22. FIG. 27 illustrates example embodiments where the measuring operation 2220 may include at least one additional operation. Additional operations may include operation 2700, and/or operation 2702.

Operation 2700 depicts measuring at least one brain activity surrogate marker of the at least one member of the population, the at least one brain activity surrogate marker proximate to the at least one presented avatar among the plurality of avatars associated with at least one instance of media content. For example, the device 206, physiologic activity measurement unit 210, surrogate marker measurement unit 230, iris response module 232, gaze tracking module 234, skin response module 236, and/or voice response module can measure at least one brain activity surrogate marker of the at least one member of the population, the at least one brain activity surrogate marker proximate to the at least one presented avatar among the plurality of avatars associated with at least one instance of media content. In one embodiment, surrogate marker measurement unit 230 can measure any of a variety of physiological responses proximate to a presented avatar or avatars associated with the at least one instance of media content, the physiological responses indicative of a brain activation and/or mental state proximate to the presented avatar associated with at least one instance of media content.

For example, surrogate marker measurement unit 230 can measure a physiological attribute such as heart rate, respiration, perspiration, temperature, skin coloring, skin electrical response, eye movement, pupil dilation, voice stress, body or facial tic, or the like, before, during, and/or after presentation to a member of population 105 of an avatar associated with at least one instance of media content. Such measurements may include, for example, an increase in heart rate over a time interval as measured by a heart rate monitor embedded in a user interface; increased eye movements as measured by an image capture device such as a video camera, or changes in the galvanic skin response as measured by electrodes embedded in a user interface or included in device 106.

Operation 2702 depicts measuring at least one brain activity surrogate marker of the at least one member of the population using at least one of iris dilation or constriction, gaze tracking, skin response, or voice response, the at least one brain activity surrogate marker proximate to the at least one presented avatar among the plurality of avatars associated with at least one instance of media content. For example, the device 206, physiologic activity measurement unit 210, surrogate marker measurement unit 230, iris response module 232, gaze tracking module 234, skin response module 236, and/or voice response module can measure at least one brain activity surrogate marker of the at least one member of the population using at least one of iris dilation or constriction, gaze tracking, skin response, or voice response, the at least one brain activity surrogate marker proximate to the at least one presented avatar among the plurality of avatars associated with at least one instance of media content.

In one embodiment, an iris response module 232 and/or gaze tracking module 234 may acquire data from a user monitoring device such as a video capture device or a video communication device, for example, when a subject's image is captured as a photograph or video when using an application, such as a webcam, or when a subject's image is captured when communicating via a photography or video-based application. Other sources of image data may include biometric data such as facial pattern data, eye scanning data, or the like. Such image data may indicate, for example, alertness, attention, approval, disapproval, or the like, as discussed below.

Image data may include results of visual spectrum imaging that can image changes in facial expression, body movement, or the like that can be indicative of a physiological activity, brain activity, and/or mental state. User image data may also be obtained from other kinds of imaging such as infrared imaging that can read a heat signature and/or ultrasound imaging. Further, reflected image or refracted image data may also be obtained by physiologic activity measurement unit 210 and/or surrogate marker measurement unit 230. Near infrared imaging may be used to test for baseline physiologic states and metabolism, as well as physiologic and metabolic changes. Image data may be of all or a portion of a member of population 105 such as a head-to-toe image, a face image, an image of fingers, an image of an eye, or the like. Such images may be in the visual or non-visual wavelength range of the electromagnetic spectrum.

In one embodiment, alertness or attention can be measured, for example, by measuring eye movements, body movements, pointing device manipulation, and/or task proficiency (e.g., are a subject's eyelids drooping, is a subject's head nodding, is a subject failing or succeeding to activate on-screen items when prompted by an avatar, does a subject respond to a sound, or the like). Alertness or attention to, for example, an avatar associated with an advertisement may be gauged from a subject's interaction with the avatar. Interest in the avatar associated with an advertisement may be inferred from face pattern data (e.g., a smile on an image of the subject's face), pointing device manipulation data (e.g., a mouse click on an onscreen advertisement icon associated with the avatar), and/or eye movement data (e.g., repeated eye movements toward the avatar), or the like.

In one embodiment, a voice response module can measure speech captured by a microphone during presentation of an avatar associated with the at least one instance of media content. Speech or voice can be measured, for example, by examining voice, song, and/or other vocal utterances of a subject before, during, and/or after presentation of an avatar associated with the at least one instance of media content to a member of population 105. Such measurements may include, for example, as discussed above, layered voice analysis, voice stress analysis, or the like.

The reaction of a subject to a presented avatar associated with at least one instance of media content such as an advertisement in a computerized game world or in another virtual world may be a recognizable vocal exclamation such as "Wow, that's nice!" that may be detectable by a voice response module 338 such as a microphone monitoring an interaction between the member of population 105 and, for example, a presentation device 364 and/or device 306. A voice response module 338 may also include a speech recognition function such as a software program or computational device that can identify and/or record an utterance of a member of population 105 as speech or voice data.

In another embodiment, an iris response module may record changes in the movement of a subject's iris (with corresponding changes in the size of the pupil) before, during, and/or after presentation of an avatar associated with at least one instance of media content to a member of a population 105. Such measurements of physiologic activity that indicate brain activity and/or mental state may be carried out at a time that is proximate to presentation of the avatar associated with at least one instance of media content to a member of population 105.

In one embodiment, a gaze tracking module 334 may include a camera that can monitor a subject's eye movements in order to determine whether and/or how many times the subject looks at a presented avatar associated with at least one instance of media content, for example, during a certain time period.

A surrogate marker measurement unit 230 may also measure face pattern, for example, by measuring user facial features, perhaps in relation to a control user face pattern image captured when the user was not interacting with a presented avatar associated with at least one instance of media content. Alternatively, a subject's face pattern may be compared to a consensus face pattern compiled from a large number of faces in a population 105 or a population cohort 104. In one embodiment, the reaction of a member of population cohort 102 to an onscreen avatar may be a smile or a frown that may be detectable by a camera monitoring the interaction. Information suggesting that a user smiles in response to viewing a presented characteristic may be transmitted to association unit 340.

A surrogate marker measurement unit 330 may include a pen including electronic sensing capability that may include the capability to monitor a subject's hand for temperature, blood flow, tremor, fingerprints, or other attributes. For example, reaction time among young males aged 18-28 that play video games with some frequency may be distinguishable from average reaction times of women and/or users in older age groups.

In another embodiment, a surrogate marker measurement unit 330 and/or device 306 may anonymize physiologic activity measurement data acquired during a subject's interaction with one or more presented avatars associated with at least one instance of media content. Anonymization of member of population 105 data may be accomplished through various methods known in the art, including data coding, k-anonymization, de-association, pseudonymization, or the like.

FIG. 28 illustrates alternative embodiments of the example operational flow 2200 of FIG. 22. FIG. 28 illustrates example embodiments where the measuring operation 2220 may include at least one additional operation. Additional operations may include operation 2800 and/or 2802.

Operation 2800 depicts measuring at least one physiologic activity of the at least one member of the population in near real time, the at least one physiologic activity proximate to the at least one presented avatar among the plurality of avatars associated with at least one instance of media content. For example, the device 206, physiologic activity measurement unit 210, brain activity measurement unit 212, and/or surrogate marker measurement unit 230 can measure at least one physiologic activity of the at least one member of the population in near real time, the at least one physiologic activity proximate to the at least one presented avatar among the plurality of avatars associated with at least one instance of media content. In one embodiment, the brain activity measurement unit 212 can measure brain activity in the member of population 105 at the milliseconds-to-seconds time frame, inclusive of processing time. Accordingly, the methods discussed herein, including surrogate marker measurement functions, can measure responses of a member of the population 105 in near real time, which may include a delay between the occurrence of a proximate and/or response event and the use of the processed proximal measurement data, e.g., for further processing and/or for subsequent display, or for output to a display device or to a memory.

Operation 2802 depicts measuring at least one brain activity and at least one eye movement activity of the at least one member of the population, the at least one brain activity and the at least one eye movement proximate to the at least one presented avatar among the plurality of avatars associated with at least one instance of media content. For example, the device 206, physiologic activity measurement unit 210, brain activity measurement unit 212, gaze tracking module 234, and/or surrogate marker measurement unit 230 can measure at least one brain activity and at least one eye movement activity of the at least one member of the population, the at least one brain activity and the at least one eye movement proximate to the at least one presented avatar among the plurality of avatars associated with at least one instance of media content. In one embodiment, more than one avatar and/or avatar attribute such as an instance of media content may be presented to a member of population 105 at one time. In such a case, eye movement analysis and/or gaze tracking analysis of the member of population 105 may be used to determine which avatar is being viewed at a given point in time.

Alternatively, eye movement analysis and/or gaze tracking analysis may be used to determine an overall pattern of viewing with respect to one or more presented avatars. A time-stamped measurement of eye movement analysis and/or gaze tracking analysis may be matched with other coincident physiologic activity such as brain activity measurements to link, for example, viewing of a specific avatar among many with a particular brain activity measurement.

Gaze tracking module 334 and/or iris response module 332 may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, a display 372. (e.g., http://jp.hamamatsu.com/en/rd/publication/scientific_american/common/pdf/scientific_06 08.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an user 106.

Two types of gaze tracking or eye tracking techniques include bright pupil eye tracking and dark pupil eye tracking. Their difference is based on the location of the illumination source with respect to the optics. If the illumination is coaxial with the optical path, then the eye acts as a retroreflector as the light reflects off the retina, creating a bright pupil effect similar to red eye. If the illumination source is offset from the optical path, then the pupil appears dark.

Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright light. However, bright pupil techniques are not recommended for tracking outdoors as extraneous IR sources may interfere with monitoring.

Eye tracking configurations can vary; in some cases the measurement apparatus may be head-mounted, in some cases the head should be stable (e.g., stabilized with a chin rest), and in some cases the eye tracking may be done remotely to automatically track the head during motion. Most eye tracking systems use a sampling rate of at least 30 Hz. Although 50/60 Hz is most common, many video-based eye trackers run at 240, 350 or even 1000/1250 Hz, which is recommended in order to capture the detail of the very rapid eye movements during reading, or during studies of neurology.

Eye movements are typically divided into fixations, when the eye gaze pauses in a certain position, and saccades, when the eye gaze moves to another position. A series of fixations and saccades is called a scanpath. Most information from the eye is made available during a fixation, not during a saccade. The central one or two degrees of the visual angle (the fovea) provide the bulk of visual information; input from larger eccentricities (the periphery) generally is less informative. Therefore the locations of fixations along a scanpath indicate what information loci on the stimulus were processed during an eye tracking session. On average, fixations last for around 200 milliseconds during the reading of linguistic text, and 350 milliseconds during the viewing of a scene. Preparing a saccade towards a new goal takes around 200 milliseconds.

Scanpaths are useful for analyzing cognitive intent, interest, and salience. Other biological factors (some as simple as gender) may affect the scanpath as well. Eye tracking in human-computer interaction typically investigates the scanpath for usability purposes, or as a method of input in gaze-contingent displays, also known as gaze-based interfaces.

There are two primary components to most eye tracking studies: statistical analysis and graphic rendering. These are both based mainly on eye fixations on specific elements. Statistical analyses generally sum the number of eye data observations that fall in a particular region. Commercial software packages may analyze eye tracking and show the relative probability of eye fixation on each feature in a website. This allows for a broad analysis of which site elements received attention and which ones were ignored. Other behaviors such as blinks, saccades, and cognitive engagement can be reported by commercial software packages. Statistical comparisons can be made to test, for example, competitors, prototypes or subtle changes to an avatar and/or web design. They can also be used to compare participants in different demographic groups and/or population cohorts. Statistical analyses may quantify where subjects look, sometimes directly, and sometimes based on models of higher-order phenomena (e.g., cognitive engagement).

In addition to statistical analysis, it is often useful to provide visual depictions of eye tracking results. One method is to create a video of an eye tracking testing session with the gaze of a participant superimposed upon it. This allows one to effectively see through the eyes of the subject during interaction with a presented avatar associated with at least one instance of media content. Another method graphically depicts the scanpath of a single participant during a given time interval. Analysis may show each fixation and eye movement of a participant during a search on a virtual shelf display of breakfast cereals, analyzed and rendered with a commercial software package. For example, a different color may represent one second of viewing time, allowing for a determination of the order in which products are seen. Analyses such as these may be used as evidence of specific trends in visual behavior.

A similar method sums the eye data of multiple participants during a given time interval as a heat map. A heat map may be produced by a commercial software package, and shows the density of eye fixations for several participants superimposed on the original stimulus, for example, a magazine cover. Red and orange spots represent areas with high densities of eye fixations. This allows one to examine which regions attract the attention and focus of the viewer.

Commercial eye tracking applications include web usability, advertising, sponsorship, package design and automotive engineering. Eye tracking studies often present a target stimulus to a sample of consumers while an eye tracker is used to record the activity of the eye. Examples of target stimuli may include websites, television programs, sporting events, films, commercials, magazines, newspapers, packages, shelf displays, consumer systems (e.g., ATMs, checkout systems, kiosks), and software. The resulting data can be statistically analyzed and graphically rendered to provide evidence of specific visual patterns. By examining fixations, saccades, pupil dilation, blinks, and a variety of other behaviors, researchers can determine a great deal about the effectiveness of a given medium or product.

A prominent field of eye tracking research is web usability. While traditional usability techniques are often quite powerful in providing information on clicking and scrolling patterns, eye tracking offers the ability to analyze user interaction between the clicks. This provides insight into which features of a given avatar associated with at least one instance of media content are the most eye-catching, which features cause confusion, and which ones are ignored altogether. Specifically, eye tracking can be used to assess search efficiency, branding, online advertisement, navigation usability, overall design, and many other site components, including a wide range of avatar attributes. Analyses may target a prototype avatar or competitor avatars in addition to a primary avatar.

Eye tracking is commonly used in a variety of different advertising media. Commercials, print ads, online ads, and sponsored programs are all conducive to analysis with eye tracking technology. Analyses may focus on visibility of a target product or logo in the context of a magazine, newspaper, website, virtual world, or televised event. This allows researchers to assess in great detail how often a sample of consumers fixates on the target logo, product, or advertisement. In this way, an advertiser can quantify the success of a given campaign in terms of actual visual attention.

Eye tracking also provides package designers with the opportunity to examine the visual behavior of a consumer while interacting with a target package. This may be used to analyze distinctiveness, attractiveness and the tendency of the package to be chosen for purchase. Eye tracking is often used while the target product is in the prototype stage. Prototypes are tested against each other and against competitors to examine which specific elements are associated with high visibility and/or appeal.

Another application of eye tracking research is in the field of automotive design. Eye tracking cameras may be integrated into automobiles to provide the vehicle with the capacity to assess in real-time the visual behavior of the driver. The National Highway Traffic Safety Administration (NHTSA) estimates that drowsiness is the primary causal factor in 100,000 police-reported accidents per year. Another NHTSA study suggests that 80% of collisions occur within three seconds of a distraction. By equipping automobiles with the ability to monitor drowsiness, inattention, and cognitive engagement driving safety could be dramatically enhanced. Lexus® claims to have equipped its LS 460 automobile with the first driver monitor system in 2006, providing a warning if the driver takes his or her eye off the road.

Eye tracking is also used in communication systems for disabled persons, allowing the user to speak, mail, surf the web and so with only the eyes as tool. Eye control works even when the user has involuntary body movement as a result of cerebral palsy or other disability, and/or when the user wears glasses.

FIG. 29 illustrates alternative embodiments of the example operational flow 2200 of FIG. 22. FIG. 29 illustrates example embodiments where the measuring operation 2220 may include at least one additional operation. Additional operations may include operation 2900 and/or 2902.

Operation 2900 depicts measuring the at least one physiologic activity of the at least one member of the population, the at least one physiologic activity responsive to at least one presented avatar among the plurality of avatars associated with at least one instance of media content relevant to the population. For example, the device 206, physiologic activity measurement unit 210, brain activity measurement unit 212, gaze tracking and/or surrogate marker measurement unit 230 can measure the at least one physiologic activity of the at least one member of the population, the at least one physiologic activity responsive to at least one presented avatar among the plurality of avatars associated with at least one instance of media content relevant to the population. In one embodiment, brain activity measurement unit 312 can measure brain activity during presentation of an avatar associated with at least one instance of relevant media content, such as presenting an avatar associated with a medical product to a member of an elderly population 105 and/or a member of a population known to be afflicted with a specific pathology. Measured proximate physiologic activity may indicate population cohorts that most favorably regard the avatar associated with the medical product, through association of the physiologic activity with a mental state, as discussed below. This may occur as other presented avatars with similar instances of media content ignored and/or elicit a different pattern of physiologic activity. As a further example, brain activity measurement unit 212 can measure brain activity during presentation of an avatar associated with at least one instance of French media content to a French population 105.

Operation 2902 depicts measuring the at least one physiologic activity of the at least one member of the population, the at least one physiologic activity responsive to at least one avatar among the plurality of avatars associated with at least one instance of media content relevant to a population cohort. For example, the device 206, physiologic activity measurement unit 210, brain activity measurement unit 212, and/or surrogate marker measurement unit 230 can measure the at least one physiologic activity of the at least one member of the population, the at least one physiologic activity responsive to at least one avatar among the plurality of avatars associated with at least one instance of media content relevant to a population cohort. In one embodiment, brain activity measurement unit 312 can measure brain activity during presentation of an avatar associated with at least one instance of relevant media content, such as a toy designed for girls to play with. Measured proximate physiologic activity among a group of girls aged 5-15 may be associated (as discussed below) with a population cohort such as a narrower age range (e.g., girls aged 7-10) that most favorably regard the avatar associated with the toy. As a further example, brain activity measurement unit 212 can measure brain activity during presentation of an avatar associated with a specific sports team to a population cohort 104 of, for example, men living in the state where the sports team is located.

FIG. 30 illustrates alternative embodiments of the example operational flow 2200 of FIG. 22. FIG. 30 illustrates example embodiments where the measuring operation 2220 may include at least one additional operation. Additional operations may include operation 3000.

Operation 3000 depicts measuring with permission the at least one physiologic activity of the at least one member of the population, the at least one physiologic activity responsive to the at least one presented avatar among the plurality of avatars associated with at least one instance of media content. For example, the device 206, physiologic activity measurement unit 210, brain activity measurement unit 212, and/or surrogate marker measurement unit 230 can measure with permission the at least one physiologic activity of the at least one member of the population, the at least one physiologic activity responsive to the at least one presented avatar among the plurality of avatars associated with at least one instance of media content. In one embodiment, after receiving permission from a member of population 105, brain activity measurement unit 312 can measure brain activity during presentation of a plurality of avatars associated with at least one instance of media content to the member of population 105. For example, a member of population 105 may click an acceptance box asking for permission to measure a physiologic activity, for example, during a virtual world session, an online gaming session, an online shopping session, a social networking session, or the like.

FIG. 31 illustrates alternative embodiments of the example operational flow 2200 of FIG. 22. FIG. 31 illustrates example embodiments where the associating operation 2230 may include at least one additional operation. Additional operations may include operation 3100, 3102, 3104, 3106, and/or 3108.

Operation 3100 depicts associating at least one electrical brain activity with the at least one mental state. For example, the device 106, association unit 140, emotion association module 242, attention association module 244, and/or cognition association module 346 can associate at least one electrical brain activity with at least one mental state. In one embodiment, association unit 240 can receive an electrical brain activity measurement, such as measurement of electrical activation of the hippocampus, in response to presentation of one of a plurality of avatars associated with at least one instance of media content to a member of population 105. The electrical brain activity measurement may be received from, for example, EEG module 220. As discussed below, association unit 240 can then search, for example, one or more functional brain mapping databases based on the electrical brain activity measurement to find one or more matching mental states. For example, activation of the hippocampus is associated in the literature with enhanced motivational drive for food and drugs. Thus an association may be made between hippocampus activation and enhanced motivational drive, for example, based on research findings (e.g., Wang et al., "Gastric stimulation in obese subjects activates the hippocampus and other regions involved in brain reward circuitry," PNAS, vol. 103, pp. 15641-45 (2006).

In another embodiment, attention association module 244 can receive a brain activity measurement based on electrical brain activity, such as a measurement from MEG module 218. In this embodiment, an avatar with a specific set of facial features found in media content (e.g., a celebrity's likeness) may be presented to a member of population 105, during which presentation MEG module 218 can measure the brain's electrical activity based on induced magnetic fields. For example, presentation of the avatar with the specific set of facial features may elicit electrical activity in the prefrontal and/or parietal areas of the brain. Association unit 240 may thus match the activation measurement pattern with a known pattern of brain activation from research indicating which brain areas are activated when attention is required. For example, activation of the thalamic reticular nucleus is also associated with selective attention. See Contreras et al., "Inactivation of the Interoceptive Insula Disrupts Drug Craving and Malaise Induced by Lithium," Science, vol. 318, pp. 655-658 (26 Oct. 2007).

Operation 3102 depicts associating at least one brain blood oxygen level with the at least one mental state. For example, the device 106, association unit 140, emotion association module 242, attention association module 244, and/or cognition association module 346 can associate at least one brain blood oxygen level with the at least one mental state. In one embodiment, association unit 240 can receive a brain blood oxygen level activity measurement, such as measurement of activation of the right prefrontal and parietal areas, in response to presentation of one of a set of avatars associated with at least one instance of media content to a member of population 105. The hemodynamic brain activity measurement indicating activation of the right prefrontal and parietal areas may be received from, for example, fNIR module 214. Association unit 240 can then search one or more functional brain mapping databases based on the brain activity measurement to find one or more matching mental states. For example, activation of the right prefrontal and parietal areas is associated in the literature with attention. Thus an association may be made between right prefrontal and parietal areas activation and increased attention to the presented avatar associated with at least one instance of media content by association unit 240, for example, based on research findings. See Cabeza et al, "Imaging Cognition II: An Empirical Review of 275 PET and fMRI Studies," J. Cognitive Neurosci., vol. 12, pp. 1-47 (2000).

Operation 3104 depicts associating at least one of glucose metabolism or blood flow with the at least one mental state. For example, the device 106, association unit 140, emotion association module 242, attention association module 244, and/or cognition association module 346 can associate at least one of glucose metabolism or blood flow with at least one mental state. In one embodiment, association unit 240 can receive a glucose metabolism measurement, such as measurement of activation of the right hemisphere of the bilateral fusiform gyrus, that is proximate to presentation of one of a plurality of avatars having a celebrity face characteristic to a member of population 105. The glucose metabolism brain activity measurement indicating activation of the right hemisphere of the bilateral fusiform gyrus may be received from, for example, PET module 222. Attention association module 244 can then match the brain activity measurement to one or more corresponding mental states. For example, activation of the right hemisphere of the bilateral fusiform gyrus is associated in the literature with increased attention to faces. Thus an association can be made between activation of the right hemisphere of the bilateral fusiform gyrus and increased attention to the presented avatar having a celebrity face characteristic by association unit 240, for example, based on research findings. See Cabeza et al, "Imaging Cognition II: An Empirical Review of 275 PET and fMRI Studies," J. Cognitive Neurosci., vol. 12, pp. 1-47 (2000).

Operation 3106 depicts associating activity in the ventromedial prefrontal cortex with a mental state indicating approval. For example, the device 106, association unit 140, emotion association module 242, attention association module 244, and/or cognition association module 346 can associate activity in the ventromedial prefrontal cortex with a mental state indicating approval. In one embodiment, association unit 240 can receive a brain activity measurement indicating activation of the ventromedial prefrontal cortex that is proximate to presentation to a member of population 105 of an avatar having a characteristic of interest from the news media, among a set of presented avatars. The brain activity measurement indicating activation of the ventromedial prefrontal cortex may be received from, for example, fMRI module 216. Emotion association module 242 and/or attention association module 244 can then match the ventromedial prefrontal cortex activation measurement to one or more corresponding mental states. For example, activation of the ventromedial prefrontal cortex is associated in the literature with preference or approval. Thus an association unit 240 can make an association between activation of the ventromedial prefrontal cortex and approval of the presented avatar having the characteristic of interest from the news media, for example, based on research findings. See Cabeza et al, "Imaging Cognition II: An Empirical Review of 275 PET and fMRI Studies," J. Cognitive Neurosci., vol. 12, pp. 1-47 (2000).

Operation 3108 depicts associating activity in at least one of the frontopolar cortex, the prefrontal cortex, the ventral striatum, the orbitofrontal prefrontal cortex, the amygdala, or the nucleus accumbens with a mental state indicating approval. For example, the device 106, association unit 140, emotion association module 242, attention association module 244, and/or cognition association module 346 can associate activity in at least one of the frontopolar cortex, the prefrontal cortex, the ventral striatum, the orbitofrontal prefrontal cortex, the amygdala, or the nucleus accumbens with a mental state indicating approval. In one embodiment, association unit 240 can receive a brain activity measurement indicating activation of the nucleus accumbens in response to presentation to a member of population 105 of an avatar possessing a product as the at least one instance of media content, the avatar being one of a group of presented avatars possessing various products. The brain activity measurement indicating activation of the nucleus accumbens may be received from, for example, MEG module 218. Emotion association module 242 and/or attention association module 244 can then match the nucleus accumbens activation measurement to one or more corresponding mental states. For example, activation of the nucleus accumbens is associated in the literature with product preference. Thus an association can be made between activation of the nucleus accumbens and preference for the presented avatar possessing a product, by association unit 240, for example, based on research findings. See Wise, "Thought Police: How Brain Scans Could Invade Your Private Life," Popular Mechanics, (November 2007).

FIG. 32 illustrates alternative embodiments of the example operational flow 2200 of FIG. 22. FIG. 32 illustrates example embodiments where the associating operation 2230 may include at least one additional operation. Additional operations may include operation 3200, 3202, 3204, and/or 3206.

Operation 3200 depicts associating activity in the prefrontal cortex with a mental state indicating brand preference. For example, the device 106, association unit 140, emotion association module 242, attention association module 244, and/or cognition association module 346 can associate activity in the prefrontal cortex with a mental state indicating brand preference. In one embodiment, association unit 240 can receive a brain activity measurement indicating activation of the prefrontal cortex proximate to presentation to a member of population 105 of one of a set of avatars associated with an image of a product brand as the avatar associated with at least one instance of media content. The brain activity measurement indicating activation of the prefrontal cortex may be received from, for example, fNIR module 314. Emotion association module 242, attention association module 244, and/or cognition association module 346 can then match the prefrontal cortex activation measurement to one or more corresponding mental states. For example, activation of the prefrontal cortex is associated in the literature with brand preference. Thus an association can be made between activation of the prefrontal cortex and preference for the presented avatar associated with an image of a product brand, by association unit 240, for example, based on research findings. See Kenning et al., "Neuroeconomics: an overview from an economic perspective," Brain Res. Bull., vol. 67, pp. 343-354 (2005).

Operation 3202 depicts associating activity in the dorsolateral prefrontal cortex, the posterior parietal cortex, the occipital cortex, and the left premotor area with a mental state indicating brand preference. For example, the device 106, association unit 140, emotion association module 242, attention association module 244, and/or cognition association module 346 can associate activity in the dorsolateral prefrontal cortex, the posterior parietal cortex, the occipital cortex, and the left premotor area with a mental state indicating brand preference. In one embodiment, association unit 240 can receive a brain activity measurement indicating activation of the dorsolateral prefrontal cortex, the posterior parietal cortex, the occipital cortex, and the left premotor area in response to presentation to a member of population 105 of a brand embodied in an avatar as the avatar associated with at least one instance of media content. The brain activity measurement indicating activation of the dorsolateral prefrontal cortex, the posterior parietal cortex, the occipital cortex, and the left premotor area may be received from, for example, fNIR module 314. Emotion association module 242, attention association module 244, and/or cognition association module 346 can then match the dorsolateral prefrontal cortex, the posterior parietal cortex, the occipital cortex, and the left premotor area activation measurement to one or more corresponding mental states.

For example, activation of the dorsolateral prefrontal cortex, the posterior parietal cortex, the occipital cortex, and the left premotor area is associated in the literature with brand preference. Thus an association can be made by association unit 240 between preference for the presented brand embodied in an avatar and activation of the dorsolateral prefrontal cortex, the posterior parietal cortex, the occipital cortex, and the left premotor area, for example, based on research findings. This may be particularly true when the target brand is the subject's favorite brand. See Kenning et al., "Neuroeconomics: an overview from an economic perspective," Brain Res. Bull., vol. 67, pp. 343-354 (2005). Further, there is evidence for a large-scale neural system for visuospatial attention that includes the right posterior parietal cortex. See Cabeza et al, "Imaging Cognition II: An Empirical Review of 275 PET and fMRI Studies," J. Cognitive Neurosci., vol. 12, pp. 1-47 (2000).

Operation 3204 depicts associating activity in at least one of the inferior precuneus, posterior cingulate, right parietal cortex, right superior frontal gyrus, right supramarginal gyrus, or the ventromedial prefrontal cortex with a mental state indicating brand preference. For example, the device 106, association unit 140, emotion association module 242, attention association module 244, and/or cognition association module 346 can associate activity in at least one of the inferior precuneus, posterior cingulate, right parietal cortex, right superior frontal gyrus, right supramarginal gyrus, or the ventromedial prefrontal cortex with a mental state indicating brand preference. In one embodiment, association unit 240 can receive a brain activity measurement indicating activation of the inferior precuneus and the ventromedial prefrontal cortex proximate to presentation to a member of population 105 of an avatar associated with a product brand among a group of avatars associated with at least one instance of media content. The brain activity measurement indicating activation of the inferior precuneus and the ventromedial prefrontal cortex may be received from, for example, EEG module 320 and/or fMRI module 316. Emotion association module 242, attention association module 244, and/or cognition association module 346 can then match the inferior precuneus and ventromedial prefrontal cortex activation measurement to one or more corresponding mental states. For example, activation of the inferior precuneus and the ventromedial prefrontal cortex is associated in the literature with brand preference. Thus an association can be made between preference for the presented avatar associated with a product brand and activation of the inferior precuneus and the ventromedial prefrontal cortex, by association unit 240, for example, based on research findings. See Kenning et al., "Neuroeconomics: an overview from an economic perspective," Brain Res. Bull., vol. 67, pp. 343-354 (2005).

Operation 3206 depicts associating activity in at least one of the insula, the lateral orbital frontal cortex, or the amygdala with a mental state indicating emotional disapproval. For example, the device 106, association unit 140, and/or emotion association module 242 can associate activity in at least one of the insula, the lateral orbital frontal cortex, or the amygdala with a mental state indicating emotional disapproval. In one embodiment, association unit 240 and/or emotion association module 342 can receive a brain activity measurement indicating activation of the insula in response to presentation of a plurality of avatars associated with at least one instance of media content to a member of population cohort 102. The brain activity measurement indicating activation of the insula may be received from, for example, fNIR module 314 and/or EEG module 320. Emotion association module 242 and/or association unit 340 can then match the insula activation measurement to one or more corresponding mental states. For example, activation of the insula is associated in the literature with pain, distress, and other negative emotional states. Thus an association can be made between emotional disapproval of the presented avatar associated with an instance of media content and activation of the insula, by emotional association module 242 and/or association unit 240, for example, based on research findings. See Kenning et al., "Neuroeconomics: an overview from an economic perspective," Brain Res. Bull., vol. 67, pp. 343-354 (2005).

FIG. 33 illustrates alternative embodiments of the example operational flow 2200 of FIG. 22. FIG. 33 illustrates example embodiments where the associating operation 2230 may include at least one additional operation. Additional operations may include operation 3300, 3302, 3304, 3306, and/or 3308.

Operation 3300 depicts associating activity in the dorsolateral prefrontal cortex with a mental state indicating objective approval. For example, the device 106, association unit 140, emotion association module 242, attention association module 244, and/or cognition association module 346 can associate activity in the dorsolateral prefrontal cortex with a mental state indicating objective approval. In one embodiment, association unit 240 can receive a brain activity measurement indicating activation of the dorsolateral prefrontal cortex proximate to presentation of a group of avatars associated with at least one instance of media content to a member of population 105. The brain activity measurement indicating activation of the dorsolateral prefrontal cortex may be received from, for example, MEG module 218. Emotion association module 242 and/or association unit 340 can then match the dorsolateral prefrontal cortex activation measurement to one or more corresponding mental states. For example, activation of the dorsolateral prefrontal cortex is associated in the literature with objective recognition of benefit despite an emotional perception of unfairness. Thus an association can be made between activation of the DLPFC and objective approval of a presented avatar associated with at least one instance of media content, for example by emotion association module 342, for example, based on research findings. See Kenning et al., "Neuroeconomics: an overview from an economic perspective," Brain Res. Bull., vol. 67, pp. 343-354 (2005).

Operation 3302 depicts associating activity in the caudate nucleus with a mental state indicating trust. For example, the device 106, association unit 140, emotion association module 242, attention association module 244, and/or cognition association module 346 can associate activity in the caudate nucleus with a mental state indicating trust. In one embodiment, association unit 240 can receive a brain activity measurement indicating activation of the caudate nucleus proximate to presentation of, for example, two avatars associated with at least one instance of media content to a member of population 105. The brain activity measurement indicating activation of the caudate nucleus may be received from, for example, MEG module 218 and/or fNIR module 214. Emotion association module 242 and/or association unit 340 can then match the caudate nucleus activation measurement to one or more corresponding mental states. For example, activation of the caudate nucleus is associated in the literature with trust-building and reciprocity in economic exchange. Thus an association can be made between activation of the caudate nucleus and a mental state indicating trust in the context of presentation of the avatar associated with at least one instance of media content, for example by emotion association module 342, for example, based on research findings.

See Kenning et al., "Neuroeconomics: an overview from an economic perspective," Brain Res. Bull., vol. 67, pp. 343-354 (2005).

Operation 3304 depicts associating activity in the hippocampus with a mental state indicating novelty in a perceived object. For example, the device 106, association unit 140, emotion association module 242, attention association module 244, and/or cognition association module 346 can associate activity in the hippocampus with a mental state indicating novelty in a perceived object. In one embodiment, association unit 240 can receive a brain activity measurement indicating activation of the hippocampus proximate to presentation of, for example, three avatars associated with at least one instance of media content to a member of population 105, in sequence. The brain activity measurement indicating activation of the hippocampus may be received from, for example, MEG module 218 and/or fMRI module 316 in response to viewing only the second presented avatar associated with at least one instance of media content.

Emotion association module 242, cognition association module 346, and/or association unit 340 can then match the hippocampus activation measurement to one or more corresponding mental states. For example, activation of the hippocampus is associated in the literature with a central role in processing novel stimuli. Thus an association can be made between activation of the hippocampus and a mental state indicating perceived novelty in the context of presentation of the second presented avatar associated with at least one instance of media content, for example by cognition association module 346, for example, based on research findings. See Martin et al., "Human experience seeking correlates with hippocampus volume: Convergent evidence from manual tracing and voxel-based morphometry," Neuropsychologia, vol. 45, pp. 2874-81 (2007).

Operation 3306 depicts associating activity in the hippocampus with a mental state indicating lack of inhibition toward a perceived object. For example, the device 106, association unit 140, emotion association module 242, attention association module 244, and/or cognition association module 346 can associate activity in the hippocampus with a mental state indicating lack of inhibition toward a perceived object. In one embodiment, association unit 240 can receive a brain activity measurement indicating activation of the hippocampus proximate to presentation of an avatar associated with at least one instance of media content to a member of population 105. The brain activity measurement indicating activation of the hippocampus may be received from, for example, PET module 222 and/or fNIR module 214. Emotion association module 242, cognition association module 346, and/or association unit 340 can then match the hippocampus activation measurement to one or more corresponding mental states. For example, activation of the hippocampus is associated in the literature with a lack of inhibition toward a perceived object. Thus an association can be made between activation of the hippocampus and a mental state indicating a lack of inhibition toward a perceived object in the context of presentation of an avatar associated with at least one instance of media content, for example by emotion association module 342, for example, based on research findings. See Wang et al., "Gastric stimulation in obese subjects activates the hippocampus and other regions involved in brain reward circuitry," PNAS, vol. 103, pp. 15641-45 (2006).

Operation 3308 depicts associating at least one brain activity surrogate marker with at least one mental state. For example, the device 106, association unit 140, emotion association module 242, attention association module 244, and/or cognition association module 346 can associate at least one brain activity surrogate marker with at least one mental state. In one embodiment, association unit 240 can receive a brain activity surrogate marker such as a skin response measurement, voice stress measurement, eye movement measurement, and/or iris response measurement proximate to presentation of an avatar associated with at least one instance of media content to a member of population 105. The brain activity surrogate marker may be received from, for example, iris response module 232, gaze tracking module 234, skin response module 236, and/or voice response module 238. Emotion association module 242, attention association module 244, cognition association module 246, and/or association unit 240 can then match the brain activity surrogate marker to one or more corresponding mental states. For example, detection of voice patterns indicative of a calm mental state may indicate approval toward a characteristic, particularly in combination with brain activation measurement of caudate nucleus activation as a predictor of trust toward the characteristic. Thus an association can be made between a calm voice pattern and a mental state indicating approval toward a presented avatar associated with at least one instance of media content, for example by emotion association module 342, for example, based on research findings. See Sanfey, "Social Decision-Making: Insights from Game Theory and Neuroscience," Science, vol. 318, pp. 598-601 (26 Oct. 2007).

FIG. 34 illustrates alternative embodiments of the example operational flow 2200 of FIG. 22. FIG. 34 illustrates example embodiments where the associating operation 2230 may include at least one additional operation. Additional operations may include operation 3400 and/or operation 3402.

Operation 3400 depicts associating at least one physiologic activity that is at or above a defined threshold with at least one mental state. For example, the device 106, association unit 140, emotion association module 242, attention association module 244, and/or cognition association module 346 can associate at least one physiologic activity that is at or above a defined threshold with at least one mental state. In one embodiment, association unit 140 can associate a mental state with, for example, activity in the frontopolar cortex above a specified intensity level, as measured by, for example, fMRI or fNIR. Because low level activations of the frontopolar cortex may occur frequently having little or no significance in terms of indicating mental state (an association unit 240 may nevertheless make an association based on low level activation of a brain area or surrogate marker), a filter may be employed to allow only mental state associations founded on activations above a certain threshold to pass to an attribute specification unit 250. Such a filter also may be employed at the level of the physiologic measurement unit 210 such that measurements that do not meet or exceed the defined threshold level or intensity are not transmitted to the association unit 240. Alternatively, a filter may be employed at the stage of the association unit 240 such that only associations between mental state and physiologic measurements at or above the defined threshold are transmitted to media content identification unit 166. In addition or alternatively, a filter may be employed at the level of the media content identification unit 166 such that mental states grounded on physiological measurements below the defined threshold are not identified, withheld, and/or discounted.

Operation 3402 depicts associating at least one pattern of physiologic activity with at least one mental state that is known to be associated with the pattern of physiologic activity. For example, the device 106, association unit 140, emotion association module 242, attention association module 244, and/or cognition association module 346 can associate at least one pattern of physiologic activity with at least one mental state that is known to be associated with the pattern of physiologic activity. In one embodiment, association unit 240 can associate a specific mental state with, for example, a specific constellation of brain activity and/or surrogate marker(s) of brain activity known to signify the specific mental state, as measured by, for example, fMRI module 216, fNIR module 214, and/or by surrogate marker measurement unit 230. For example, presentation of an avatar with a celebrity face characteristic to a member of population 105 may coincide with detection of activation of the visual cortex (perhaps indicating visual contact with the characteristic); activation of the right prefrontal and parietal areas (perhaps indicating visual vigilance, i.e., attention); activation of the right hemisphere of the bilateral fusiform gyrus (perhaps indicating perception of the face characteristic); activation of the medial temporal regions (perhaps indicating retrieval of an item-specific memory); and activation of the ventral striatum and decreased activity in the insula (perhaps indicating a positive emotional response such as approval); increased frequency of eye movements to the face characteristic; and iris dilation. In one embodiment, an association unit 240 may associate some or all of the above physiological activity measurements with one or more mental states, in effect creating a signature mental state for the proximate reaction of member of population 105 to the avatar with a celebrity face characteristic. Alternatively, association unit 240 may associate a physiologic activity measurement with a known physiologic activity signature or pattern that corresponds to a known mental state, i.e., a known association.

FIG. 35 illustrates alternative embodiments of the example operational flow 2200 of FIG. 22. FIG. 35 illustrates example embodiments where the identifying operation 2240 may include at least one additional operation. Additional operations may include operation 3500, 3502, 3504, and/or operation 3506.

Operation 3500 depicts identifying at least one of an instance of movie content, an instance of television content, an instance of music content, an instance of literature content, an instance of internet content, or an instance of advertising content based on the at least one mental state. For example, the device 106 and/or media content identification unit 266 may identify at least one of an instance of movie content, an instance of television content, an instance of music content, an instance of literature content, an instance of internet content, or an instance of advertising content based on the at least one mental state. In one embodiment, media content identification unit 366 can assimilate information from association unit 340 and/or physiologic activity measurement unit 310 indicating mental state with respect to a presented avatar or avatars associated with an instance of media content, to identify an instance of media content that, for example, was presented proximate to an approving mental state and underlying physiological activity detected in the member of population 105. Further, an identified instance of media content may be selected relative to physiologic activity and attendant association with mental state identified for other presented avatars with an instance of media content, so as to provide a comparative value to the identification. This comparative may be quantified by media content identification unit 266 based on, for example, underlying physiological activity measurement such as intensity of VMPFC, number of dwells counted for a particular instance of media content, degree of modulation of voice stress, or the like.

For example, among presented avatars, each showing a different trailer clip for a to-be-released movie, presentation of one avatar showing one clip in particular may be proximate to the most reward center brain activity relative to others in the group of clip-bearing avatars. In one embodiment, media content identification unit 266 may identify an instance of media content that is associated with a mental state that is based on physiologic activity that is statistically significant relative to that of other presented avatars with associated media content. Accordingly, the media content identification unit 266 may identify a relative confidence level or statistical significance of an associated mental state with respect to an identified instance of media content.

Operation 3502 depicts identifying at least one preferred instance of media content based on the at least one mental state. For example, the device 106 and/or media content identification unit 266 may identify at least one preferred instance of media content based on the at least one mental state. In one embodiment the media content identification unit 266 may identify an instance of media content such as a product packaging design associated with a presented avatar, the avatar being one of a group of presented avatars each having a different product packaging design. In this embodiment, comparative advertising may thus be carried out on a related set of, for example, product packaging designs as way to identify a most preferred packaging design among a set of candidates.

Operation 3504 depicts identifying at least one instance of advertising content based on at least one approving mental state relative to that of a competitor's advertising content. For example, the device 106 and/or media content identification unit 266 may identify at least one instance of advertising content based on at least one approving mental state relative to that of a competitor's advertising content. In one embodiment the media content identification unit 266 may identify an instance of media content such as an advertising attribute associated with a presented avatar, the avatar associated with approval based on a measured presentation-proximate physiologic activity in the member of population 105. In this example, a second presented avatar associated with a competitor's advertising attribute may be associated with a neutral or disapproving mental state based on a measured presentation-proximate physiologic activity in the member of population 105. In this embodiment, comparative advertising may thus be carried out between competing advertising attributes.

Operation 3506 depicts identifying the at least one instance of a product design based on at least one approving mental state relative to that of at least one alternative product design. For example, the device 106 and/or media content identification unit 266 may identify at least one instance of a product design based on at least one approving mental state relative to that of at least one alternative product design. In one embodiment the media content identification unit 266 may identify an instance of media content such as a shoe design associated with a presented avatar based on a mental state indicating approval of the presented shoe design, the avatar being one of a group of presented avatars each having a different shoe design. In this embodiment, a comparison of shoe design candidates may thus be carried out on a related set of designs as way to identify those that may elicit approval in a population member 105.

FIG. 36 illustrates a partial view of an example computer program product 3600 that includes a computer program 3604 for executing a computer process on a computing device. An embodiment of the example computer program product 3600 is provided using a signal bearing medium 3602, and may include one or more instructions for presenting to at least one member of a population a plurality of avatars associated with at least one instance of media content; one or more instructions for measuring at least one physiologic activity of the at least one member of the population, the at least one physiologic activity proximate to at least one presented avatar among the plurality of avatars associated with at least one instance of media content; one or more instructions for associating the at least one physiologic activity with at least one mental state; and one or more instructions for identifying at least one instance of media content based on the at least one mental state. The one or more instructions may be, for example, computer executable and/or logic-implemented instructions. In one implementation, the signal-bearing medium 3602 may include a computer-readable medium 3606. In one implementation, the signal bearing medium 3602 may include a recordable medium 3608. In one implementation, the signal bearing medium 3602 may include a communications medium 3610.

FIG. 37 illustrates an example system 3700 in which embodiments may be implemented. The system 3700 includes a computing system environment. The system 3700 also illustrates a member of population 3705 using a device 3704, which is optionally shown as being in communication with a computing device 3702 by way of an optional coupling 3706. The optional coupling 3706 may represent a local, wide-area, or peer-to-peer network, or may represent a bus that is internal to a computing device (e.g., in example embodiments in which the computing device 3702 is contained in whole or in part within the device 3704). A storage medium 3708 may be any computer storage media. In one embodiment, the computing device 3702 may include a virtual machine operating within another computing device. In an alternative embodiment, the computing device 3702 may include a virtual machine operating within a program running on a remote server.

The computing device 3702 includes computer-executable instructions 3710 that when executed on the computing device 3702 cause the computing device 3702 to (a) present to at least one member of a population a plurality of avatars associated with at least one instance of media content; (b) measure at least one physiologic activity of the at least one member of the population, the at least one physiologic activity proximate to at least one presented avatar among the plurality of avatars associated with at least one instance of media content; (c) associate the at least one physiologic activity with at least one mental state; and (d) identify at least one instance of media content based on the at least one mental state. As referenced above and as shown in FIG. 37, in some examples, the computing device 3702 may optionally be contained in whole or in part within the device 3704.

In FIG. 37, then, the system 3700 includes at least one computing device (e.g., 3702 and/or 3704). The computer-executable instructions 3710 may be executed on one or more of the at least one computing device. For example, the computing device 3702 may implement the computer-executable instructions 3710 and output a result to (and/or receive data from) the computing device 3704. Since the computing device 3702 may be wholly or partially contained within the computing device 3704, the device 3704 also may be said to execute some or all of the computer-executable instructions 3710, in order to be caused to perform or implement, for example, various ones of the techniques described herein, or other techniques.

The device 3704 may include, for example, a portable computing device, workstation, or desktop computing device. In another example embodiment, the computing device 3702 is operable to communicate with the device 3704 associated with the member of population 3705 to receive information about physiologic activity of the member of population 3705 for performing data access and data processing, and to identify at least one instance of media content based on the at least one mental state, the mental state based on physiologic activity of the member of population 3705.

Although a member of population 3705 is shown/described herein as a single illustrated figure, those skilled in the art will appreciate that a member of population 3705 may be composed of two or more entities. Those skilled in the art will appreciate that, in general, the same may be said of "sender" and/or other entity-oriented terms as such terms are used herein.

FIG. 38 illustrates an operational flow 3800 representing example operations related to specifying an avatar attribute. In FIG. 38, discussion and explanation may be provided with respect to the above-described system environments of FIGS. 1-4, and/or with respect to other examples and contexts. However, it should be understood that the operational flows may be executed in a number of other environment and contexts and/or in modified versions of FIGS. 1-3. Also, although the various operational flows are presented in the sequences illustrated, it should be understood that the various operations may be performed in other orders than those which are illustrated, or may be performed concurrently.

After a start operation, operation 3810 depicts presenting to at least one member of a population a plurality of avatars associated with at least one instance of media content. Operation 3820 depicts measuring at least one physiologic activity of the at least one member of the population, the at least one physiologic activity proximate to at least one presented avatar among the plurality of avatars associated with at least one instance of media content. Operation 3830 depicts searching at least one database to identify at least one mental state corresponding to the at least one physiologic activity. Such searching may be carried out by association unit 240 and/or device 206. Searchable databases may include one or more biomedical literature databases, neuroeconomic databases, functional brain imaging databases, functional brain mapping databases, face pattern databases, voice pattern databases, skin response databases, or the like. Operation 3840 depicts associating the at least one physiologic activity with the at least one mental state. Operation 3850 depicts identifying at least one instance of media content based on the at least one mental state.

One skilled in the art will recognize that the herein-described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet are incorporated herein by reference, to the extent not inconsistent herewith.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

What is claimed is:

1. A system comprising:
    circuitry for presenting to at least one member of a population a plurality of avatars associated with at least one instance of media content;
    circuitry for measuring at least one physiologic activity of the at least one member of the population, the at least one physiologic activity proximate to at least one presented avatar among the plurality of avatars associated with at least one instance of media content;
    circuitry for associating the at least one physiologic activity with at least one mental state, including circuitry for identifying at least one preferred instance of media content based on the at least one mental state; and
    circuitry for identifying at least one instance of media content based on the at least one mental state.

2. The system of claim 1 wherein the circuitry for presenting to at least one member of a population a plurality of avatars associated with at least one instance of media content comprises:
    circuitry for presenting to the at least one member of the population a plurality of avatars, each avatar associated with at least one of an instance of movie content, an instance of television content, an instance of music content, an instance of literature content, an instance of internet content, an instance of news content, or an instance of advertising content.

3. The system of claim 1 wherein the circuitry for presenting to at least one member of a population a plurality of avatars associated with at least one instance of media content comprises:
    circuitry for presenting to the at least one member of the population a plurality of substantially similar avatars, each avatar associated with a substantially different instance of media content.

4. The system of claim 1 wherein the circuitry for presenting to at least one member of a population a plurality of avatars associated with at least one instance of media content comprises:
    circuitry for presenting to the at least one member of the population a plurality of substantially distinct avatars, each avatar associated with a substantially similar instance of media content.

5. The system of claim 1 wherein the circuitry for presenting to at least one member of a population a plurality of avatars associated with at least one instance of media content comprises:
    circuitry for presenting to at least one member of a family group the plurality of avatars associated with at least one instance of media content.

6. The system of claim 1 wherein the circuitry for presenting to at least one member of a population a plurality of avatars associated with at least one instance of media content comprises:
    circuitry for presenting to at least one member of a population cohort the plurality of avatars associated with at least one instance of media content.

7. The system of claim 1 wherein the circuitry for presenting to at least one member of a population a plurality of avatars associated with at least one instance of media content comprises:
    circuitry for presenting to at least one member of at least one of an age cohort, a gender cohort, an ethnicity cohort, or a purchasing cohort the plurality of avatars associated with at least one instance of media content.

8. The system of claim 1 wherein the circuitry for presenting to at least one member of a population a plurality of avatars associated with at least one instance of media content comprises:
    circuitry for presenting to the at least one member of the population the plurality of avatars, each avatar associated with at least one of an image instance of media content, an audio instance of media content, a video instance of media content, or an animation instance of media content.

9. The system of claim 1 wherein the circuitry for presenting to at least one member of a population a plurality of avatars associated with at least one instance of media content comprises:
    circuitry for presenting to the at least one member of the population a plurality of avatars in sequence, each avatar associated with at least one instance of media content.

10. The system of claim 1 wherein the circuitry for presenting to the at least one member of the population the plurality of avatars, each avatar associated with at least one of an image instance of media content, an audio instance of media content, a video instance of media content, or an animation instance of media content comprises:
    circuitry for presenting to at least one of a virtual world participant, a computer game participant, an online shopping participant, or a social networking website participant a plurality of avatars associated with at least one instance of media content.

11. The system of claim 1 wherein the circuitry for measuring at least one physiologic activity of the at least one member of the population, the at least one physiologic activity proximate to at least one presented avatar among the plurality of avatars associated with at least one instance of media content comprises:
    circuitry for measuring at least one physiologic activity of the at least one member of the population using functional near-infrared imaging, the at least one physiologic activity proximate to the at least one presented avatar among the plurality of avatars associated with at least one instance of media content.

12. The system of claim 1 wherein the circuitry for measuring at least one physiologic activity of the at least one member of the population, the at least one physiologic activity proximate to at least one presented avatar among the plurality of avatars associated with at least one instance of media content comprises:
    circuitry for measuring at least one physiologic activity of the at least one member of the population using at least one of electroencephalography, positron emission tomography, magnetic resonance imaging, functional magnetic resonance imaging, functional near-infrared imaging, or magnetoencephalography, the at least one physiologic activity proximate to the at least one presented avatar among the plurality of avatars associated with at least one instance of media content.

13. The system of claim 1 wherein the circuitry for measuring at least one physiologic activity of the at least one member of the population, the at least one physiologic activity proximate to at least one presented avatar among the plurality of avatars associated with at least one instance of media content comprises:

circuitry for measuring at least one brain activity surrogate marker of the at least one member of the population, the at least one brain activity surrogate marker proximate to the at least one presented avatar among the plurality of avatars associated with at least one instance of media content.

14. The system of claim 13 wherein the circuitry for measuring at least one brain activity surrogate marker of the at least one member of the population, the at least one brain activity surrogate marker proximate to the at least one presented avatar among the plurality of avatars associated with at least one instance of media content comprises:

circuitry for measuring at least one brain activity surrogate marker of the at least one member of the population using at least one of iris dilation or constriction, gaze tracking, skin response, or voice response, the at least one brain activity surrogate marker proximate to the at least one presented avatar among the plurality of avatars associated with at least one instance of media content.

15. The system of claim 1 wherein the circuitry for measuring at least one physiologic activity of the at least one member of the population, the at least one physiologic activity proximate to at least one presented avatar among the plurality of avatars associated with at least one instance of media content comprises:

circuitry for measuring at least one physiologic activity of the at least one member of the population in near real time, the at least one physiologic activity proximate to the at least one presented avatar among the plurality of avatars associated with at least one instance of media content.

16. The system of claim 1 wherein the circuitry for measuring at least one physiologic activity of the at least one member of the population, the at least one physiologic activity proximate to at least one presented avatar among the plurality of avatars associated with at least one instance of media content comprises:

circuitry for measuring at least one brain activity and at least one eye movement activity of the at least one member of the population, the at least one brain activity and the at least one eye movement proximate to the at least one presented avatar among the plurality of avatars associated with at least one instance of media content.

17. The system of claim 1 wherein the circuitry for measuring at least one physiologic activity of the at least one member of the population, the at least one physiologic activity proximate to at least one presented avatar among the plurality of avatars associated with at least one instance of media content comprises:

circuitry for measuring the at least one physiologic activity of the at least one member of the population, the at least one physiologic activity responsive to at least one presented avatar among the plurality of avatars associated with at least one instance of media content relevant to the population.

18. The system of claim 1 wherein the circuitry for measuring at least one physiologic activity of the at least one member of the population, the at least one physiologic activity proximate to at least one presented avatar among the plurality of avatars associated with at least one instance of media content comprises:

circuitry for measuring the at least one physiologic activity of the at least one member of the population, the at least one physiologic activity responsive to at least one avatar among the plurality of avatars associated with at least one instance of media content relevant to a population cohort.

19. The system of claim 1 wherein the circuitry for measuring at least one physiologic activity of the at least one member of the population, the at least one physiologic activity proximate to at least one presented avatar among the plurality of avatars associated with at least one instance of media content comprises:

circuitry for measuring with permission the at least one physiologic activity of the at least one member of the population, the at least one physiologic activity responsive to the at least one presented avatar among the plurality of avatars associated with at least one instance of media content.

20. The system of claim 1 wherein the circuitry for associating the at least one physiologic activity with at least one mental state comprises:

circuitry for associating at least one electrical brain activity with the at least one mental state.

21. The system of claim 1 wherein the circuitry for associating the at least one physiologic activity with at least one mental state comprises:

circuitry for associating at least one brain blood oxygen level with the at least one mental state.

22. The system of claim 1 wherein the circuitry for associating the at least one physiologic activity with at least one mental state comprises:

circuitry for associating at least one of glucose metabolism or blood flow with the at least one mental state.

23. The system of claim 1 wherein the circuitry for associating the at least one physiologic activity with at least one mental state comprises:

circuitry for associating activity in the ventromedial prefrontal cortex with a mental state indicating approval.

24. The system of claim 1 wherein the circuitry for associating the at least one physiologic activity with at least one mental state comprises:

circuitry for associating activity in at least one of the frontopolar cortex, the prefrontal cortex, the ventral striatum, the orbitofrontal prefrontal cortex, the amygdala, or the nucleus accumbens with a mental state indicating approval.

25. The system of claim 1 wherein the circuitry for associating the at least one physiologic activity with at least one mental state comprises:

circuitry for associating activity in the prefrontal cortex with a mental state indicating brand preference.

26. The system of claim 1 wherein the circuitry for associating the at least one physiologic activity with at least one mental state comprises:

circuitry for associating activity in the dorsolateral prefrontal cortex, the posterior parietal cortex, the occipital cortex, and the left premotor area with a mental state indicating brand preference.

27. The system of claim 1 wherein the circuitry for associating the at least one physiologic activity with at least one mental state comprises:

circuitry for associating activity in at least one of the inferior precuneus, posterior cingulate, right parietal cortex, right superior frontal gyrus, right supramarginal gyrus, or the ventromedial prefrontal cortex with a mental state indicating brand preference.

28. The system of claim 1 wherein the associating the at least one physiologic activity with at least one mental state comprises:

circuitry for associating activity in at least one of the insula, the lateral orbital frontal cortex, or the amygdala with a mental state indicating emotional disapproval.

29. The system of claim 1 wherein the circuitry for associating the at least one physiologic activity with at least one mental state comprises:
   circuitry for associating activity in the dorsolateral prefrontal cortex with a mental state indicating objective approval.

30. The system of claim 1 wherein the circuitry for associating the at least one physiologic activity with at least one mental state comprises:
   circuitry for associating activity in the caudate nucleus with a mental state indicating trust.

31. The system of claim 1 wherein the circuitry for associating the at least one physiologic activity with at least one mental state comprises:
   circuitry for associating activity in the hippocampus with a mental state indicating novelty in a perceived object.

32. The system of claim 1 wherein the circuitry for associating the at least one physiologic activity with at least one mental state comprises:
   circuitry for associating activity in the hippocampus with a mental state indicating lack of inhibition toward a perceived object.

33. The system of claim 1 wherein the circuitry for associating the at least one physiologic activity with at least one mental state comprises:
   circuitry for associating at least one brain activity surrogate marker with at least one mental state.

34. The system of claim 1 wherein the circuitry for associating the at least one physiologic activity with at least one mental state comprises:
   circuitry for associating at least one physiologic activity that is at or above a defined threshold with at least one mental state.

35. The system of claim 1 wherein the circuitry for associating the at least one physiologic activity with at least one mental state comprises:
   circuitry for associating at least one pattern of physiologic activity with at least one mental state that is known to be associated with the pattern of physiologic activity.

36. The system of claim 1 wherein the circuitry for identifying at least one instance of media content based on the at least one mental state comprises:
   circuitry for identifying at least one of an instance of movie content, an instance of television content, an instance of music content, an instance of literature content, an instance of internet content, or an instance of advertising content based on the at least one mental state.

37. The system of claim 1 wherein the circuitry for associating the at least one physiologic activity with at least one mental state comprises:
   circuitry for identifying at least one instance of advertising content based on at least one approving mental state relative to that of a competitor's advertising content.

38. The system of claim 1 wherein the circuitry for associating the at least one physiologic activity with at least one mental state comprises:
   circuitry for identifying the at least one instance of a product design based on at least one approving mental state relative to that of at least one alternative product design.

39. A computer program product comprising:
   a non-transitory signal-bearing medium bearing
   (a) one or more instructions for presenting to at least one member of a population a plurality of avatars associated with at least one instance of media content;
   (b) one or more instructions for measuring at least one physiologic activity of the at least one member of the population, the at least one physiologic activity proximate to at least one presented avatar among the plurality of avatars associated with at least one instance of media content;
   (c) one or more instructions for associating the at least one physiologic activity with at least one mental state, including one or more instructions for identifying at least one preferred instance of media content based on the at least one mental state; and
   (d) one or more instructions for identifying at least one instance of media content based on the at least one mental state.

40. The computer program product of claim 39, wherein the signal-bearing medium includes a computer-readable medium.

41. The computer program product of claim 39, wherein the signal-bearing medium includes a recordable medium.

42. The computer program product of claim 39, wherein the signal-bearing medium includes a communications medium.

43. A system comprising:
   a computing device; and
   instructions that when executed on the computing device cause the computing device to
   (a) present to at least one member of a population a plurality of avatars, each avatar associated with at least one instance of media content;
   (b) measure at least one physiologic activity of the at least one member of the population, the at least one physiologic activity proximate to at least one avatar among the plurality of avatars associated with at least one instance of media content;
   (c) associate the at least one physiologic activity with at least one mental state, including identifying at least one preferred instance of media content based on the at least one mental state; and
   (c) identify at least one instance of media content based on the at least one mental state.

44. The system of claim 43 wherein the computing device comprises:
   one or more of a personal digital assistant (PDA), a personal entertainment device, a mobile phone, a laptop computer, a tablet personal computer, a networked computer, a computing system comprised of a cluster of processors, a computing system comprised of a cluster of servers, a workstation computer, and/or a desktop computer.

45. The system of claim 43 wherein the computing device is operable to present to at least one member of a population a plurality of avatars, each avatar associated with at least one instance of media content from at least one memory.

46. The system of claim 43 wherein the computing device is operable to identify from at least one memory the at least one instance of media content based on the at least one mental state.

* * * * *